US011186596B2

(12) United States Patent
Boyd et al.

(10) Patent No.: US 11,186,596 B2
(45) Date of Patent: Nov. 30, 2021

(54) ANTICANCER INDENES, INDANES, AZAINDENES, AZAINDANES, PHARMACEUTICAL COMPOSITIONS AND USES

(71) Applicant: ADT PHARMACEUTICALS, LLC, Orange Beach, AL (US)

(72) Inventors: Michael Boyd, Orange Beach, AL (US); Xi Chen, Hoover, AL (US)

(73) Assignee: ADT Pharmaceuticals, LLC, Orange Beach, AL (US)

( * ) Notice: Subject to any disclaimer, the term of this patent is extended or adjusted under 35 U.S.C. 154(b) by 0 days.

(21) Appl. No.: 17/047,787

(22) PCT Filed: Apr. 26, 2019

(86) PCT No.: PCT/US2019/029430
§ 371 (c)(1),
(2) Date: Oct. 15, 2020

(87) PCT Pub. No.: WO2019/210223
PCT Pub. Date: Oct. 31, 2019

(65) Prior Publication Data
US 2021/0261572 A1    Aug. 26, 2021

Related U.S. Application Data

(60) Provisional application No. 62/662,999, filed on Apr. 26, 2018.

(51) Int. Cl.
| | | |
|---|---|---|
| C07F 5/02 | (2006.01) | |
| C07C 235/32 | (2006.01) | |
| C07D 213/40 | (2006.01) | |
| C07D 213/56 | (2006.01) | |
| C07D 231/40 | (2006.01) | |
| C07D 261/08 | (2006.01) | |
| C07D 277/28 | (2006.01) | |
| C07D 307/52 | (2006.01) | |
| C07D 317/12 | (2006.01) | |
| C07D 327/04 | (2006.01) | |

(52) U.S. Cl.
CPC ........... *C07F 5/025* (2013.01); *C07C 235/32* (2013.01); *C07D 213/40* (2013.01); *C07D 213/56* (2013.01); *C07D 231/40* (2013.01); *C07D 261/08* (2013.01); *C07D 277/28* (2013.01); *C07D 307/52* (2013.01); *C07D 317/12* (2013.01); *C07D 327/04* (2013.01); *C07B 2200/07* (2013.01)

(58) Field of Classification Search
CPC ..... C07F 5/025; C07C 235/32; C07D 213/40; C07D 213/56; C07D 231/40; C07D 261/08; C07D 277/28; C07D 307/52; C07D 317/12; C07D 327/04; C07B 2200/07

USPC .......................................................... 514/64
See application file for complete search history.

(56) References Cited

U.S. PATENT DOCUMENTS

| | | | |
|---|---|---|---|
| 3,642,785 | A | 2/1972 | Shen et al. |
| 3,888,902 | A | 6/1975 | Shen et al. |
| 5,093,356 | A | 3/1992 | Girard |
| 5,401,774 | A | 3/1995 | Pamukcu et al. |
| 5,965,582 | A | 10/1999 | Lebaut |
| 5,965,619 | A | 10/1999 | Pamukcu et al. |
| 6,028,116 | A | 2/2000 | Sperl et al. |
| 6,063,818 | A | 5/2000 | Sperl et al. |
| 6,071,934 | A | 6/2000 | Sperl et al. |
| 6,121,321 | A | 9/2000 | Sperl et al. |
| 6,166,053 | A | 12/2000 | Sperl et al. |
| 6,403,831 | B1 | 6/2002 | Sperl et al. |
| 6,538,029 | B1 | 3/2003 | Thompson et al. |
| 6,649,629 | B2 | 11/2003 | Bandarage et al. |
| 7,166,618 | B2 | 1/2007 | Bandarage et al. |
| 7,211,598 | B2 | 5/2007 | Ranatunge et al. |
| 7,432,285 | B2 | 10/2008 | Bandarage et al. |
| 7,491,744 | B2 | 2/2009 | Marnett et al. |
| 8,044,048 | B2 | 10/2011 | Piazza et al. |

(Continued)

FOREIGN PATENT DOCUMENTS

| | | |
|---|---|---|
| AU | 2013/206215 A1 | 6/2013 |
| AU | 2013/206218 A1 | 6/2013 |

(Continued)

OTHER PUBLICATIONS

"All RAS Mutation Panel," *TrimGen Genetic Diagnostics*, 2 pp. (Retrieved Jan. 28, 2017).

(Continued)

*Primary Examiner* — Kristin A Vajda
(74) *Attorney, Agent, or Firm* — Leydig, Voit & Mayer, Ltd.

(57) ABSTRACT

Disclosed are compounds for medical uses, for example, compounds of formula (Ia), wherein $A_1$, $A_2$, $A_3$, $A_4$, $A_5$, $A_6$, $A_7$, $R_6$, $R_7$ and E are as described herein, pharmaceutical compositions containing such compounds, and methods of treating or preventing a disease or condition, for example, cancer.

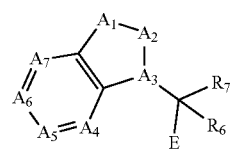

(Ia)

20 Claims, 3 Drawing Sheets

(56) References Cited

U.S. PATENT DOCUMENTS

| | | |
|---|---|---|
| 9,862,698 B2 | 1/2018 | Piazza et al. |
| 9,931,315 B2 | 4/2018 | Piazza et al. |
| 10,526,307 B2 | 1/2020 | Piazza et al. |
| 10,975,054 B2 | 4/2021 | Piazza et al. |
| 10,981,886 B2 | 4/2021 | Piazza et al. |
| 2003/0009033 A1 | 1/2003 | Sperl et al. |
| 2003/0176316 A1 | 9/2003 | Whitehead et al. |
| 2003/0194750 A1 | 10/2003 | Li et al. |
| 2007/0155734 A1 | 7/2007 | Ranatunge et al. |
| 2009/0099139 A1 | 4/2009 | Bandarage et al. |
| 2009/0221703 A1 | 9/2009 | Yu et al. |
| 2016/0168108 A1 | 6/2016 | Piazza et al. |
| 2016/0168113 A1 | 6/2016 | Piazza et al. |
| 2016/0175275 A1 | 6/2016 | Piazza et al. |
| 2017/0342021 A1 | 11/2017 | Piazza et al. |
| 2018/0208573 A1 | 7/2018 | Piazza et al. |
| 2018/0251443 A9 | 9/2018 | Piazza et al. |
| 2020/0031795 A1 | 1/2020 | Piazza et al. |
| 2020/0048217 A1 | 2/2020 | Piazza et al. |
| 2020/0223815 A1 | 7/2020 | Piazza et al. |
| 2020/0223816 A1 | 7/2020 | Piazza et al. |
| 2020/0223817 A1 | 7/2020 | Piazza et al. |

FOREIGN PATENT DOCUMENTS

| | | |
|---|---|---|
| AU | 2013/231152 A1 | 10/2013 |
| AU | 2014/201024 A1 | 3/2014 |
| AU | 2016/219617 A1 | 9/2016 |
| CN | 101031289 A | 9/2007 |
| CN | 103491772 A | 1/2014 |
| DE | 2020762 A1 | 11/1970 |
| DE | 10163426 A1 | 7/2003 |
| EP | 0 132 690 A1 | 2/1985 |
| EP | 0142801 A2 | 5/1985 |
| EP | 1 044 187 B1 | 1/2004 |
| GB | 1370028 | 10/1974 |
| HU | 9903620 A2 | 2/2000 |
| JP | 2000-514417 A | 10/2000 |
| JP | 2002-508358 A | 3/2002 |
| JP | 2004-510762 A | 4/2004 |
| JP | 2007-534702 A | 11/2007 |
| JP | 2009-522364 A | 6/2009 |
| JP | 2013-518060 A | 5/2013 |
| WO | WO 97/47303 A1 | 12/1997 |
| WO | WO 2001/045703 A1 | 6/2001 |
| WO | WO 2001/047939 A1 | 7/2001 |
| WO | WO 2004/002420 A2 | 1/2004 |
| WO | WO 2005/112921 A2 | 12/2005 |
| WO | WO 2006/124874 A1 | 11/2006 |
| WO | WO 2007/065924 A1 | 6/2007 |
| WO | WO 2007/081694 A2 | 7/2007 |
| WO | WO 2008/007171 A1 | 1/2008 |
| WO | WO 2008/010025 A1 | 1/2008 |
| WO | WO 2008/012602 A1 | 1/2008 |
| WO | WO 2008/012603 A1 | 1/2008 |
| WO | WO 2008/012605 A1 | 1/2008 |
| WO | WO 2008/017903 A1 | 2/2008 |
| WO | WO 2008/019357 A2 | 2/2008 |
| WO | WO 2008/020270 A1 | 2/2008 |
| WO | WO 2008/029199 A1 | 3/2008 |
| WO | WO 2008/029200 A1 | 3/2008 |
| WO | WO 2008/044095 A1 | 4/2008 |
| WO | WO 2008/149181 A1 | 12/2008 |
| WO | WO 2011/091417 A1 | 7/2011 |
| WO | WO 2012/135650 A1 | 10/2012 |
| WO | WO 2014/047592 A2 | 3/2014 |
| WO | WO 2014/169080 A1 | 10/2014 |
| WO | WO 2015/126462 A1 | 8/2015 |
| WO | WO 2016/099452 A1 | 6/2016 |
| WO | WO 2016/100542 A1 | 6/2016 |
| WO | WO 2016/100546 A1 | 6/2016 |
| WO | WO 2017/106520 A1 | 6/2017 |
| WO | WO 2019/210223 A1 | 10/2019 |

OTHER PUBLICATIONS

"ASCO Updates Guideline to Include Testing for New RAS Mutations," *Gastrointestinal Cancers Symposium*, 3 pp. (2016).

"Cobas KRAS Mutation Test—P140023," www.fda.gov, 2 pp. (Retrieved Jan. 28, 2017).

"KRAS Mutation Testing," www.trovagene.com, 5 pp. (Retrieved Jan. 28, 2017).

"Therascreen KRAS RGQ PCR Kit—P110027," www.fda.gov, 2 pp. (Retrieved Jan. 28, 2017).

Alcalde et al., "Indene-based scaffolds. Design and synthesis of novel serotonin 5-HT$_6$receptor ligands," *Org. Biomol. Chem.* 6: 3795-3810 (2008).

Al-Saeed, "Gastrointestinal and Cardiovascular Risk of Nonsteroidal Anti-inflammatory Drugs," *Oman Medical Journal*, 26(6): 385-391 (2011).

Andreyev et al., "Antisense treatment directed against mutated Ki-ras in human colorectal adenocarcinoma," *Gut.* 48: 230-237 (2001).

Antman et al., "Use of Nonsteroidal Antiinflammatory Drugs: An Update for Clinicians—A Scientific Statement From the American Heart Association," *Circulation* 115: 1634-1642 (2007).

Aparoy et al., "Pharmacophore modeling and virtual screening for designing potential 5-Lipoxygenase inhibitors," *Bioorganic and Medicinal Chemistry Letter* 20: 1013-1018 (2010).

Arber et al., "A K-ras Oncogene Increases Resistance to Sulindac-Induced Apoptosis in Rat Enterocytes," *Gastroenterology* 113: 1892-1900 (1997).

Arisawa et al., "Design and Synthesis of Indomethacin Analogues That Inhibit P-Glycoprotein and/or Multidrug Resistant Protein without Cox Inhibitory Activity," *Journal of Medicinal Chemistry* 55: 8152-8163 (2012).

Baldwin et al., "Structural requirements for the binding of non-steroidal anti-inflammatory drugs to the 78 kDa gastrin binding protein," *Biochimica et Biophysica Acta (BBA)*, 1428(1): 68-76 (1999).

Berge et al., "Pharmaceutical Salts," *Journal of Pharmaceutical Sciences* 66(1): 1-19 (1977).

Bittker et al., "Screen for RAS-Selective Lethal Compounds and VDAC Ligands," Probe Reports from NIH Molecular Libraries Program, Bethesda, ML210, Dec. 12, 2011 update, http://www.ncbi.nlm.nih.gov/books/NBK98919/.

Brink et al., "K-ras oncogene mutations in sporadic colorectal cancer in The Netherlands Cohort Study," *Carcinogenesis* 24(4): 703-710 (2003).

Chabner, Bruce A.,"Clinical Strategies for Cancer Treatment: The Role of Drugs," Chapter 1 of *Cancer Chemotherapy and Biotherapy: Principles and Practice*, Lippincott Williams & Wilkins, a Wolters Kluwer business, Philadelphia, PA, pp. 3-14 (2011).

Chen et al., "A novel series of substituted indene derivatives that potently and selectively inhibit growth of tumor cells harboring mutant Ras," *American Association for Cancer Research—Special Conference on Ras Oncogenes: From Biology to Therapy*, Disney Yacht Club Resort, Lake Buena Vista, Florida (Feb. 24-27, 2014)—1 pg.

Chennamaneni et al., "COX inhibitors Indomethacin and Sulindac derivatives as antiproliferative agents: Synthesis, biological evaluation, and mechanism investigation," *European Journal of Medicinal Chemistry* 56: 17-29 (2012).

Clark, "Molecular Targeted Drugs," Chapter 29 of *Cancer Chemotherapy and Biotherapy: Principles and Practice*, Lippincott Williams & Wilkins, a Wolters Kluwer business, Philadelphia, PA, pp. 526-546 (2011).

Collins et al., "Principles of Pharmacokinetics," Chapter 4 of *Cancer Chemotherapy and Biotherapy: Principles and Practice*, Lippincott Williams & Wilkins, a Wolters Kluwer business, Philadelphia, PA, pp. 50-61 (2011).

Cox et al., "Drugging the undruggable RAS: Mission Possible?," *Nature Reviews* 13: 828-840 (2014).

Database Chemcats [Online], May 16, 2014 (May 16, 2014), "TimeTec Stock Building Blocks and Screening Compounds," XP002767898, Database accession No. 1287187215 abstract.

(56) References Cited

OTHER PUBLICATIONS

De Jong et al., "Inhibition of rat colon tumors by sulindac and sulindac sulfone is independent of K-ras (codon 12) mutation," *American Journal of Physiology—Gastrointestinal and Liver Physiology* 278: G266-G272 (2000).

Decker et al., "Target Identification and Drug Discovery," Chapter 2 of *Cancer Chemotherapy and Biotherapy: Principles and Practice*, Lippincott Williams & Wilkins, a Wolters Kluwer business, Philadelphia, PA, pp. 15-27 (2011).

Dolma et al., "Identification of genotype-selective antitumor agents using synthetic lethal chemical screening in engineered human tumor cells," *Cancer Cell* 3: 285-296 (2003).

Downward, Julian, "Targeting RAS Signalling Pathways in Cancer Therapy," *Nature Reviews—Cancer* 3: 11-22 (Jan. 2003).

Gala et al., "Inhibition of cell transformation in sulindac sulfide is confined to specific oncogenic pathways," *Cancer Letters* 175: 89-94 (2002).

Goldstein et al., "Overexpression of protein kinase C β1 in the SW480 colon cancer cell line causes growth suppression," *Carcinogenesis* 16(5): 1121-1126 (1995).

Greig et al., "Tumorigenic and metastatic properties of "normal" and ras-transfected NIH/3T3 cells," *Proc. Natl. Acad. Sci. USA* 82: 3698-3701 (1985).

Guo et al., "Antitumor Activity of a Novel Oncrasin Analogue Is Mediated by JNK Activation and STAT3 Inhibition," *PLoS One* 6(12): 1-10 (2011).

Guo et al., "Identification of a Small Molecule with Synthetic Lethality for K-Ras and Protein Kinase C Iota," *Cancer Research* 68(18): 7403-7408 (2008).

Gurpinar et al., "A Novel Sulindac Derivative Inhibits Lung Adenocarcinoma Cell Growth through Suppression of Akt/mTOR Signaling and Induction of Autophagy," *Molecular Cancer Therapeutics* 12(5): 663-674 (2013).

Gurpinar et al., "NSAIDs Inhibit Tumorigenesis, but How?," *Clinical Cancer Research* 20(5): 1104-1113 (2014).

Gysin et al., "Therapeutic Strategies for Targeting Ras Proteins," *Genes & Cancer* 2(3): 359-372 (2011).

Herrmann et al., "Sulindac sulfide inhibits Ras signaling," *Oncogene* 17: 1769-1776 (1998).

Igarashi et al., "Synthesis and Evaluation of Carbamate Prodrugs of a Phenolic Compound," *Chem. Pharm. Bull.* 55(2): 328-333 (2007).

Ito et al., "A medium-term rat liver bioassay for rapid in vivo detection of carcinogenic potential of chemicals," *Cancer Sci.* 94(1): 3-8 (2003).

Jemal et al. "Cancer Statistics, 2003," *CA Cancer J Clin* 53: 5-26 (2003).

Jemal et al., "Cancer Statistics, 2008," *CA: A Cancer Journal for Clinicians* 58: 71-96 (2008).

Karaguni, Ioanna-Maria, et al., "New Indene-Derivatives with Anti-Proliferative Properties," *Bioorganic & Medicinal Chemistry Letters* 12: 709-713 (2002).

Kaufman, Dwight C., et al., "Clinical Strategies for Cancer Treatment: The Role of Drugs," Chapter 1, *Cancer Chemotherapy and Biotherapy: Principles and Practice*, Lippincott, Williams and Wilkins, pp. 1-16 (2011).

Keeton et al., "Search for Inhibitors of Ras-Driven Cancers," *Conquering RAS, 1st Edition. From Biology to Cancer Therapy*, Ch. 8, pp. 135-154 (2016).

Kong et al., "Structure-Based Discovery of a Boronic Acid Bioisostere of Combretastatin A-4," *Chem. Biol.* 12: 1007-1014 (2005).

Lawson et al., "Influence of K-ras Activation on the Survival Responses of Caco-2 Cells to the Chemopreventive Agents Sulindac and Difluoromethylornithine," *Cancer Epidemiology, Biomarkers & Prevention* 9: 1155-1162 (2000).

Ledford, "The RAS Renaissance," *Nature* 520: 278-280 (2015).

Lee et al., "Effect of Simbastatin on Cetuximab Resistance in Human Colorectal Cancer With KRAS Mutations," *JNCI* 103(8): 674-688 (2011).

Liedtke et al., "Cyclooxygenase-1-Selective Inhibitors Based on the (E)-2'-Des-methyl-sulindac Sulfide Scaffold," *Journal of Medicinal Chemistry* 55(5): 2287-2300 (2012).

Lim et al., "Exisulind and Related Compounds Inhibit Expression and Function of the Androgen Receptor in Human Prostate Cancer Cells," *Clinical Cancer Research* 9: 4972-4982 (2003).

Lim et al., "Sulindac Derivatives Inhibit Growth and Induce Apoptosis in Human Prostate Cancer Cell Lines," *Biochemical Pharmacology* 58(7): 1097-1107 (1999).

Magar et al., "Synthesis of Diverse Indene Derivatives from 1-Diazonaphthalen-2(1H)-ones via Thermal Cascade Reactions," *Organic Letters*, (2013) 4 pages.

McGettigan et al., "Cardiovascular Risk and Inhibition of Cyclooxygenase: A Systematic Review of the Observational Studies of Selective and Nonselective Inhibitors of Cyclooxygenase 2," *Journal of American Medical Association* 296(13): E1-E12 (2006—Reprinted).

Mielgo et al., "A MEK-independent role for CRAF in mitosis and tumor progression," *Nature Medicine* 17(12): 1641-1646 (2011).

Moon et al., "Benzylamide Sulindac Analogues Induce Changes in Cell Shape, Loss of Microtubules and $G_2$-M Arrest in a Chronic Lymphocytic Leukemia (CLL) Cell Line and Apoptosis in Primary CLL Cells 1," *Cancer Research* 62: 5711-5719 (2002).

Mulcahy et al., "Anti-EGFR Agents Detrimental in Colorectal Cancer Patients With KRAS Mutation," *Medscape Medical News*, 3 pp. (2009).

Müller et al., "Identification of Potent Ras Signaling Inhibitors by Pathway-Selective Phenotype-Based Screening," *Angewandte Chemie International Edition* 43(4): 450-454 (2004).

Murata et al., "An Efficient Catalyst System for Palladium-Catalyzed Borylation of Aryl Halides with Pinacolborane," *Synlett* 12: 1867-1870 (2006).

Nagase et al., "Abstract 2602: KRAS G12D and G12V specific alkylating agent (KR12) inhibits growth of colon cancer with those KRAS mutations in vitro as well as in vivo," Proceedings: AACR Annual Meeting 2014, *Cancer Research* 74(19 Suppl): Abstract nr. 2602 (2014)—1 pg.

O'Bryant et al., "A dose-ranging study of pharmacokinetics and pharmacodynamics of the selective apoptotic antineoplastic drug (SAAND), OSI-461, in patients with advanced cancer, in the fasted and fed state," *Cancer Chemotherapy and Pharmacology* 63(3): 477-489 (2008).

Okedula et. al., "K-ras Gene Mutation Enhances Motility of Immortalized Airway Cells and Lung Adenocarcinoma Cells via Akt Activation," *Am. J. Pathol* 164(1): 91-100 (2004).

Ostrem et al., "K-Ras(G12C) inhibitors allosterically control GTP affinity and effector interactions," *Nature* 503: 548-551 (2013).

Pan et al., "Non-steroidal anti-inflammatory drugs suppress the ERK signaling pathway via block of Ras/c-Raf interaction and activation of MAP kinase phosphatases," *Cellular Signalling* 20: 1134-1141 (2008).

Pekol et al., "Human Metabolism of the Proteasome Inhibitor Bortezomib: Identification of Circulating Metabolites," *Drug Metab. Dispos.* 33: 771-777 (2005).

Pettit et al., "Antineoplastic agents 322. Synthesis of combretastatin A-4 prodrugs," *Anticancer Drug Des.* 10: 299-309 (1995).

Pettit et. al., "Antineoplastic Agents. 291. Isolation and Synthesis of Combretastatins A-4, A-5, and A-6," *J. Med. Chem.* 38: 1666-1672 (1995).

Piazza et al., "A Novel Sulindac Derivative That Does Not Inhibit Cyclooxygenases but Potently Inhibits Colon Tumor Cell Growth and Induces Apoptosis with Antitumor Activity," *Cancer Prevention Research* 2(6): 572-580 (2009).

Pubchem, Compound Summary for CID 70682824, Create Date: Feb. 4, 2013, [retrieved on Apr. 2, 2015]. Retrieved from the Internet, <URL: https://pubchem.ncbi.nlm.nih.gov/compound/70682824.?from=summary>. entire document.

Qiagen Manchester Ltd., "TheraScreen: K-RAS Mutation Kit: For the Detection of 7 Mutations in the K-RAS Gene," *DxS Diagnostic Innovations*, pp. 1-24 (2012).

*Remington's Pharmaceutical Sciences*, Mack Publishing Company, Easton, Pennsylvania, $18^{th}$ edition, pp. 1445 (1990).

(56) References Cited

OTHER PUBLICATIONS

Rickles et al., "Adenosine A2A receptor agonists and PDE inhibitors: a synergistic multitarget mechanism discovered through systematic combination screening in B-cell malignancies," *Blood* 116: 593-602 (2010).

Roberts Jr., "Clinical Drug Development and Marketing Approval," Chapter 3 of *Cancer Chemotherapy and Biotherapy: Principles and Practice*, Lippincott Williams & Wilkins, a Wolters Kluwer business, Philadelphia, PA, pp. 28-49 (2011).

Romeiro, Nelilma C., et al., "Synthesis, pharmacological evaluation and docking studies of new sulindac analogues," *European Journal of Medicinal Chemistry* 44: 1959-1971 (2009).

Satta et al., "Establishment of drug resistance in human gastric and colon carcinoma xenograft lines.," *Jpn. J. Cancer Res.* 82(5): 593-598 (1991) Abstract only.

Schacter, Lee, "Etoposide phosphate: What, Why, Where, and How?," *Semin. Oncol.* 23(6 Suppl. 13): 1-7 (1996).

Schramm et al., "Activated K-ras is Involved in Regulation of Integrin Expression in Human Colon Carcinoma Cells," *In. J. Cancer* 87: 155-164 (2000).

Scudellari, "Mix and Match: Doctors face a maze of drug options and genetic markers to find the right treatment for people with advanced colorectal cancer," *Nature* 521: 512-514 (2015).

Shaw et al., "Selective killing of K-ras mutant cancer cells by small molecule inducers of oxidative stress," *Proceedings of the National Academy of Sciences of the United States of America* 108(21): 8773-8778 (2011).

Sheridan, "The Most Common Chemical Replacements in Drug-Like Compounds," *J. Chem. Inf. Comput. Sci.* 42: 103-108 (2002).

Shigaki et al., "KRAS and BRAF Mutations in 203 Esophageal Squamous Cell Carcinomas: Pyrosequencing Technology and Literature Review," *Annals of Surgical Oncology*, 8 pp. (Dec. 2012).

Shirasawa et al., "Altered Growth of Human Colon Cancer Cell Lines Disrupted at Activated Ki-ras," *Science* 260: 85-88 (1993).

Slatter et al., "Pharmacokinetics, Metabolism, and Excretion of Irinotecan (CPT-11) Following I.V. Infusion of [$^{14}$C]CPT-11 in Cancer Patients," *Drug Metab. Dispos.* 28(4): 423-433 (2000).

Snyder et al., "Reductive Coupling and Polymerization of Unsaturated Amides. II. Effect of Substituents," *J. Am. Chem. Soc.* 76: 1893-1898 (1954).

Spiegel, Jochen, et al., "Small-molecule modulation of Ras signaling," *Nature Chemical Biology* 10: 613-622 (2014).

Stephen, Andrew G., et al., "Dragging Ras Back in the Ring," *Cancer Cell* 25: 272-281 (2014).

Stoneman et al., "Induction of intercellular adhesion molecule I and class II histocompatibility antigens in colorectal tumour cells expressing activated ras oncogene," *Journal of Clinical Pathology—Molecular Pathology* 48: M326-M332 (1995).

Suhasani et al., "Cyclic-GMP-Dependent Protein Kinase Inhibits the Ras/Mitogen-Activated Protein Kinase Pathway," *Molecular and Cellular Biology* 18(12): 6983-6994 (1998).

Takashima et al., "Targeting the RAS oncogene," *Expert Opinion on Therapeutic Targets* 17(5): 507-531 (2013).

Teicher et al., *Anticancer Drug Development Guide: Preclinical Screening, Clinical Trials, and Approval*, Second Edition, Humana Press, Inc., Totowa, NJ, pp. 1-450 (2004).

Thompson et al., "Exisulind Induction of Apoptosis Involves Guanosine 3', 5'-Cyclic Monophosphate Phosphodiesterase Inhibition, Protein Kinase G Activation, and Attenuated β-Catenin," *Cancer Research* 60: 3338-3342 (2000).

Thompson et al., "Sulfone Metabolite of Sulindac Inhibits Mammary Carcinogenesis," *Cancer Research* 57: 267-271 (1997).

Thompson, "US National Cancer Institute's new Ras project targets an old foe," *Nature Medicine* 19(8): 949-950 (2013).

Tidyman et al., "The RASopathies: Developmental syndromes of Ras/MAPK pathway dysregulation," *Current Opinion in Genetics & Development* 19(3): 230-236 (Jun. 2009).

Waldmann, "Sulindac-Derived Ras Pathway Inhibitors Target the Ras-Raf Interaction and Downstream Effectors in the Ras Pathway," *Angewandte Chemie International Edition* 43: 454-458 (2004).

Wu et al., "Prodrug oncrasin-266 improves the stability, pharmacokinetics, and safety of NSC-743380," *Bioorganic & Medicinal Chemistry* 22: 5234-5240 (2014).

Xiao et al., "The sulindac derivatives OSI-461, OSIP486823, and OSIP487703 arrest colon cancer cells in mitosis by causing microtubule depolymerization," *Molecular Cancer Therapeutics* 5(1): 60-67 (2006).

Yamaguchi et al., "Efficient Heterogeneous Aerobic Oxidation of Amines by a Supported Ruthenium Catalyst," *Angew. Chem. Int. Ed..* 42: 1480-1483 (2003).

Yang et al., "Synthetic Lethal Screening Identifies Compounds Activating Iron-Dependent, Nonapoptotic Cell Death in Oncogenic-RAS-Harboring Cancer Cells," *Chemistry & Biology* 15: 234-245 (2008).

Yoon et al., "CP248, a Derivative of Exisulind, Causes Growth Inhibition, Mitotic Arrest, and Abnormalities in Microtubule Polymerization in Glioma Cells," *Molecular Cancer Therapeutics* 1: 393-404 (2002).

Zimmermann, Gunther, et al., "Structure Guided Design and Kinetic Analysis of Highly Potent Benzimidazole Inhibitors Targeting the PDEδ Prenyl Binding Site," *Journal of Medicinal Chemistry* 57: 5435-5448 (2014).

US Patent and Trademark Office, International Search Report in International Application No. PCT/US2014/070511 (dated Apr. 20, 2015).

US Patent and Trademark Office, Written Opinion in International Application No. PCT/US2014/070511 (dated Apr. 20, 2015).

U.S. Patent and Trademark Office, International Preliminary Report on Patentability Chapter II with Annexes in International Application No. PCT/US2014/070511 (dated Jun. 21, 2017).

European Patent Office, International Search Report in International Application No. PCT/US2015/066146 (dated Feb. 25, 2016).

European Patent Office, Written Opinion in International Application No. PCT/US2015/066146 (dated Feb. 25, 2016).

European Patent Office, International Preliminary Report on Patentability in International Application No. PCT/US2015/066146 (dated Apr. 6, 2017).

European Patent Office, Written Opinion of the International Preliminary Examining Authority in International Application No. PCT/US2015/066146 (dated Nov. 9, 2016).

European Patent Office, International Search Report in International Application No. PCT/US2016/066962 (dated Apr. 4, 2017).

European Patent Office, Written Opinion in International Application No. PCT/US2016/066962 (dated Apr. 4, 2017).

International Bureau of WIPO, International Preliminary Report on Patentability in International Application No. PCT/US2016/066962 (dated Jun. 28, 2018).

European Patent Office, International Search Report in International Application No. PCT/US2019/029430 (dated Oct. 4, 2019).

European Patent Office, Written Opinion in International Application No. PCT/US2019/029430 (dated Oct. 4, 2019).

European Patent Office, Written Opinion of the International Preliminary Examining Authority in International Application No. PCT/US2019/029430 (dated Mar. 20, 2020).

European Patent Office, International Preliminary Report on Patentability in International Application No. PCT/US2019/029430 (dated Aug. 28, 2020).

European Patent Office, International Search Report in International Application No. PCT/US2015/066154 (dated Apr. 26, 2016).

European Patent Office, Written Opinion in International Application No. PCT/US2015/066154 (dated Apr. 26, 2016).

European Patent Office, International Preliminary Report on Patentability in International Application No. PCT/US2015/066154 (dated Dec. 6, 2016).

European Patent Office, Communication Pursuant to Article 94(3) EPC in European Application No. 15821218.3 (dated Jul. 19, 2018).

European Patent Office, Communication Pursuant to Article 94(3) EPC in European Application No. 15823453.4 (dated Mar. 20, 2019).

European Patent Office, Extended European Search Report in European Application No. 19197686.9 (dated May 14, 2020).

(56) References Cited

OTHER PUBLICATIONS

European Patent Office, second Communication Pursuant to Article 94(3) EPC issued in European Application No. 15823453.4 (dated Oct. 13, 2020).
Intellectual Property India, First Examination Report in Indian Patent Application No. 201717021093 (dated Nov. 4, 2019).
IP Australia, Examination Report No. 1 in Australian Patent Application No. 2015364696 (dated Nov. 1, 2019).
IP Australia, Examination Report No. 2 in Australian Patent Application No. 2015364696 (dated Mar. 6, 2020).
IP Australia, Examination Report No. 3 in Australian Patent Application No. 2015364696 (dated Apr. 28, 2020).
IP Australia, Notice of Acceptance in Australian Patent Application No. 2015364696 (dated Oct. 1, 2020).
Japan Patent Office, Notice of Reasons for Rejection in Japanese Patent Application No. 2017-533501 (dated Sep. 11, 2019).
Japan Patent Office, Notice of Reasons for Rejection in Japanese Patent Application No. 2017-533501 (dated Jan. 9, 2020).
Japan Patent Office, Notice of Reasons for Rejection in Japanese Patent Application No. 2017-533502 (dated Aug. 21, 2019).
Japan Patent Office, Notice of Final Rejection in Japanese Patent Application No. 2017-533502 (dated Feb. 5, 2020).
Japan Patent Office, Notice of Reasons for Refusal in Japanese Patent Application No. 2020-005245 (dated Nov. 12, 2020).
Mexico Institute of the Industrial Property, First Office Action in Mexican Patent Application No. MX/a/2017/007840 (dated Feb. 25, 2020).
Mexico Institute of the Industrial Property, Second Office Action in Mexican Patent Application No. MX/a/2017/007840 (dated Nov. 17, 2020).
Brazilian National Institute of Industrial Property, Office Action in Brazilian Patent Application No. BR112017013012-2 (dated Oct. 13, 2020).
Superintendence of Industry and Commerce, Office Action in Colombian Patent Application No. NC2017/0007076 (dated Aug. 2, 2017).
China National Intellectual Property Administration, First Office Action in Chinese Patent Application No. 201580076204.6 (dated Dec. 11, 2019).
China National Intellectual Property Administration, Second Office Action in Chinese Patent Application No. 201580076204.6 (dated Jul. 21, 2020).
State Intellectual Property Office of the People's Republic of China, Office Action in Chinese Patent Application No. 201580076108.1 (dated Feb. 2, 2019).
State Intellectual Property Office of the People's Republic of China, Office Action in Chinese Patent Application No. 201580076108.1 (dated Jul. 18, 2019).
State Intellectual Property Office of the People's Republic of China, Third Office Action in Chinese Patent Application No. 201580076108.1 (dated Dec. 31, 2019).
Vietnamese National Office of Intellectual Property, Office Action in Vietnamese Patent Application No. 1-2017-02611 (dated Feb. 12, 2018).
U.S. Appl. No. 14/571,647, filed Dec. 16, 2014, Patented.
U.S. Appl. No. 14/571,690, filed Dec. 16, 2014, Abandoned/Expired.
U.S. Appl. No. 15/056,202, filed Feb. 29, 2016, Patented.
U.S. Appl. No. 15/537,222, filed Jun. 16, 2017, Abandoned/Expired.
U.S. Appl. No. 15/537,283, filed Jun. 16, 2017, Pending.
U.S. Appl. No. 15/537,292, filed Jun. 16, 2017, Patented.
U.S. Appl. No. 15/863,285, filed Jan. 5, 2018, Abandoned/Expired.
U.S. Appl. No. 15/900,213, filed Feb. 20, 2018, Abandoned/Expired.
U.S. Appl. No. 16/593,776, filed Oct. 4, 2019, Pending.
U.S. Appl. No. 16/593,806, filed Oct. 4, 2019, Pending.
U.S. Appl. No. 16/834,267, filed Mar. 30, 2020, Pending.
U.S. Appl. No. 16/834,348, filed Mar. 30, 2020, Pending.
U.S. Appl. No. 16/837,757, filed Apr. 1, 2020, Pending.

ANTICANCER INDENES, INDANES, AZAINDENES, AZAINDANES, PHARMACEUTICAL COMPOSITIONS AND USES

CROSS-REFERENCE TO RELATED APPLICATIONS

This patent application is the U.S. national phase of International Application No. PCT/US2019/029430, filed on Apr. 26, 2019, which claims the benefit of U.S. Provisional Application No. 62/662,999, filed Apr. 26, 2018, the disclosures of which are incorporated herein by reference in their entireties for all purposes.

BACKGROUND OF THE INVENTION

Cancer is a leading cause of death in the developed world, with over one million people diagnosed and more than 500,000 deaths per year in the United States alone. Overall it is estimated that at least one in three people will develop some form of cancer during their lifetime. There are more than 200 different histopathological types of cancer, four of which (breast, lung, colorectal, and prostate) account for over half of all new cases in the U.S. (Jemal et al., *Cancer J. Clin.*, 53, 5-26 (2003)).

Many of these tumors arise from mutations that activate Ras proteins, which control critically important cellular signaling pathways that regulate growth and other processes associated with tumorigenesis. The name "Ras" is an abbreviation of "Rat sarcoma" reflecting the way the first members of the Ras protein family were discovered. The name "ras" also is used to refer to the family of genes encoding these proteins.

Ras-driven cancers have remained the most intractable diseases to any available treatment. New therapeutic and preventative strategies are urgently needed for such cancers (Stephen et al., *Cancer Cell*, 25: 272-281 (2014)). Drug discovery programs worldwide have sought Ras-selective drugs for many years, but heretofore no avail (Spiegel et al., *Nature Chem. Biol.*, 10: 613-622 (2014)). New drugs that selectively target abnormal or mutant Ras and/or Ras-mediated pathological processes in patients' tumors will enable highly efficacious treatments of such patients while minimizing toxicity to cells and tissues with normal Ras functions (Stephen et al., supra; Spiegel et al., supra).

Ras proteins are key regulators of several aspects of normal cell growth and malignant transformation, including cellular proliferation, survival and invasiveness, tumor angiogenesis and metastasis (Downward, *Nature Rev. Cancer*, 3: 11-22 (2003)). Ras proteins are abnormally active in most human tumors due to mutations in the ras genes themselves, or in upstream or downstream Ras pathway components, or other alterations in Ras signaling. Targeted therapies that inhibit Ras-mediated pathways therefore are expected to inhibit the growth, proliferation, survival and spread of tumor cells having activated or mutant Ras. Some such new experimental therapeutic agents have shown promising activity in preclinical studies, albeit with only modest activity in human clinical trials.

Genetic mutations in ras genes were first identified in human cancer over 3 decades ago. Such mutations result in the activation of one or more of three major Ras protein isoforms, including H-Ras, N-Ras, or K-Ras, that turn on signaling pathways leading to uncontrolled cell growth and tumor development. Activating ras gene mutations occur de novo in approximately one third of all human cancers and are especially prevalent in pancreatic, colorectal, and lung tumors. Ras mutations also develop in tumors that become resistant to chemotherapy and/or radiation, as well as to targeted therapies, such as receptor tyrosine kinase inhibitors (Gysin et al., *Genes Cancer*, 2: 359-372 (2011)). While ras mutations are relatively infrequent in other tumor types, for example, breast cancer, Ras can be pathologically activated by certain growth factor receptors that signal through Ras.

Although ras gene mutations have been known for many years, there currently are no available cancer therapeutics approved by the U.S. Food and Drug Administration that are known to selectively suppress the growth of tumors driven by activated Ras. In fact, Ras has been described as "undruggable" because of the relative abundance in cells and high affinity for its substrate, GTP (Takashima and Faller, *Expert Opin. Ther. Targets*, 17: 507-531 (2013)).

In addition to its role in cancer, activated Ras is important in a variety of other diseases, collectively referred to as "rasopathies." One such disease, neurofibromatosis type 1 (NF1), a very prevalent autosomal dominant heritable disease, is caused by a mutation in neurofibromin, a Ras GAP (inactivating protein), which results in Ras hyperactivation in the relatively common event of loss of the second NF1 allele. Such mutations reportedly affect 1:3000 live births. The worst symptoms associated with NF1 include numerous benign tumors (neurofibromas) arising from precursor nerve cells and Schwann cells of the peripheral nervous system. These tumors can cause severe problems depending on their location within the body, such as hearing or vision loss, as well as disfiguring masses on visible areas. Less common but extremely serious complications may arise when central nervous system gliomas develop or plexiform neurofibromas become transformed, resulting in the development of metastatic peripheral nerve sheath tumors (Tidyman and Rauen, *Curr. Opin. Genet. Dev.*, 19: 230-236 (2009)). Another rare developmental disease which is attributable to hyperactive H-Ras is Costello syndrome. This condition causes a range of developmental abnormalities as well as predisposing patients to a variety of benign and malignant neoplasms (Tidyman and Rauen, supra).

Several approaches to treat diseases that arise from activating ras mutations have been undertaken. Because full maturation of the Ras protein requires lipid modification, attempts have been made to target this enzymatic process with inhibitors of farnesyl transferase and geranylgeranyl-transferase, but with limited success and significant toxicity. Targeting of downstream components of Ras signaling with inhibitors of Raf/Mek/Erk kinase components of the cascading pathway has been an extremely active area of pharmaceutical research, but also fraught with difficulties and paradoxes arising from complex feedback systems within the pathways (Takashima and Faller, supra).

Inhibitors targeting components within the PI3K/Akt pathway also have not been successful as single agents, but presumably might synergize with Raf/Mek/Erk pathway inhibitors to block Ras-dependent tumor growth and survival. Similarly, several other molecular targets have been identified from RNAi screening, which might provide new opportunities to inhibit the growth of Ras-driven tumors; such other potential targets include CDK4, Cyclin D1, Tiam1, Myc, STK33, and TBK, as well as several genes involved in mitosis (Takashima and Faller, supra).

The nonsteroidal anti-inflammatory drug, sulindac (FIG. 1) has been reported to selectively inhibit proliferation of cultured tumor cells having ras mutations (Herrmann et al., *Oncogene*, 17: 1769-1776 (1998)). Extensive chemical modifications of sulindac and the related NSAID, indomethacin, have been aimed at removing cyclooxygenase-inhibitory activity, while improving anticancer activity (Gurpinar et al., *Mol. Cancer Ther.*, 12: 663-674 (2013); Romeiro et al., *Eur. J. Med. Chem.*, 44: 1959-1971 (2009); Chennamaneni et al., *Eur. J. Med. Chem.*, 56: 17-29 (2012)). An example of a highly potent antiproliferative derivative is a hydroxy-substituted indene derivative of sulindac, OSIP-487703 (FIG. 1), that was reported to arrest colon cancer cells in mitosis by causing microtubule depolymerization (Xiao et al., *Mol. Cancer Ther.*, 5: 60-67 (2006)). OSIP-487703 also was reported to inhibit the growth and induce apoptosis of human SW480 colon cancer cells. These properties of mitotic arrest and microtubule disruption were shared by several additional related compounds, including a pyridine (CP461) and trimethoxy (CP248) substituted variants (FIG. 1) (Lim et al., *Clin. Cancer Res*, 9: 4972-4982 (2003); Yoon et al., *Mol. Cancer Ther.*, 1: 393-404 (2002)). However, there was no reported association of antitumor properties of these compounds (FIG. 1) with Ras function, but rather such properties were attributed to direct binding to the microtubule subunit, tubulin, thereby causing mitotic arrest and blocking cell division. Still other reports describe their ability to induce apoptosis by inhibition of cGMP phosphodiesterase (Thompson et al., *Cancer Research*, 60: 3338-3342 (2000)).

Other investigators reported that sulindac sulfide (FIG. 1) can inhibit Ras-induced malignant transformation, possibly by decreasing the effects of activated Ras on its main effector, the c-Raf-1kinase, due to direct binding to the ras gene product p21 in a non-covalent manner (Herrmann et al., supra). Sulindac sulfide also can inhibit focus formation, a marker of malignant transformation, by rat or mouse fibroblasts by forced Ras expression, but not by other transformation pathways (Gala et al., *Cancer Lett.*, 175: 89-94 (2002); Herrmann et al., supra). Sulindac sulfide was reported also to bind Ras directly and interfere with nucleotide exchange. Several groups additionally reported that sulindac interferes with Ras binding to the downstream signaling kinase c-Raf, and blocks activation of downstream signaling or transcription (Herrmann et al., supra; Pan et al., *Cell Signal.*, 20: 1134-1141 (2008)).

The previous findings led to efforts to improve the Ras inhibitory activity of sulindac sulfide through chemical modifications (Karaguni et al., *Bioorg. Med. Chem. Lett.*, 12: 709-713 (2002)). Several derivatives were identified that were more potent inhibitors of tumor cell proliferation, and four related compounds (FIG. 2) exhibited selectivity towards a Ras-transfected MDCK cell line compared to the parental cell line. Three of these compounds also potently disrupted the Ras-Raf interaction. However, none of the four were more potent toward the mutant K-Ras-bearing SW-480 cell line, although they did inhibit Erk phosphorylation and bound weakly to the G-domain of H-Ras (Waldmann et al., *Angew. Chem. Int. Ed. Engl.*, 43: 454-458 (2004)).

In addition to sulindac sulfide, the non-COX inhibitory sulfone metabolite of sulindac has been reported to have selective effects on tumor cells with mutant Ras. For example, transfection of Caco-2 colon tumor cells with the activated K-Ras oncogene caused cells treated with either sulindac sulfide or sulfone to undergo apoptosis earlier than non-transfected cells. (Lawson et al., *Cancer Epidemiol. Biomarkers Prev.*, 9: 1155-62 (2000)). Other investigators have reported that sulindac sulfone can inhibit mammary tumorigenesis in rats and that the effect was greater on tumors with the mutant H-Ras genotype (Thompson et al., *Cancer Research* 57: 267-271 (1997)). However, other investigators report that the inhibition of colon tumorigenesis in rats by either sulindac or sulindac sulfone occurs independently of K-Ras mutations (de Jong et al., *Amer. J Physio. Gastro and Liver Phys.* 278: 266-272 (2000)). Yet other investigators report that the K-Ras oncogene increases resistance to sulindac-induced apoptosis in rat enterocytes (Arber et al., *Gastroenterology,* 113: 1892-1900 (1997)). As such, the influence of Ras mutations on the anticancer activity of sulindac and its metabolites is controversial and unresolved, and not exploited to improve anticancer potency or selectivity.

Certain other compounds have been described with selective toxicity toward cells expressing activated Ras. A high-throughput phenotypic screen of over 300,000 compounds was conducted within NIH Molecular Libraries Screening Center program to identify compounds which were synthetically lethal to cells expressing oncogenic H-Ras. A lead compound, ML210, inhibited growth of cells expressing mutant Ras with an IC50 of 71 nM, and was 4-fold selective versus cells lacking oncogenic Ras. Though the specific molecular target of ML210 (FIG. 3) is unknown, the compound was chemically optimized to eliminate reactive groups and improve pharmacologic properties (ML210, Dec. 12, 2011 update, Probe Reports from NIH Molecular Libraries Program, Bethesda, http://www.ncbi.nlm.nih.gov/books/NBK98919/).

A separate high-throughput screen identified two compounds, RSL3 and RSL5 which induce non-apoptotic, Mek-dependent, oxidative cell death (Yang and Stockwell, *Chem. Biol.*, 15: 234-245 (2008). RSL5, like a previously identified Ras synthetic lethal compound, erastin, binds the voltage-dependent anion channel (VDAC) (Dolma et al., *Cancer Cell,* 3: 285-296 (2003)). Yet another small-molecule screen identified oncrasin, a compound selectively active against K-Ras mutant cell lines (Guo et al., *Cancer Res.*, 68: 7403-7408 (2008)). One analog, NSC-743380 (FIG. 3), is highly potent and has shown anti-tumor activity in a pre-clinical model of K-Ras driven renal cancer (Guo et al., *PLoS One,* 6: e28487 (2011)). A prodrug approach has recently been described for oncrasin derivatives, to improve stability, pharmacokinetics, and safety (Wu et al., *Bioorg. Med. Chem.*, 22: 5234-5240 (2014)). A synthetic lethal screen using embryonic fibroblasts derived from mice expressing the oncogenic K-Ras (G12D) identified a compound, lanperisone (FIG. 3), that induced non-apoptotic cell death via a mechanism involving oxidative stress (Shaw et al., *Proc. Natl. Acad. Sci. USA,* 108: 8773-8778 (2011)). In contrast to the synthetic lethal approach, a fragment-based screening approach paired with crystallographic studies has been used to identify compounds which irreversibly bind to and inhibit K-Ras in lung tumor cells having the relatively rare G12C ras gene mutation (Ostrem et al., *Nature,* 503: 548-551 (2013)). While compounds of this series potently inhibit Ras through a covalent interaction, the low frequency of this mutation may limit the utility of such compounds. Finally, a new investigational strategy for targeting oncogenic Ras has been described (Zimmerman et al., *J. Med. Chem.*, 57: 5435-5448 (2014)) which involves structure guided design and kinetic analysis of benzimidazole inhibitors targeting the PDE5 prenyl binding site.

WO 97/47303 and WO 2014/047592, U.S. Patent Application Publication Nos. 2003/0009033 and 2003/0194750, U.S. Pat. Nos. 6,063,818; 6,071,934, 5,965,619; 5,401,774; 6,538,029, 6,121,321, and UK Patent No. GB 1370028 disclose certain anticancer compounds; however, these documents do not disclose that the compounds have any Ras-specific activity, nor any basis for a selective Ras-directed method of use.

We have disclosed (2015-2018) a series of compounds having an indene or indene-related core structure, such compounds having antitumor properties, including Ras-inhibitory properties (U.S. Pat. Nos. 9,862,698 and 9,931,315; U.S. Pat. App. Pub. Nos. US 2017/0342021 and US 2018/0251443; PCT Intl. Pat. App. Nos. WO 2016/100542, WO 2016/100546; WO 2016/099452; WO 2017/106520). Chemical structures of all these previously disclosed compounds are encompassed by the generic structure I shown in FIG. 4 wherein the substituents for R, $R_0$, $R_1$-$R_8$, n, X, Y, Y', and E are as described in the WO 2016/100542. Here we disclose novel, indene-related compounds designed to further improve druglike attributes, Ras-inhibitory antitumor properties and medical utility.

Cancer still is among the most prevalent causes of human deaths and suffering worldwide, and there remains a vast unmet medical need for new compounds that can be developed or made suitable for treating or preventing cancers. There especially exists an unmet need for novel compounds that inhibit Ras-dependent diseases or undesirable conditions. The present invention discloses new Ras-inhibitory antitumor compounds with unique chemical structures, properties, medical utility and commercial applicability distinct from any prior art.

BRIEF SUMMARY OF THE INVENTION

The invention provides a compound of formula Ia:

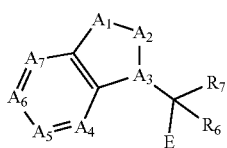

Ia wherein:

$A_1$ is a nitrogen atom bonded to $R_{21}$ when $R_{21}$ is not bonded to $A_2$, or $A_1$ is a nitrogen atom bonded to $R_9$ when $R_{21}$ is bonded to $A_2$; or, $A_1$ is a carbon atom bonded to $R_9$ and $R_{21}$ when $R_{21}$ is not bonded to $A_2$, or $A_1$ is a carbon atom bonded to $R_8$ and $R_9$ when $R_{21}$ is bonded to $A_2$;

$A_2$ is a nitrogen atom bonded to $R_{21}$ when $R_{21}$ is not bonded to $A_1$, or $A_2$ is a nitrogen atom bonded to $R_8$ when $R_{21}$ is bonded to $A_1$; or, $A_2$ is a carbon atom bonded to $R_8$ and $R_{21}$ when $R_{21}$ is not bonded to $A_1$, or $A_2$ is a carbon atom bonded to $R_8$ and $R_{20}$ when $R_{21}$ is bonded to $A_1$;

$A_3$ is a nitrogen atom; or, or $A_3$ is a carbon atom bonded to $R_5$;

$A_4$ is a nitrogen atom; or, or $A_4$ is a carbon atom bonded to $R_4$;

$A_5$ is a nitrogen atom; or, or $A_5$ is a carbon atom bonded to $R_3$;

$A_6$ is a nitrogen atom; or, or $A_6$ is a carbon atom bonded to $R_2$;

$A_7$ is a nitrogen atom; or, or $A_7$ is a carbon atom bonded to $R_1$;

each of $R_1$, $R_2$, $R_3$, and $R_4$ is independently selected from hydrogen, halo, alkyl, hydroxyl, haloalkyl, alkylmercapto, cyano and a substituted or unsubstituted alkyloxy group;

$R_{21}$ is selected from —$(CH_2)_nC(O)X$ and —$(CH_2)_n NR_{22}C(O)X$;

each of $R_5$, $R_6$, $R_7$, $R_8$, $R_9$, $R_{20}$, and $R_{22}$ is independently selected from hydrogen, alkyl, halo and hydroxyl; or $R_5$ and $R_6$ together is a carbon-carbon bond when $A_3$ is a carbon atom; or $R_5$ and $R_{20}$ together is a carbon-carbon bond when $A_2$ and $A_3$ are carbon atoms; or $R_9$ and $R_{20}$ together is a carbon-carbon bond when $A_1$ and $A_2$ are carbon atoms; or $R_9$ and $R_8$ together is a carbon-nitrogen bond when $A_1$ is carbon and $A_2$ is nitrogen or when $A_1$ is nitrogen and $A_2$ is carbon; or $R_5$ and $R_6$ together is a carbon-nitrogen bond when $A_2$ is nitrogen and $A_3$ is carbon; or, $R_6$ and $R_7$ together with the atom to which they are attached form a ring; or, when $A_3$ is carbon, $R_5$ and $R_6$ together with the atoms to which they are attached form a ring;

n is 0, 1 or 2, or n is 1 or 2 when $A_7$ is a nitrogen atom;

X is selected from aryl, arylalkyl, heterocyclyl and heterocyclylalkyl, or X is NR'R" where R' is selected from aryl, arylalkyl, heterocyclyl, and heterocyclylalkyl, where the heterocyclyl of the heterocyclyl and of the heterocyclylalkyl of the X, and the heterocyclyl of the heterocyclyl and of the heterocyclylalkyl of the R' when X is NR'R", is selected from 7-membered, 6-membered and 5-membered heterocyclic rings, and the aryl of the aryl and arylalkyl, and the heterocyclyl of the heterocyclyl and of the heterocyclylalkyl, is optionally substituted with one or more of halo, alkyl, haloalkyl, hydroxyl, alkyloxy, amino, alkylamino, dialkylamino, mercapto, alkylmercapto, carboxamido, aldehydo, cyano, oxo, alkylcarbonyloxy and sulfonamido;

R" is selected from hydrogen, alkyl and haloalkyl;

E is a substituted or unsubstituted, saturated or unsaturated, 9-membered, 8-membered, 7-membered, 6-membered, 5-membered, 4-membered or 3-membered, carbocyclic or heterocyclic, monocyclic or bicyclic ring; or (Z)- or (E)-isomer, epimer, diastereomer, rotamer, or pharmaceutically acceptable salt of said compound;

with the proviso that when $R_{21}$ is —$(CH_2)_nC(O)X$, and each of $A_2$, $A_4$, $A_5$, $A_6$ and $A_7$ is a carbon atom, and $R_9$ and $R_{20}$ together is a carbon-carbon bond, and E is a substituted or unsubstituted, saturated or unsaturated, 7-membered, 6-membered, 5-membered, 4-membered or 3-membered carbocyclic or heterocyclic, monocyclic or bicyclic ring, then at least one of $R_5$, $R_6$ and $R_7$ is halo, or $R_6$ and $R_7$ together with the atom to which they are attached form a ring, or $R_5$ and $R_6$ together with the atoms to which they are attached form a ring, or at least one of $R_1$, $R_2$, $R_3$, and $R_4$ or at least one substituent on the ring at E is haloalkyloxy or is a substituted or unsubstituted group selected from polyethyleneglycoxy, polyethyleneglycoxyalkyl, thioureido, borono, boronoalkyl, boronoalkyloxy, arylalkyloxy, aminosulfonyloxy, aminocarboxyl, aminocarbonylalkyloxy, aminocarbonylalkylthio, alkylcarbonylamino, aminoalkenylamino, alkylsulfonylamino, phosphono, phosphonothio, phosphonoamino, phosphonoalkyl, phosphonoalkylthio, phosphonoalkylamino, carboxyalkyl, carboxyalkenyl, carboxyalkynyl, carboxyalkyloxy, carboxyalkylamino, carboxyalkylthio, aminocarbonylthio, hydroxyalkyloxy, hydroxyalkylamino, hydroxyalkylthio, dialkylaminoalkyl, aminoalkylamino, alkylaminoalkylamino, dialkylaminoalkylamino, aminoalkyloxy, alkylaminoalkyloxy, dialkylaminoalkyloxy, alkyloxyaminocarbonyloxy, aminoalkylthio, alkylaminoalkylthio and dialkylaminoalkylthio, or any two substituents on E, together with the atoms to which they are attached, comprise an optionally substituted, saturated or unsaturated 3-, 4-, 5-, 6- or 7-membered carbocyclic or heterocyclic ring that is not alkylenedioxy.

In a preferred embodiment, the invention provides a compound of formula Ia or a pharmaceutical composition thereof for use in treating a cancer patient whose cancer has been assayed and found to contain a hyperactive Ras protein or a mutant ras gene encoding for a hyperactive Ras protein.

The invention also provides pharmaceutical compositions comprising at least one novel compound of formula Ia for use in treating cancer, especially Ras-driven cancer, and methods of treating a cancer patient, particularly a cancer patient having a Ras-driven, with a compound of formula Ia or IIa.

BRIEF DESCRIPTION OF THE SEVERAL VIEWS OF THE DRAWING(S)

DETAILED DESCRIPTION OF THE INVENTION

Figure 1:
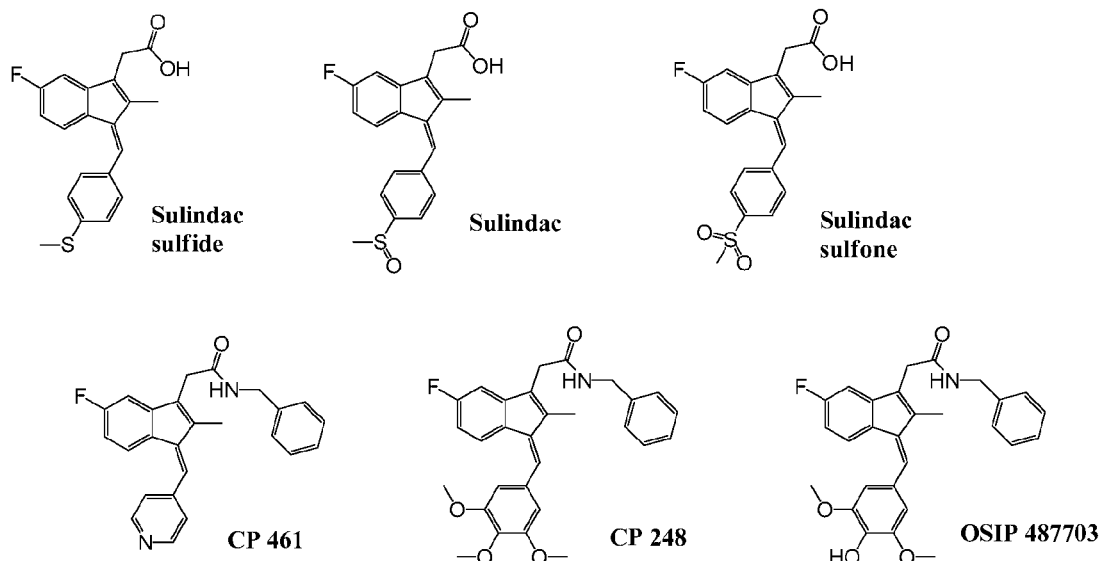
FIG. 1 depicts the chemical structures of sulindac and certain derivatives thereof reportedly having anticancer activity.
Figure 2:
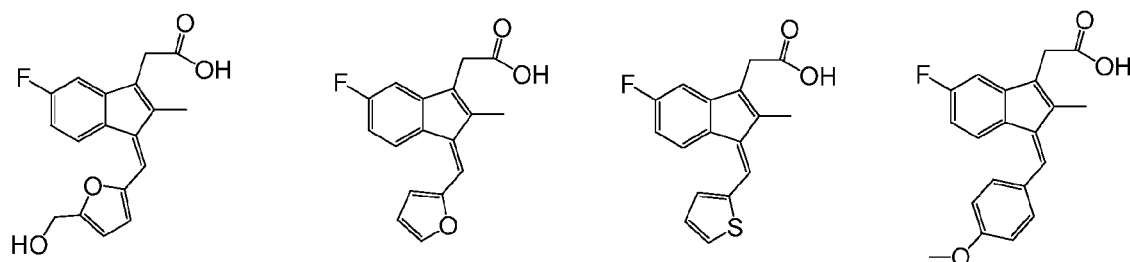
FIG. 2 depicts chemical structures of certain other sulindac derivatives reported to inhibit Ras.
Figure 3:
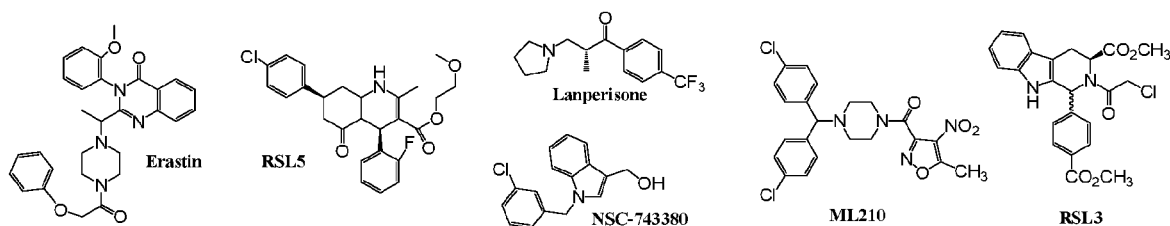
FIG. 3 shows chemical structures of selective Ras-inhibitory compounds identified by synthetic lethal screening.
Figure 4:
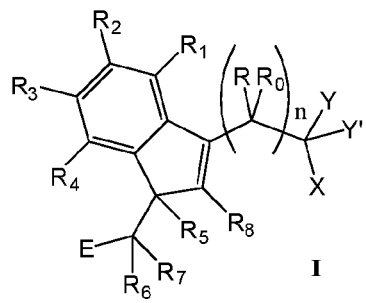
FIG. 4 depicts the generic structure I from WO 2016/100542 wherein the substituents for R, $R_0$, $R_1$-$R_8$, n, X, Y, Y', and E are as described in the WO 2016/100542.

The invention provides a compound of formula Ia:

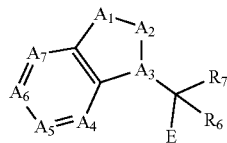

Ia wherein:

$A_1$ is a nitrogen atom bonded to $R_{21}$ when $R_{21}$ is not bonded to $A_2$, or $A_1$ is a nitrogen atom bonded to $R_9$ when $R_{21}$ is bonded to $A_2$; or, $A_1$ is a carbon atom bonded to $R_9$ and $R_{21}$ when $R_{21}$ is not bonded to $A_2$, or $A_1$ is a carbon atom bonded to $R_8$ and $R_9$ when $R_{21}$ is bonded to $A_2$;

$A_2$ is a nitrogen atom bonded to $R_{21}$ when $R_{21}$ is not bonded to $A_1$, or $A_2$ is a nitrogen atom bonded to $R_8$ when $R_{21}$ is bonded to $A_1$; or, $A_2$ is a carbon atom bonded to $R_8$ and $R_{21}$ when $R_{21}$ is not bonded to $A_1$, or $A_2$ is a carbon atom bonded to $R_8$ and $R_{20}$ when $R_{21}$ is bonded to $A_1$;

$A_3$ is a nitrogen atom; or, or $A_3$ is a carbon atom bonded to $R_5$;

$A_4$ is a nitrogen atom; or, or $A_4$ is a carbon atom bonded to $R_4$;

$A_5$ is a nitrogen atom; or, or $A_5$ is a carbon atom bonded to $R_3$;

$A_6$ is a nitrogen atom; or, or $A_6$ is a carbon atom bonded to $R_2$;

$A_7$ is a nitrogen atom; or, or $A_7$ is a carbon atom bonded to $R_1$;

each of $R_1$, $R_2$, $R_3$, and $R_4$ is independently selected from hydrogen, halo, alkyl, hydroxyl, haloalkyl, alkylmercapto, cyano and a substituted or unsubstituted alkyloxy group;

$R_{21}$ is selected from —$(CH_2)_nC(O)X$ and —$(CH_2)_nNR_{22}C(O)X$;

each of $R_5$, $R_6$, $R_7$, $R_8$, $R_9$, $R_{20}$, and $R_{22}$ is independently selected from hydrogen, alkyl, halo and hydroxyl; or $R_5$ and $R_6$ together is a carbon-carbon bond when $A_3$ is a carbon atom; or $R_5$ and $R_{20}$ together is a carbon-carbon bond when $A_2$ and $A_3$ are carbon atoms; or $R_9$ and $R_{20}$ together is a carbon-carbon bond when $A_1$ and $A_2$ are carbon atoms; or $R_9$ and $R_8$ together is a carbon-nitrogen bond when $A_1$ is carbon and $A_2$ is nitrogen or when $A_1$ is nitrogen and $A_2$ is carbon; or $R_5$ and $R_8$ together is a carbon-nitrogen bond when $A_2$ is nitrogen and $A_3$ is carbon; or, $R_6$ and $R_7$ together with the atom to which they are attached form a ring; or, when $A_3$ is carbon, $R_5$ and $R_6$ together with the atoms to which they are attached form a ring;

n is 0, 1 or 2, or n is 1 or 2 when $A_7$ is a nitrogen atom;

X is selected from aryl, arylalkyl, heterocyclyl and heterocyclylalkyl, or X is NR'R" where R' is selected from aryl, arylalkyl, heterocyclyl, and heterocyclylalkyl, where the heterocyclyl of the heterocyclyl and of the heterocyclylalkyl of the X, and the heterocyclyl of the heterocyclyl and of the heterocyclylalkyl of the R' when X is NR'R", is selected from 7-membered, 6-membered and 5-membered heterocyclic rings, and the aryl of the aryl and arylalkyl, and the heterocyclyl of the heterocyclyl and of the heterocyclylalkyl, is optionally substituted with one or more of halo, alkyl, haloalkyl, hydroxyl, alkyloxy, amino, alkylamino, dialkylamino, mercapto, alkylmercapto, carboxamido, aldehydo, cyano, oxo, alkylcarbonyloxy and sulfonamido;

R" is selected from hydrogen, alkyl and haloalkyl;

E is a substituted or unsubstituted, saturated or unsaturated, 9-membered, 8-membered, 7-membered, 6-membered, 5-membered, 4-membered or 3-membered, carbocyclic or heterocyclic, monocyclic or bicyclic ring; or (Z)- or (E)-isomer, epimer, diastereomer, rotamer, or pharmaceutically acceptable salt of said compound;

with the proviso that when $R_{21}$ is —$(CH_2)_nC(O)X$, and each of $A_2$, $A_4$, $A_5$, $A_6$ and $A_7$ is a carbon atom, and $R_9$ and $R_{20}$ together is a carbon-carbon bond, and E is a substituted or unsubstituted, saturated or unsaturated, 7-membered, 6-membered, 5-membered, 4-membered or 3-membered carbocyclic or heterocyclic, monocyclic or bicyclic ring, then at least one of $R_5$, $R_6$ and $R_7$ is halo, or $R_6$ and $R_7$ together with the atom to which they are attached form a ring, or $R_5$ and $R_6$ together with the atoms to which they are attached form a ring, or at least one of $R_1$, $R_2$, $R_3$, and $R_4$ or at least one substituent on the ring at E is haloalkyloxy or is a substituted or unsubstituted group selected from polyethyleneglycoxy, polyethyleneglycoxyalkyl, thioureido, borono, boronoalkyl, boronoalkyloxy, arylalkyloxy, aminosulfonyloxy, aminocarboxyl, aminocarbonylalkyloxy, aminocarbonylalkylthio, alkylcarbonylamino, aminoalkenylamino, alkylsulfonylamino, phosphono, phosphonothio, phosphonoamino, phosphonoalkyl, phosphonoalkylthio, phosphonoalkylamino, carboxyalkyl, carboxyalkenyl, carboxyalkynyl, carboxyalkyloxy, carboxyalkylamino, carboxyalkylthio, aminocarbonylthio, hydroxyalkyloxy, hydroxyalkylamino, hydroxyalkylthio, dialkylaminoalkyl, aminoalkylamino, alkylaminoalkylamino, dialkylaminoalkylamino, aminoalkyloxy, alkylaminoalkyloxy, dialkylaminoalkyloxy, alkyloxyaminocarbonyloxy, aminoalkylthio, alkylaminoalkylthio and dialkylaminoalkylthio, or any two substituents on E, together with the atoms to which they are attached, comprise an optionally substituted, saturated or unsaturated 3-, 4-, 5-, 6- or 7-membered carbocyclic or heterocyclic ring that is not alkylenedioxy.

In an embodiment, the compound is of formula Ia wherein $A_7$ is a carbon atom.

In another embodiment, the compound is of formula Ia wherein $A_1$ and $A_3$ are carbon atoms.

In a further embodiment, the compound is of formula Ia wherein each of $A_1$, $A_2$, $A_3$, $A_4$, As, $A_6$ and $A_7$ is a carbon atom.

In an additional embodiment, the compound is of formula Ia wherein $R_{21}$ is —$(CH_2)_n NR_{22}C(O)X$.

In yet another embodiment, the compound is of formula Ia wherein $R_{21}$ is —$(CH_2)_n C(O)X$.

In a preferred embodiment of any one or more of the above embodiments either individually or combined, the compound is of formula Ia where the heterocyclyl of the heterocyclyl and of the heterocyclylalkyl of X, or the heterocyclyl of the heterocyclyl and of the heterocyclylalkyl of R' when X is NR'R", is selected from azepanyl, oxazepanyl, thiazepanyl, azepinyl, oxepinyl, thiepanyl, homopiperazinyl, diazepinyl, thiazepinyl, piperidinyl, oxanyl, thianyl, pyridinyl, pyranyl, thiopyranyl, piperazinyl, morpholinyl, thiomorpholinyl, dioxanyl, dithianyl, pyrimidinyl, pyrazinyl, pyridizinyl, oxazinyl, thiazinyl, dioxinyl, dithiinyl, trioxanyl, trithianyl, triazinyl, tetrazinyl, pyrrolidinyl, tetrahydrofuranyl, tetrahydrothiaphenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl.

In a preferred embodiment of the previous embodiment, the compound is of formula Ia wherein X is selected from heterocyclyl and heterocyclylalkyl, or X is NR'R" where R' is selected from heterocyclyl, and heterocyclylalkyl, where the heterocyclyl of the heterocyclyl and of the heterocyclylalkyl of the X, and the heterocyclyl of the heterocyclyl and of the heterocyclylalkyl of the R' when X is NR'R", is selected from oxanyl, thianyl, pyranyl, thiopyranyl, thiomorpholinyl, dioxanyl, dithianyl, pyrimidinyl, pyrazinyl, pyridizinyl, oxazinyl, thiazinyl, dioxinyl, dithiinyl, trioxanyl, trithianyl, triazinyl, tetrazinyl, tetrahydrofuranyl, tetrahydrothiaphenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl.

In a preferred embodiment of the previous embodiment, the compound is of formula Ia wherein the heterocyclyl of the heterocyclyl and of the heterocyclylalkyl of the X, and the heterocyclyl of the heterocyclyl and of the heterocyclylalkyl of the R' when X is NR'R", is selected from oxanyl, thianyl, pyranyl, thiopyranyl, thiomorpholinyl, dioxanyl, dithianyl, pyrimidinyl, pyrazinyl, pyridizinyl, oxazinyl, thiazinyl, dioxinyl, dithiinyl, trioxanyl, trithianyl, triazinyl, tetrazinyl, tetrahydrofuranyl, tetrahydrothiaphenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl.

In a preferred embodiment of the previous embodiment, the compound is of formula Ia wherein the heterocyclyl of the heterocyclyl and of the heterocyclylalkyl of the X, and the heterocyclyl of the heterocyclyl and of the heterocyclylalkyl of the R' when X is NR'R", is selected from dioxolanyl, imidazolyl, pyrazolyl, oxazolyl, isoxazolyl, thiazolyl and isothiazolyl.

In a preferred embodiment of any one or more of the above embodiments either individually or combined, the compound is of formula Ia wherein E is selected from aryl, pyridinyl, pyridizinyl, pyrimidinyl, pyrazinyl, benzpyrazolyl, benztriazolyl, indolyl, benzimidazolyl and indenyl, each of which is substituted or unsubstituted.

In a preferred embodiment of the previous embodiment, E is phenyl and each of $A_1$, $A_2$, $A_3$, $A_4$, As, $A_6$ and $A_7$ is a carbon atom.

In another preferred embodiment, the compound is of formula Ia wherein each of $A_1$, $A_2$, $A_3$, $A_4$, As, $A_6$ and $A_7$ is a carbon atom and the phenyl at E substituted with one or more substituents selected from hydrogen, halo, alkyl, cycloalkyl, haloalkyl, hydroxyl, carboxyl, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkyloxy, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, phosphonooxyalkyloxy, aminosulfonyl, aminosulfonyloxy, polyethyleneglycoxy, polyethyleneglycoxyalkyl, thioureido, borono, boronoalkyl, boronoalkyloxy, arylalkyloxy, aminocarboxyl, aminocarbonylalkyloxy, aminocarbonylalkylthio, alkylcarbonylamino, aminoalkenylamino, alkylsulfonylamino, phosphono, phosphonothio, phosphonoamino, phosphonoalkyl, phosphonoalkylthio, phosphonoalkylamino, carboxyalkyl, carboxyalkenyl, carboxyalkynyl, carboxyalkyloxy, carboxyalkylamino, carboxyalkylthio, aminocarbonylthio, hydroxyalkyloxy, hydroxyalkylamino, hydroxyalkylthio, dialkylaminoalkyl, aminoalkylamino, alkylaminoalkylamino, dialkylaminoalkylamino, aminoalkyloxy, alkylaminoalkyloxy, dialkylaminoalkyloxy, alkyloxyaminocarbonyloxy, aminoalkylthio, alkylaminoalkylthio, dialkylaminoalkylthio, and a cleavable alcohol prodrug moiety, or any two substituents on E, together with the atoms to which they are attached, form and an optionally substituted, saturated or unsaturated 3-, 4-, 5-, 6- or 7-membered carbocyclic or heterocyclic ring.

In a preferred embodiment of the prior embodiment, the compound above is of the formula Ia, wherein $R_9$ and $R_{20}$ are independently selected from hydrogen and alkyl, or $R_9$ and $R_{20}$ together is a carbon-carbon bond.

In a preferred embodiment of the preceeding embodiment, the compound is of formula Ia wherein n is 1; at least one of $R_1$, $R_2$, $R_3$ and $R_4$ is hydrogen and two of $R_1$, $R_2$, $R_3$ and $R_4$ are independently selected from hydrogen, hydroxyl, halo, alkyloxy, alkyl and alkylmercapto; $R_5$ and $R_6$ together form a carbon-carbon bond; $R_7$ is hydrogen; and $R_8$ is selected from hydrogen, alkyl and alkoxy; and, E is phenyl substituted with at least two alkyloxy groups, each of which may be substituted or unsubstituted.

In a preferred embodiment of the preceeding embodiment, the compound is of formula Ia wherein E is phenyl substituted with at least one trifluoromethoxy group.

In another preferred embodiment, the compound is a compound of formula Ia of any one or more of any of the aforementioned embodiments either individually or combined, wherein $R_{21}$ is either —$(CH_2)_nNR_{22}C(O)X$ or —$(CH_2)_nC(O)X$.

In a preferred embodiment of the preceeding embodiment, the compound is of formula Ia wherein $R_{21}$ is —$(CH_2)_nNR_{22}C(O)X$.

In another embodiment, the compound is of formula IIa:

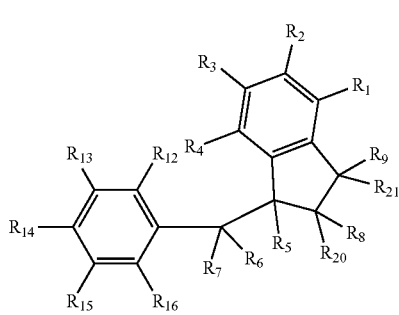

IIa wherein:

each of $R_1$, $R_2$, $R_3$, and $R_4$ is independently selected from hydrogen, halo, alkyl, hydroxyl, haloalkyl, alkylmercapto, cyano, alkyloxy and haloalkyloxy;

$R_{21}$ is selected from —$(CH_2)_nC(O)X$ and —$(CH_2)_nNR_{22}C(O)X$;

each of $R_5$, $R_6$, $R_7$, $R_8$, $R_9$, $R_{20}$, and $R_{22}$ is independently selected from hydrogen, alkyl, halo, and hydroxyl; or $R_5$ and $R_6$ together is a carbon-carbon bond; or $R_9$ and $R_{20}$ together is a carbon-carbon bond; or $R_6$ and $R_7$ together with the atom to which they are attached form a ring; or $R_5$ and $R_6$ together with the atoms to which they are attached, form a ring;

n is 1 or 2;

X is selected from aryl, arylalkyl, heterocyclyl and heterocyclylalkyl, or X is NR'R" where R' is selected from aryl, arylalkyl, heterocyclyl, and heterocyclylalkyl, where the heterocyclyl of the heterocyclyl and heterocyclylalkyl of the X, and the heterocyclyl of the heterocyclyl and the heterocyclylalkyl of the R' when X is NR'R", is selected from 7-membered, 6-membered and 5-membered heterocyclic rings, and the aryl of the aryl and arylalkyl, and the heterocyclyl of the heterocyclyl and heterocyclylalkyl, is optionally substituted with one or more of halo, alkyl, haloalkyl, hydroxyl, alkyloxy, amino, alkylamino, dialkylamino, mercapto, alkylmercapto, carboxamido, aldehydo, cyano, oxo, alkylcarbonyloxy and sulfonamide; R" is selected from hydrogen, alkyl and haloalkyl;

each of $R_{12}$, $R_{13}$, $R_{15}$ and $R_{16}$ is independently selected from hydrogen, halo, alkyl, cycloalkyl, haloalkyl, alkyloxy, haloalkyloxy, hydroxyl, carboxyl, formyloxy, hydroxyalkyl, aldehydo, amino, alkylamino, aminoalkyl, alkylaminoalkyl, dialkylamino, mercapto, alkylmercapto, cyano, cyanoalkyl, nitro and azido;

$R_{14}$ is hydroxyl or is a cleavable alcohol prodrug moiety, or is a substituted or unsubstituted group selected from alkylsulfinyloxy, alkylsulfonyloxy, carbamate, alkyloxy, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, phosphonooxyalkyloxy, aminosulfonyloxy, polyethyleneglycoxy, borono, boronoalkyl, boronoalkyloxy, arylalkyloxy, aminocarbonylalkyloxy, carboxyalkyloxy, hydroxyalkyloxy, aminoalkyloxy, alkylaminoalkyloxy, dialkylaminoalkyloxy and alkyloxyaminocarbonyloxy;

(Z)- or (E)-isomer, epimer, diastereomer, rotamer, or pharmaceutically acceptable salt of said compound;

with the proviso that when $R_{21}$ is —$(CH_2)_nC(O)X$, and $R_9$ and $R_{20}$ together is a carbon-carbon bond, then at least one of $R_5$, $R_6$ and $R_7$ is halo, or $R_6$ and $R_7$ together with the atom to which they are attached form a ring, or $R_5$ and $R_6$ together with the atoms to which they are attached form a ring, or at least one of $R_1$, $R_2$, $R_3$, and $R_4$ or at least one $R_{12}$, $R_{13}$, $R_{14}$, $R_{15}$ and $R_{16}$ is haloalkyloxy, or $R_{14}$ is a substituted or unsubstituted group selected from polyethyleneglycoxy, borono, boronoalkyl, aminosulfonyloxy and alkyloxyaminocarbonyloxy.

In a preferred embodiment, the compound is of formula IIa wherein X is selected from phenyl, benzyl, heterocyclyl and heterocyclylmethyl, or X is NR'R" where R' is selected from phenyl, benzyl, heterocyclyl and heterocyclylmethyl, where the heterocyclyl of the heterocyclyl and of the heterocyclylmethyl of the X, and the heterocyclyl of the heterocyclyl and of the heterocyclylmethyl of the R' when X is NR'R", is selected from piperidinyl, oxanyl, thianyl, pyridinyl, pyranyl, thiopyranyl, piperazinyl, morpholinyl, thiomorpholinyl, dioxanyl, dithianyl, pyrimidinyl, pyrazinyl, pyridizinyl, oxazinyl, thiazinyl, dioxinyl, dithiinyl, trioxanyl, trithianyl, triazinyl, tetrazinyl, pyrrolidinyl, tetrahydrofuranyl, tetrahydrothiaphenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl, wherein the phenyl and the phenyl ring of the benzyl, and the heterocyclyl of the heterocyclyl and heterocyclylmethyl, is optionally substituted with one or more of halo, alkyl, haloalkyl, hydroxyl, alkyloxy, amino, alkylamino, dialkylamino, mercapto, alkylmercapto, carboxamido, aldehydo, cyano, oxo, alkylcarbonyloxy and sulfonamide; R" is selected from hydrogen, alkyl and trifluoromethyl.

In a more preferred embodiment, the preceeding compound is of formula IIa where the heterocyclyl of the heterocyclyl and of the heterocyclylmethyl of the X, and the heterocyclyl of the heterocyclyl and of the heterocyclylmethyl of the R' when X is NR'R", is selected from furanyl, pyrrolyl, thiophenyl, oxazolyl, isoxazolyl, thiazolyl, isothiazolyl, dioxolanyl, pyrazolyl, pyridinyl and imidazolyl, and the phenyl and the phenyl ring of the benzyl, and the heterocyclyl of the heterocyclyl and heterocyclylalkyl, is optionally substituted with one or more of halo, alkyl, haloalkyl, hydroxy, alkyloxy, amino, alkylamino, dialkylamino, mercapto, alkylmercapto, and carboxamido.

In a further preferred embodiment, the preceeding compound is of formula IIa wherein X is selected from heterocyclyl and heterocyclylmethyl, or X is NR'R" where R' is selected from heterocyclyl and heterocyclylmethyl, where the heterocyclyl of the heterocyclyl and of the heterocyclylmethyl of the X, and the heterocyclyl of the heterocyclyl and of the heterocyclylmethyl of the R' when X is NR'R", is selected from furanyl, pyrrolyl, pyridinyl, oxazolyl, thiazolyl, dioxolanyl, imidazolyl, pyrazolyl and thiophenyl, and the heterocyclyl of the heterocyclyl and of the heterocyclylmethyl is optionally substituted with one or more of halo, alkyl, trifluoromethyl, hydroxy and methoxy.

In an even more preferred embodiment, the preceeding compound is of formula IIa wherein the heterocyclyl or heterocyclylmethyl is selected from 2-furanyl, 3-furanyl, furan-2-ylmethyl, furan-3-ylmethyl, 2-oxazolyl, 4-oxazolyl, 5-oxazolyl, oxazol-2-ylmethyl, oxazol-4-ylmethyl, oxazol-5-ylmethyl, 2-thiazolyl, 4-thiazolyl, 5-thiazolyl, thiazol-2-ylmethyl, thiazol-4-ylmethyl, thiazol-5-ylmethyl, 2-imidazolyl, 4-imidazolyl, 5-imidazolyl, imidazol-2-ylmethyl, imidazol-4-ylmethyl, imidazol-5-ylmethyl, 3-pyrazolyl, 4-pyrazolyl, 5-pyrazolyl, pyrazol-3-ylmethyl, pyrazol-4-ylmethyl, pyrazol-5-ylmethyl, 2-dioxlanyl, 4-dioxlanyl, dixolan-2-ylmethyl, and dioxolan-4-ylmethyl; and, R" is hydrogen.

In a more specific embodiment, the preceeding compound is of formula IIa wherein the heterocyclyl or heterocyclylmethyl is selected from 2-oxazolyl, oxazol-2-ylmethyl, 2-thiazolyl, thiazol-2-ylmethyl, 2-imidazolyl, imidazol-2-ylmethyl, 4-pyrazolyl, pyrazol-4-ylmethyl, 2-dioxlanyl and dioxolan-2-ylmethyl.

In an even more specific embodiment, the heterocyclyl or heterocyclylmethyl of the preceeding compound is selected from 2-furanyl, 4-pyrazolyl and pyridin-3-ylmethyl.

In a more general embodiment of any one or more of the above embodiments either individually or combined, the compound is of formula IIa wherein each of $R_1$, $R_2$, $R_3$ and $R_4$ is independently selected from hydrogen, halo, alkyloxy and alkyl; n is 1; each of $R_{12}$, $R_{13}$, $R_{15}$ and $R_{16}$ is independently selected from hydrogen, halo, alkyl, alkyloxy and haloalkyloxy; $R_{14}$ is selected from alkyloxy, hydroxyl, and a cleavable alcohol prodrug moiety.

In a preferred embodiment of the preceeding embodiment, the compound is of formula IIa wherein $R_2$ is selected from halo and alkyloxy; $R_1$, $R_3$ and $R_4$ are hydrogen; two of $R_{12}$, $R_{13}$, $R_{15}$ and $R_{16}$ are independently selected from hydrogen, alkyloxy and haloalkyloxy.

In a preferred embodiment of the preceeding embodiment, the compound is of formula IIa wherein $R_2$ is selected from fluoro and methoxy; $R_{12}$ and $R_{16}$ are hydrogens, In a preferred embodiment of the prior embodiment, each of $R_{13}$ and $R_{15}$ is independently selected from methoxy and trifluoromethoxy; $R_{14}$ is selected from hydroxyl and methoxy;

In a preferred embodiment of the preceeding embodiment, each of $R_{13}$ and $R_{15}$ is methoxy; $R_7$ is hydrogen; $R_8$ is alkyl; $R_{14}$ is hydroxyl; X is selected from heterocyclyl and heterocyclylmethyl, or X is NR'R" where R' is selected from heterocyclyl and heterocyclylmethyl, where the heterocyclyl or the heterocyclylmethyl of the X, and the heterocyclyl or the heterocyclylmethyl of the R' when X is NR'R", is selected from 2-furanyl, 4-pyrazolyl and pyridin-3-ylmethyl.

In a preferred embodiment, the compound is a compound of any of the above embodiments of formula IIa wherein $R_9$ and $R_{20}$ together is a carbon-carbon bond.

In yet another preferred embodiment, the compound is a compound of any of the above embodiments of formula IIa wherein $R_5$ and $R_6$ together is a carbon-carbon bond.

In a further preferred embodiment, the compound is a compound of any of the above embodiments of formula IIa wherein $R_9$ and $R_{20}$ together is a carbon-carbon bond and $R_5$ and $R_6$ together is a carbon-carbon bond.

In an additional preferred embodiment, the compound is a compound of any of the above embodiments of formula IIa, wherein $R_{21}$ is selected from —$(CH_2)_nC(O)X$ or —$(CH_2)_nNR_{22}C(O)X$.

In a different aspect of the preceeding embodiment, $R_{14}$ cannot be aminosulfonyl when $R_{21}$ is —$(CH_2)_nC(O)X$.

In a preferred embodiment of the preceeding embodiment wherein $R_{21}$ is selected from —$(CH_2)_nC(O)X$ or —$(CH_2)_nNR_{22}C(O)X$, the compound is of formula IIa, wherein $R_{21}$ is —$(CH_2)_nNR_{22}C(O)X$.

In a preferred embodiment of any of the above embodiments of formula Ia and IIa, the compound is selected from:
(E)-1-(5-fluoro-1-(4-(hydroxymethyl)-3,5-dimethoxybenzylidene)-2-methyl-1H-inden-3-yl)-3-(furan-2-ylmethyl) urea (1664);
2-(4-((5-fluoro-3-(3-(furan-2-ylmethyl)ureido)-2-methyl-2,3-dihydro-1H-inden-1-yl)methyl)-2,6-dimethoxyphenyl) acetic acid (1666);
(E)-2-((4-((5-fluoro-3-(3-(furan-2-ylmethyl)ureido)-2-methyl-1H-inden-1-ylidene)methyl)-2,6-dimethoxyphenyl)amino)acetic acid (1668);
(E)-2-(4-((5-fluoro-2-methyl-3-(3-(pyridin-3-yl)ureido)-1H-inden-1-ylidene)methyl)-2,6-dimethoxyphenoxy)acetic acid (1669);
(E)-2-(4-((5-fluoro-2-methyl-3-(3-(pyridin-3-yl)ureido)-1H-inden-1-ylidene)methyl)-2,6-dimethoxyphenyl)acetic acid (1670);
2-((4-((3-(3-(1H-pyrazol-5-yl)ureido)-5-fluoro-2-methyl-2,3-dihydro-1H-inden-1-yl)methyl)-2,6-dimethoxyphenyl)thio)acetic acid (1671);
(Z)-2-((4-((5-fluoro-2-methyl-3-(2-oxo-2-(pyridin-3-ylamino)ethyl)-1H-inden-1-ylidene)methyl)-2,6-dimethoxyphenyl)amino)acetic acid (1673);
(Z)-2-(4-((5-fluoro-2-methyl-3-(2-oxo-2-(pyrazin-2-ylamino)ethyl)-1H-inden-1-ylidene)methyl)-2,6-dimethoxyphenyl)acetic acid (1674);
2-(4-((3-(2-((1H-pyrazol-5-yl)amino)-2-oxoethyl)-5-fluoro-2-methyl-2,3-dihydro-1H-inden-1-yl)methyl)-2,6-dimethoxyphenyl)acetic acid (1675);
(Z)-2-(4-((3-(2-(((1H-pyrazol-5-yl)methyl)amino)-2-oxoethyl)-5-fluoro-2-methyl-1H-inden-1-ylidene)methyl)-2,6-dimethoxyphenyl)acetic acid (1676);
(Z)-1,4-dimethylpiperazin-2-yl 2-((4-((5-fluoro-3-(2-((furan-2-ylmethyl)amino)-2-oxoethyl)-2-methyl-1H-inden-1-ylidene)methyl)-2-methoxyphenyl)amino)acetate (1677);
2-(4-((3-(2-((furan-2-ylmethyl)amino)-2-oxoethyl)-5-methoxy-2-methyl-1H-inden-1-yl)methyl)-2,6-dimethoxyphenyl)acetic acid (1678);
(Z)-2-(4-((5-fluoro-2-methyl-3-(2-(((1-methyl-1H-pyrrol-2-yl)methyl)amino)-2-oxoethyl)-1H-inden-1-ylidene) methyl)-2,6-dimethoxyphenyl)acetic acid (1679);
(Z)-3-(2,6-dimethoxy-4-((5-methoxy-2-methyl-3-(2-(((1-methyl-1H-pyrrol-2-yl)methyl)amino)-2-oxoethyl)-1H-inden-1-ylidene)methyl)phenyl)propanoic acid (1680);
(Z)-2-((2,6-dimethoxy-4-((5-methoxy-2-methyl-3-(2-oxo-2-((pyridin-3-ylmethyl)amino)ethyl)-1H-inden-1-ylidene)methyl)phenyl)amino)acetic acid (1683);
(Z)-3-(4-((5-fluoro-2-methyl-3-(2-oxo-2-((pyridin-2-ylmethyl)amino)ethyl)-1H-inden-1-ylidene)methyl)-2,6-dimethoxyphenyl)propanoic acid (1685);
(Z)-2-((4-((3-(2-(benzylamino)-2-oxoethyl)-5-methoxy-2-methyl-1H-inden-1-ylidene)methyl)-2,6-dimethoxyphenyl)amino)acetic acid (1687);
(Z)-2-((4-((3-(2-(benzylamino)-2-oxoethyl)-5-fluoro-2-methyl-1H-inden-1-ylidene)methyl)-2-methoxyphenyl) amino)acetic acid (1688);
(Z)-3-((4-((5-cyano-3-(2-((furan-2-ylmethyl)amino)-2-thioxoethyl)-2-methyl-1H-inden-1-ylidene)methyl)-2,6-dimethoxyphenyl)thio)propanoic acid (1689);
(Z)-2-(4-((5-fluoro-2-methyl-3-(2-(((1-methyl-1H-pyrrol-2-yl)methyl)amino)-2-oxoethyl)-1H-inden-1-ylidene) methyl)-2,6-dimethoxyphenyl)acetic acid (1692);

(Z)-2-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl)acetic acid (1693);

(Z)-3-((4-((5-fluoro-2-methyl-3-(2-oxo-2-((pyridin-3-ylmethyl)amino)ethyl)-1H-inden-1-ylidene)methyl)phenyl)amino)propanoic acid (1694);

(Z)-3-((4-((5-fluoro-2-methyl-3-(2-oxo-2-((pyridin-2-ylmethyl)amino)ethyl)-1H-inden-1-ylidene)methyl)-2,6-dimethoxyphenyl)amino)propanoic acid (1696);

(Z)-3-((2,6-dimethoxy-4-((5-methoxy-2-methyl-3-(2-oxo-2-((pyridin-2-ylmethyl)amino)ethyl)-1H-inden-1-ylidene)methyl)phenyl)thio)propanoic acid (1697);

(Z)-3-((4-((3-(2-(benzylamino)-2-oxoethyl)-5-fluoro-2-methyl-1H-inden-1-ylidene)methyl)-2,6-dimethoxyphenyl)amino)propanoic acid (1698);

(Z)-3-((2,6-dimethoxy-4-((5-methoxy-2-methyl-3-(2-oxo-2-(phenylamino)ethyl)-1H-inden-1-ylidene)methyl)phenyl)amino)propanoic acid (1699);

(Z)-(4-((5-fluoro-3-(2-((furan-2-ylmethyl)amino)-2-oxoethyl)-2-methyl-1H-inden-1-ylidene)methyl)-2,6-dimethoxyphenyl)boronic acid (1732);

(Z)-(4-((3-(2-((furan-2-ylmethyl)amino)-2-oxoethyl)-5-methoxy-2-methyl-1H-inden-1-ylidene)methyl)-2,6-dimethoxyphenyl)boronic acid (1733);

(Z)-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl)boronic acid (1734);

(Z)-(2,6-dimethoxy-4-((5-methoxy-2-methyl-3-(2-(((1-methyl-1H-pyrrol-2-yl)methyl)amino)-2-oxoethyl)-1H-inden-1-ylidene)methyl)phenyl)boronic acid (1735);

(Z)-(4-((5-fluoro-2-methyl-3-(2-oxo-2-((pyridin-3-ylmethyl)amino)ethyl)-1H-inden-1-ylidene)methyl)-2,6-dimethoxyphenyl)boronic acid (1736);

(Z)-(2,6-dimethoxy-4-((5-methoxy-2-methyl-3-(2-oxo-2-((pyridin-3-ylmethyl)amino)ethyl)-1H-inden-1-ylidene)methyl)phenyl)boronic acid (1737);

(Z)-(4-((5-fluoro-2-methyl-3-(2-oxo-2-((pyridin-2-ylmethyl)amino)ethyl)-1H-inden-1-ylidene)methyl)-2,6-dimethoxyphenyl)boronic acid (1738);

(Z)-(2,6-dimethoxy-4-((5-methoxy-2-methyl-3-(2-oxo-2-((pyridin-2-ylmethyl)amino)ethyl)-1H-inden-1-ylidene)methyl)phenyl)boronic acid (1739);

(Z)-(4-((3-(2-(benzylamino)-2-oxoethyl)-5-fluoro-2-methyl-1H-inden-1-ylidene)methyl)-2,6-dimethoxyphenyl)boronic acid (1740);

(Z)-(4-((3-(2-(benzylamino)-2-oxoethyl)-5-methoxy-2-methyl-1H-inden-1-ylidene)methyl)-2,6-dimethoxyphenyl)boronic acid (1741);

(Z)-2-(4-((5-fluoro-3-(2-((furan-2-ylmethyl)amino)-2-oxoethyl)-2-methyl-1H-inden-1-ylidene)methyl)-2,6-dimethoxyphenoxy)acetic acid (1742);

(Z)-2-(4-((3-(2-((furan-2-ylmethyl)amino)-2-oxoethyl)-5-methoxy-2-methyl-1H-inden-1-ylidene)methyl)-2,6-dimethoxyphenoxy)acetic acid (1743);

(Z)-2-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)acetic acid (1744);

(Z)-2-(2,6-dimethoxy-4-((5-methoxy-2-methyl-3-(2-(((1-methyl-1H-pyrrol-2-yl)methyl)amino)-2-oxoethyl)-1H-inden-1-ylidene)methyl)phenoxy)acetic acid (1745);

(Z)-2-(4-((5-fluoro-2-methyl-3-(2-oxo-2-((pyridin-3-ylmethyl)amino)ethyl)-1H-inden-1-ylidene)methyl)-2,6-dimethoxyphenoxy)acetic acid (1746);

(Z)-2-(2,6-dimethoxy-4-((5-methoxy-2-methyl-3-(2-oxo-2-((pyridin-3-ylmethyl)amino)ethyl)-1H-inden-1-ylidene)methyl)phenoxy)acetic acid (1747);

(Z)-2-(4-((5-fluoro-2-methyl-3-(2-oxo-2-((pyridin-2-ylmethyl)amino)ethyl)-1H-inden-1-ylidene)methyl)-2,6-dimethoxyphenoxy)acetic acid (1748);

(Z)-2-(2,6-dimethoxy-4-((5-methoxy-2-methyl-3-(2-oxo-2-((pyridin-2-ylmethyl)amino)ethyl)-1H-inden-1-ylidene)methyl)phenoxy)acetic acid (1749);

(Z)-2-(4-((3-(2-(benzylamino)-2-oxoethyl)-5-methoxy-2-methyl-1H-inden-1-ylidene)methyl)-2,6-dimethoxyphenoxy)acetic acid (1750);

(Z)-2-(4-((3-(2-(benzylamino)-2-oxoethyl)-5-fluoro-2-methyl-1H-inden-1-ylidene)methyl)-2,6-dimethoxyphenoxy)acetic acid (1751);

(Z)-3-(4-((5-fluoro-3-(2-((furan-2-ylmethyl)amino)-2-oxoethyl)-2-methyl-1H-inden-1-ylidene)methyl)-2,6-dimethoxyphenoxy)propanoic acid (1752);

(Z)-3-(4-((3-(2-((furan-2-ylmethyl)amino)-2-oxoethyl)-5-methoxy-2-methyl-1H-inden-1-ylidene)methyl)-2,6-dimethoxyphenoxy)propanoic acid (1754);

(Z)-3-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)propanoic acid (1755);

(Z)-3-(2,6-dimethoxy-4-((5-methoxy-2-methyl-3-(2-(((1-methyl-1H-pyrrol-2-yl)methyl)amino)-2-oxoethyl)-1H-inden-1-ylidene)methyl)phenoxy)propanoic acid (1756);

(Z)-3-(4-((5-fluoro-2-methyl-3-(2-oxo-2-((pyridin-3-ylmethyl)amino)ethyl)-1H-inden-1-ylidene)methyl)-2,6-dimethoxyphenoxy)propanoic acid (1757);

(Z)-3-(2,6-dimethoxy-4-((5-methoxy-2-methyl-3-(2-oxo-2-((pyridin-3-ylmethyl)amino)ethyl)-1H-inden-1-ylidene)methyl)phenoxy)propanoic acid (1758);

(Z)-3-(4-((5-fluoro-2-methyl-3-(2-oxo-2-((pyridin-2-ylmethyl)amino)ethyl)-1H-inden-1-ylidene)methyl)-2,6-dimethoxyphenoxy)propanoic acid (1759);

(Z)-3-(2,6-dimethoxy-4-((5-methoxy-2-methyl-3-(2-oxo-2-((pyridin-2-ylmethyl)amino)ethyl)-1H-inden-1-ylidene)methyl)phenoxy)propanoic acid (1760);

(Z)-3-(4-((3-(2-(benzylamino)-2-oxoethyl)-5-fluoro-2-methyl-1H-inden-1-ylidene)methyl)-2,6-dimethoxyphenoxy)propanoic acid (1761);

(Z)-3-(4-((3-(2-(benzylamino)-2-oxoethyl)-5-methoxy-2-methyl-1H-inden-1-ylidene)methyl)-2,6-dimethoxyphenoxy)propanoic acid (1762);

2-(6-fluoro-3-(4-hydroxy-3,5-dimethoxybenzyl)-2-methyl-2,3-dihydro-1H-inden-1-yl)-N-(furan-2-ylmethyl)acetamide (1765);

2-(6-fluoro-3-(4-hydroxy-3,5-dimethoxybenzyl)-2-methyl-1H-inden-1-yl)-N-(furan-2-ylmethyl)acetamide (1767);

N-(furan-2-ylmethyl)-2-(3-(4-hydroxy-3,5-dimethoxybenzyl)-6-methoxy-2-methyl-1H-inden-1-yl)acetamide (1768);

N-(furan-2-ylmethyl)-2-(3-(4-hydroxy-3,5-dimethoxybenzyl)-2-methyl-6-(trifluoromethyl)-2,3-dihydro-1H-inden-1-yl)acetamide (1769);

2-(6-cyano-3-(4-hydroxy-3,5-dimethoxybenzyl)-2-methyl-2,3-dihydro-1H-inden-1-yl)-N-(furan-2-ylmethyl)acetamide (1771);

(Z)-2-(6-fluoro-3-(4-hydroxy-3,5-dimethoxybenzylidene)-2-methyl-2,3-dihydro-1H-inden-1-yl)-N-(furan-2-ylmethyl)acetamide (1772);

(Z)—N-(furan-2-ylmethyl)-2-(3-(4-hydroxy-3,5-dimethoxybenzylidene)-6-methoxy-2-methyl-2,3-dihydro-1H-inden-1-yl)acetamide (1773);

2-(5,6-difluoro-3-(4-hydroxy-3,5-dimethoxybenzyl)-2-methyl-2,3-dihydro-1H-inden-1-yl)-N-(furan-2-ylmethyl)acetamide (1774);

2-(6-fluoro-3-(4-hydroxy-3,5-dimethoxybenzyl)-2-methyl-2,3-dihydro-1H-inden-1-yl)-N-((1-methyl-1H-pyrrol-2-yl)methyl)acetamide (1776);

2-(6-fluoro-3-(4-hydroxy-3,5-dimethoxybenzyl)-2-methyl-1H-inden-1-yl)-N-((1-methyl-1H-pyrrol-2-yl)methyl)acetamide (1777);

(Z)-2-(6-cyano-3-(4-hydroxy-3,5-dimethoxybenzylidene)-2-methyl-2,3-dihydro-1H-inden-1-yl)-N-((1-methyl-H-pyrrol-2-yl)methyl)acetamide (1779);

(Z)-2-(6-fluoro-3-(4-hydroxy-3,5-dimethoxybenzylidene)-2-methyl-2,3-dihydro-1H-inden-1-yl)-N-((1-methyl-H-pyrrol-2-yl)methyl)acetamide (1780);

2-(6-fluoro-3-(4-hydroxy-3,5-dimethoxybenzyl)-2-methyl-2,3-dihydro-1H-inden-1-yl)-N-(pyridin-3-ylmethyl)acetamide (1782);

2-(6-fluoro-3-(4-hydroxy-3,5-dimethoxybenzyl)-2-methyl-1H-inden-1-yl)-N-(pyridin-3-ylmethyl)acetamide (1783);

(Z)-2-(3-(4-hydroxy-3,5-dimethoxybenzylidene)-2-methyl-2,3-dihydro-1H-inden-1-yl)-N-(pyridin-3-ylmethyl)acetamide (1784);

2-(5,6-difluoro-3-(4-hydroxy-3,5-dimethoxybenzyl)-2-methyl-2,3-dihydro-1H-inden-1-yl)-N-(pyridin-3-ylmethyl)acetamide (1785);

(Z)-2-(6-fluoro-3-(4-hydroxy-3,5-dimethoxybenzylidene)-2-methyl-2,3-dihydro-1H-inden-1-yl)-N-(pyridin-3-ylmethyl)acetamide (1787);

2-(6-fluoro-3-(4-hydroxy-3,5-dimethoxybenzyl)-2-methyl-2,3-dihydro-1H-inden-1-yl)-N-(pyridin-2-ylmethyl)acetamide (1789);

2-(6-fluoro-3-(4-hydroxy-3,5-dimethoxybenzyl)-2-methyl-1H-inden-1-yl)-N-(pyridin-2-ylmethyl)acetamide (1790);

2-(3-(4-hydroxy-3,5-dimethoxybenzyl)-2-methyl-6-(trifluoromethyl)-1H-inden-1-yl)-N-(pyridin-2-ylmethyl)acetamide (1791);

(Z)-2-(6-cyano-3-(4-hydroxy-3,5-dimethoxybenzylidene)-2-methyl-2,3-dihydro-1H-inden-1-yl)-N-(pyridin-2-ylmethyl)acetamide (1792);

(Z)-2-(6-fluoro-3-(4-hydroxy-3,5-dimethoxybenzylidene)-2-methyl-2,3-dihydro-1H-inden-1-yl)-N-(pyrazin-2-ylmethyl)acetamide (1793);

(Z)-2-(6-fluoro-3-(4-hydroxy-3,5-dimethoxybenzylidene)-2-methyl-2,3-dihydro-1H-inden-1-yl)-N-(pyridin-2-ylmethyl)acetamide (1794);

N-benzyl-2-(6-fluoro-3-(4-hydroxy-3,5-dimethoxybenzyl)-2-methyl-2,3-dihydro-1H-inden-1-yl)acetamide (1796);

N-benzyl-2-(6-fluoro-3-(4-hydroxy-3,5-dimethoxybenzyl)-2-methyl-1H-inden-1-yl) acetamide (1797);

(Z)—N-benzyl-2-(3-(4-hydroxy-3,5-dimethoxybenzylidene)-2-methyl-6-(trifluoromethyl)-2,3-dihydro-1H-inden-1-yl)acetamide (1798);

(Z)—N-benzyl-2-(6-fluoro-3-(4-hydroxy-3,5-dimethoxybenzylidene)-2-methyl-2,3-dihydro-1H-inden-1-yl)acetamide (1800);

(Z)-(4-((5-fluoro-3-(2-((furan-2-ylmethyl)amino)-2-oxoethyl)-2-methyl-2,3-dihydro-1H-inden-1-ylidene)methyl)-2,6-dimethoxyphenyl)boronic acid (1801);

(Z)-4-((5-fluoro-3-(2-((furan-2-ylmethyl)amino)-2-oxoethyl)-2-methyl-2,3-dihydro-1H-inden-1-ylidene)methyl)-2,6-dimethoxyphenyl dihydrogen phosphate (1802);

(Z)-4-((5-fluoro-3-(2-((furan-2-ylmethyl)amino)-2-oxoethyl)-2-methyl-2,3-dihydro-1H-inden-1-ylidene)methyl)-2,6-dimethoxyphenyl dimethylcarbamate (1803);

(Z)-4-((5-fluoro-3-(2-((furan-2-ylmethyl)amino)-2-oxoethyl)-2-methyl-2,3-dihydro-1H-inden-1-ylidene)methyl)-2,6-dimethoxyphenyl 4-methylpiperazine-1-carboxylate (1804);

(Z)-(4-((3-(2-((furan-2-ylmethyl)amino)-2-oxoethyl)-5-methoxy-2-methyl-2,3-dihydro-1H-inden-1-ylidene)methyl)-2,6-dimethoxyphenyl)boronic acid (1805);

(Z)-4-((3-(2-((furan-2-ylmethyl)amino)-2-oxoethyl)-5-methoxy-2-methyl-2,3-dihydro-1H-inden-1-ylidene)methyl)-2,6-dimethoxyphenyl dihydrogen phosphate (1806);

(Z)-4-((3-(2-((furan-2-ylmethyl)amino)-2-oxoethyl)-5-methoxy-2-methyl-2,3-dihydro-1H-inden-1-ylidene)methyl)-2,6-dimethoxyphenyl dimethylcarbamate (1807);

(Z)-4-((3-(2-((furan-2-ylmethyl)amino)-2-oxoethyl)-5-methoxy-2-methyl-2,3-dihydro-1H-inden-1-ylidene)methyl)-2,6-dimethoxyphenyl 4-methylpiperazine-1-carboxylate (1808);

(Z)-(4-((5-fluoro-2-methyl-3-(2-(((1-methyl-1H-pyrrol-2-yl)methyl)amino)-2-oxoethyl)-2,3-dihydro-1H-inden-1-ylidene)methyl)-2,6-dimethoxyphenyl)boronic acid (1809);

(Z)-4-((5-fluoro-2-methyl-3-(2-(((1-methyl-1H-pyrrol-2-yl)methyl)amino)-2-oxoethyl)-2,3-dihydro-1H-inden-1-ylidene)methyl)-2,6-dimethoxyphenyl dihydrogen phosphate (1810);

(Z)-4-((5-fluoro-2-methyl-3-(2-(((1-methyl-1H-pyrrol-2-yl)methyl)amino)-2-oxoethyl)-2,3-dihydro-1H-inden-1-ylidene)methyl)-2,6-dimethoxyphenyl dimethylcarbamate (1811);

(Z)-4-((5-fluoro-2-methyl-3-(2-(((1-methyl-1H-pyrrol-2-yl)methyl)amino)-2-oxoethyl)-2,3-dihydro-1H-inden-1-ylidene)methyl)-2,6-dimethoxyphenyl 4-methylpiperazine-1-carboxylate (1812);

(Z)-(4-((5-fluoro-2-methyl-3-(2-oxo-2-((pyridin-3-ylmethyl)amino)ethyl)-2,3-dihydro-1H-inden-1-ylidene)methyl)-2,6-dimethoxyphenyl)boronic acid (1813);

(Z)-4-((5-fluoro-2-methyl-3-(2-oxo-2-((pyridin-3-ylmethyl)amino)ethyl)-2,3-dihydro-1H-inden-1-ylidene)methyl)-2,6-dimethoxyphenyl dihydrogen phosphate (1814);

(Z)-4-((5-fluoro-2-methyl-3-(2-oxo-2-((pyridin-3-ylmethyl)amino)ethyl)-2,3-dihydro-1H-inden-1-ylidene)methyl)-2,6-dimethoxyphenyl dimethylcarbamate (1815);

(Z)-4-((5-fluoro-2-methyl-3-(2-oxo-2-((pyridin-3-ylmethyl)amino)ethyl)-2,3-dihydro-1H-inden-1-ylidene)methyl)-2,6-dimethoxyphenyl 4-methylpiperazine-1-carboxylate (1816);

(Z)-(4-((5-fluoro-2-methyl-3-(2-oxo-2-((pyridin-2-ylmethyl)amino)ethyl)-2,3-dihydro-1H-inden-1-ylidene)methyl)-2,6-dimethoxyphenyl)boronic acid (1817);

(Z)-4-((5-fluoro-2-methyl-3-(2-oxo-2-((pyridin-2-ylmethyl)amino)ethyl)-2,3-dihydro-1H-inden-1-ylidene)methyl)-2,6-dimethoxyphenyl dihydrogen phosphate (1818);

(Z)-4-((5-fluoro-2-methyl-3-(2-oxo-2-((pyridin-2-ylmethyl)amino)ethyl)-2,3-dihydro-1H-inden-1-ylidene)methyl)-2,6-dimethoxyphenyl dimethylcarbamate (1819);

(Z)-4-((5-fluoro-2-methyl-3-(2-oxo-2-((pyridin-2-ylmethyl)amino)ethyl)-2,3-dihydro-1H-inden-1-ylidene)methyl)-2,6-dimethoxyphenyl 4-methylpiperazine-1-carboxylate (1820);

(Z)-(4-((3-(2-(benzylamino)-2-oxoethyl)-5-fluoro-2-methyl-2,3-dihydro-1H-inden-1-ylidene)methyl)-2,6-dimethoxyphenyl)boronic acid (1821);

(Z)-4-((3-(2-(benzylamino)-2-oxoethyl)-5-fluoro-2-methyl-2,3-dihydro-1H-inden-1-ylidene)methyl)-2,6-dimethoxyphenyl dihydrogen phosphate (1822);

(Z)-4-((3-(2-(benzylamino)-2-oxoethyl)-5-fluoro-2-methyl-2,3-dihydro-1H-inden-1-ylidene)methyl)-2,6-dimethoxyphenyl dimethylcarbamate (1823);

(Z)-4-((3-(2-(benzylamino)-2-oxoethyl)-5-fluoro-2-methyl-2,3-dihydro-1H-inden-1-ylidene)methyl)-2,6-dimethoxyphenyl 4-methylpiperazine-1-carboxylate (1824);

(Z)—S-(4-((5-fluoro-3-(2-((furan-2-ylmethyl)amino)-2-oxoethyl)-2-methyl-1H-inden-1-ylidene)methyl)-2,6-dimethoxyphenyl) dimethylcarbamothioate (1831);

(Z)—S-(4-((5-fluoro-3-(2-((furan-2-ylmethyl)amino)-2-oxoethyl)-2-methyl-1H-inden-1-ylidene)methyl)-2,6-dimethoxyphenyl) 4-methylpiperazine-1-carbothioate (1832);

(Z)—S-(4-((3-(2-((furan-2-ylmethyl)amino)-2-oxoethyl)-5-methoxy-2-methyl-1H-inden-1-ylidene)methyl)-2,6-dimethoxyphenyl) dimethylcarbamothioate (1833);

(Z)—S-(4-((3-(2-((furan-2-ylmethyl)amino)-2-oxoethyl)-5-methoxy-2-methyl-1H-inden-1-ylidene)methyl)-2,6-dimethoxyphenyl) 4-methylpiperazine-1-carbothioate (1834);

(Z)—S-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl) dimethylcarbamothioate (1835);

(Z)—S-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl) 4-methylpiperazine-1-carbothioate (1836);

(Z)—S-(4-((5-fluoro-2-methyl-3-(2-oxo-2-((pyridin-2-ylmethyl)amino)ethyl)-1H-inden-1-ylidene)methyl)-2,6-dimethoxyphenyl) dimethylcarbamothioate (1837);

(Z)—S-(4-((5-fluoro-2-methyl-3-(2-oxo-2-((pyridin-2-ylmethyl)amino)ethyl)-1H-inden-1-ylidene)methyl)-2,6-dimethoxyphenyl) 4-methylpiperazine-1-carbothioate (1838);

(Z)—S-(4-((5-fluoro-2-methyl-3-(2-oxo-2-((pyridin-3-ylmethyl)amino)ethyl)-1H-inden-1-ylidene)methyl)-2,6-dimethoxyphenyl) dimethylcarbamothioate (1839);

(Z)—S-(4-((5-fluoro-2-methyl-3-(2-oxo-2-((pyridin-3-ylmethyl)amino)ethyl)-1H-inden-1-ylidene)methyl)-2,6-dimethoxyphenyl) 4-methylpiperazine-1-carbothioate (1840);

(Z)—S-(4-((3-(2-(benzylamino)-2-oxoethyl)-5-fluoro-2-methyl-1H-inden-1-ylidene)methyl)-2,6-dimethoxyphenyl) dimethylcarbamothioate (1841);

(Z)—S-(4-((3-(2-(benzylamino)-2-oxoethyl)-5-fluoro-2-methyl-1H-inden-1-ylidene)methyl)-2,6-dimethoxyphenyl) 4-methylpiperazine-1-carbothioate (1842);

(Z)-2-((4-((5-fluoro-3-(2-((furan-2-ylmethyl)amino)-2-oxoethyl)-2-methyl-1H-inden-1-ylidene)methyl)-2,6-dimethoxyphenyl)amino)acetic acid (1849);

(Z)-3-((4-((5-fluoro-3-(2-((furan-2-ylmethyl)amino)-2-oxoethyl)-2-methyl-1H-inden-1-ylidene)methyl)-2,6-dimethoxyphenyl)amino)propanoic acid (1850);

(Z)-2-(dimethylamino)ethyl 2-((4-((5-fluoro-3-(2-((furan-2-ylmethyl)amino)-2-oxoethyl)-2-methyl-1H-inden-1-ylidene)methyl)-2,6-dimethoxyphenyl)amino)acetate (1851);

(Z)-2-(dimethylamino)ethyl 3-((4-((5-fluoro-3-(2-((furan-2-ylmethyl)amino)-2-oxoethyl)-2-methyl-1H-inden-1-ylidene)methyl)-2,6-dimethoxyphenyl)amino)propanoate (1852);

(Z)-2-(4-methylpiperazin-1-yl)ethyl 2-((4-((5-fluoro-3-(2-((furan-2-ylmethyl)amino)-2-oxoethyl)-2-methyl-1H-inden-1-ylidene)methyl)-2,6-dimethoxyphenyl)amino)acetate (1853);

(Z)-1-methylpiperidin-4-yl 2-((4-((5-fluoro-3-(2-((furan-2-ylmethyl)amino)-2-oxoethyl)-2-methyl-1H-inden-1-ylidene)methyl)-2,6-dimethoxyphenyl)amino)acetate (1854);

(Z)-2-((4-((5-fluoro-3-(2-((furan-2-ylmethyl)amino)-2-oxoethyl)-2-methyl-1H-inden-1-ylidene)methyl)-2,6-dimethoxyphenyl)amino)-4-guanidinobutanoic acid (1855);

(Z)-2-((4-((5-fluoro-3-(2-((furan-2-ylmethyl)amino)-2-oxoethyl)-2-methyl-1H-inden-1-ylidene)methyl)-2,6-dimethoxyphenyl)thio)acetic acid (1856);

(Z)-3-((4-((5-fluoro-3-(2-((furan-2-ylmethyl)amino)-2-oxoethyl)-2-methyl-1H-inden-1-ylidene)methyl)-2,6-dimethoxyphenyl)thio)propanoic acid (1857);

(Z)-2-((4-((3-(2-((furan-2-ylmethyl)amino)-2-oxoethyl)-5-methoxy-2-methyl-1H-inden-1-ylidene)methyl)-2,6-dimethoxyphenyl)thio)acetic acid (1858);

(Z)-3-((4-((3-(2-((furan-2-ylmethyl)amino)-2-oxoethyl)-5-methoxy-2-methyl-1H-inden-1-ylidene)methyl)-2,6-dimethoxyphenyl)thio)propanoic acid (1859);

(Z)-2-(dimethylamino)ethyl 2-((4-((5-fluoro-3-(2-((furan-2-ylmethyl)amino)-2-oxoethyl)-2-methyl-1H-inden-1-ylidene)methyl)-2,6-dimethoxyphenyl)thio)acetate (1860);

(Z)-2-(dimethylamino)ethyl 3-((4-((5-fluoro-3-(2-((furan-2-ylmethyl)amino)-2-oxoethyl)-2-methyl-1H-inden-1-ylidene)methyl)-2,6-dimethoxyphenyl)thio)propanoate (1861);

(Z)-2-(4-methylpiperazin-1-yl)ethyl 2-((4-((5-fluoro-3-(2-((furan-2-ylmethyl)amino)-2-oxoethyl)-2-methyl-1H-inden-1-ylidene)methyl)-2,6-dimethoxyphenyl)thio)acetate (1862);

(Z)-2-(dimethylamino)ethyl 2-(4-((5-fluoro-3-(2-((furan-2-ylmethyl)amino)-2-oxoethyl)-2-methyl-1H-inden-1-ylidene)methyl)-2,6-dimethoxyphenoxy)acetate (1863);

(Z)-2-(dimethylamino)ethyl 3-(4-((5-fluoro-3-(2-((furan-2-ylmethyl)amino)-2-oxoethyl)-2-methyl-1H-inden-1-ylidene)methyl)-2,6-dimethoxyphenoxy)propanoate (1864);

(Z)-2-(4-methylpiperazin-1-yl)ethyl 2-(4-((5-fluoro-3-(2-((furan-2-ylmethyl)amino)-2-oxoethyl)-2-methyl-1H-inden-1-ylidene)methyl)-2,6-dimethoxyphenoxy)acetate (1865);

(Z)-2-morpholinoethyl 2-(4-((5-fluoro-3-(2-((furan-2-ylmethyl)amino)-2-oxoethyl)-2-methyl-1H-inden-1-ylidene)methyl)-2,6-dimethoxyphenoxy)acetate (1866);

(Z)-2-(1-(3,5-dimethoxy-4-(2-(4-methylpiperazin-1-yl)-2-oxoethoxy)benzylidene)-5-fluoro-2-methyl-1H-inden-3-yl)-N-(furan-2-ylmethyl)acetamide (1867);

(Z)-2-(1-(3,5-dimethoxy-4-(2-oxo-2-(piperidin-4-ylamino)ethoxy)benzylidene)-5-fluoro-2-methyl-1H-inden-3-yl)-N-(furan-2-ylmethyl)acetamide (1868);

(Z)-2-(1-(3,5-dimethoxy-4-(2-((1-methylpyrrolidin-3-yl)amino)-2-oxoethoxy)benzylidene)-5-fluoro-2-methyl-1H-inden-3-yl)-N-(furan-2-ylmethyl)acetamide (1869);

(Z)-1-methylpiperidin-4-yl 2-(4-((5-fluoro-3-(2-((furan-2-ylmethyl)amino)-2-oxoethyl)-2-methyl-1H-inden-1-ylidene)methyl)-2,6-dimethoxyphenoxy)acetate (1870);

(Z)-2-(1-(4-(2-(dimethylamino)ethoxy)-3,5-dimethoxybenzylidene)-5-fluoro-2-methyl-1H-inden-3-yl)-N-(furan-2-ylmethyl)acetamide (1871);

(Z)-2-(5-fluoro-1-(4-(2-hydroxyethoxy)-3,5-dimethoxybenzylidene)-2-methyl-1H-inden-3-yl)-N-(furan-2-ylmethyl)acetamide (1872);

(Z)-(2-(4-((5-fluoro-3-(2-((furan-2-ylmethyl)amino)-2-oxoethyl)-2-methyl-1H-inden-1-ylidene)methyl)-2,6-dimethoxyphenoxy)ethyl)boronic acid (1873);

(Z)-2-(dimethylamino)ethyl 2-(4-((3-(2-((furan-2-ylmethyl)amino)-2-oxoethyl)-5-methoxy-2-methyl-1H-inden-1-ylidene)methyl)-2,6-dimethoxyphenoxy)acetate (1874);

(Z)-2-(dimethylamino)ethyl 3-(4-((3-(2-((furan-2-ylmethyl)amino)-2-oxoethyl)-5-methoxy-2-methyl-1H-inden-1-ylidene)methyl)-2,6-dimethoxyphenoxy)propanoate (1875);

(Z)-2-(4-methylpiperazin-1-yl)ethyl 2-(4-((3-(2-((furan-2-ylmethyl)amino)-2-oxoethyl)-5-methoxy-2-methyl-1H-inden-1-ylidene)methyl)-2,6-dimethoxyphenoxy)acetate (1876);

(Z)-2-(1-(3,5-dimethoxy-4-(2-oxo-2-(piperidin-4-ylamino)ethoxy)benzylidene)-5-methoxy-2-methyl-1H-inden-3-yl)-N-(furan-2-ylmethyl)acetamide (1877);

(Z)-2-(1-(3,5-dimethoxy-4-(2-(4-methylpiperazin-1-yl)-2-oxoethoxy)benzylidene)-5-methoxy-2-methyl-1H-inden-3-yl)-N-(furan-2-ylmethyl)acetamide (1878);

(Z)-1-methylpiperidin-4-yl 2-(4-((3-(2-((furan-2-ylmethyl)amino)-2-oxoethyl)-5-methoxy-2-methyl-1H-inden-1-ylidene)methyl)-2,6-dimethoxyphenoxy)acetate (1879);

(Z)-2-(1-(4-(2-(dimethylamino)ethoxy)-3,5-dimethoxybenzylidene)-5-methoxy-2-methyl-1H-inden-3-yl)-N-(furan-2-ylmethyl)acetamide (1880);

(Z)—N-(furan-2-ylmethyl)-2-(1-(4-(2-hydroxyethoxy)-3,5-dimethoxybenzylidene)-5-methoxy-2-methyl-1H-inden-3-yl)acetamide (1881);

(Z)-(2-(4-((3-(2-((furan-2-ylmethyl)amino)-2-oxoethyl)-5-methoxy-2-methyl-1H-inden-1-ylidene)methyl)-2,6-dimethoxyphenoxy)ethyl)boronic acid (1882);

(Z)-2-(dimethylamino)ethyl 2-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)acetate (1883);

(Z)-2-(dimethylamino)ethyl 3-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)propanoate (1884);

(Z)-2-(4-methylpiperazin-1-yl)ethyl 2-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)acetate (1885);

(Z)-2-(1-(3,5-dimethoxy-4-(2-oxo-2-(piperidin-4-ylamino)ethoxy)benzylidene)-5-fluoro-2-methyl-1H-inden-3-yl)-N-((1-methyl-1H-pyrrol-2-yl)methyl)acetamide (1886);

(Z)-2-(1-(3,5-dimethoxy-4-(2-(4-methylpiperazin-1-yl)-2-oxoethoxy)benzylidene)-5-fluoro-2-methyl-1H-inden-3-yl)-N-((1-methyl-1H-pyrrol-2-yl)methyl)acetamide (1887);

(Z)-1-methylpiperidin-4-yl 2-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)acetate (1888);

(Z)-2-(1-(4-(2-(dimethylamino)ethoxy)-3,5-dimethoxybenzylidene)-5-fluoro-2-methyl-1H-inden-3-yl)-N-((1-methyl-1H-pyrrol-2-yl)methyl)acetamide (1889);

(Z)-2-(5-fluoro-1-(4-(2-hydroxyethoxy)-3,5-dimethoxybenzylidene)-2-methyl-1H-inden-3-yl)-N-((1-methyl-1H-pyrrol-2-yl)methyl)acetamide (1890);

(Z)-(2-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)ethyl)boronic acid (1891);

(Z)-2-(4-methylpiperazin-1-yl)ethyl 2-(4-((5-fluoro-2-methyl-3-(2-oxo-2-((pyridin-3-ylmethyl)amino)ethyl)-1H-inden-1-ylidene)methyl)-2,6-dimethoxyphenoxy)acetate (1892);

(Z)-2-(1-(3,5-dimethoxy-4-(2-oxo-2-(piperidin-4-ylamino)ethoxy)benzylidene)-5-fluoro-2-methyl-1H-inden-3-yl)-N-(pyridin-3-ylmethyl)acetamide (1893);

(Z)-2-(1-(3,5-dimethoxy-4-(2-(4-methylpiperazin-1-yl)-2-oxoethoxy)benzylidene)-5-fluoro-2-methyl-1H-inden-3-yl)-N-(pyridin-3-ylmethyl)acetamide (1894);

(Z)-1-methylpiperidin-4-yl 2-(4-((5-fluoro-2-methyl-3-(2-oxo-2-((pyridin-3-ylmethyl)amino)ethyl)-1H-inden-1-ylidene)methyl)-2,6-dimethoxyphenoxy)acetate (1895);

(Z)-2-(1-(4-(2-(dimethylamino)ethoxy)-3,5-dimethoxybenzylidene)-5-fluoro-2-methyl-1H-inden-3-yl)-N-(pyridin-3-ylmethyl)acetamide (1896);

(Z)-2-(5-fluoro-1-(4-(2-hydroxyethoxy)-3,5-dimethoxybenzylidene)-2-methyl-1H-inden-3-yl)-N-(pyridin-3-ylmethyl)acetamide (1897);

(Z)-(2-(4-((5-fluoro-2-methyl-3-(2-oxo-2-((pyridin-3-ylmethyl)amino)ethyl)-1H-inden-1-ylidene)methyl)-2,6-dimethoxyphenoxy)ethyl)boronic acid (1898);

(Z)-2-(dimethylamino)ethyl 2-(4-((5-fluoro-2-methyl-3-(2-oxo-2-((pyridin-3-ylmethyl)amino)ethyl)-1H-inden-1-ylidene)methyl)-2,6-dimethoxyphenoxy)acetate (1899);

(Z)-2-(dimethylamino)ethyl 3-(4-((5-fluoro-2-methyl-3-(2-oxo-2-((pyridin-3-ylmethyl)amino)ethyl)-1H-inden-1-ylidene)methyl)-2,6-dimethoxyphenoxy)propanoate (1900);

(Z)-2-(dimethylamino)ethyl 2-(4-((5-fluoro-2-methyl-3-(2-oxo-2-((pyridin-2-ylmethyl)amino)ethyl)-1H-inden-1-ylidene)methyl)-2,6-dimethoxyphenoxy)acetate (1901);

(Z)-2-(dimethylamino)ethyl 3-(4-((5-fluoro-2-methyl-3-(2-oxo-2-((pyridin-2-ylmethyl)amino)ethyl)-1H-inden-1-ylidene)methyl)-2,6-dimethoxyphenoxy)propanoate (1902);

(Z)-2-(4-methylpiperazin-1-yl)ethyl 2-(4-((5-fluoro-2-methyl-3-(2-oxo-2-((pyridin-2-ylmethyl)amino)ethyl)-1H-inden-1-ylidene)methyl)-2,6-dimethoxyphenoxy)acetate (1903);

(Z)-2-(1-(3,5-dimethoxy-4-(2-oxo-2-(piperidin-4-ylamino)ethoxy)benzylidene)-5-fluoro-2-methyl-1H-inden-3-yl)-N-(pyridin-2-ylmethyl)acetamide (1904);

(Z)-2-(1-(3,5-dimethoxy-4-(2-(4-methylpiperazin-1-yl)-2-oxoethoxy)benzylidene)-5-fluoro-2-methyl-1H-inden-3-yl)-N-(pyridin-2-ylmethyl)acetamide (1905);

(Z)-1-methylpiperidin-4-yl 2-(4-((5-fluoro-2-methyl-3-(2-oxo-2-((pyridin-2-ylmethyl)amino)ethyl)-1H-inden-1-ylidene)methyl)-2,6-dimethoxyphenoxy)acetate (1906);

(Z)-2-(1-(4-(2-(dimethylamino)ethoxy)-3,5-dimethoxybenzylidene)-5-fluoro-2-methyl-1H-inden-3-yl)-N-(pyridin-2-ylmethyl)acetamide (1907);

(Z)-2-(5-fluoro-1-(4-(2-hydroxyethoxy)-3,5-dimethoxybenzylidene)-2-methyl-1H-inden-3-yl)-N-(pyridin-2-ylmethyl)acetamide (1908);

(Z)-(2-(4-((5-fluoro-2-methyl-3-(2-oxo-2-((pyridin-2-ylmethyl)amino)ethyl)-1H-inden-1-ylidene)methyl)-2,6-dimethoxyphenoxy)ethyl)boronic acid (1909);

(Z)-2-(dimethylamino)ethyl 2-(4-((3-(2-(benzylamino)-2-oxoethyl)-5-fluoro-2-methyl-1H-inden-1-ylidene)methyl)-2,6-dimethoxyphenoxy)acetate (1910);

(Z)-2-(dimethylamino)ethyl 3-(4-((3-(2-(benzylamino)-2-oxoethyl)-5-fluoro-2-methyl-1H-inden-1-ylidene)methyl)-2,6-dimethoxyphenoxy)propanoate (1911);

(Z)-2-(4-methylpiperazin-1-yl)ethyl 2-(4-((3-(2-(benzylamino)-2-oxoethyl)-5-fluoro-2-methyl-1H-inden-1-ylidene)methyl)-2,6-dimethoxyphenoxy)acetate (1912);

(Z)—N-benzyl-2-(1-(3,5-dimethoxy-4-(2-oxo-2-(piperidin-4-ylamino)ethoxy)benzylidene)-5-fluoro-2-methyl-1H-inden-3-yl)acetamide (1913);

(Z)—N-benzyl-2-(1-(3,5-dimethoxy-4-(2-(4-methylpiperazin-1-yl)-2-oxoethoxy)benzylidene)-5-fluoro-2-methyl-1H-inden-3-yl)acetamide (1914);

(Z)-1-methylpiperidin-4-yl 2-(4-((3-(2-(benzylamino)-2-oxoethyl)-5-fluoro-2-methyl-1H-inden-1-ylidene)methyl)-2,6-dimethoxyphenoxy)acetate (1915);

(Z)—N-benzyl-2-(1-(4-(2-(dimethylamino)ethoxy)-3,5-dimethoxybenzylidene)-5-fluoro-2-methyl-1H-inden-3-yl)acetamide (1916);

(Z)—N-benzyl-2-(5-fluoro-1-(4-(2-hydroxyethoxy)-3,5-dimethoxybenzylidene)-2-methyl-1H-inden-3-yl)acetamide (1917);

(Z)-(2-(4-((3-(2-(benzylamino)-2-oxoethyl)-5-fluoro-2-methyl-1H-inden-1-ylidene)methyl)-2,6-dimethoxyphenoxy)ethyl)boronic acid (1918);

(Z)-2-(2-fluoro-5-(4-hydroxy-3,5-dimethoxybenzylidene)-6-methyl-5H-cyclopenta[b]pyridin-7-yl)-N-(furan-2-ylmethyl)acetamide (1965);

(Z)-2-(3-fluoro-7-(4-hydroxy-3,5-dimethoxybenzylidene)-6-methyl-7H-cyclopenta[b]pyridin-5-yl)-N-(furan-2-ylmethyl)acetamide (1966);

(Z)-2-(3-fluoro-7-(4-hydroxy-3,5-dimethoxybenzylidene)-6-methyl-7H-cyclopenta[c]pyridin-5-yl)-N-(furan-2-ylmethyl)acetamide (1967);

2-(3-fluoro-7-(4-hydroxy-3,5-dimethoxybenzyl)-6-methyl-7H-cyclopenta[c]pyridin-5-yl)-N-(furan-2-ylmethyl)acetamide (1968);

(Z)—N-(furan-2-ylmethyl)-2-(7-(4-hydroxy-3,5-dimethoxybenzylidene)-3-methoxy-6-methyl-7H-cyclopenta[b]pyridin-5-yl)acetamide (1969);

(E)-2-(7-(4-hydroxy-3,5-dimethoxybenzylidene)-3-methoxy-7H-pyrrolo[3,4-b]pyridin-5-yl)-N-((1-methyl-1H-pyrrol-2-yl)methyl)acetamide (1970);

2-(3-cyano-7-(4-hydroxy-3,5-dimethoxybenzyl)-6-methyl-5H-cyclopenta[c]pyridin-5-yl)-N-((1-methyl-1H-pyrrol-2-yl)methyl)acetamide (1971);

(Z)—N-(furan-2-ylmethyl)-2-(5-(4-hydroxy-3,5-dimethoxybenzylidene)-3-methoxy-6-methyl-5H-cyclopenta[c]pyridin-7-yl)acetamide (1972);

(Z)-2-(3-fluoro-7-(4-hydroxy-3,5-dimethoxybenzylidene)-6-methyl-7H-cyclopenta[c]pyridin-5-yl)-N-(pyridin-4-ylmethyl)acetamide (1973);

(Z)-2-(1-fluoro-5-(4-hydroxy-3,5-dimethoxybenzylidene)-6-methyl-5H-cyclopenta[c]pyridin-7-yl)-N-(pyridin-2-ylmethyl)acetamide (1974);

(E)-2-(3-fluoro-7-(4-hydroxy-3,5-dimethoxybenzylidene)-6-methyl-6,7-dihydro-5H-pyrrolo[3,4-b]pyridin-5-yl)-N-(pyridin-3-ylmethyl)acetamide (1975);

(E)-2-(6-fluoro-3-(4-hydroxy-3,5-dimethoxybenzylidene)-2-methylisoindolin-1-yl)-N-(pyridin-3-ylmethyl)acetamide (1976);

(E)-2-(2-fluoro-5-(4-hydroxy-3,5-dimethoxybenzylidene)-6-methyl-6,7-dihydro-5H-pyrrolo[3,4-b]pyridin-7-yl)-N-(pyridin-3-ylmethyl)acetamide (1978);

(Z)-2-(3-fluoro-7-(4-hydroxy-3,5-dimethoxybenzylidene)-6-methyl-7H-cyclopenta[c]pyridin-5-yl)-N-(pyridin-2-ylmethyl)acetamide (1979);

(Z)-2-(2-fluoro-5-(4-hydroxy-3,5-dimethoxybenzylidene)-6-methyl-5H-cyclopenta[b]pyrazin-7-yl)-N-(pyridin-2-ylmethyl)acetamide (1980);

(Z)—N-benzyl-2-(2-fluoro-5-(4-hydroxy-3,5-dimethoxybenzylidene)-6-methyl-5H-cyclopenta[b]pyridin-7-yl)acetamide (1981);

(Z)—N-benzyl-2-(3-fluoro-7-(4-hydroxy-3,5-dimethoxybenzylidene)-6-methyl-7H-cyclopenta[b]pyridin-5-yl)acetamide (1982);

(E)-N-benzyl-2-(6-fluoro-3-(4-hydroxy-3,5-dimethoxybenzylidene)-3H-pyrrolo[3,4-c]pyridin-1-yl)acetamide (1983);

(E)-N-benzyl-2-(6-fluoro-3-(4-hydroxy-3,5-dimethoxybenzylidene)-2-methyl-2,3-dihydro-1H-pyrrolo[3,4-c]pyridin-1-yl)acetamide (1984);

(E)-1-benzyl-3-(3-fluoro-5-(4-hydroxy-3,5-dimethoxybenzylidene)-6-methyl-5H-cyclopenta[c]pyridin-7-yl)urea (1985);

2-(3-fluoro-7-(4-hydroxy-3,5-dimethoxybenzyl)-6-methyl-5H-cyclopenta[b]pyridin-5-yl)-N-((1-methyl-1H-pyrrol-2-yl)methyl)acetamide (1986);

(E)-2-(6-fluoro-3-(4-hydroxy-3,5-dimethoxybenzylidene)-2-methylisoindolin-1-yl)-N-((1-methyl-1H-pyrrol-2-yl)methyl)acetamide (1987);

(E)-2-(4,6-difluoro-1-(4-hydroxy-3,5-dimethoxybenzylidene)-2-methyl-2,3-dihydro-1H-pyrrolo[3,4-c]pyridin-3-yl)-N-((1-methyl-1H-pyrrol-2-yl)methyl)acetamide (1988);

(Z)-2-(4-((2-fluoro-7-(2-((furan-2-ylmethyl)amino)-2-oxoethyl)-6-methyl-5H-cyclopenta[b]pyridin-5-ylidene)methyl)-2,6-dimethoxyphenoxy)acetic acid (1989);

(Z)-2-(4-((3-fluoro-5-(2-((furan-2-ylmethyl)amino)-2-oxoethyl)-6-methyl-5H-cyclopenta[c]pyridin-7-ylidene)methyl)-2,6-dimethoxyphenoxy)acetic acid (1990);

(Z)-2-(4-((3-fluoro-5-(2-((furan-2-ylmethyl)amino)-2-oxoethyl)-6-methyl-7H-cyclopenta[b]pyridin-7-ylidene)methyl)-2,6-dimethoxyphenoxy)acetic acid (1991);

(Z)-2-(4-((3-fluoro-7-(2-((furan-2-ylmethyl)amino)-2-oxoethyl)-6-methyl-5H-cyclopenta[c]pyridin-5-ylidene)methyl)-2,6-dimethoxyphenoxy)acetic acid (1992);

2-(4-((6-fluoro-1-(2-((furan-2-ylmethyl)amino)-2-oxoethyl)-1H-pyrrolo[3,4-c]pyridin-3-yl)methyl)-2,6-dimethoxyphenoxy)acetic acid (1993);

(E)-2-(4-((5-fluoro-3-(2-((furan-2-ylmethyl)amino)-2-oxoethyl)-1H-isoindol-1-ylidene)methyl)-2,6-dimethoxyphenoxy)acetic acid (1994);

(E)-2-(2,6-dimethoxy-4-((2-methyl-3-(2-(((1-methyl-1H-pyrrol-2-yl)methyl)amino)-2-oxoethyl)-5-(trifluoromethyl)isoindolin-1-ylidene)methyl)phenoxy)acetic acid (1995);

(E)-2-(4-((5-fluoro-3-(2-((furan-2-ylmethyl)amino)-2-oxoethyl)-2-methylisoindolin-1-ylidene)methyl)-2,6-dimethoxyphenoxy)acetic acid (1996);

2-(4-((6-fluoro-1-(2-((furan-2-ylmethyl)amino)-2-oxoethyl)-1H-isoindol-3-yl)methyl)-2,6-dimethoxyphenoxy)acetic acid (1997);

2-(4-((2-fluoro-7-(2-((furan-2-ylmethyl)amino)-2-oxoethyl)-7H-pyrrolo[3,4-b]pyridin-5-yl)methyl)-2,6-dimethoxyphenoxy)acetic acid (1998);

(E)-2-((4-((5-cyano-3-(2-((furan-2-ylmethyl)amino)-2-oxoethyl)-2-methylisoindolin-1-ylidene)methyl)-2,6-dimethoxyphenyl)amino)acetic acid (1999);

(Z)-2-(4-((2-fluoro-6-methyl-7-(2-(((1-methyl-1H-pyrrol-2-yl)methyl)amino)-2-oxoethyl)-5H-cyclopenta[b]pyridin-5-ylidene)methyl)-2,6-dimethoxyphenoxy)acetic acid (2000);

(Z)-2-(4-((5-(2-((furan-2-ylmethyl)amino)-2-oxoethyl)-3-methoxy-6-methyl-7H-cyclopenta[c]pyridin-7-ylidene)methyl)-2,6-dimethoxyphenoxy)acetic acid (2001);

(Z)-2-(4-((3-fluoro-6-methyl-5-(2-(((1-methyl-1H-pyrrol-2-yl)methyl)amino)-2-oxoethyl)-7H-cyclopenta[b]pyridin-7-ylidene)methyl)-2,6-dimethoxyphenoxy)acetic acid (2002);

(Z)-2-(4-((3-fluoro-6-methyl-7-(2-oxo-2-((pyridin-3-ylmethyl)amino)ethyl)-5H-cyclopenta[c]pyridin-5-ylidene)methyl)-2,6-dimethoxyphenoxy)acetic acid (2003);

(Z)-2-(4-((5-(2-(benzylamino)-2-oxoethyl)-3-bromo-6-methyl-7H-cyclopenta[b]pyridin-7-ylidene)methyl)-2,6-dimethoxyphenoxy)acetic acid (2004);
(E)-2-(4-((7-(2-(benzylamino)-2-oxoethyl)-2-fluoro-5H-pyrrolo[3,4-b]pyridin-5-ylidene)methyl)-2,6-dimethoxyphenoxy)acetic acid (2005);
(Z)-2-(2,6-dimethoxy-4-((3-methoxy-6-methyl-5-(2-oxo-2-((pyridin-4-ylmethyl)amino)ethyl)-7H-cyclopenta[c]pyridin-7-ylidene)methyl)phenoxy)acetic acid (2006);
(Z)-2-(4-((3-fluoro-6-methyl-5-(2-oxo-2-((pyridin-2-ylmethyl)amino)ethyl)-7H-cyclopenta[b]pyridin-7-ylidene)methyl)-2,6-dimethoxyphenoxy)acetic acid (2007);
(Z)-2-(4-((1,3-difluoro-6-methyl-7-(2-oxo-2-((pyridin-3-ylmethyl)amino)ethyl)-5H-cyclopenta[c]pyridin-5-ylidene)methyl)-2,6-dimethoxyphenoxy)acetic acid (2008);
(Z)-(4-((2-fluoro-7-(2-((furan-2-ylmethyl)amino)-2-oxoethyl)-6-methyl-5H-cyclopenta[b]pyridin-5-ylidene)methyl)-2,6-dimethoxyphenyl)boronic acid (2009);
(Z)-(4-((3-fluoro-5-(2-((furan-2-ylmethyl)amino)-2-oxoethyl)-6-methyl-7H-cyclopenta[c]pyridin-7-ylidene)methyl)-2,6-dimethoxyphenyl)boronic acid (2010);
(Z)-(4-((3-fluoro-5-(2-((furan-2-ylmethyl)amino)-2-oxoethyl)-6-methyl-7H-cyclopenta[b]pyridin-7-ylidene)methyl)-2,6-dimethoxyphenyl)boronic acid (2011);
(Z)-4-((3-fluoro-7-(2-((furan-2-ylmethyl)amino)-2-oxoethyl)-6-methyl-5H-cyclopenta[c]pyridin-5-ylidene)methyl)-2,6-dimethoxyphenyl dihydrogen borate (2012);
(4-((6-fluoro-1-(2-((furan-2-ylmethyl)amino)-2-oxoethyl)-1H-pyrrolo[3,4-c]pyridin-3-yl)methyl)-2,6-dimethoxyphenyl)boronic acid (2013);
(E)-4-((5-fluoro-3-(2-oxo-2-((pyridin-2-ylmethyl)amino)ethyl)-1H-isoindol-1-ylidene)methyl)-2,6-dimethoxyphenyl dihydrogen borate (2014);
(E)-2-(6-chloro-3-(3,5-dimethoxy-4-sulfamoylbenzylidene)-2-methylisoindolin-1-yl)-N-(furan-2-ylmethyl)acetamide (2015);
(Z)-2-(4-((3-chloro-5-(3-(furan-2-ylmethyl)ureido)-6-methyl-7H-cyclopenta[b]pyridin-7-ylidene)methyl)-2,6-dimethoxyphenoxy)acetic acid (2016);
2-(4-((3-fluoro-5-(3-(furan-2-ylmethyl)ureido)-6-methyl-5H-cyclopenta[c]pyridin-7-yl)methyl)-2,6-dimethoxyphenoxy)acetic acid (2017);
2-((4-((2-fluoro-7-(2-(((1-methyl-1H-pyrrol-2-yl)methyl)amino)-2-oxoethyl)-7H-pyrrolo[3,4-b]pyridin-5-yl)methyl)-2-methoxyphenyl)amino)acetic acid (2018);
(4-((6-fluoro-1-(2-((furan-2-ylmethyl)amino)-2-oxoethyl)-2-methyl-2,3-dihydro-1H-pyrrolo[3,4-c]pyridin-3-yl)methyl)-2,6-dimethoxyphenyl)boronic acid (2019);
(Z)-2-((4-((2-fluoro-6-methyl-7-(2-(((1-methyl-1H-pyrrol-2-yl)methyl)amino)-2-oxoethyl)-5H-cyclopenta[b]pyridin-5-ylidene)methyl)-2,6-dimethoxyphenyl)amino)acetic acid (2020);
(Z)-2-((4-((5-(3-(furan-2-ylmethyl)ureido)-3-methoxy-6-methyl-7H-cyclopenta[c]pyridin-7-ylidene)methyl)-2,6-dimethoxyphenyl)amino)acetic acid (2021);
(Z)-(2-(4-((3-fluoro-6-methyl-5-(2-(((1-methyl-1H-pyrrol-2-yl)methyl)amino)-2-oxoethyl)-7H-cyclopenta[b]pyridin-7-ylidene)methyl)-2,6-dimethoxyphenoxy)ethyl)boronic acid (2022);
(Z)-2-((4-((3-fluoro-6-methyl-7-(2-oxo-2-((pyridin-3-ylmethyl)amino)ethyl)-5H-cyclopenta[c]pyridin-5-ylidene)methyl)-2,6-dimethoxyphenyl)amino)acetic acid (2023);
(Z)-2-((5-((5-(3-(benzylamino)-3-oxopropyl)-3-methoxy-6-methyl-5H-cyclopenta[b]pyridin-7(6H)-ylidene)methyl)-2-methoxyphenyl)amino)acetic acid (2024);
(E)-2-((4-((7-(2-(benzylamino)-2-oxoethyl)-2-fluoro-5H-pyrrolo[3,4-b]pyridin-5-ylidene)methyl)-2,6-dimethoxyphenyl)amino)acetic acid (2025);
(Z)-2-((2,6-dimethoxy-4-((3-methoxy-6-methyl-5-(2-oxo-2-((pyridin-4-ylmethyl)amino)ethyl)-7H-cyclopenta[c]pyridin-7-ylidene)methyl)phenyl)amino)acetic acid (2026);
(Z)-2-((2,6-dimethoxy-4-((3-methoxy-6-methyl-5-(2-oxo-2-((pyridin-2-ylmethyl)amino)ethyl)-7H-cyclopenta[b]pyridin-7-ylidene)methyl)phenyl)amino)acetic acid (2027);
(Z)-2-((4-((3-fluoro-6-methyl-7-(2-oxo-2-((pyridin-3-ylmethyl)amino)ethyl)-5H-cyclopenta[c]pyridin-5-ylidene)methyl)-2-methoxyphenyl)amino)acetic acid (2028);
(E)-2-((4-((7-(2-(benzylamino)-2-oxoethyl)-2-fluoro-5H-pyrrolo[3,4-b]pyridin-5-ylidene)methyl)-2,6-dimethoxyphenyl)thio)acetic acid (2029);
(Z)-3-(2,6-dimethoxy-4-((3-methoxy-6-methyl-5-(2-oxo-2-((pyridin-4-ylmethyl)amino)ethyl)-7H-cyclopenta[c]pyridin-7-ylidene)methyl)phenyl)propanoic acid (2030);
(Z)-2-(2,6-dimethoxy-4-((3-methoxy-6-methyl-5-(2-oxo-2-((pyridin-2-ylmethyl)amino)ethyl)-7H-cyclopenta[b]pyridin-7-ylidene)methyl)phenyl)acetic acid (2031);
(((4-((5-fluoro-2-methyl-3-(2-oxo-2-((pyridin-3-ylmethyl)amino)ethyl)-1H-inden-1-yl)methyl)-2,6-dimethoxyphenyl)amino)methyl)phosphonic acid (2042);
(Z)-(((4-((5-fluoro-2-methyl-3-(2-oxo-2-(pyrazin-2-ylamino)ethyl)-1H-inden-1-ylidene)methyl)-2,6-dimethoxyphenyl)amino)methyl)phosphonic acid (2043);
(Z)-(((4-((5-fluoro-2-methyl-3-(2-oxo-2-((pyridin-2-ylmethyl)amino)ethyl)-1H-inden-1-ylidene)methyl)-2,6-dimethoxyphenyl)thio)methyl)phosphonic acid (2044);
(Z)-(2-((4-((3-(2-((1H-pyrazol-5-yl)amino)-2-oxoethyl)-5-fluoro-2-methyl-1H-inden-1-ylidene)methyl)-2,6-dimethoxyphenyl)amino)ethyl)phosphonic acid (2047);
(Z)-(2-((4-((5-fluoro-2-methyl-3-(2-oxo-2-(pyridin-3-ylamino)ethyl)-1H-inden-1-ylidene)methyl)-2,6-dimethoxyphenyl)thio)ethyl)phosphonic acid (2048);
(Z)-(4-((5-fluoro-2-methyl-3-(2-((oxazol-2-ylmethyl)amino)-2-oxoethyl)-1H-inden-1-ylidene)methyl)-2,6-dimethoxyphenyl)boronic acid (2066);
(Z)-(4-((5-fluoro-2-methyl-3-(2-((oxazol-4-ylmethyl)amino)-2-oxoethyl)-1H-inden-1-ylidene)methyl)-2,6-dimethoxyphenyl)boronic acid (2067);
(Z)-(4-((5-fluoro-2-methyl-3-(2-((oxazol-5-ylmethyl)amino)-2-oxoethyl)-1H-inden-1-ylidene)methyl)-2,6-dimethoxyphenyl)boronic acid (2068);
(Z)-(4-((5-fluoro-2-methyl-3-(2-oxo-2-((thiazol-2-ylmethyl)amino)ethyl)-1H-inden-1-ylidene)methyl)-2,6-dimethoxyphenyl)boronic acid (2069);
(Z)-(4-((5-fluoro-2-methyl-3-(2-oxo-2-((thiazol-4-ylmethyl)amino)ethyl)-1H-inden-1-ylidene)methyl)-2,6-dimethoxyphenyl)boronic acid (2070);
(Z)-(4-((5-fluoro-2-methyl-3-(2-oxo-2-((thiazol-5-ylmethyl)amino)ethyl)-1H-inden-1-ylidene)methyl)-2,6-dimethoxyphenyl)boronic acid (2071);
(Z)-(4-((3-(2-(((1H-imidazol-5-yl)methyl)amino)-2-oxoethyl)-5-fluoro-2-methyl-1H-inden-1-ylidene)methyl)-2,6-dimethoxyphenyl)boronic acid (2072);
(Z)—N-((5-fluoro-1-(4-hydroxy-3,5-dimethoxybenzylidene)-2-methyl-1H-inden-3-yl)methyl)-1-methyl-1H-pyrrole-2-carboxamide (2085);
(Z)—N-((5-fluoro-1-(4-hydroxy-3,5-dimethoxybenzylidene)-2-methyl-1H-inden-3-yl)methyl)-1H-pyrrole-2-carboxamide (2086);

(Z)—N-((5-fluoro-1-(4-hydroxy-3,5-dimethoxybenzylidene)-2-methyl-1H-inden-3-yl)methyl)-1H-pyrrole-3-carboxamide (2087);

(Z)—N-((5-fluoro-1-(4-hydroxy-3,5-dimethoxybenzylidene)-2-methyl-1H-inden-3-yl)methyl)-1-methyl-1H-pyrrole-3-carboxamide (2088);

(Z)—N-((5-fluoro-1-(4-hydroxy-3,5-dimethoxybenzylidene)-2-methyl-1H-inden-3-yl)methyl)furan-3-carboxamide (2089);

(Z)—N-((5-fluoro-1-(4-hydroxy-3,5-dimethoxybenzylidene)-2-methyl-1H-inden-3-yl)methyl)furan-2-carboxamide (2090);

(Z)—N-((5-fluoro-1-(4-hydroxy-3,5-dimethoxybenzylidene)-2-methyl-1H-inden-3-yl)methyl)-2-(furan-3-yl)acetamide (2092);

(Z)—N-((5-fluoro-1-(4-hydroxy-3,5-dimethoxybenzylidene)-2-methyl-1H-inden-3-yl)methyl)-1H-imidazole-4-carboxamide (2093);

(Z)—N-((5-fluoro-1-(4-hydroxy-3,5-dimethoxybenzylidene)-2-methyl-1H-inden-3-yl)methyl)-2-(1H-imidazol-5-yl)acetamide (2094);

(Z)—N-((5-fluoro-1-(4-hydroxy-3,5-dimethoxybenzylidene)-2-methyl-1H-inden-3-yl)methyl)-2-(1H-pyrazol-5-yl)acetamide (2095);

(Z)—N-((5-fluoro-1-(4-hydroxy-3,5-dimethoxybenzylidene)-2-methyl-1H-inden-3-yl)methyl)-2-(pyridin-3-yl)acetamide (2096);

(Z)—N-((5-fluoro-1-(4-hydroxy-3,5-dimethoxybenzylidene)-2-methyl-1H-inden-3-yl)methyl)-2-(pyridin-2-yl)acetamide (2097);

(Z)—N-((5-fluoro-1-(4-hydroxy-3,5-dimethoxybenzylidene)-2-methyl-1H-inden-3-yl)methyl)-2-(pyridin-4-yl)acetamide (2098);

(Z)—N-((5-fluoro-1-(4-hydroxy-3,5-dimethoxybenzylidene)-2-methyl-1H-inden-3-yl)methyl)nicotinamide (2100);

(Z)—N-((5-fluoro-1-(4-hydroxy-3,5-dimethoxybenzylidene)-2-methyl-1H-inden-3-yl)methyl)-2-phenylacetamide (2101);

(Z)—N-((5-fluoro-1-(4-hydroxy-3,5-dimethoxybenzylidene)-2-methyl-1H-inden-3-yl)methyl)benzamide (2102);

(Z)—N-((5-fluoro-1-(4-hydroxy-3,5-dimethoxybenzylidene)-2-methyl-1H-inden-3-yl)methyl)-2-(oxazol-5-yl)acetamide (2103);

(Z)—N-((5-fluoro-1-(4-hydroxy-3,5-dimethoxybenzylidene)-2-methyl-1H-inden-3-yl)methyl)-2-(oxazol-2-yl)acetamide (2104);

(Z)—N-((5-fluoro-1-(4-hydroxy-3,5-dimethoxybenzylidene)-2-methyl-1H-inden-3-yl)methyl)-2-(oxazol-4-yl)acetamide (2105);

(Z)—N-((5-fluoro-1-(4-hydroxy-3,5-dimethoxybenzylidene)-2-methyl-1H-inden-3-yl)methyl)-2-(thiazol-5-yl)acetamide (2106);

(Z)—N-((5-fluoro-1-(4-hydroxy-3,5-dimethoxybenzylidene)-2-methyl-1H-inden-3-yl)methyl)oxazole-4-carboxamide (2107);

(Z)—N-((5-fluoro-1-(4-hydroxy-3,5-dimethoxybenzylidene)-2-methyl-1H-inden-3-yl)methyl)oxazole-5-carboxamide (2108);

(Z)—N-((5-fluoro-1-(4-hydroxy-3,5-dimethoxybenzylidene)-2-methyl-1H-inden-3-yl)methyl)oxazole-2-carboxamide (2109);

(Z)—N-((5-fluoro-1-(4-hydroxy-3,5-dimethoxybenzylidene)-2-methyl-1H-inden-3-yl)methyl)-2-(isoxazol-5-yl)acetamide (2110);

(Z)—N-((5-fluoro-1-(4-hydroxy-3,5-dimethoxybenzylidene)-2-methyl-1H-inden-3-yl)methyl)-2-(isoxazol-3-yl)acetamide (2111);

(Z)—N-((5-fluoro-1-(4-hydroxy-3,5-dimethoxybenzylidene)-2-methyl-1H-inden-3-yl)methyl)-2-(isoxazol-4-yl)acetamide (2112);

(Z)—N-((5-fluoro-1-(4-hydroxy-3,5-dimethoxybenzylidene)-2-methyl-1H-inden-3-yl)methyl)isoxazole-5-carboxamide (2113);

(Z)—N-((5-fluoro-1-(4-hydroxy-3,5-dimethoxybenzylidene)-2-methyl-1H-inden-3-yl)methyl)-2-(pyrazin-2-yl)acetamide (2114);

(Z)-(4-((3-((1H-imidazole-4-carboxamido)methyl)-5-fluoro-2-methyl-1H-inden-1-ylidene)methyl)-2,6-dimethoxyphenyl)boronic acid (2115);

(Z)-4-((3-((1H-imidazole-2-carboxamido)methyl)-5-fluoro-2-methyl-1H-inden-1-ylidene)methyl)-2,6-dimethoxyphenyl dimethylcarbamate (2116);

(Z)-(4-((3-((2-(1H-imidazol-2-yl)acetamido)methyl)-5-fluoro-2-methyl-1H-inden-1-ylidene)methyl)-2,6-dimethoxyphenyl)boronic acid (2117);

(Z)-4-((3-((2-(1H-imidazol-5-yl)acetamido)methyl)-5-fluoro-2-methyl-1H-inden-1-ylidene)methyl)-2,6-dimethoxyphenyl ethylcarbamate (2118);

(Z)-(4-((3-((2-(1H-pyrazol-5-yl)acetamido)methyl)-5-fluoro-2-methyl-1H-inden-1-ylidene)methyl)-2,6-dimethoxyphenyl)boronic acid (2119);

(Z)-4-((5-fluoro-2-methyl-3-((oxazole-4-carboxamido)methyl)-1H-inden-1-ylidene)methyl)-2,6-dimethoxyphenyl ethylcarbamate (2120);

(Z)-4-((5-fluoro-3-((2-(isoxazol-5-yl)acetamido)methyl)-2-methyl-1H-inden-1-ylidene)methyl)-2,6-dimethoxyphenyl 4-methylpiperazine-1-carboxylate (2121);

(Z)-4-((5-fluoro-2-methyl-3-((oxazole-2-carboxamido)methyl)-1H-inden-1-ylidene)methyl)-2,6-dimethoxyphenyl dimethylcarbamate (2122);

(Z)-(4-((5-fluoro-3-((2-(isoxazol-4-yl)acetamido)methyl)-2-methyl-1H-inden-1-ylidene)methyl)-2,6-dimethoxyphenyl)boronic acid (2123);

(Z)-(4-((5-fluoro-3-((2-(isoxazol-5-yl)acetamido)methyl)-2-methyl-1H-inden-1-ylidene)methyl)-2,6-dimethoxyphenyl)boronic acid (2124);

(Z)-4-((5-fluoro-2-methyl-3-((2-phenylacetamido)methyl)-1H-inden-1-ylidene)methyl)-2,6-dimethoxyphenyl 4-methylpiperazine-1-carboxylate (2125);

(Z)-4-((5-fluoro-3-((2-(pyridin-3-yl)acetamido)methyl)-1H-inden-1-ylidene)methyl)-2,6-dimethoxyphenyl morpholine-4-carboxylate (2126);

(Z)-4-((5-fluoro-3-((2-(furan-2-yl)acetamido)methyl)-2-methyl-1H-inden-1-ylidene)methyl)-2,6-dimethoxyphenyl 4-methylpiperazine-1-carboxylate (2127);

(Z)-4-((3-((2-(1H-imidazol-5-yl)acetamido)methyl)-5-fluoro-2-methyl-1H-inden-1-ylidene)methyl)-2,6-dimethoxyphenyl morpholine-4-carboxylate (2128);

(Z)-4-((5-fluoro-2-methyl-3-((2-(thiazol-5-yl)acetamido)methyl)-1H-inden-1-ylidene)methyl)-2,6-dimethoxyphenyl morpholine-4-carboxylate (2129);

(Z)-4-((5-fluoro-2-methyl-3-((2-(pyridin-2-yl)acetamido)methyl)-1H-inden-1-ylidene)methyl)-2,6-dimethoxyphenyl ethylcarbamate (2130);

(Z)-(4-((5-fluoro-2-methyl-3-((2-(pyridin-3-yl)acetamido)methyl)-1H-inden-1-ylidene)methyl)-2,6-dimethoxyphenyl)boronic acid (2131);

(Z)-(4-((5-fluoro-3-((2-(furan-2-yl)acetamido)methyl)-2-methyl-1H-inden-1-ylidene)methyl)-2,6-dimethoxyphenyl)boronic acid (2132);

(Z)-(4-((5-fluoro-2-methyl-3-((2-(1-methyl-1H-pyrrol-2-yl)acetamido)methyl)-1H-inden-1-ylidene)methyl)-2,6-dimethoxyphenyl)boronic acid (2133);

(Z)-(4-((5-fluoro-3-((furan-2-carboxamido)methyl)-2-methyl-1H-inden-1-ylidene)methyl)-2,6-dimethoxyphenyl)boronic acid (2134);

(Z)-4-((5-fluoro-2-methyl-3-((2-(pyridin-2-yl)acetamido)methyl)-1H-inden-1-ylidene)methyl)-2,6-dimethoxyphenyl [1,4'-bipiperidine]-1'-carboxylate (2135);

(Z)-4-((5-fluoro-2-methyl-3-((2-(oxazol-5-yl)acetamido)methyl)-1H-inden-1-ylidene)methyl)-2,6-dimethoxyphenyl [1,4'-bipiperidine]-1'-carboxylate (2136);

(Z)-4-((5-fluoro-2-methyl-3-((2-(oxazol-4-yl)acetamido)methyl)-1H-inden-1-ylidene)methyl)-2,6-dimethoxyphenyl [1,4'-bipiperidine]-1'-carboxylate (2137);

(Z)-4-((5-fluoro-2-methyl-3-((2-phenylacetamido)methyl)-1H-inden-1-ylidene)methyl)-2,6-dimethoxyphenyl [1,4'-bipiperidine]-1'-carboxylate (2138);

(Z)-4-((5-fluoro-2-methyl-3-((2-(pyridin-3-yl)acetamido)methyl)-1H-inden-1-ylidene)methyl)-2,6-dimethoxyphenyl [1,4'-bipiperidine]-1'-carboxylate (2139);

(Z)-4-((5-fluoro-3-((2-(isoxazol-5-yl)acetamido)methyl)-2-methyl-1H-inden-1-ylidene)methyl)-2,6-dimethoxyphenyl [1,4'-bipiperidine]-1'-carboxylate (2140);

(Z)-4-((5-fluoro-3-((2-(furan-2-yl)acetamido)methyl)-2-methyl-1H-inden-1-ylidene)methyl)-2,6-dimethoxyphenyl [1,4'-bipiperidine]-1'-carboxylate (2141);

(Z)-4-((5-fluoro-2-methyl-3-((2-(1-methyl-1H-pyrrol-2-yl)acetamido)methyl)-1H-inden-1-ylidene)methyl)-2,6-dimethoxyphenyl [1,4'-bipiperidine]-1'-carboxylate (2142);

(E)-N-((5-fluoro-1-(4-hydroxy-3,5-dimethoxybenzylidene)-1H-inden-2-yl)methyl)-2-(furan-2-yl)acetamide (2143);

(Z)-2-(5-fluoro-1-(4-hydroxy-3,5-dimethoxybenzylidene)-1H-inden-2-yl)-N-(furan-2-ylmethyl)acetamide (2144);

(E)-N-(5-fluoro-1-(4-hydroxy-3,5-dimethoxybenzylidene)-1H-inden-2-yl)-2-(furan-2-yl)acetamide (2145);

(E)-5-fluoro-N-(furan-2-ylmethyl)-1-(4-hydroxy-3,5-dimethoxybenzylidene)-1H-indene-2-carboxamide (2146);

(E)-N-((5-fluoro-1-(4-hydroxy-3,5-dimethoxybenzylidene)-1H-inden-2-yl)methyl)-2-(1-methyl-1H-pyrrol-2-yl)acetamide (2147);

(E)-N-((5-fluoro-1-(4-hydroxy-3,5-dimethoxybenzylidene)-1H-inden-2-yl)methyl)-2-phenylacetamide (2149);

(E)-N-((5-fluoro-1-(4-hydroxy-3,5-dimethoxybenzylidene)-1H-inden-2-yl)methyl)-2-(pyridin-2-yl)acetamide (2151);

(E)-N-((5-fluoro-1-(4-hydroxy-3,5-dimethoxybenzylidene)-1H-inden-2-yl)methyl)-2-(isoxazol-5-yl)acetamide (2153);

(Z)-2-(5-fluoro-1-(4-hydroxy-3,5-dimethoxybenzylidene)-1H-inden-2-yl)-N-(oxazol-5-ylmethyl)acetamide (2154);

(Z)-2-(1-(4-hydroxy-3,5-dimethoxybenzylidene)-2-methyl-5-(trifluoromethoxy)-1H-inden-3-yl)-N-(oxazol-2-ylmethyl)acetamide (2155);

(Z)-2-(1-(4-hydroxy-3,5-dimethoxybenzylidene)-2-methyl-5-(trifluoromethoxy)-1H-inden-3-yl)-N-(oxazol-5-ylmethyl)acetamide (2156);

(Z)-2-(1-(4-hydroxy-3,5-dimethoxybenzylidene)-2-methyl-5-(trifluoromethoxy)-1H-inden-3-yl)-N-(oxazol-4-ylmethyl)acetamide (2157);

(Z)-2-(1-(4-hydroxy-3,5-dimethoxybenzylidene)-2-methyl-5-(trifluoromethoxy)-1H-inden-3-yl)-N-(thiazol-2-ylmethyl)acetamide (2158);

(Z)-2-(1-(4-hydroxy-3,5-dimethoxybenzylidene)-2-methyl-5-(trifluoromethoxy)-1H-inden-3-yl)-N-(thiazol-5-ylmethyl)acetamide (2159);

(Z)-2-(1-(4-hydroxy-3,5-dimethoxybenzylidene)-2-methyl-5-(trifluoromethoxy)-1H-inden-3-yl)-N-(thiazol-4-ylmethyl)acetamide (2160);

(Z)-2-(5-fluoro-1-(4-hydroxy-3-methoxy-5-(trifluoromethoxy)benzylidene)-2-methyl-1H-inden-3-yl)-N-(oxazol-5-ylmethyl)acetamide (2161);

(Z)-2-(5-fluoro-1-(4-hydroxy-3-(trifluoromethoxy)benzylidene)-2-methyl-1H-inden-3-yl)-N-(oxazol-4-ylmethyl)acetamide (2162);

(Z)-2-(5-fluoro-1-(4-hydroxy-3,5-bis(trifluoromethoxy)benzylidene)-2-methyl-1H-inden-3-yl)-N-(oxazol-2-ylmethyl)acetamide (2163);

(Z)-2-(5-fluoro-1-(4-hydroxy-3,5-bis(trifluoromethoxy)benzylidene)-2-methyl-1H-inden-3-yl)-N-(thiazol-2-ylmethyl)acetamide (2164);

(Z)-2-(5-fluoro-1-(4-hydroxy-3-methoxy-5-(trifluoromethoxy)benzylidene)-2-methyl-1H-inden-3-yl)-N-(thiazol-5-ylmethyl)acetamide (2165);

(Z)-2-(5-fluoro-1-(4-hydroxy-3-(trifluoromethoxy)benzylidene)-2-methyl-1H-inden-3-yl)-N-(thiazol-4-ylmethyl)acetamide (2166);

(Z)—N-((1,3-dioxolan-2-yl)methyl)-2-(5-fluoro-1-(4-hydroxy-3,5-bis(trifluoromethoxy)benzylidene)-2-methyl-1H-inden-3-yl)acetamide (2167);

(Z)—N-((1,3-dioxolan-2-yl)methyl)-2-(5-fluoro-1-(4-hydroxy-3-(trifluoromethoxy)benzylidene)-2-methyl-1H-inden-3-yl)acetamide (2168);

(Z)-2-(1,3-dioxolan-2-yl)-N-((5-fluoro-1-(4-hydroxy-3,5-dimethoxybenzylidene)-2-methyl-1H-inden-3-yl)methyl)acetamide (2174);

(Z)—N-((5-fluoro-1-(4-hydroxy-3,5-dimethoxybenzylidene)-2-methyl-1H-inden-3-yl)methyl)-2-(2-methyl-1,3-dioxolan-4-yl)acetamide (2175);

(Z)—N-((5-fluoro-1-(4-hydroxy-3,5-dimethoxybenzylidene)-2-methyl-1H-inden-3-yl)methyl)-2-(thiazol-2-yl)acetamide (2176);

(Z)—N-((5-fluoro-1-(4-hydroxy-3,5-dimethoxybenzylidene)-2-methyl-1H-inden-3-yl)methyl)-2-(1,3-oxathiolan-2-yl)acetamide (2179);

(Z)—N-((1,3-dioxolan-2-yl)methyl)-2-(1-(4-hydroxy-3,5-dimethoxybenzylidene)-2-methyl-5-(trifluoromethoxy)-1H-inden-3-yl)acetamide (2181);

(Z)-(4-((3-(2-(((1,3-dioxolan-2-yl)methyl)amino)-2-oxoethyl)-5-fluoro-2-methyl-1H-inden-1-ylidene)methyl)-2,6-dimethoxyphenyl)boronic acid (2182);

(Z)—N-((5-fluoro-1-(4-hydroxy-3,5-dimethoxybenzylidene)-2-methyl-1H-inden-3-yl)methyl)-1H-pyrazole-4-carboxamide (2183);

2-(5-fluoro-1-(fluoro(4-hydroxy-3,5-dimethoxyphenyl)methyl)-2-methyl-1H-inden-3-yl)-N-(furan-2-ylmethyl)acetamide (2184);

N-benzyl-2-(5-fluoro-1-(fluoro(4-hydroxy-3,5-dimethoxyphenyl)methyl)-2-methyl-1H-inden-3-yl)acetamide (2185);

N-(furan-2-ylmethyl)-2-(2,3,6-trifluoro-3-(1-(4-hydroxy-3,5-dimethoxyphenyl)ethyl)-2-methyl-2,3-dihydro-1H-inden-1-yl)acetamide (2186);

N-benzyl-2-(2,3,6-trifluoro-3-(1-(4-hydroxy-3,5-dimethoxyphenyl)ethyl)-2-methyl-2,3-dihydro-1H-inden-1-yl)acetamide (2187);

2-(1,5-difluoro-1-(4-hydroxy-3,5-dimethoxybenzyl)-2-methyl-1H-inden-3-yl)-N-(furan-2-ylmethyl)acetamide (2188);

N-benzyl-2-(1,5-difluoro-1-(4-hydroxy-3,5-dimethoxybenzyl)-2-methyl-1H-inden-3-yl)acetamide (2189);

2-(1-(difluoro(4-hydroxy-3,5-dimethoxyphenyl)methyl)-5-fluoro-2-methyl-1H-inden-3-yl)-N-(furan-2-ylmethyl)acetamide (2190);
N-benzyl-2-(1-(difluoro(4-hydroxy-3,5-dimethoxyphenyl)methyl)-5-fluoro-2-methyl-1H-inden-3-yl)acetamide (2191);
2-(1,5-difluoro-1-(fluoro(4-hydroxy-3,5-dimethoxyphenyl)methyl)-2-methyl-1H-inden-3-yl)-N-(furan-2-ylmethyl)acetamide (2192);
N-benzyl-2-(1,5-difluoro-1-(fluoro(4-hydroxy-3,5-dimethoxyphenyl)methyl)-2-methyl-1H-inden-3-yl)acetamide (2193);
2-(2,5'-difluoro-2-(4-hydroxy-3,5-dimethoxyphenyl)-2'-methylspiro[cyclopropane-1,1'-inden]-3'-yl)-N-(furan-2-ylmethyl)acetamide (2194);
N-benzyl-2-(2,5'-difluoro-2-(4-hydroxy-3,5-dimethoxyphenyl)-2'-methylspiro[cyclopropane-1,1'-inden]-3'-yl)acetamide (2195);
N-(furan-2-ylmethyl)-2-(1,2,3,6-tetrafluoro-3-(fluoro(4-hydroxy-3,5-dimethoxyphenyl)methyl)-2-methyl-2,3-dihydro-1H-inden-1-yl)acetamide (2196);
N-benzyl-2-(1,2,3,6-tetrafluoro-3-(fluoro(4-hydroxy-3,5-dimethoxyphenyl)methyl)-2-methyl-2,3-dihydro-1H-inden-1-yl)acetamide (2197);
2-(5-fluoro-1-(1-(4-hydroxy-3,5-dimethoxyphenyl)cyclopropyl)-2-methyl-1H-inden-3-yl)-N-(furan-2-ylmethyl)acetamide (2198);
N-benzyl-2-(5-fluoro-1-(1-(4-hydroxy-3,5-dimethoxyphenyl)cyclopropyl)-2-methyl-1H-inden-3-yl)acetamide (2199);
(Z)-2-(1-(3,5-dimethoxy-4-(4,4,5,5-tetramethyl-1,3,2-dioxaborolan-2-yl)benzylidene)-5-fluoro-2-methyl-1H-inden-3-yl)-N-(pyridin-3-ylmethyl)acetamide (2200)

(Z)- or (E)-isomer thereof, epimer, diastereomer or rotamer thereof, pharmaceutically acceptable salt or prodrug thereof.

In a preferred embodiment of the preceeding embodiment, the compound is selected from compounds numbered above as 1732, 1733, 1734, 1735, 1736, 1737, 1738, 1739, 1740, 1741, 2066, 2067, 2068, 2069, 2070, 2071, 2072, 2182, 2200, 1765, 1767, 1768, 1769, 1771, 1772, 1773, 1774, 1776, 1777, 1779, 1780, 1782, 1783, 1784, 1785, 1787, 1789, 1790, 1791, 1792, 1793, 1794, 1796, 1797, 1798, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 2184, 2185, 2186, 2187, 2188, 2189, 2190, 2191, 2192, 2193, 2194, 2195, 2196, 2197, 2198, 2199, 2085, 2086, 2087, 2088, 2089, 2090, 2092, 2093, 2094, 2095, 2096, 2097, 2098, 2100, 2101, 2102, 2103, 2104, 2105, 2106, 2107, 2108, 2109, 2110, 2111, 2112, 2113, 2114, 2115, 2116, 2117, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2149, 2151, 2153, 2174, 2175, 2176, 2179, 2183, 2155, 2156, 2157, 2158, 2159, 2160, 2161, 2162, 2163, 2164, 2165, 2166, 2167, 2168 and 2181.

In a more preferred embodiment of the above embodiment, the compound is selected from compounds numbered as 1732, 1733, 1734, 1735, 1736, 1737, 1738, 1739, 1740, 1741, 2066, 2067, 2068, 2069, 2070, 2071, 2072, 2182, 2200, 1765, 1767, 1768, 1769, 1771, 1772, 1773, 1774, 1776, 1777, 1779, 1780, 1782, 1783, 1784, 1785, 1787, 1789, 1790, 1791, 1792, 1793, 1794, 1796, 1797, 1798, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 2184, 2185, 2186, 2187, 2188, 2189, 2190, 2191, 2192, 2193, 2194, 2195, 2196, 2197, 2198, 2199, 2085, 2086, 2087, 2088, 2089, 2090, 2092, 2093, 2094, 2095, 2096, 2097, 2098, 2100, 2101, 2102, 2103, 2104, 2105, 2106, 2107, 2108, 2109, 2110, 2111, 2112, 2113, 2114, 2115, 2116, 2117, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2149, 2151, 2153, 2174, 2175, 2176, 2179 and 2183.

In a more preferred embodiment of the above embodiment, the compound is selected from compounds numbered as 1765, 1767, 1768, 1769, 1771, 1772, 1773, 1774, 1776, 1777, 1779, 1780, 1782, 1783, 1784, 1785, 1787, 1789, 1790, 1791, 1792, 1793, 1794, 1796, 1797, 1798, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 2184, 2185, 2186, 2187, 2188, 2189, 2190, 2191, 2192, 2193, 2194, 2195, 2196, 2197, 2198, 2199, 2085, 2086, 2087, 2088, 2089, 2090, 2092, 2093, 2094, 2095, 2096, 2097, 2098, 2100, 2101, 2102, 2103, 2104, 2105, 2106, 2107, 2108, 2109, 2110, 2111, 2112, 2113, 2114, 2115, 2116, 2117, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2149, 2151, 2153, 2174, 2175, 2176, 2179 and 2183.

In a more preferred embodiment of the above embodiment, the compound is selected from compounds numbered as 2184, 2185, 2186, 2187, 2188, 2189, 2190, 2191, 2192, 2193, 2194, 2195, 2196, 2197, 2198, 2199, 2085, 2086, 2087, 2088, 2089, 2090, 2092, 2093, 2094, 2095, 2096, 2097, 2098, 2100, 2101, 2102, 2103, 2104, 2105, 2106, 2107, 2108, 2109, 2110, 2111, 2112, 2113, 2114, 2115, 2116, 2117, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2149, 2151, 2153, 2174, 2175, 2176, 2179 and 2183.

In a more preferred embodiment of the above embodiment, the compound is selected from compounds numbered as 2085, 2086, 2087, 2088, 2089, 2090, 2092, 2093, 2094, 2095, 2096, 2097, 2098, 2100, 2101, 2102, 2103, 2104, 2105, 2106, 2107, 2108, 2109, 2110, 2111, 2112, 2113, 2114, 2115, 2116, 2117, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2149, 2151, 2153, 2174, 2175, 2176, 2179 and 2183.

In a most preferred embodiment, the compound of the invention is of formula IIa selected from compounds numbered as 1732, 1736, 1740, 1765, 1767, 1772, 1782, 1783, 1796, 1797, 2066, 2069, 2090, 2096, 2155, 2158, 2163, 2164, 2167, 2168, 2174, 2176, 2179, 2181, 2182, 2183, 2190, 2191, 2192, 2193, 2194 and 2195.

Chemical structures of all the above-named and numbered compounds are:

1664
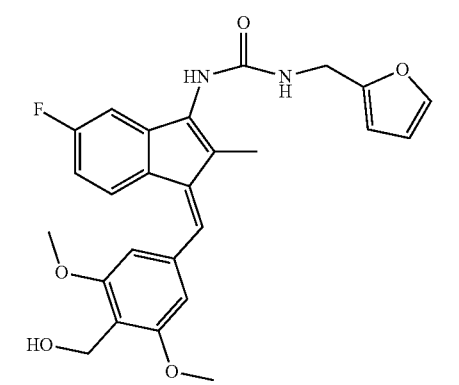
1666
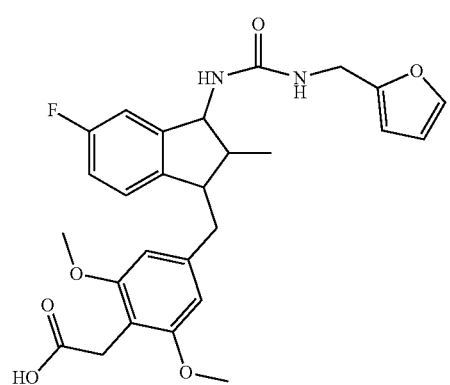
1668
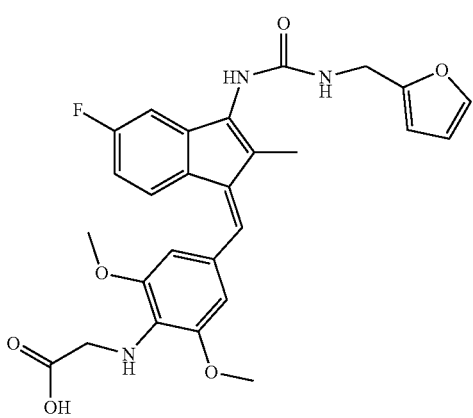
1669
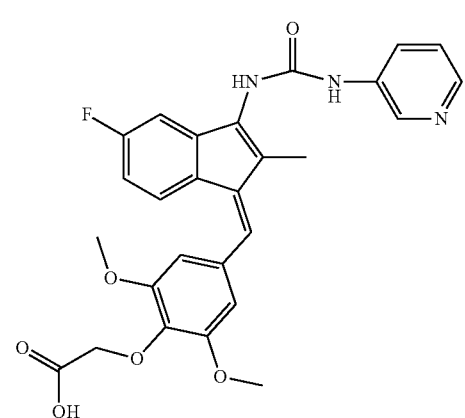
1670
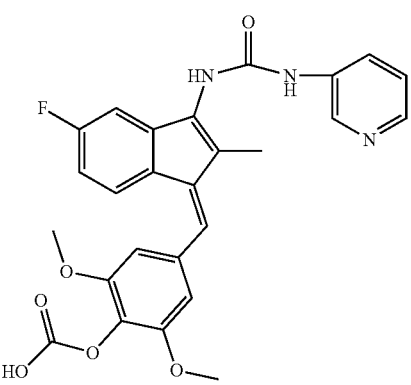
1671
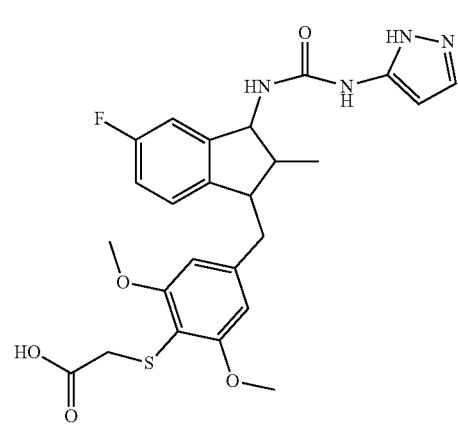
1673
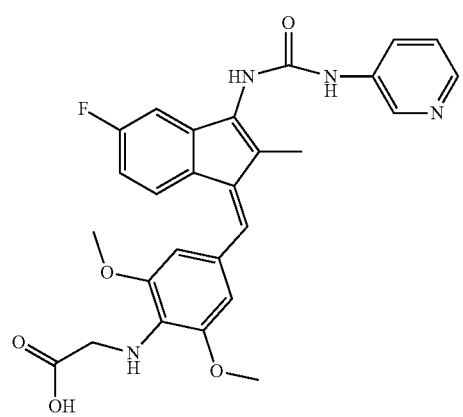
1674
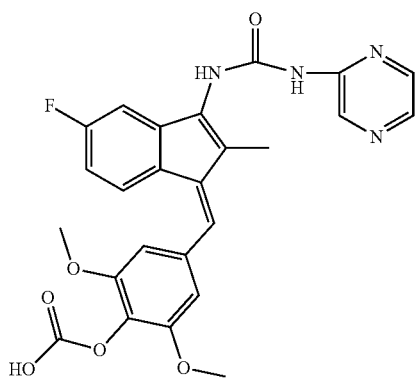

35
-continued
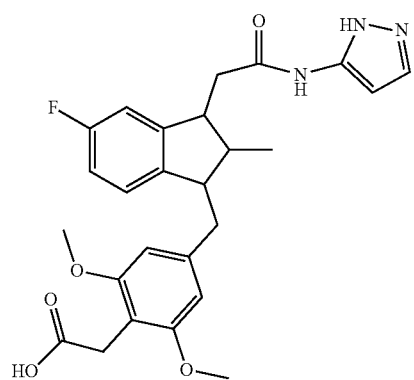
1675
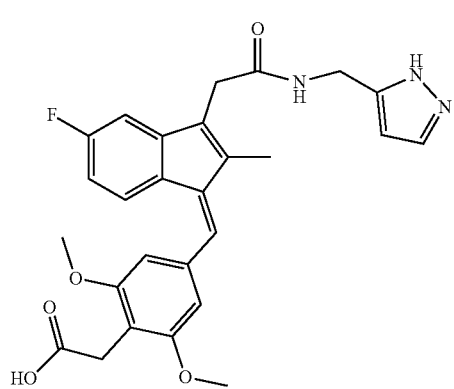
1676
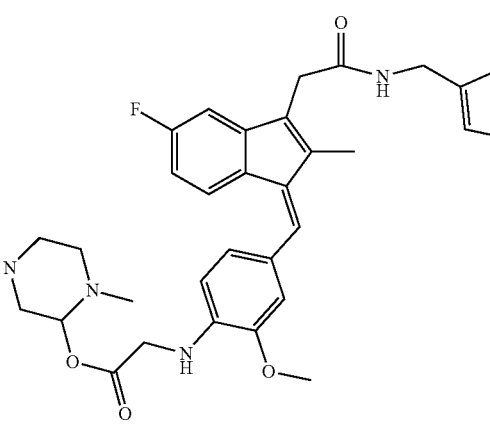
1677
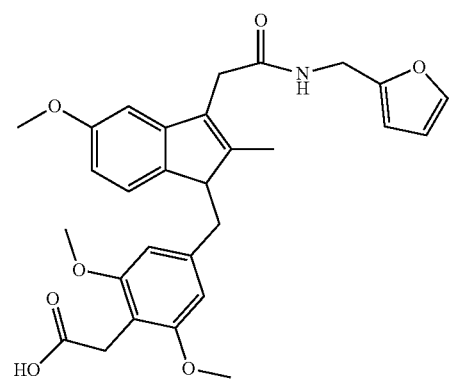
1678
36
-continued
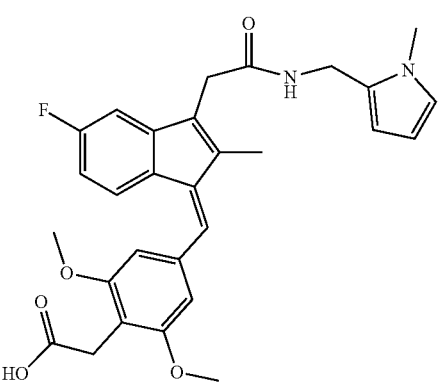
1679
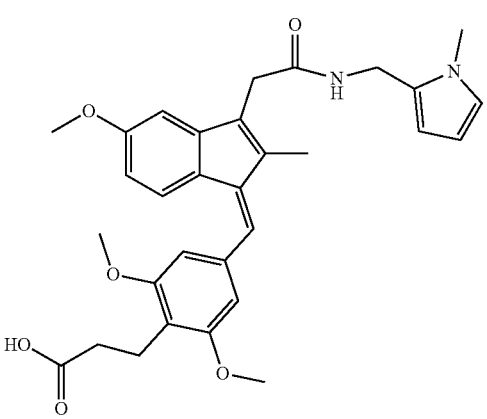
1680
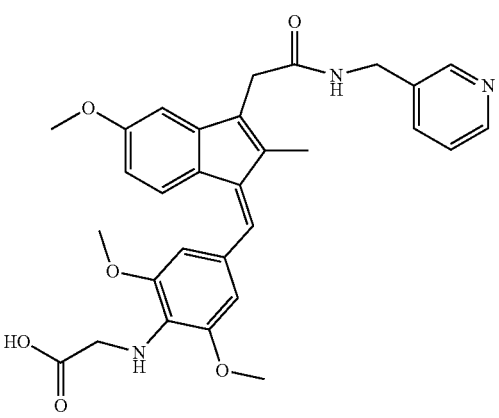
1683

37
-continued
1685
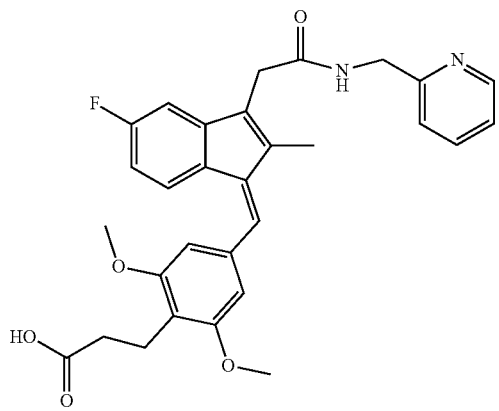
1687
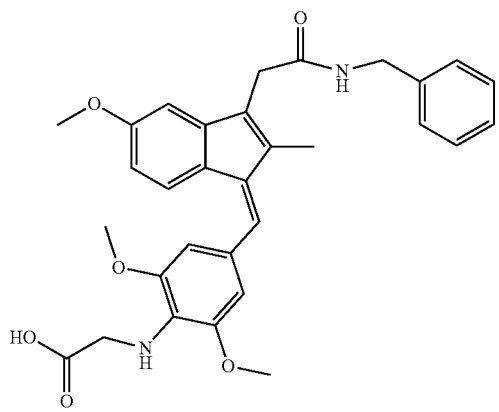
1688
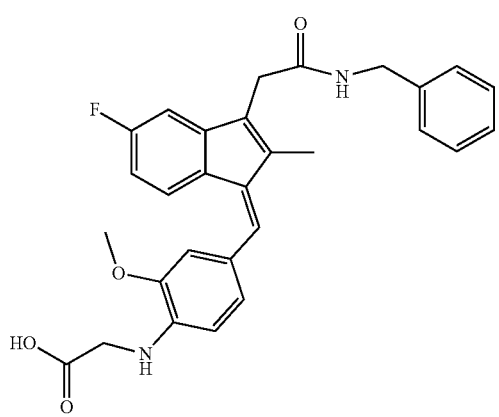
38
-continued
1689
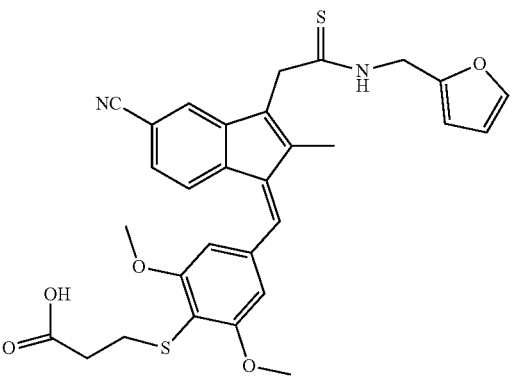

| 39 | 40 |
|---|---|
| -continued | -continued |
| 1696 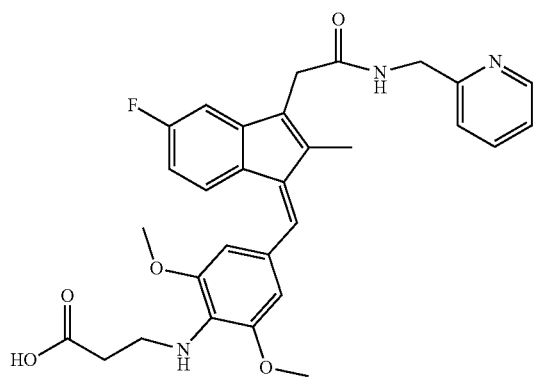 | 1732 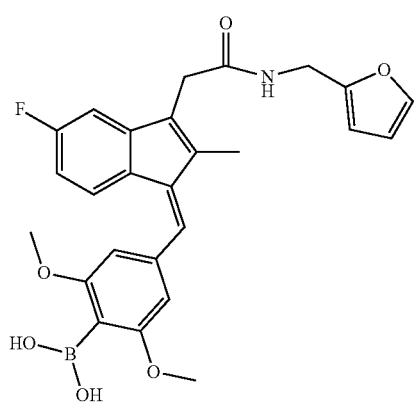 |
| 1697 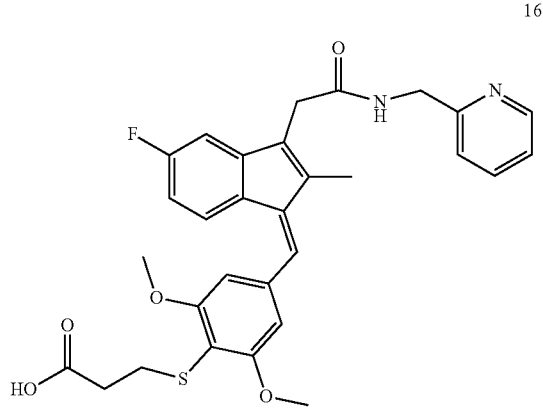 | 1733 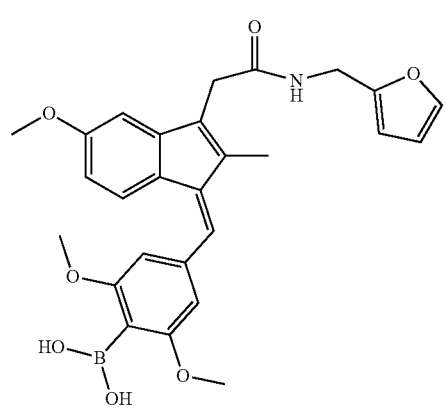 |
| 1698 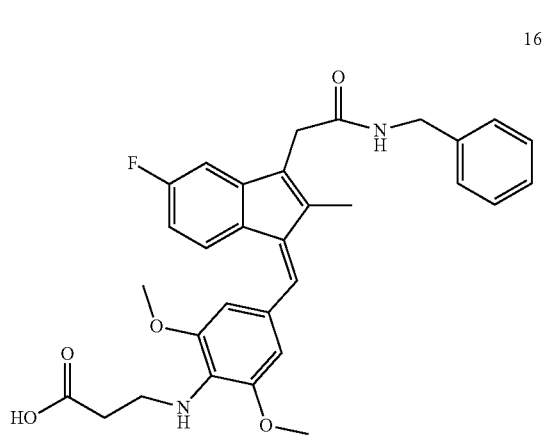 | 1734 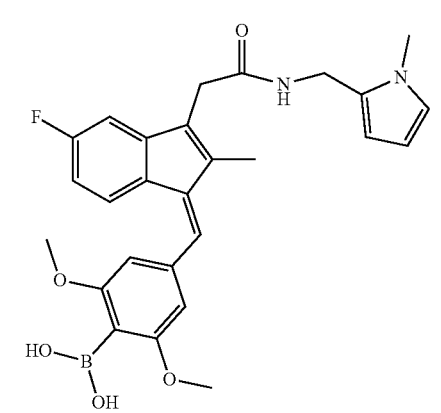 |
| 1699 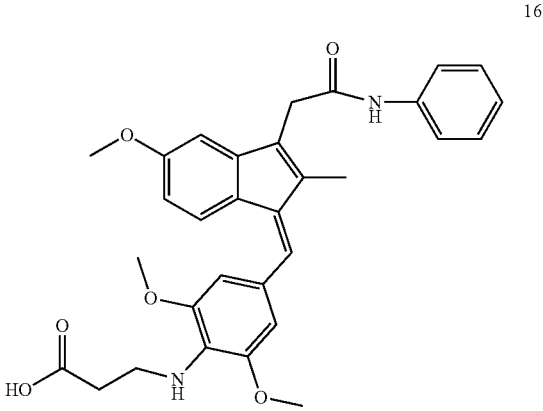 | 1735 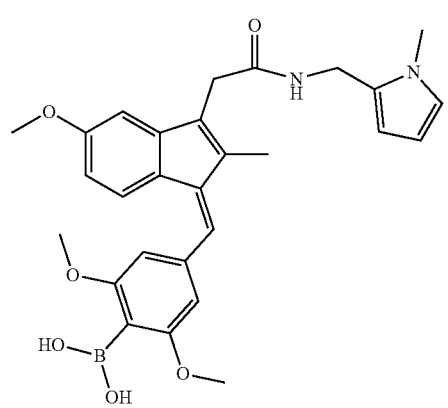 |

1736
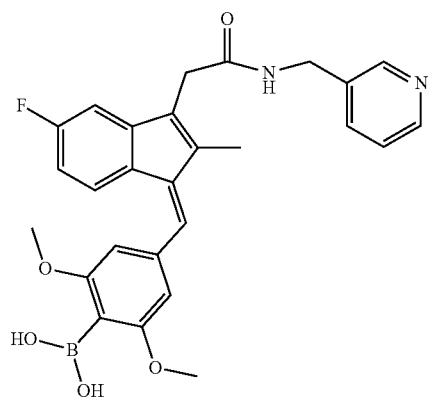
1737
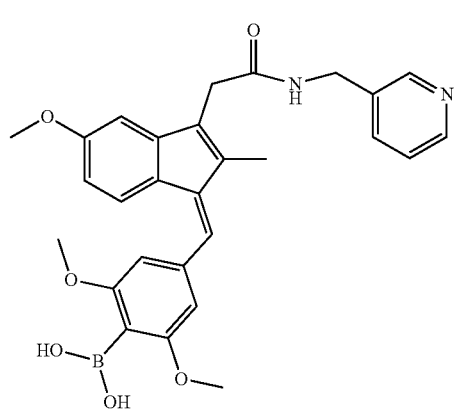
1738
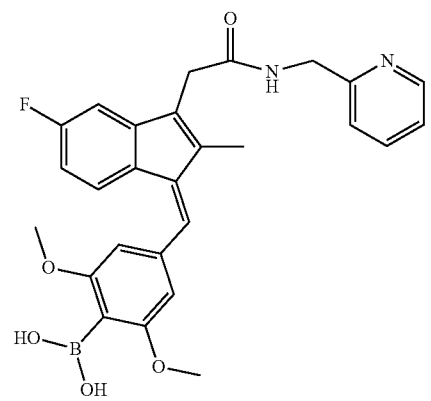
1739
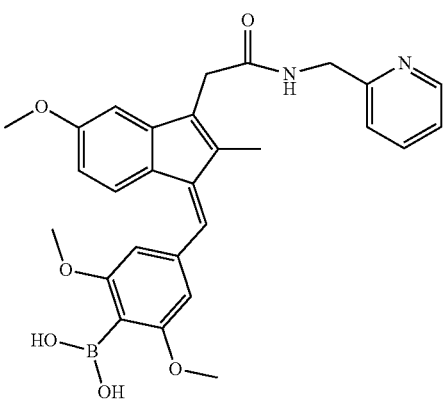
1740
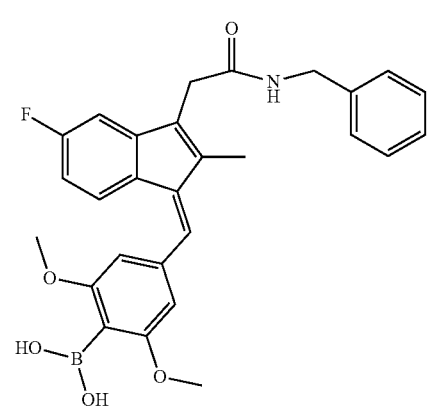
1741
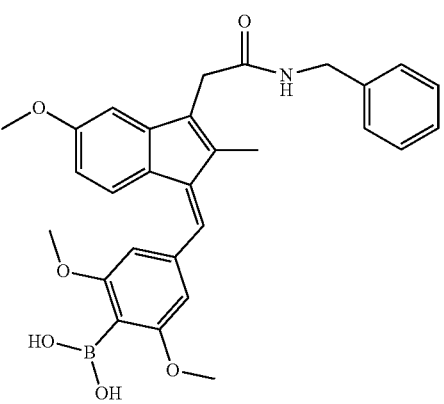
1742
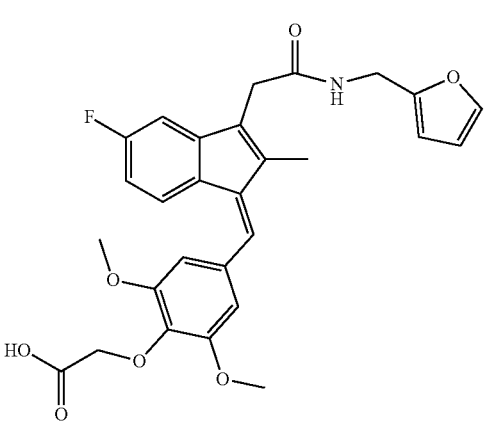

1743
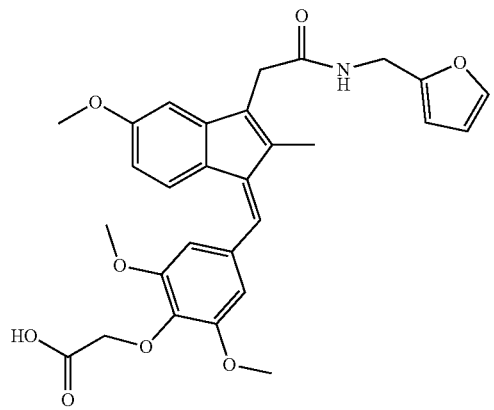
1744
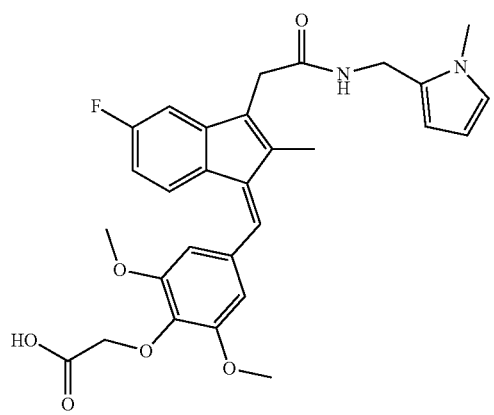
1745
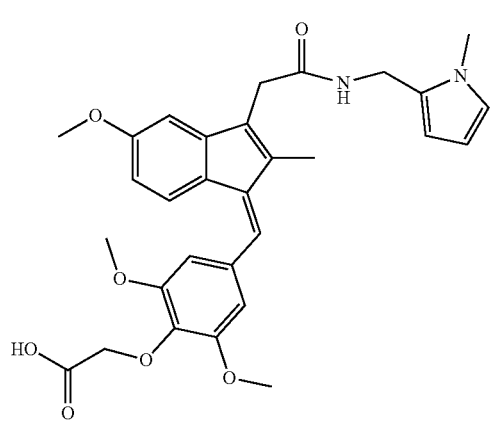
1746
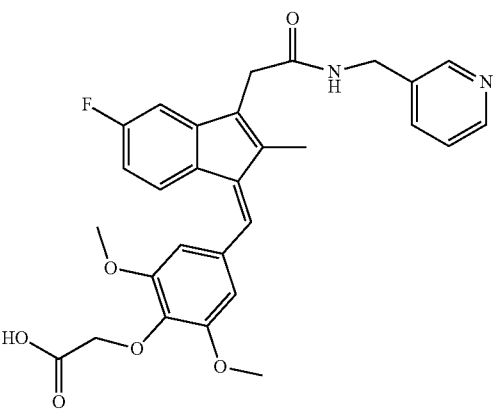
1747
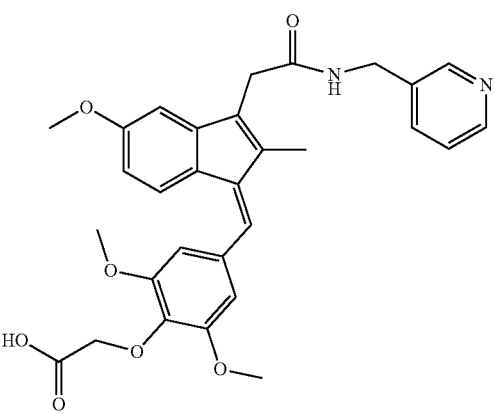
1748
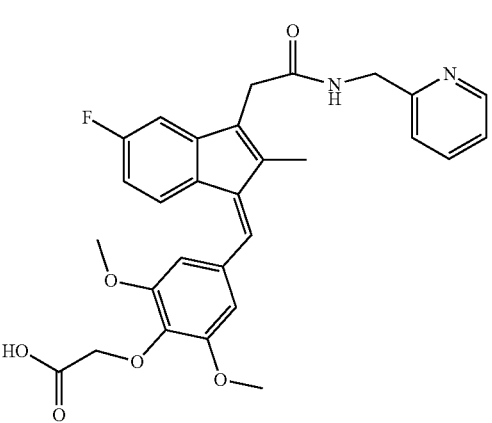

45
-continued
1749
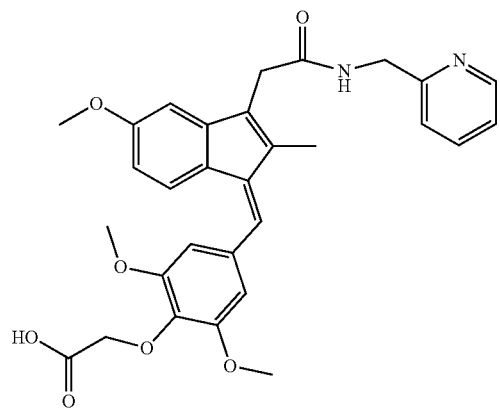
1750
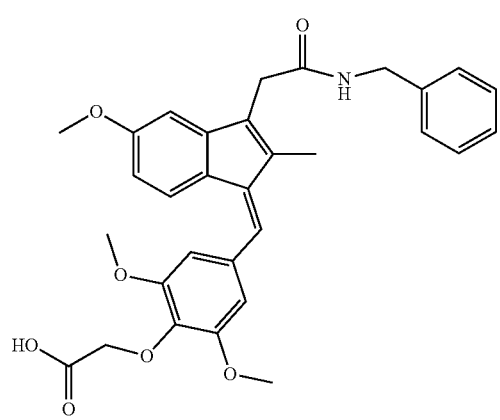
1751
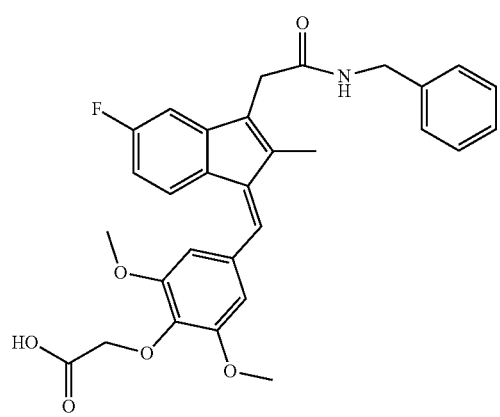
1752
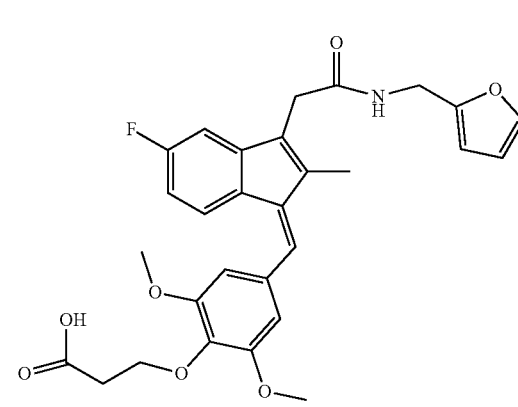
46
-continued
1754
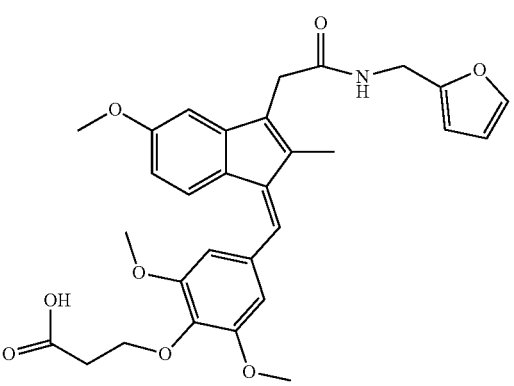
1755
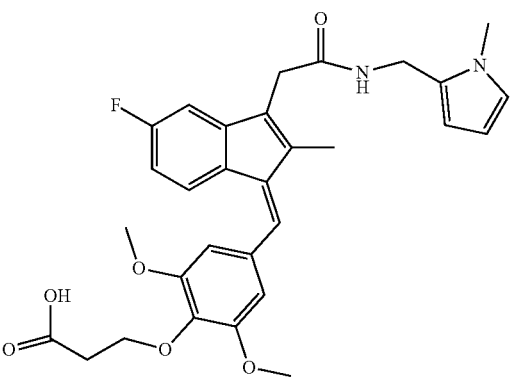
1756
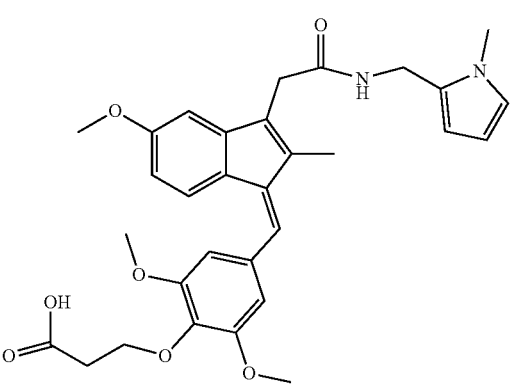
1757
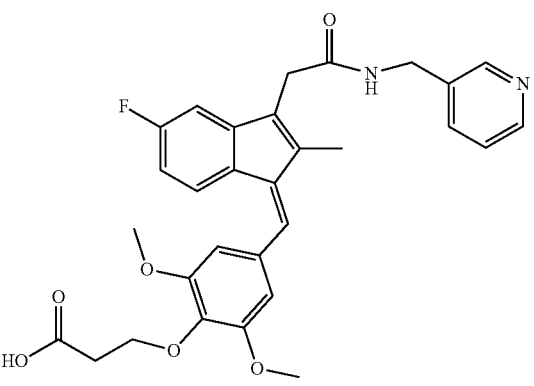

1758
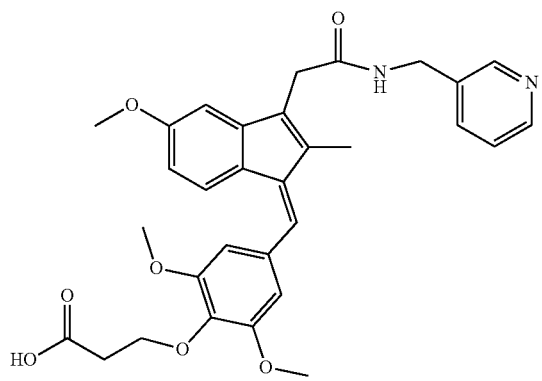
1759
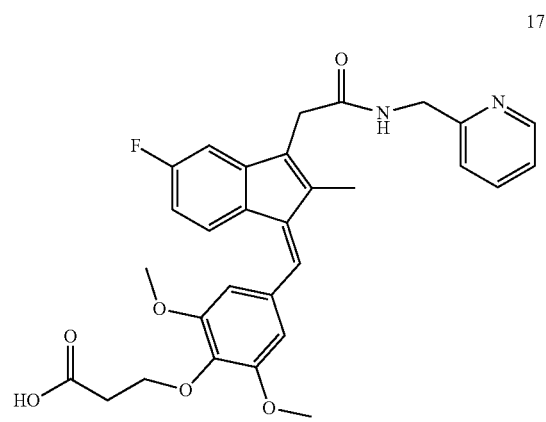
1760
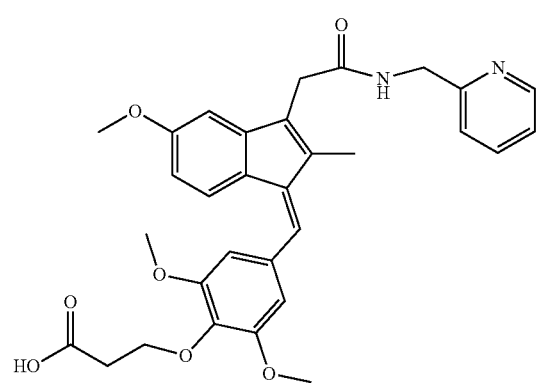
1761
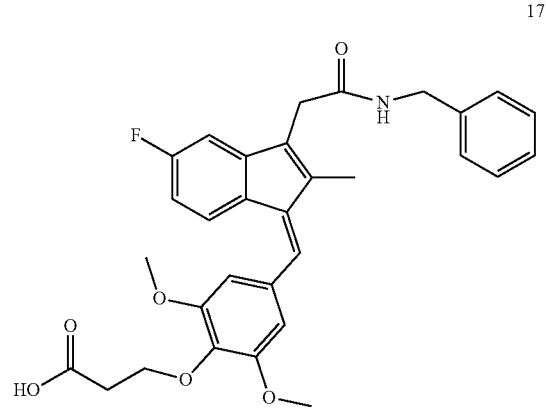
1762
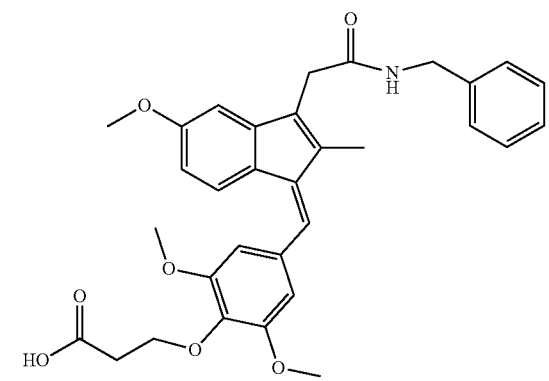
1765
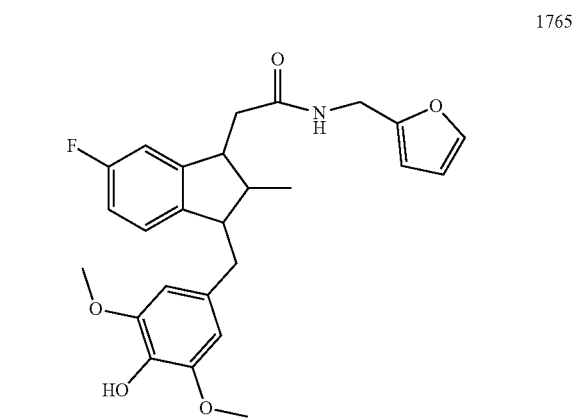
1767
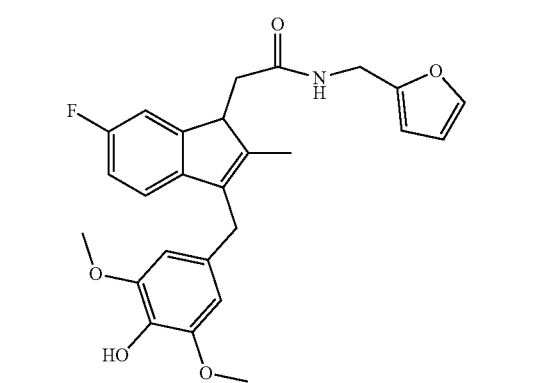
1768
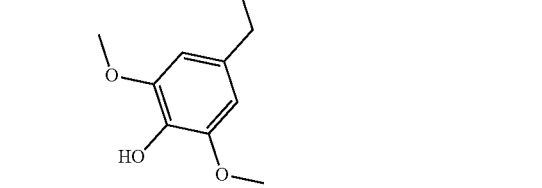

1769
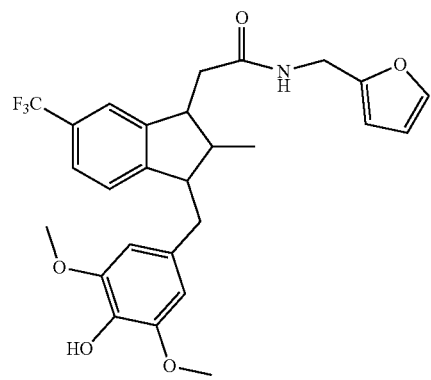
1771
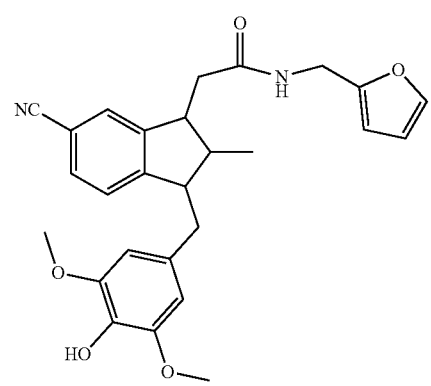
1772
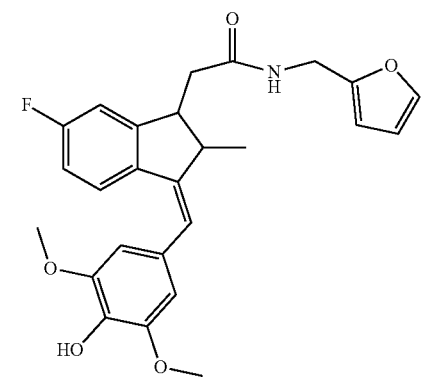
1773
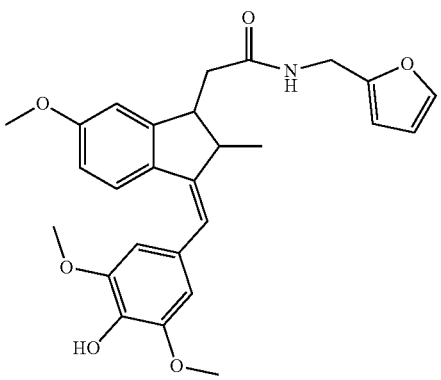
1774
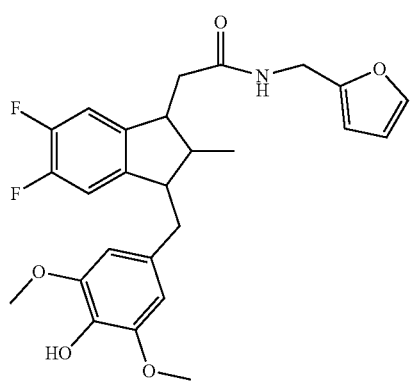
1776
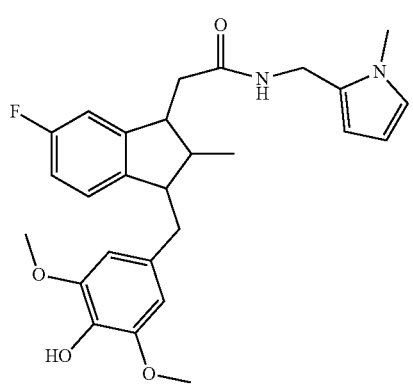
1777
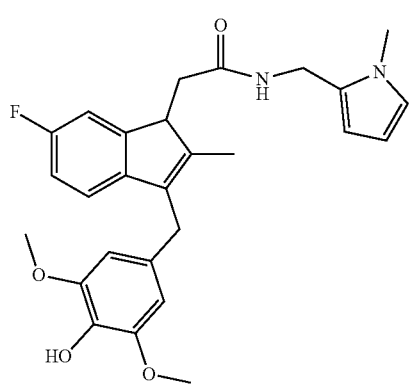
1779
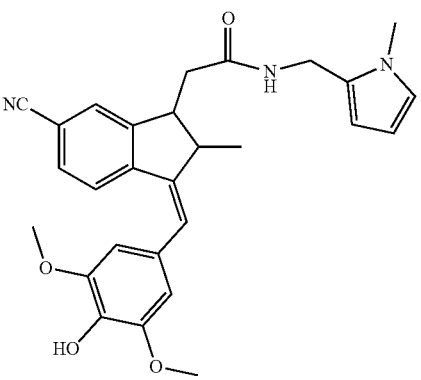

51 52
-continued -continued
1780 1785
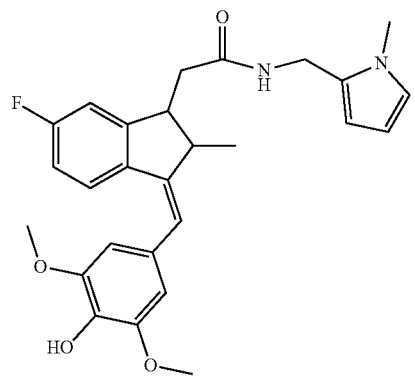 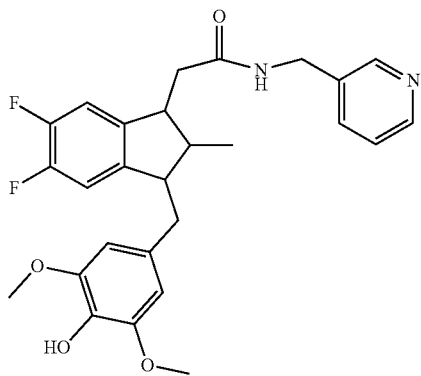
1782 1787
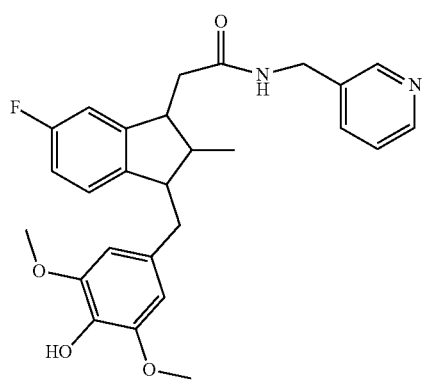 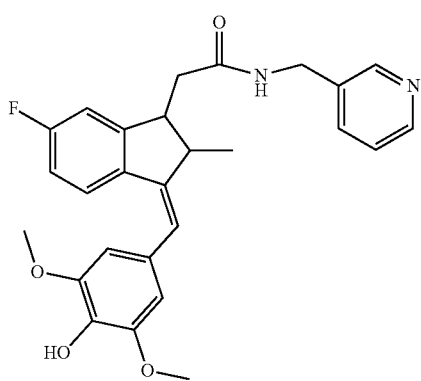
1783 1789
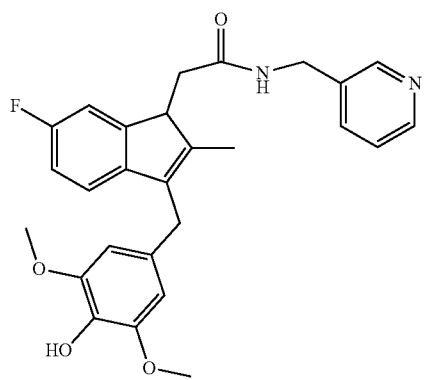 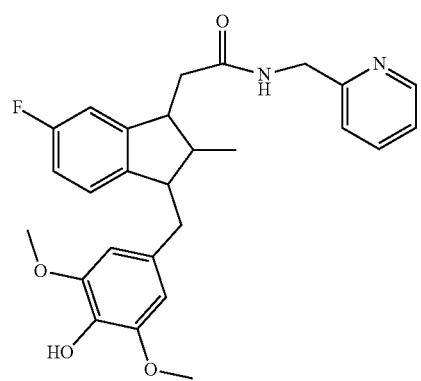
1784 1790
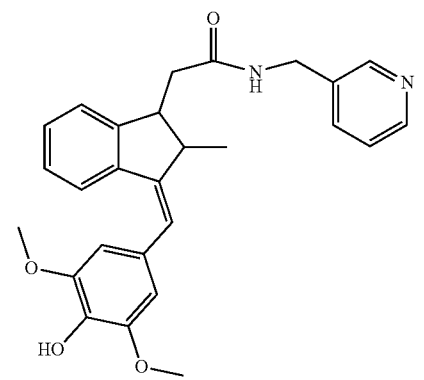 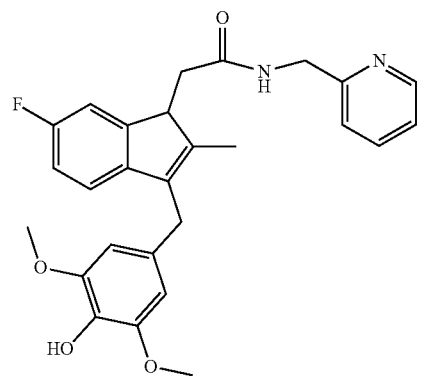

1791 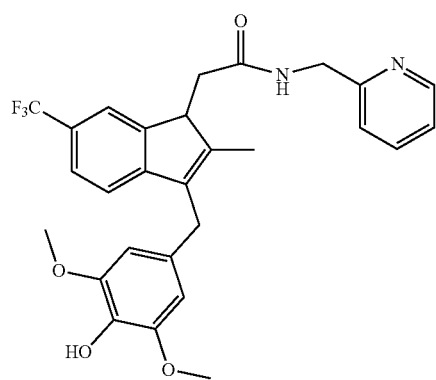
1792 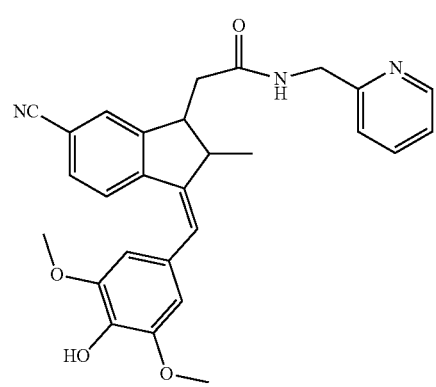
1793 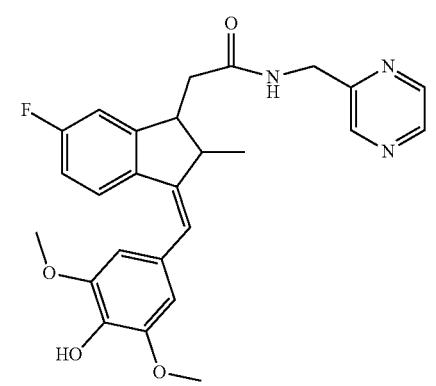
1794 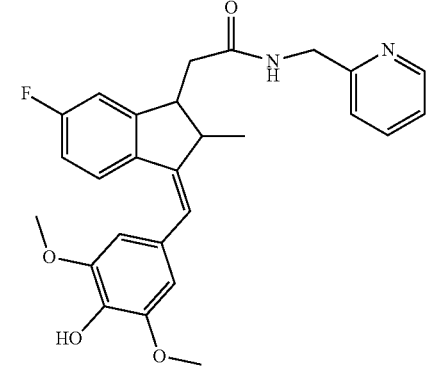
1796 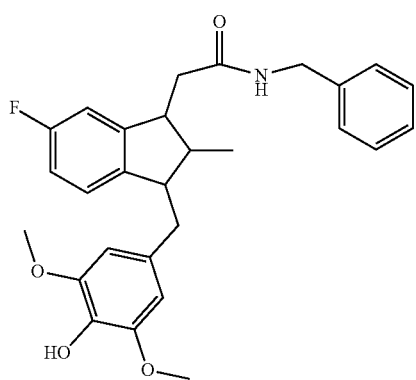
1797 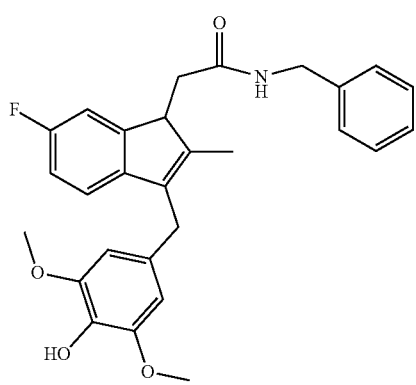
1798 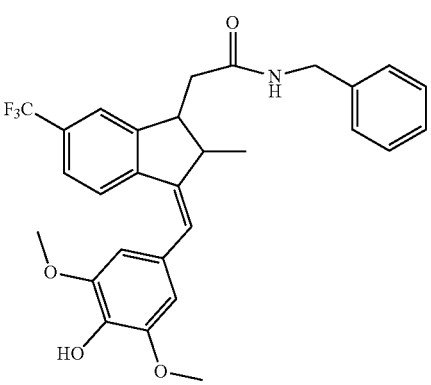
1800 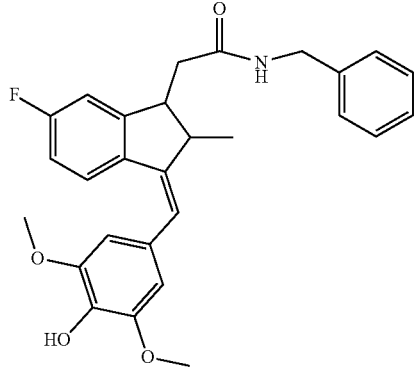

55
-continued
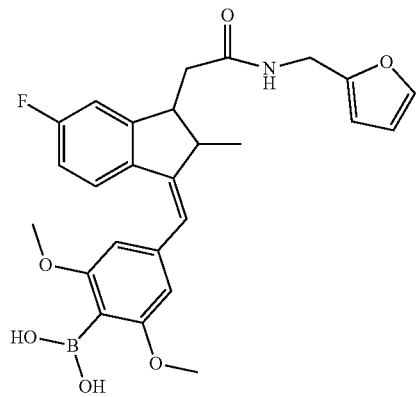
1801
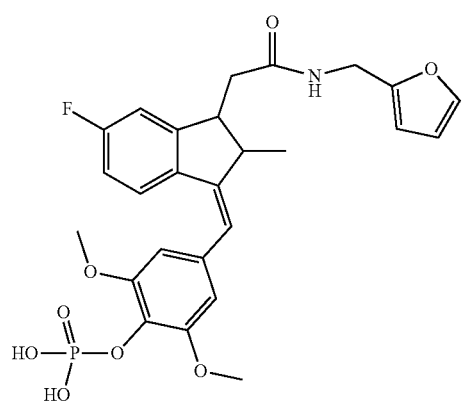
1802
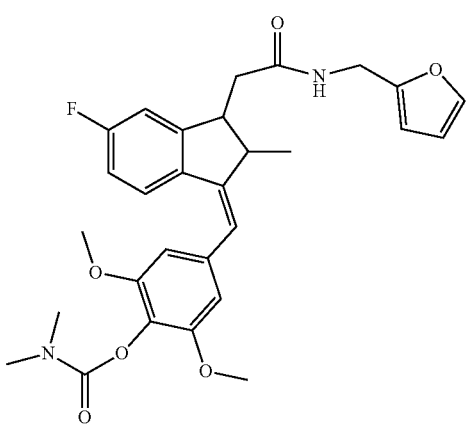
1803
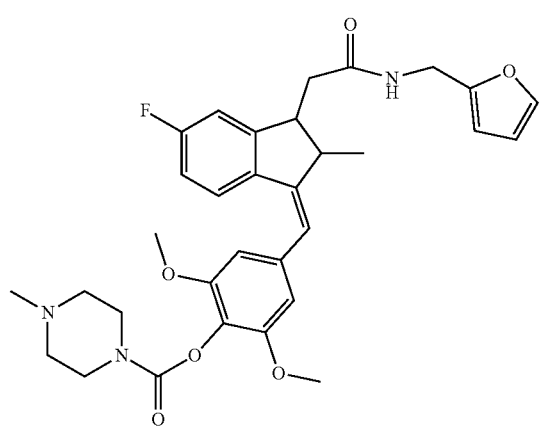
1804
56
-continued
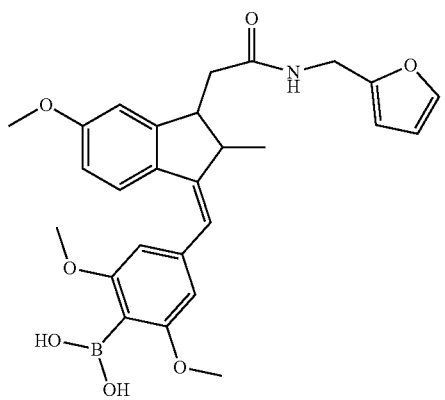
1805
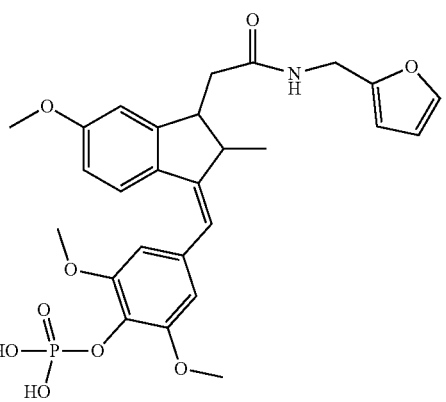
1806
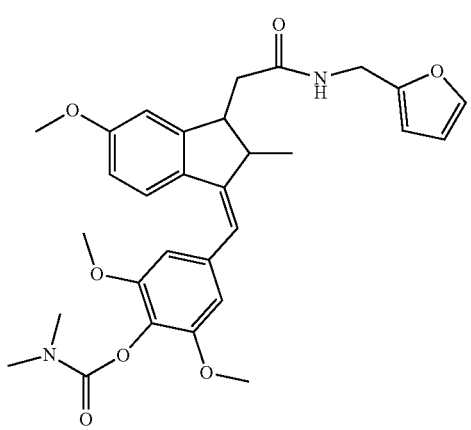
1807

-continued
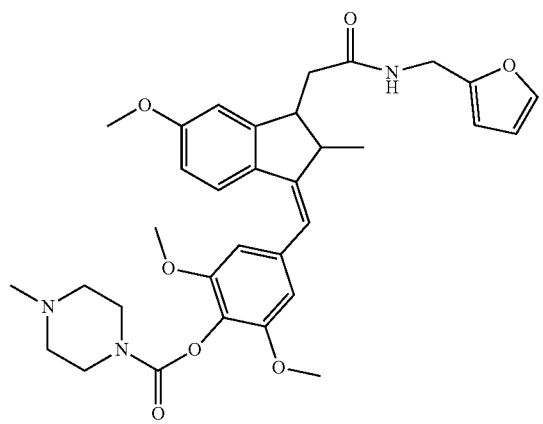
1808
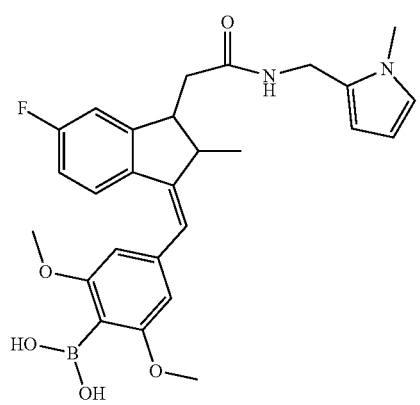
1809
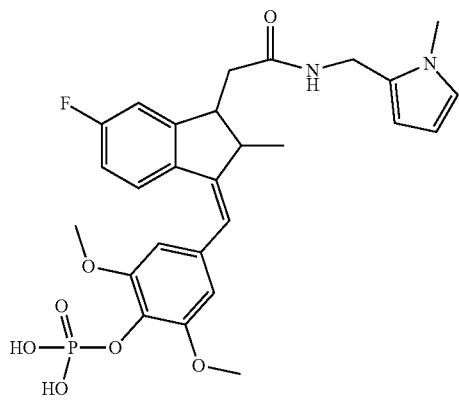
1810
-continued
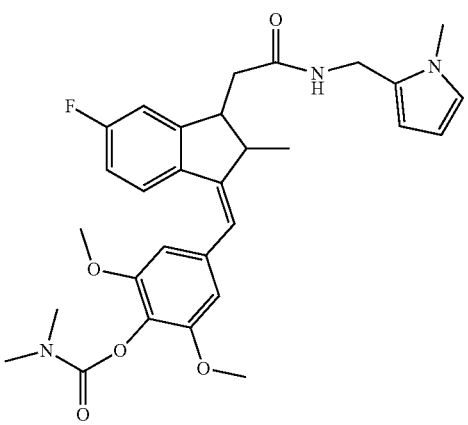
1811
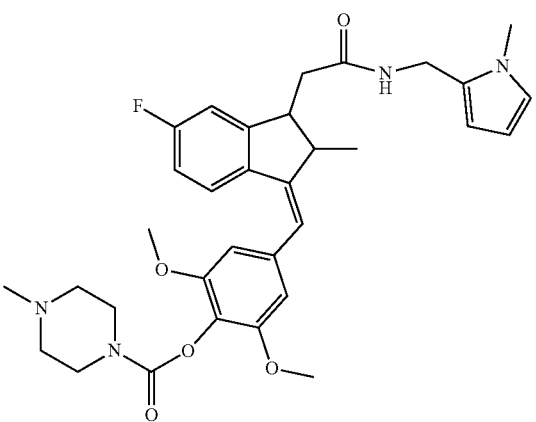
1812
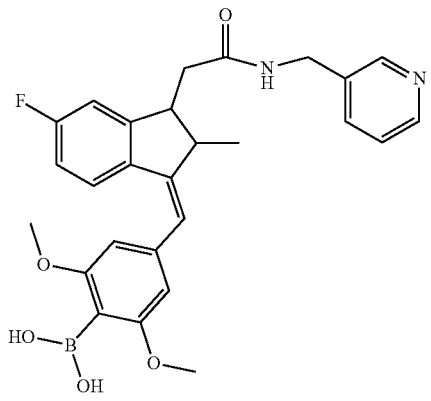
1813

1814
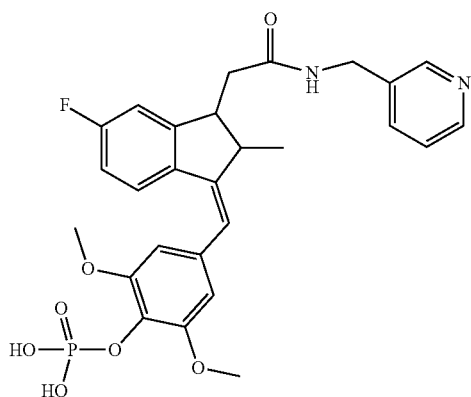
1815
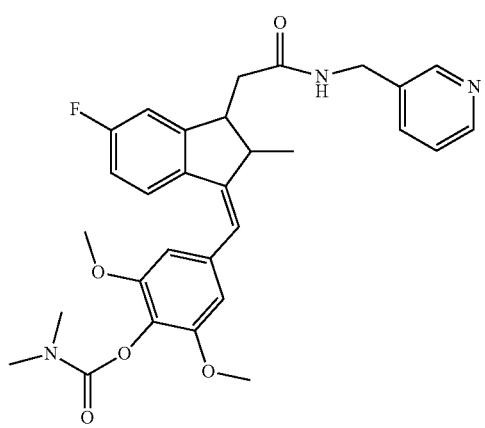
1816
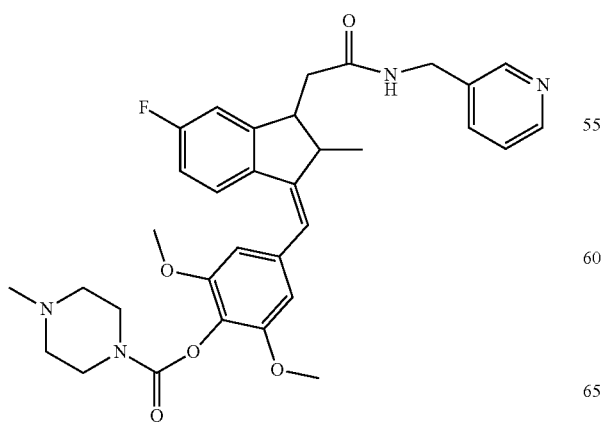
1817
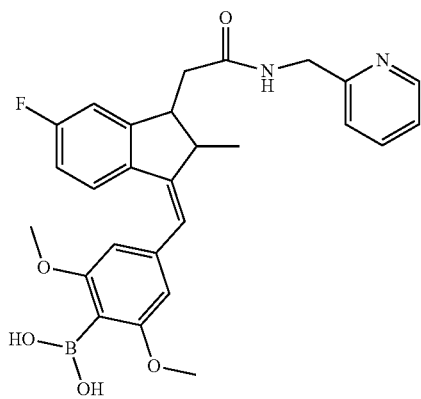
1818
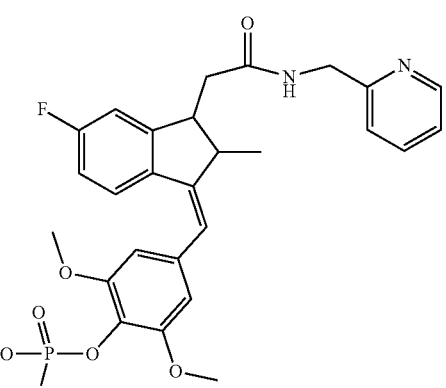
1819
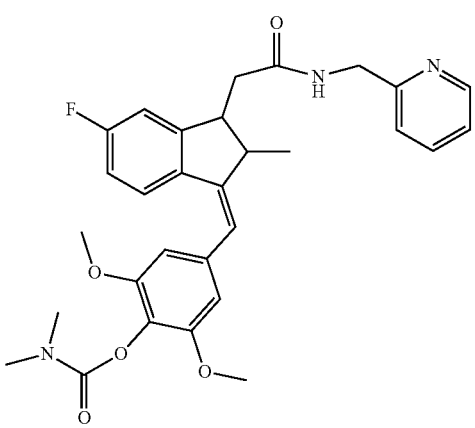

61
-continued
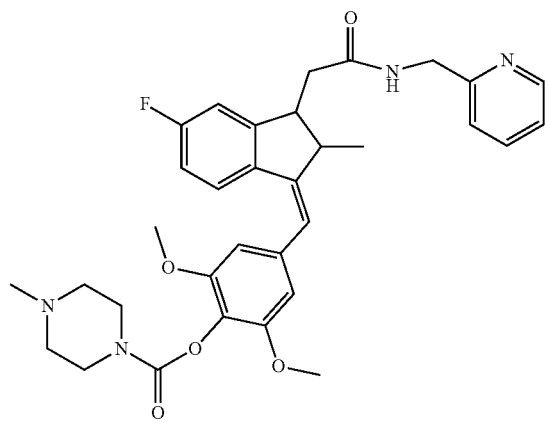
1820
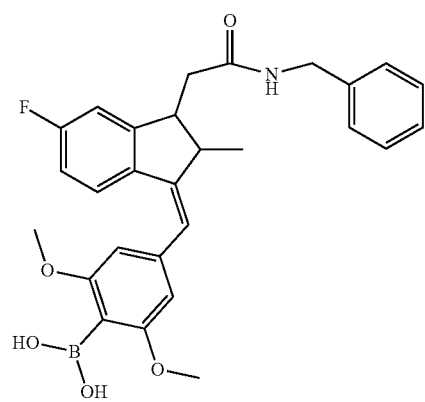
1821
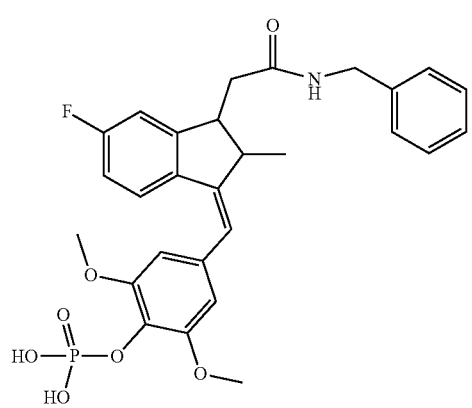
1822
62
-continued
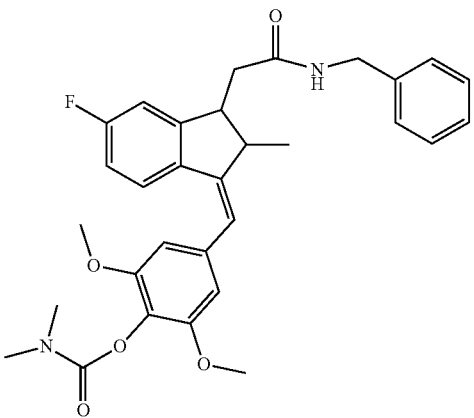
1823
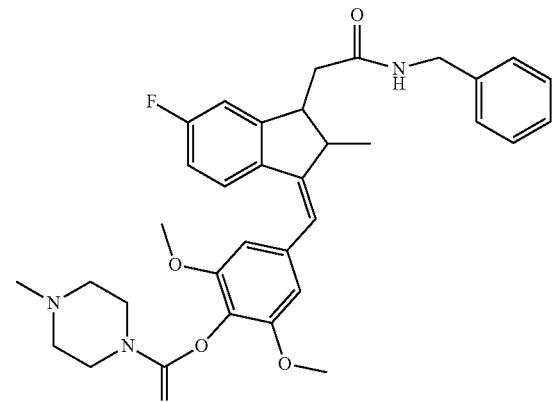
1824
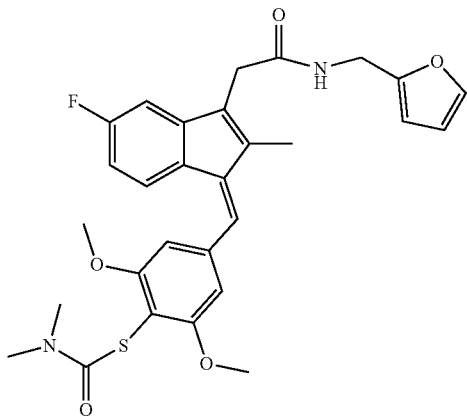
1831

1832
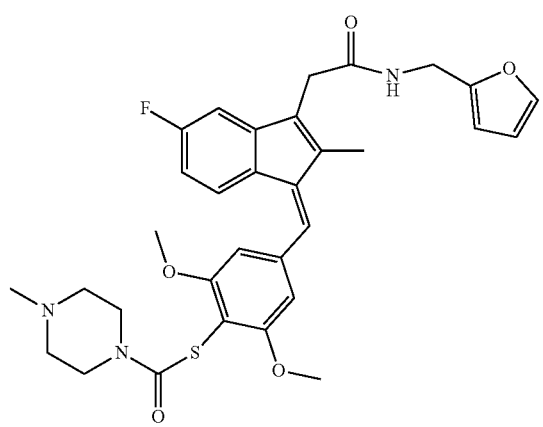
1833
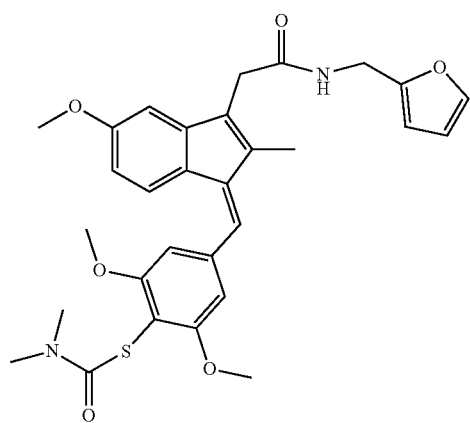
1834
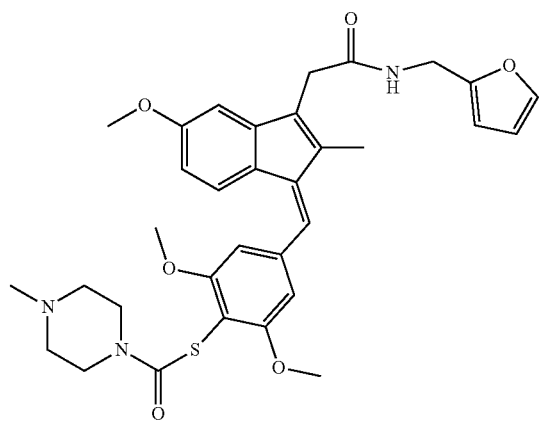
1835
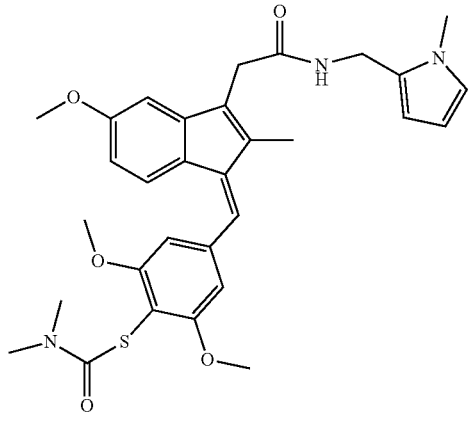
1836
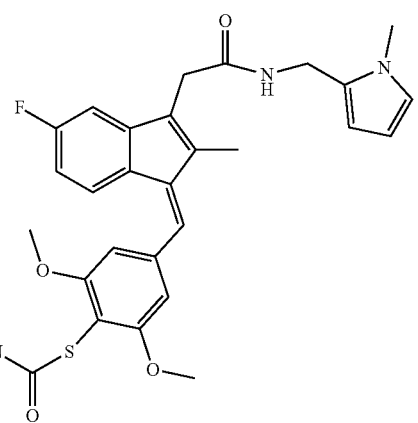
1837
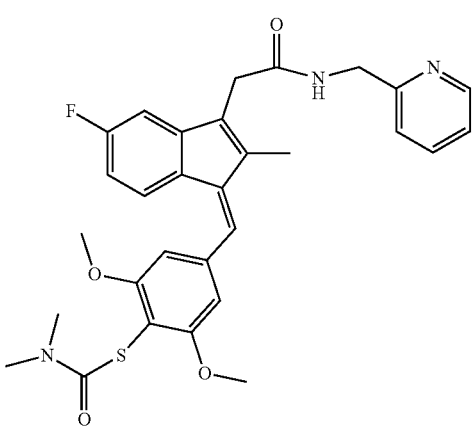

-continued
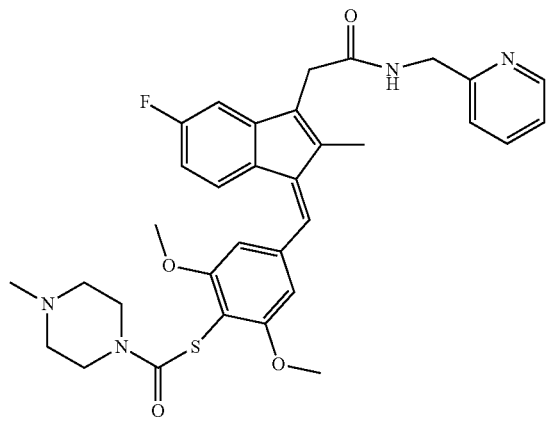
1838
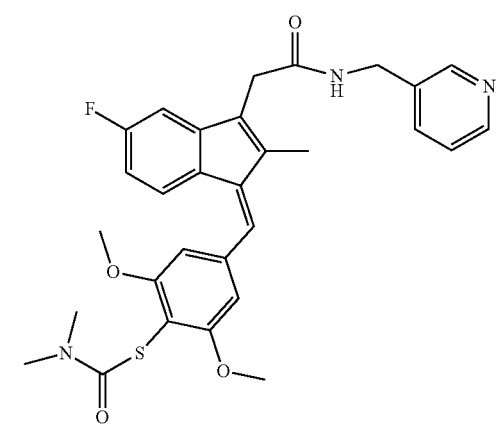
1839
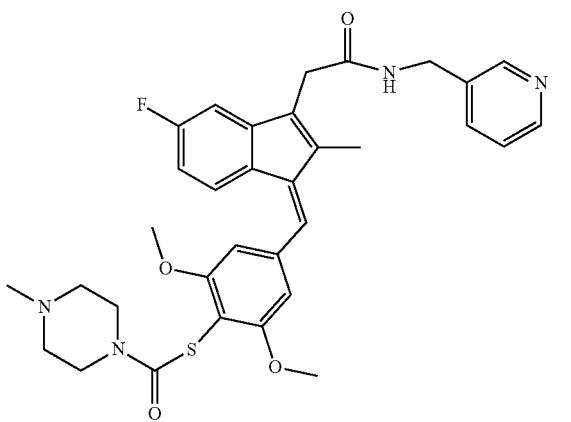
1840
-continued
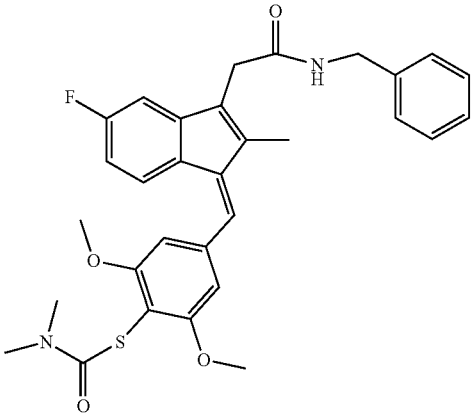
1841
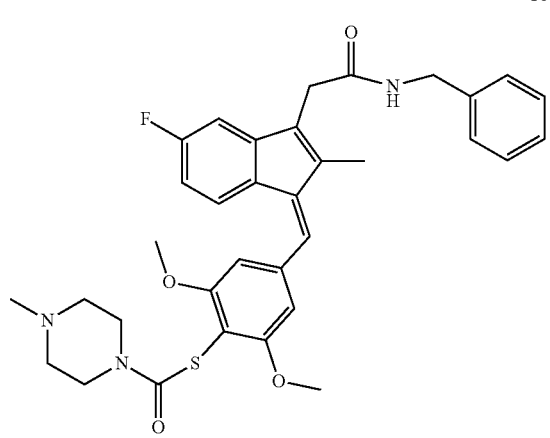
1842
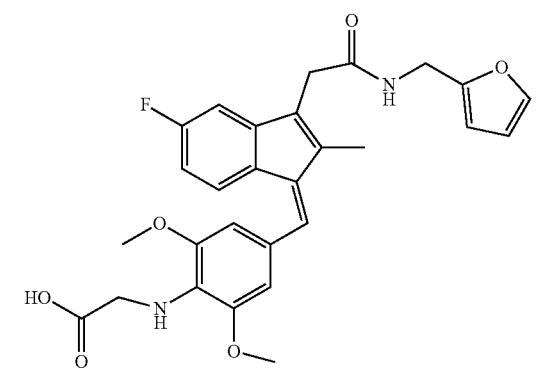
1849
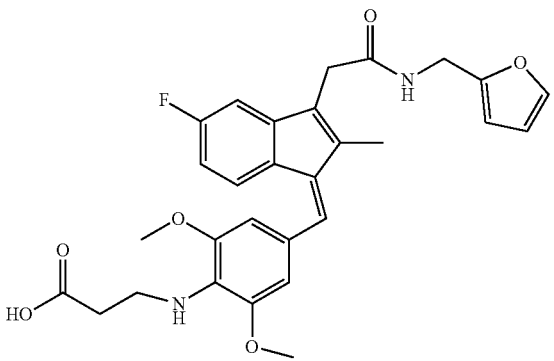
1850

1851
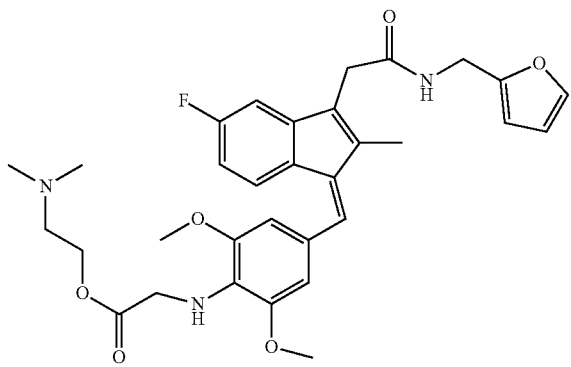
1852
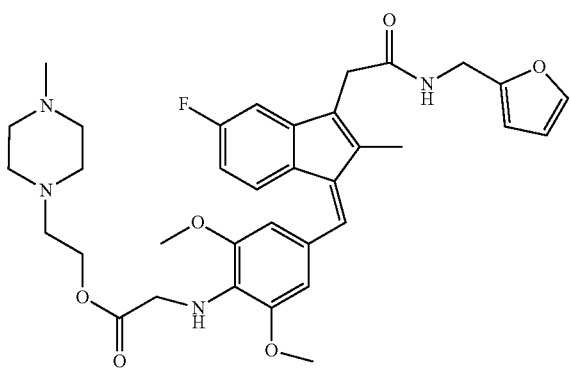
1853
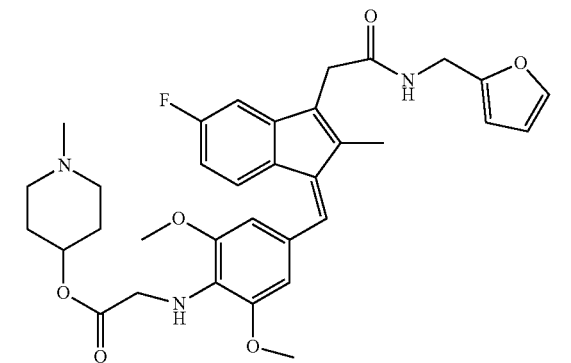
1854
1855
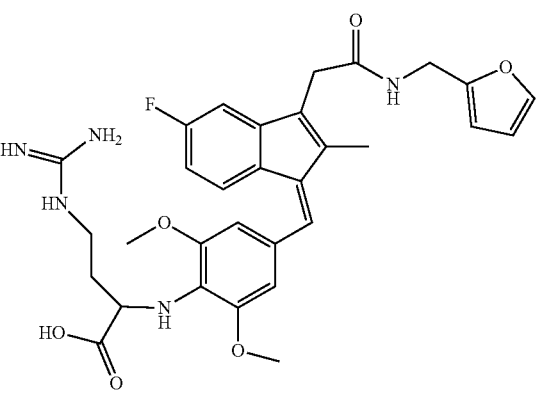
1856
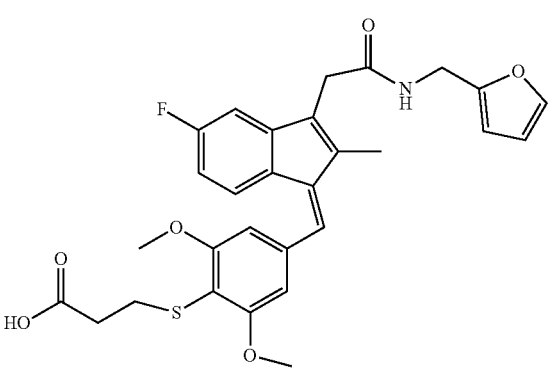
1857
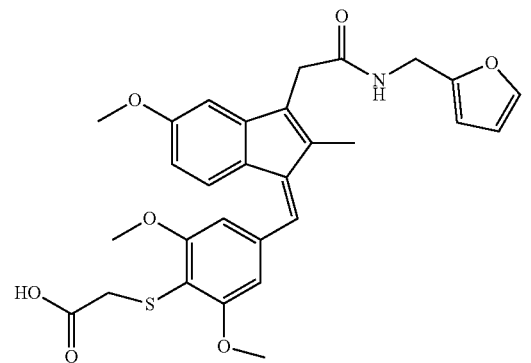
1858

69
-continued
1859
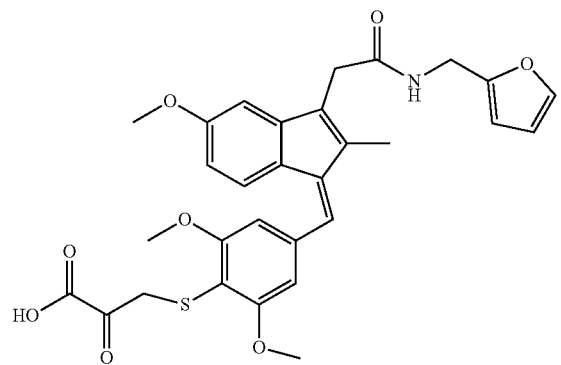
1860
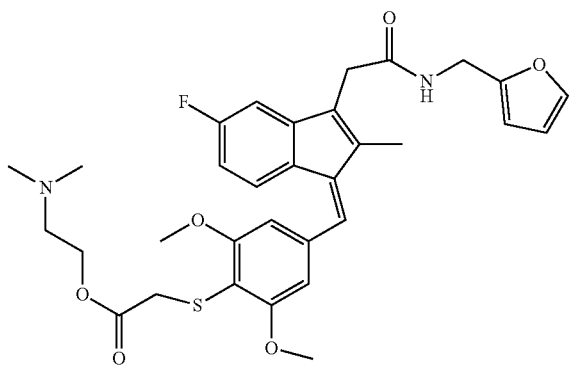
1861
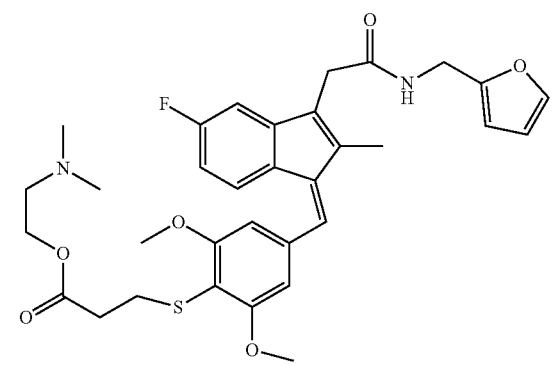
1862
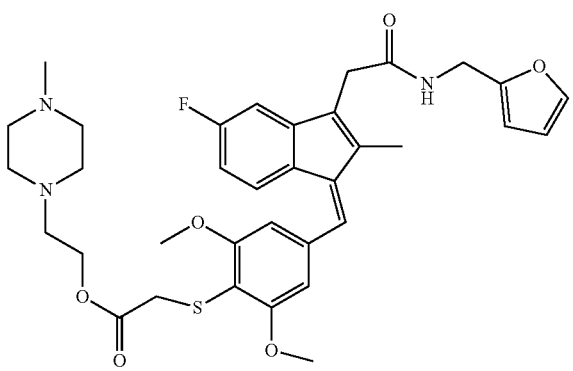
70
-continued
1863
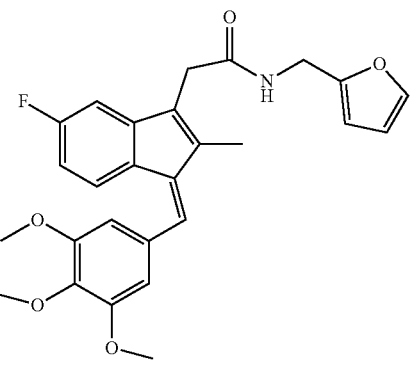
1864
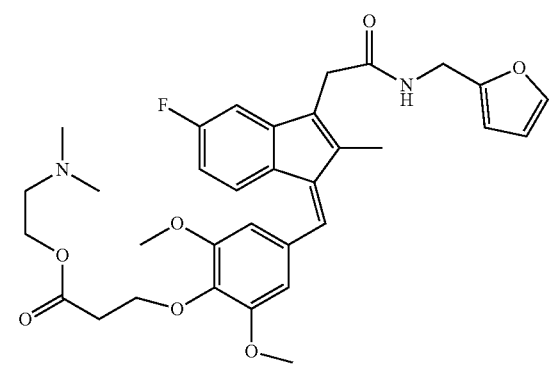
1865
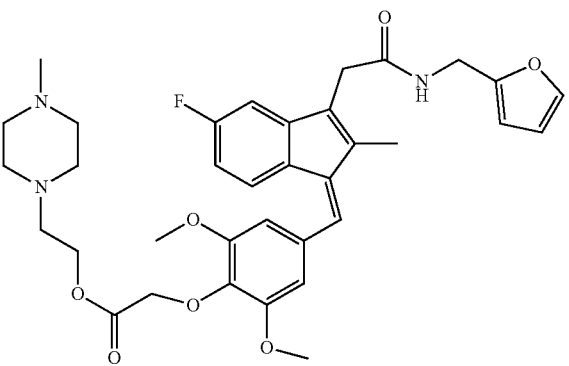
1866
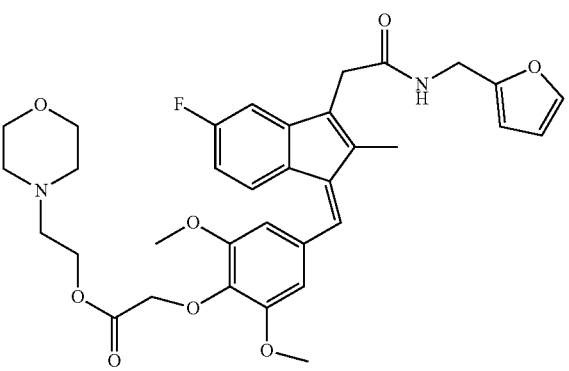

-continued
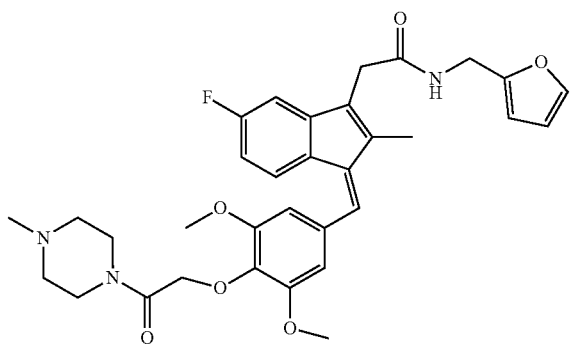
1867
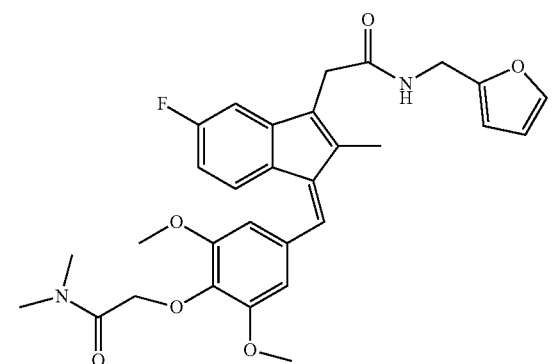
1871
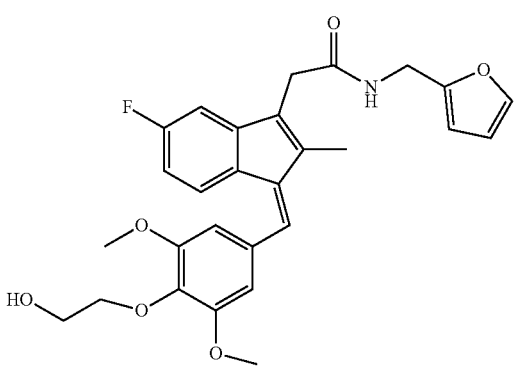
1872
1868
1869
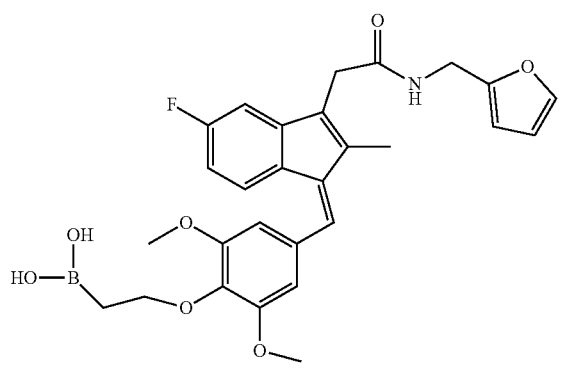
1873
1870
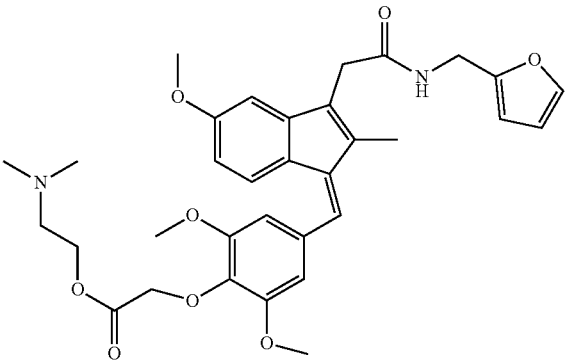
1874

-continued
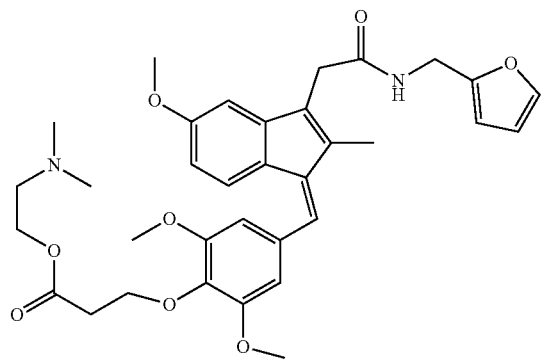
1875
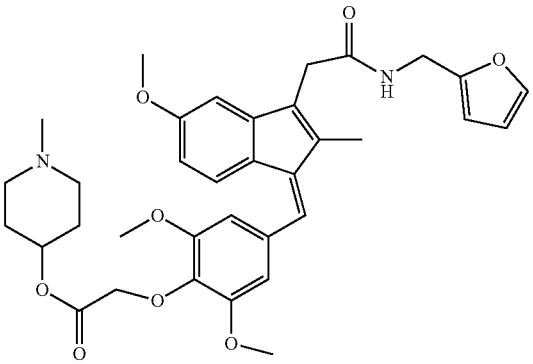
1879
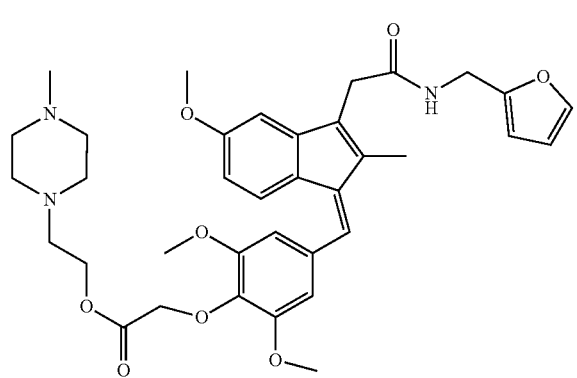
1876
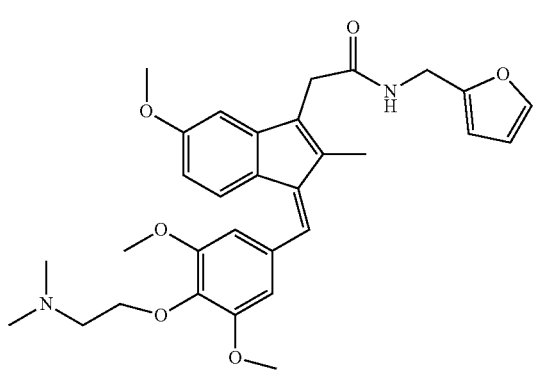
1880
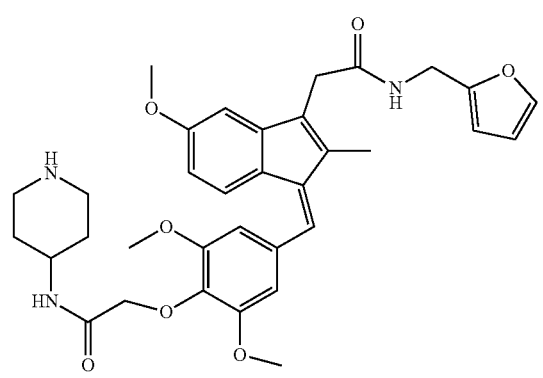
1877
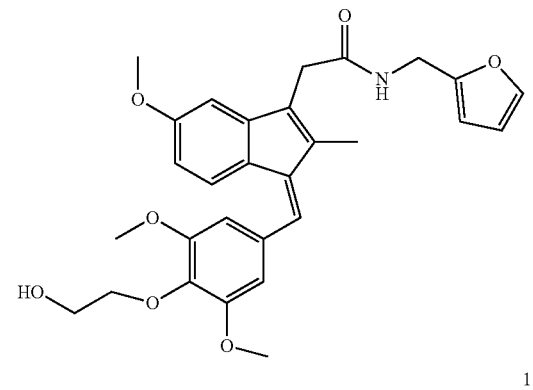
1881
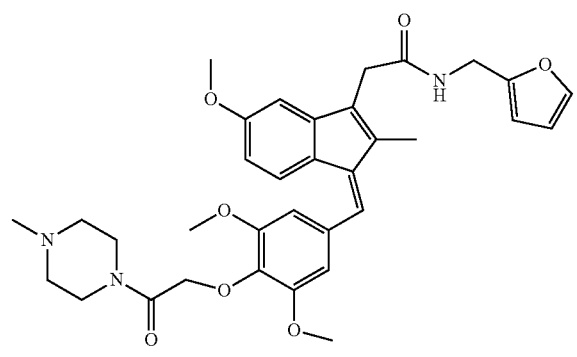
1878
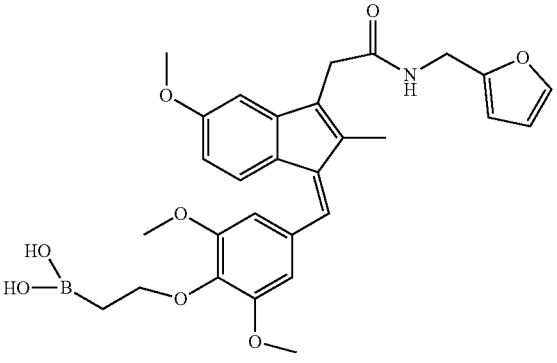
1882

1883
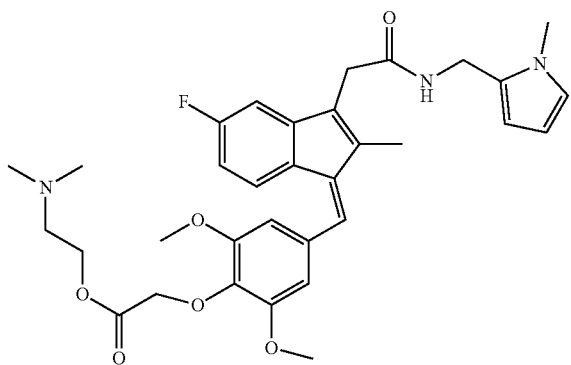
1884
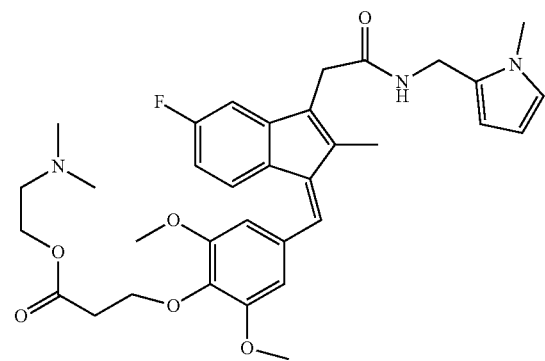
1885
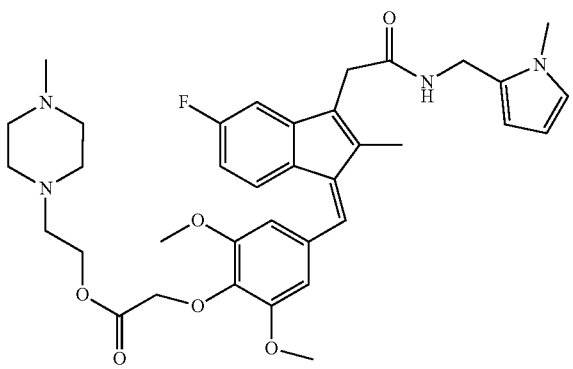
1886
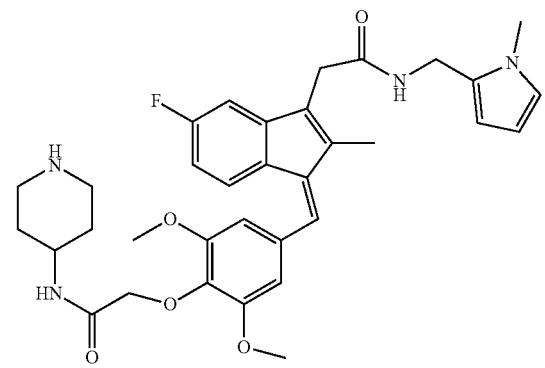
1887
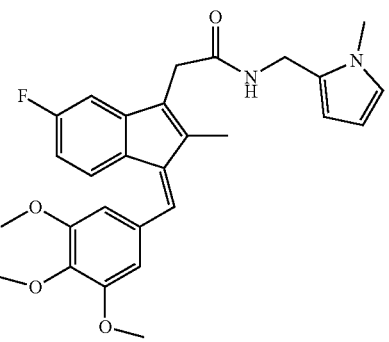
1888
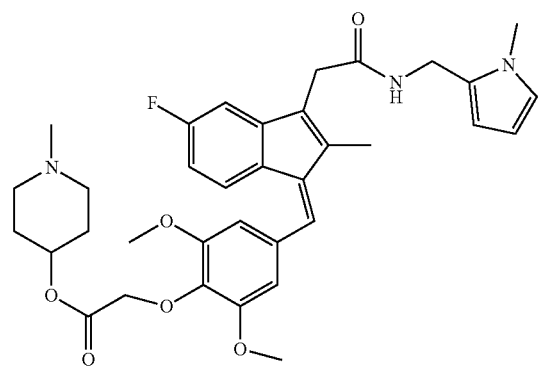
1889
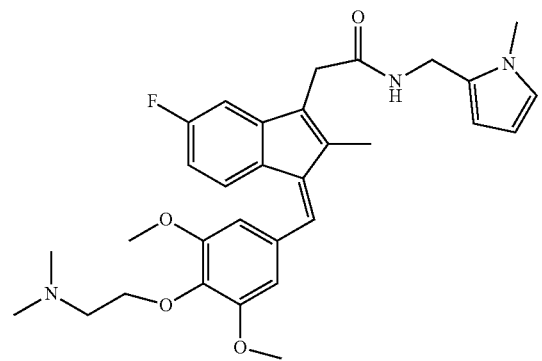
1890
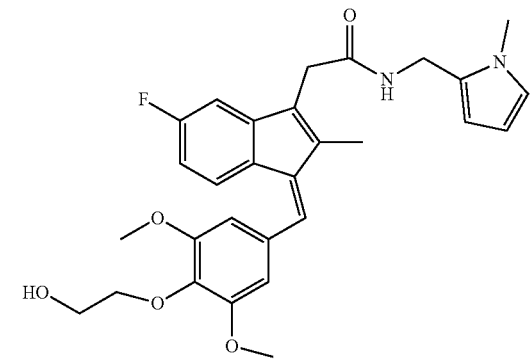

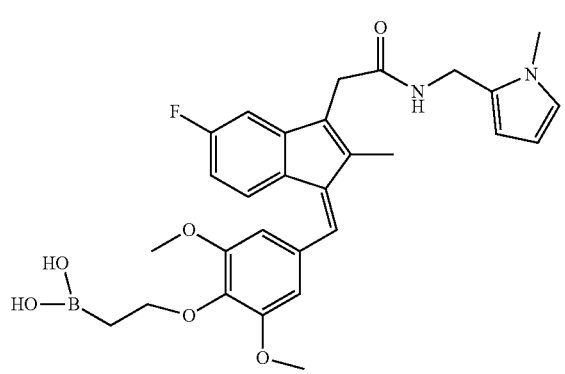
1891
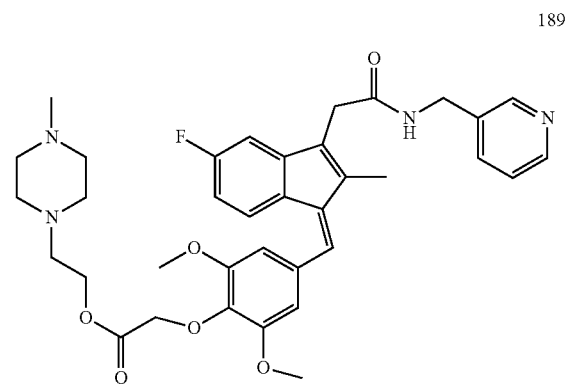
1892
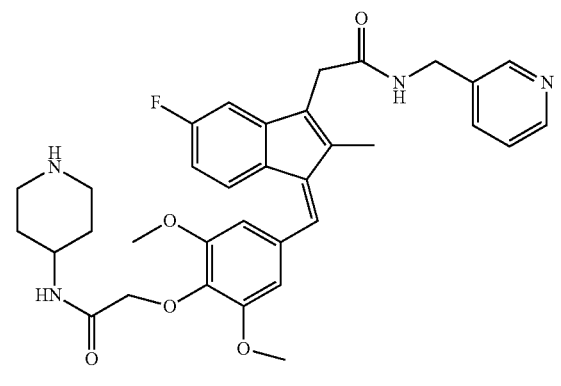
1893
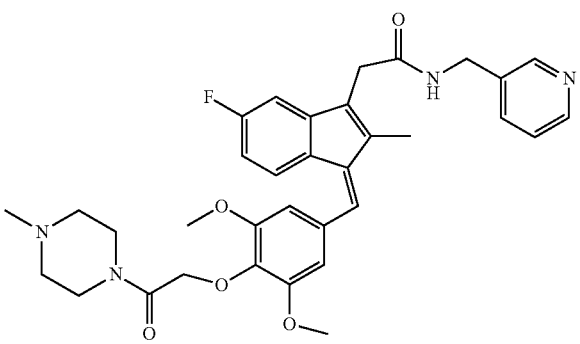
1894
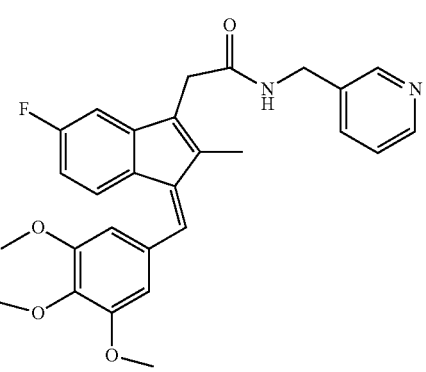
1895
1896
1897
1898

79
-continued
1899
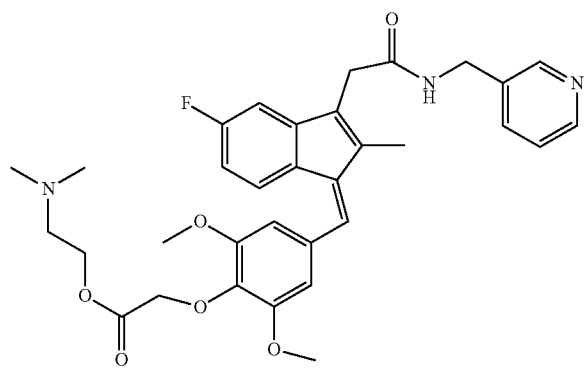
1900
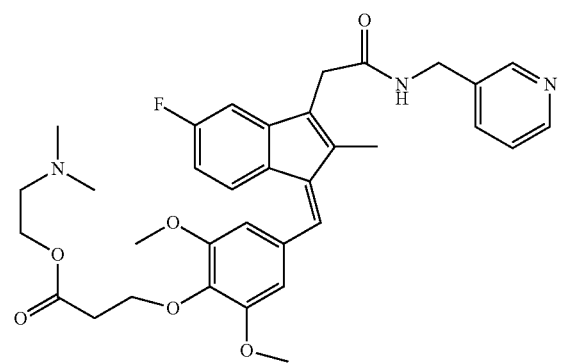
1901
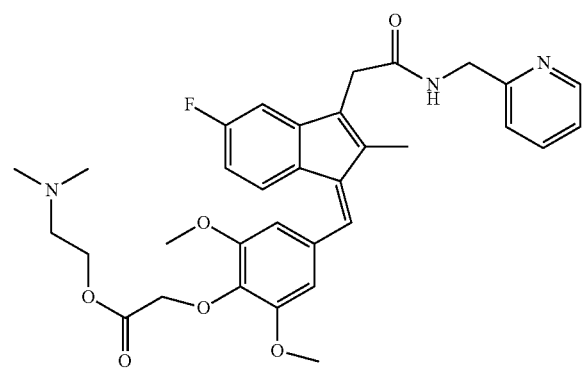
1902
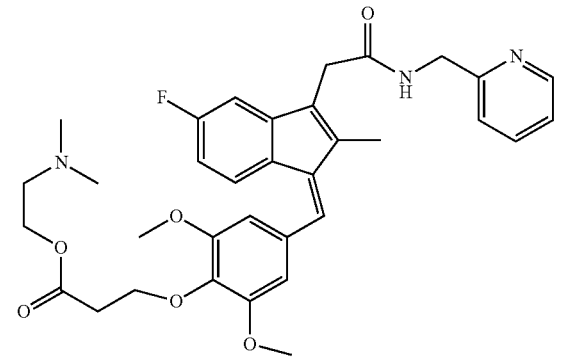
80
-continued
1903
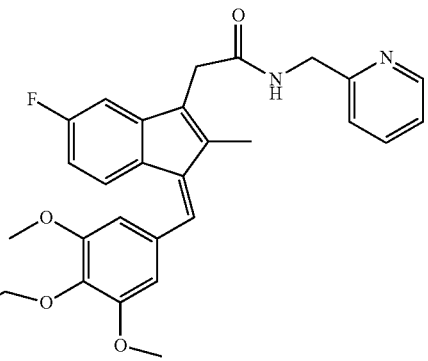
1904
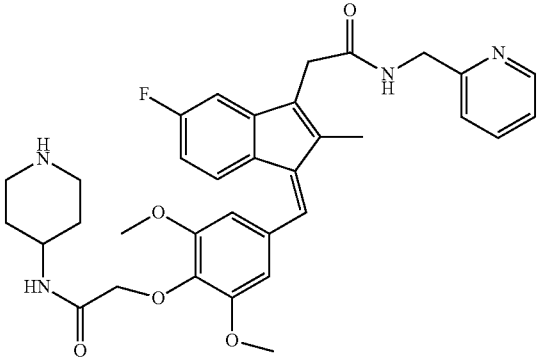
1905
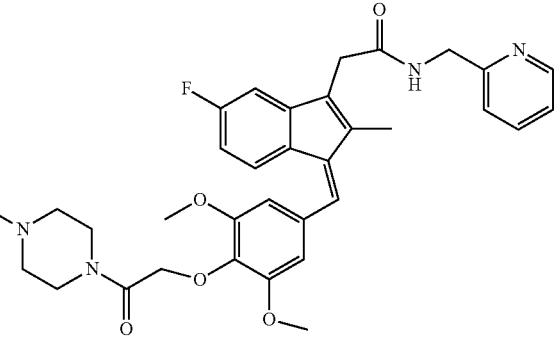
1906
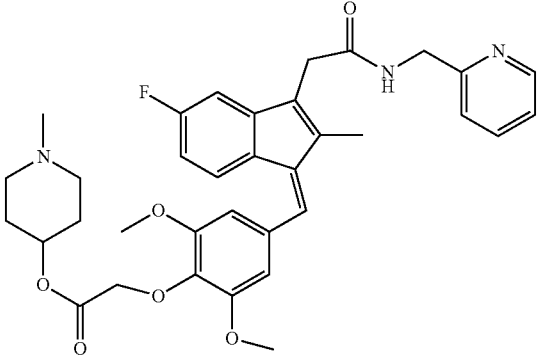

1907
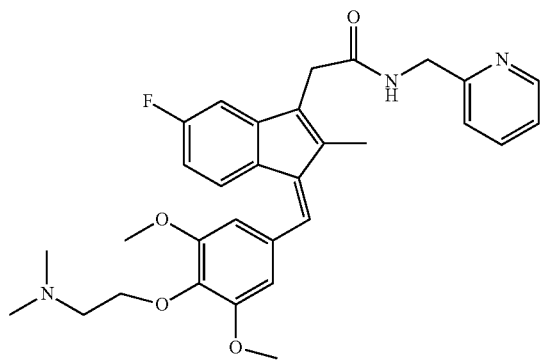
1908
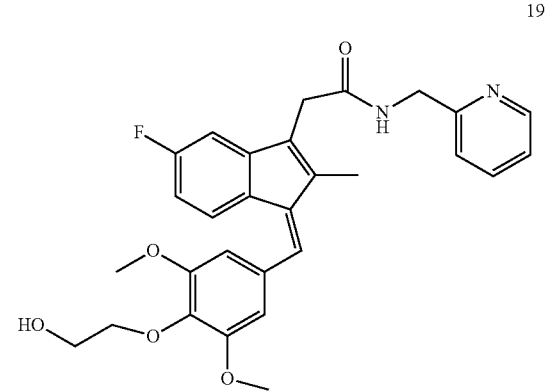
1909
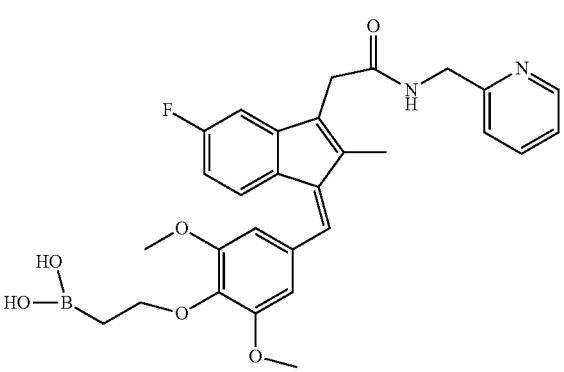
1910
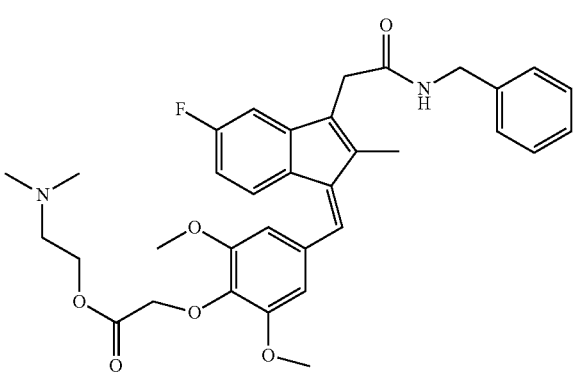
1911
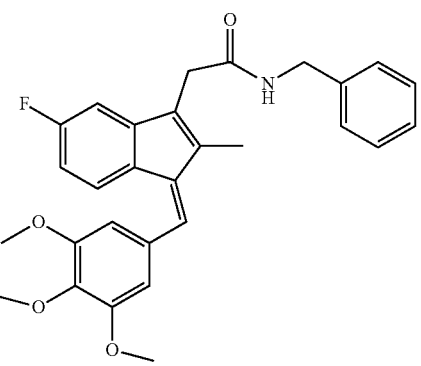
1912
1913
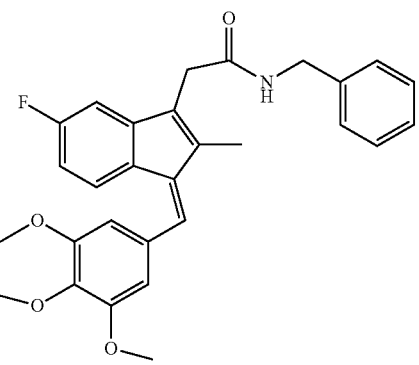
1914

1915
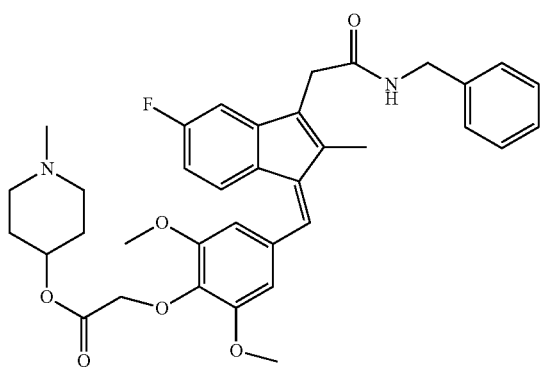
1916
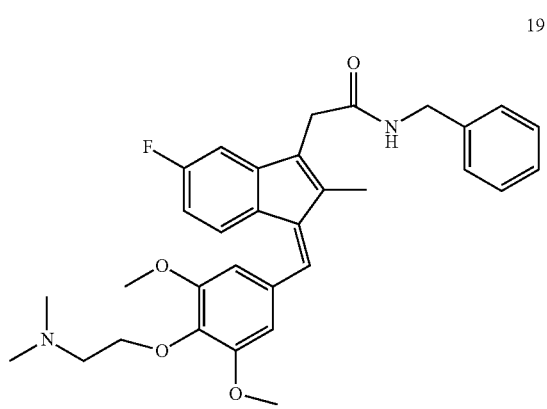
1917
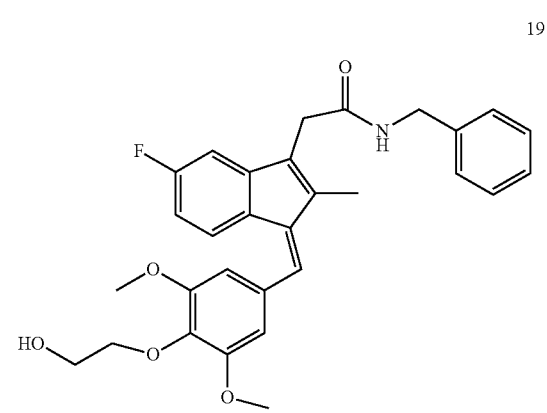
1918
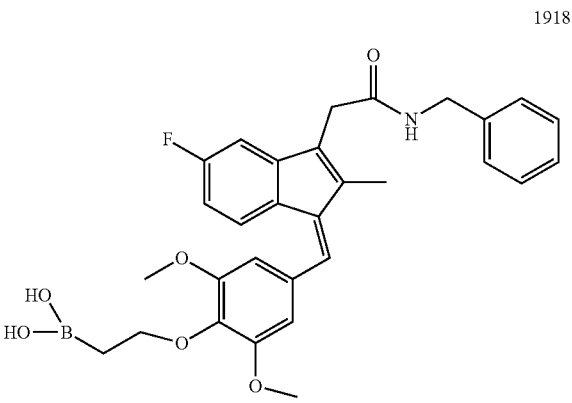
1965
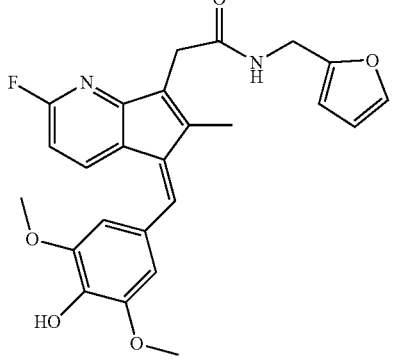
1966
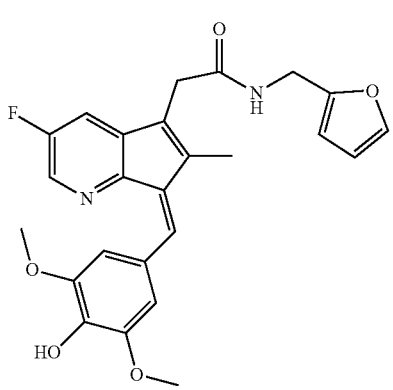
1967
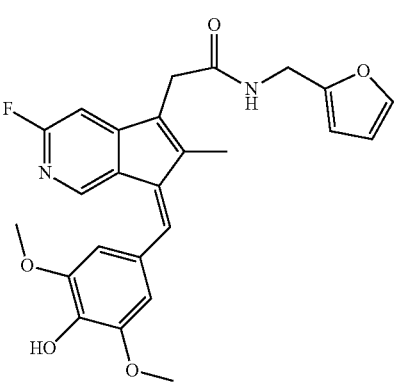
1968
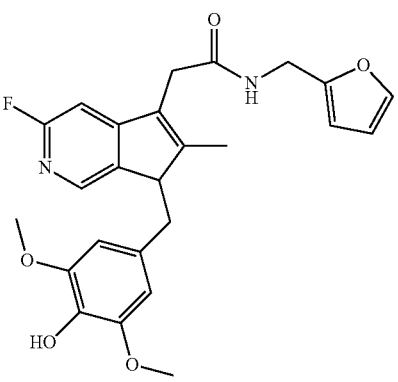

85
-continued
1969
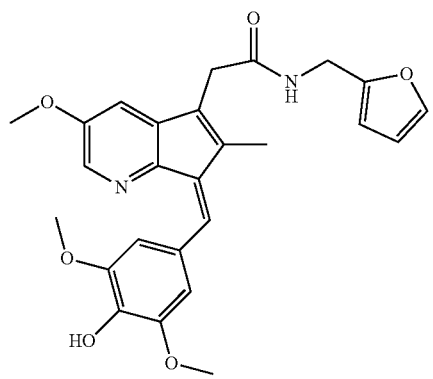
1970
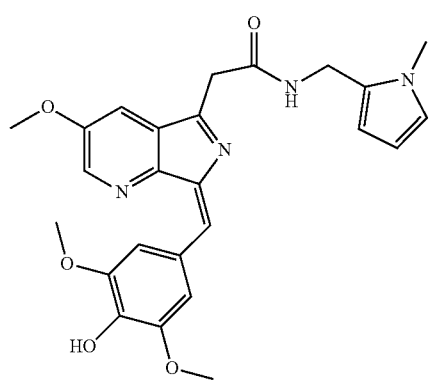
1971
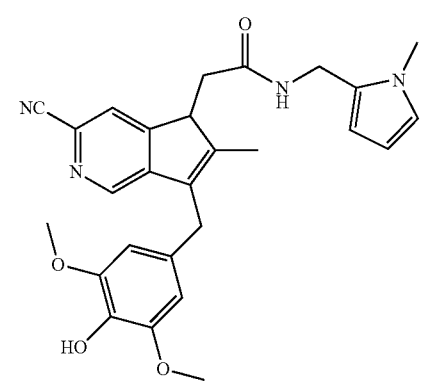
1972
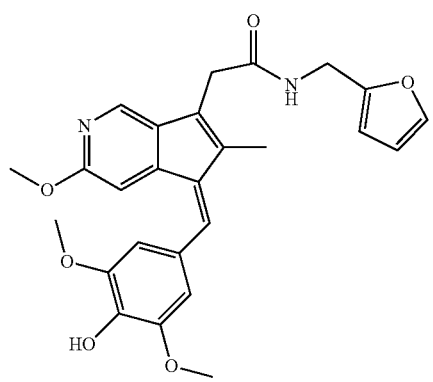
86
-continued
1973
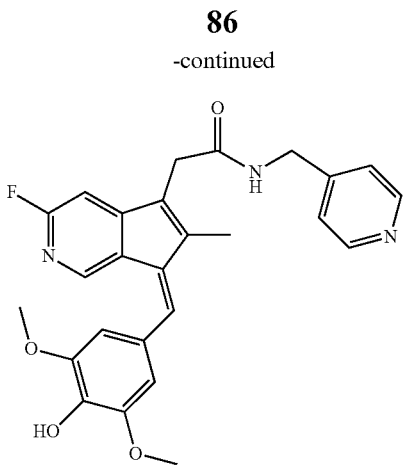
1974
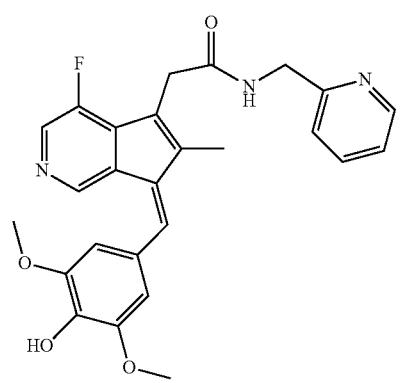
1975
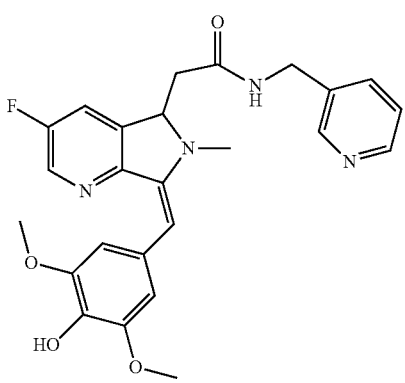
1976
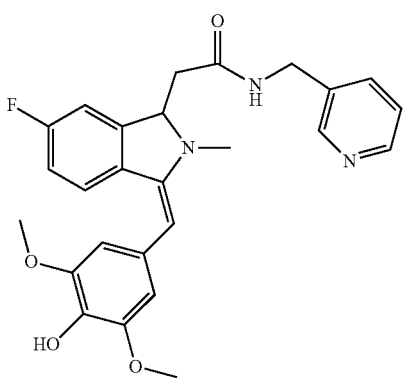

| 87 -continued | 88 -continued |
|---|---|
| 1978 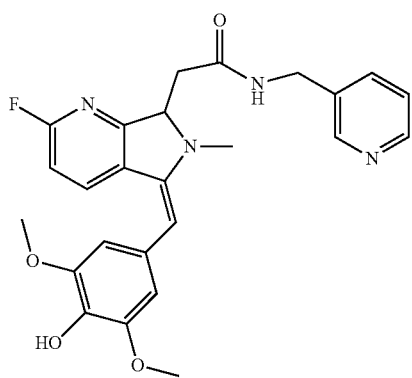 | 1982 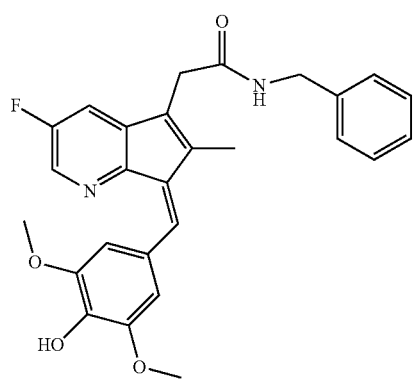 |
| 1979 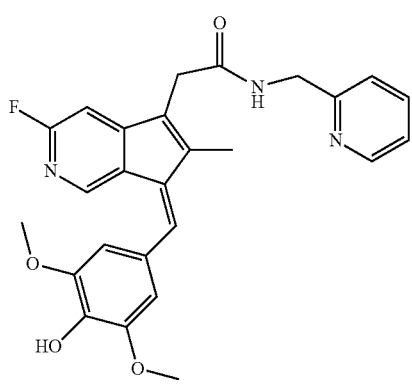 | 1983 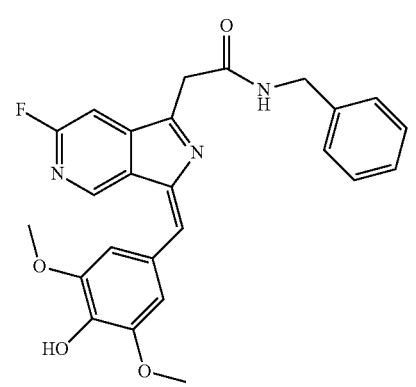 |
| 1980 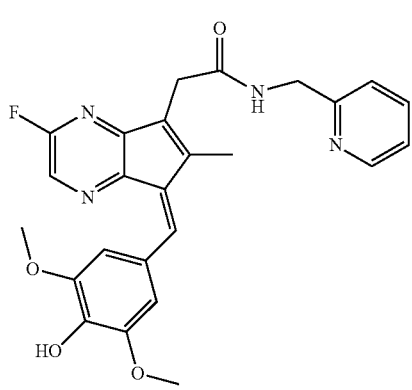 | 1984 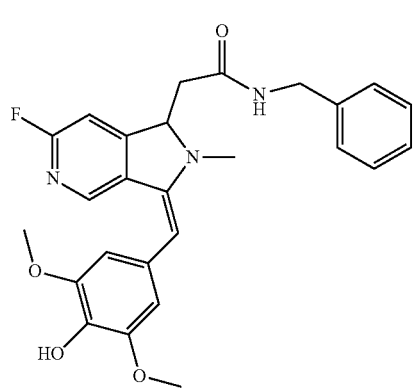 |
| 1981 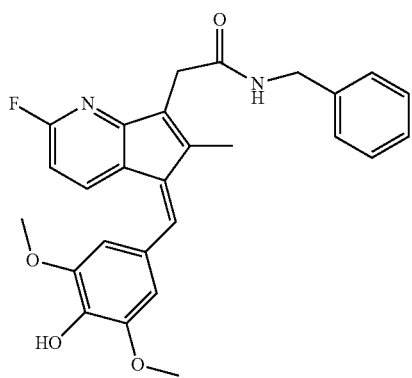 | 1985 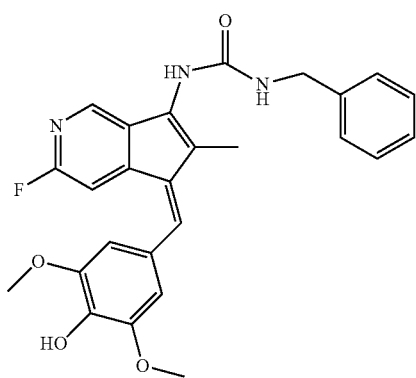 |

1986 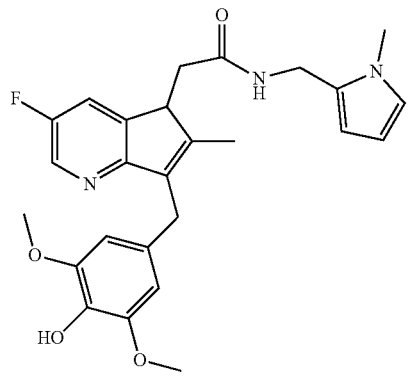
1987 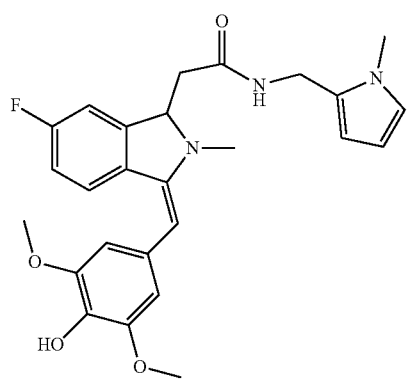
1988 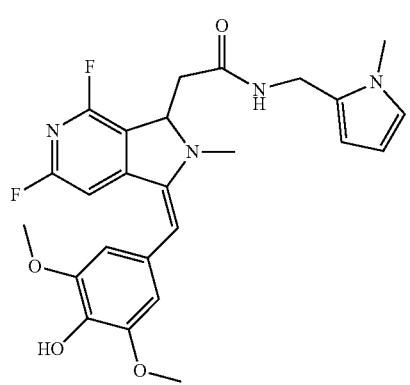
1989 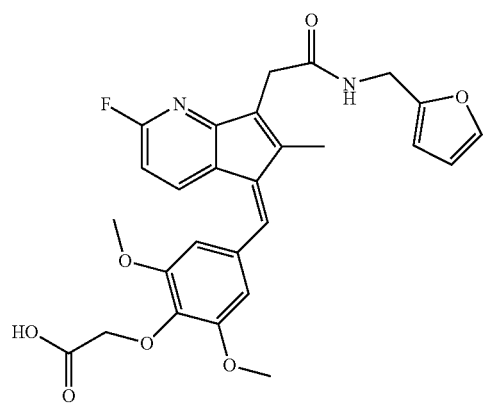
1990 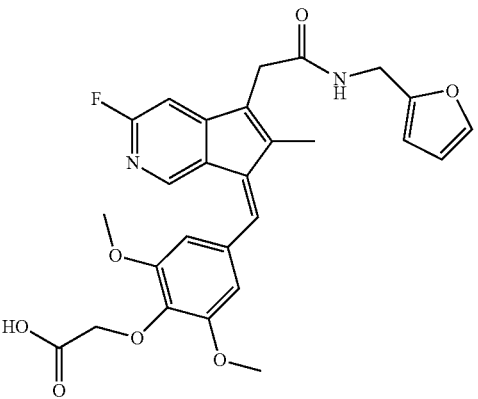
1991 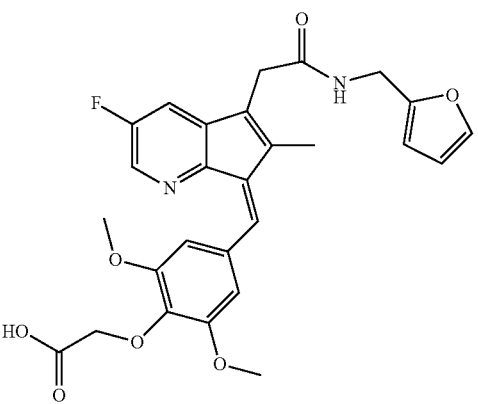
1992 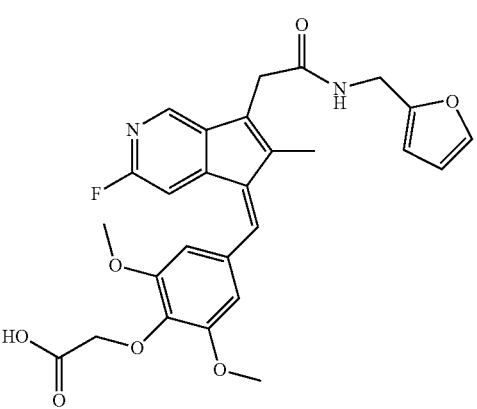

1993
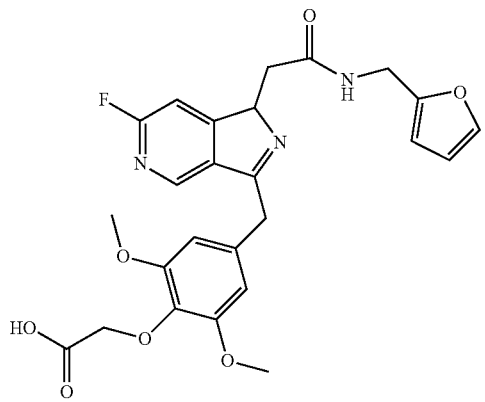
1994
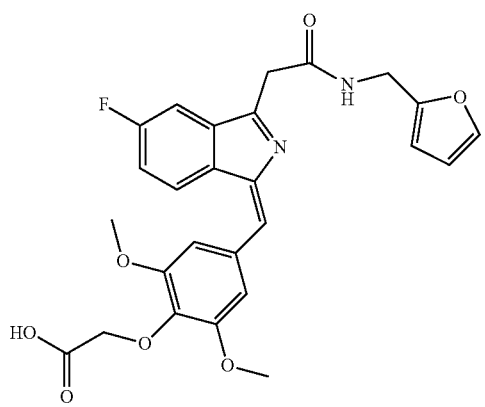
1995
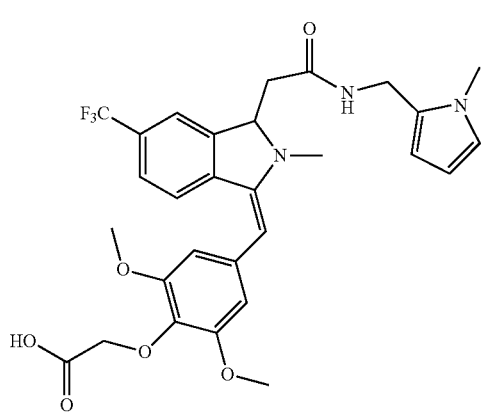
1996
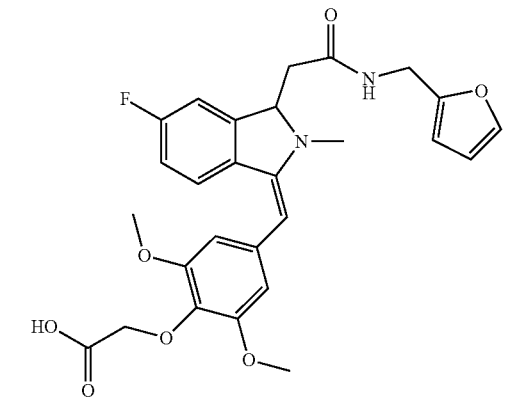
1997
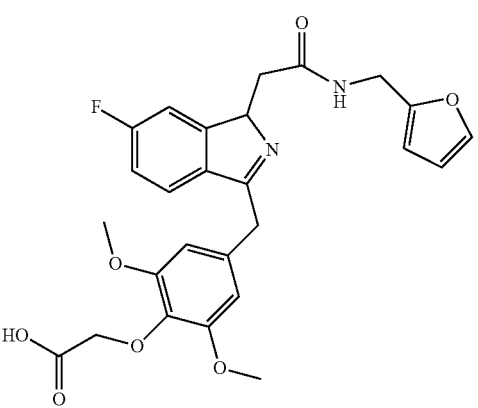
1998
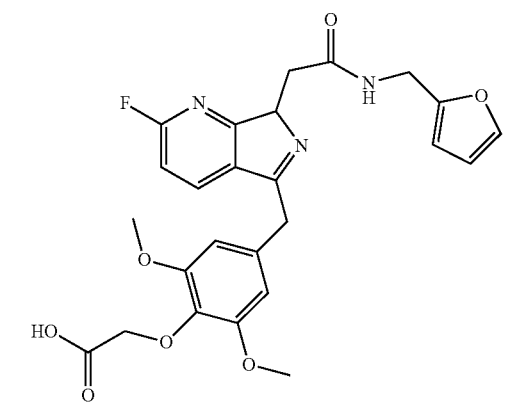

93
-continued
1999
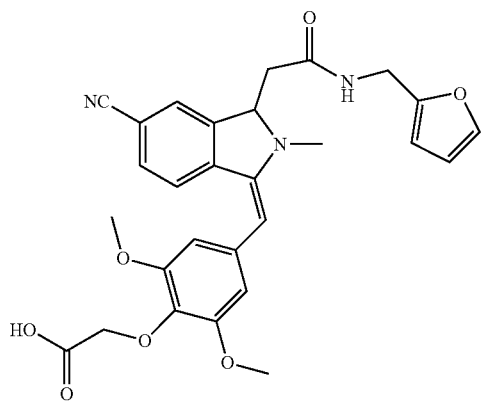
2000
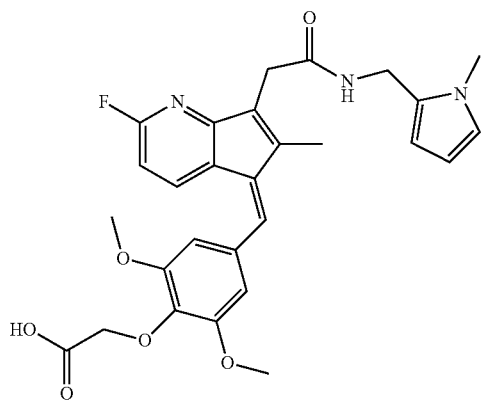
2001
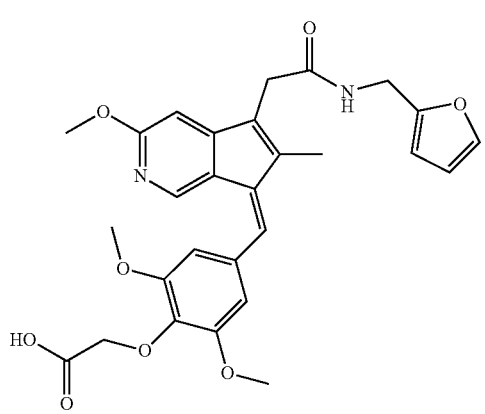
94
-continued
2002
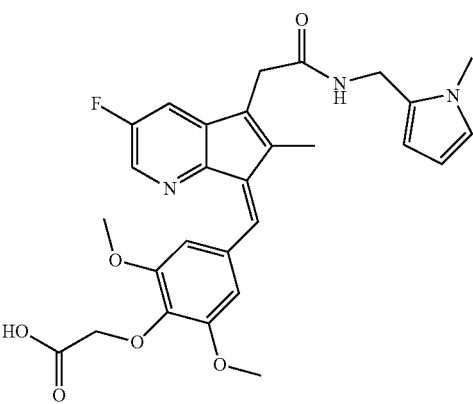
2003
2004
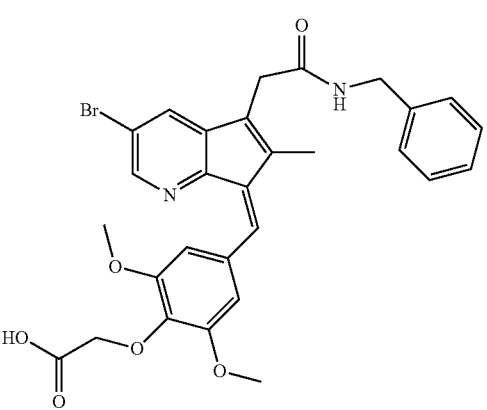

95
-continued
2005
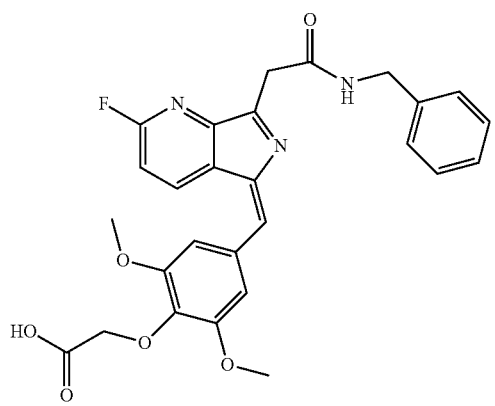
2006
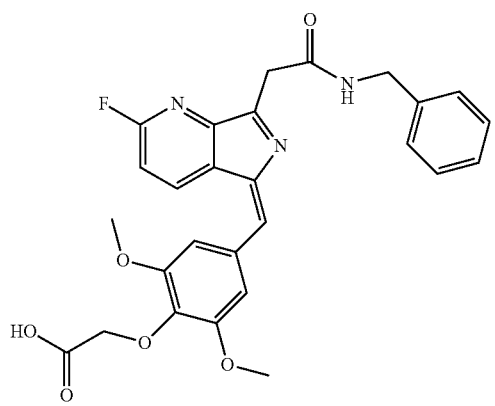
2007
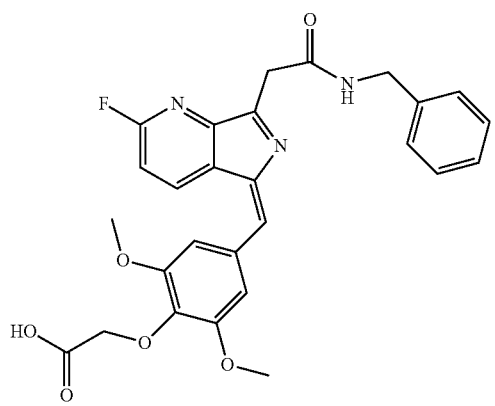
96
-continued
2008
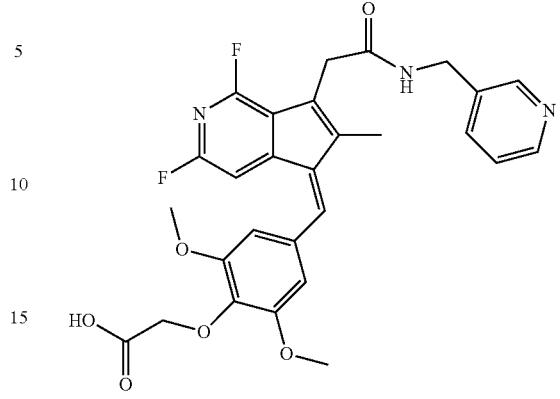
2009
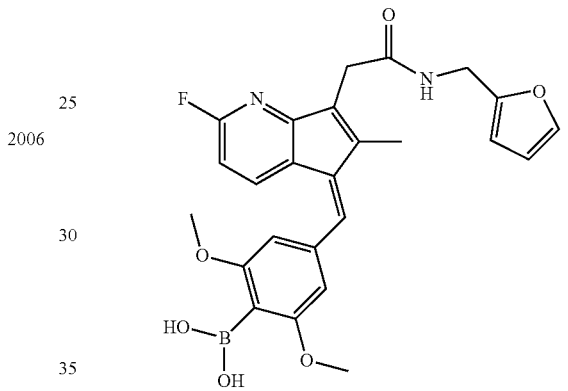
2010
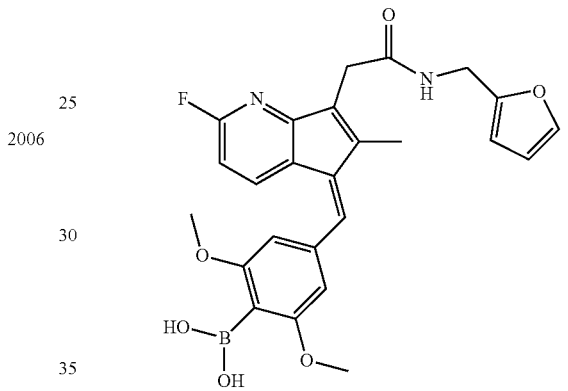
2011
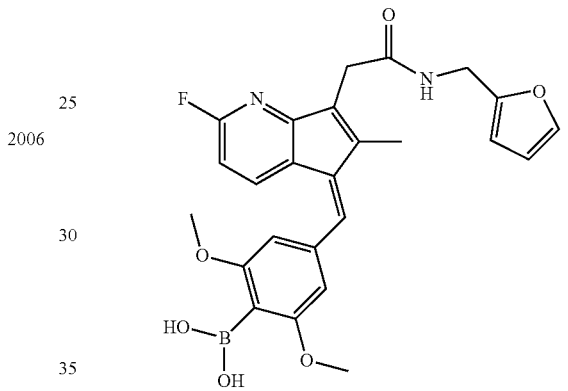

97
-continued
2012
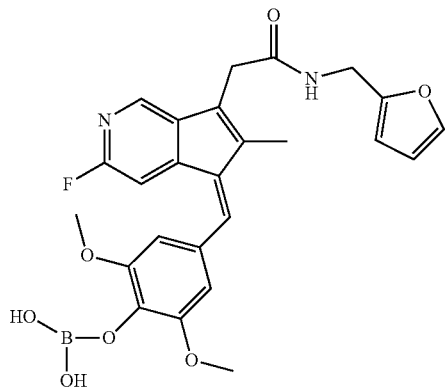
2013
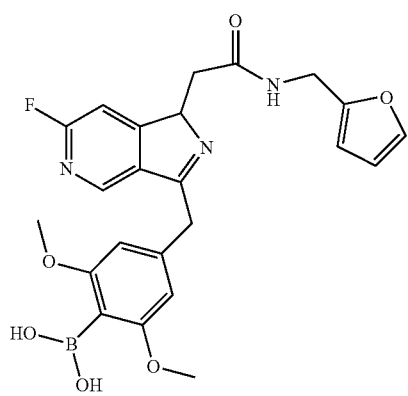
2014
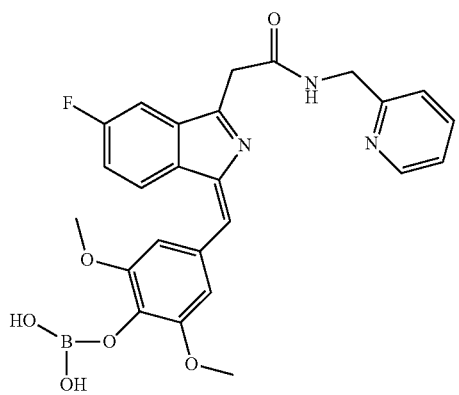
2015
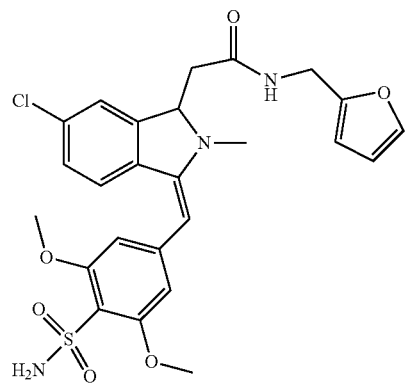
98
-continued
2016
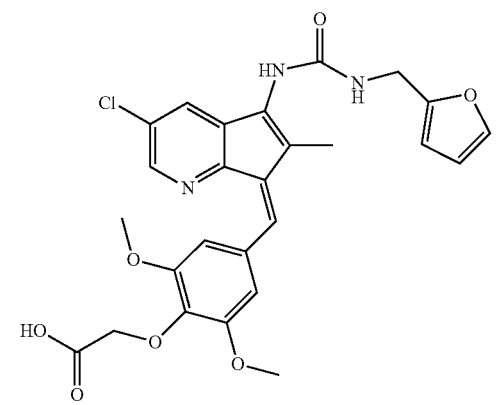
2017
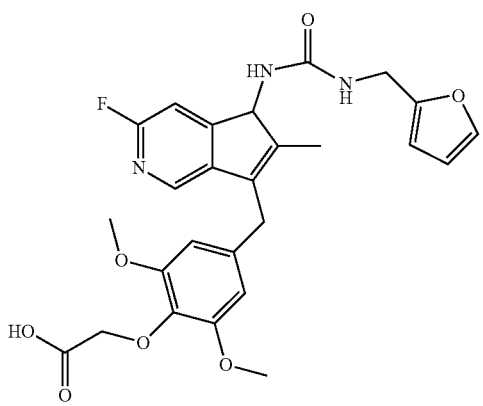
2018
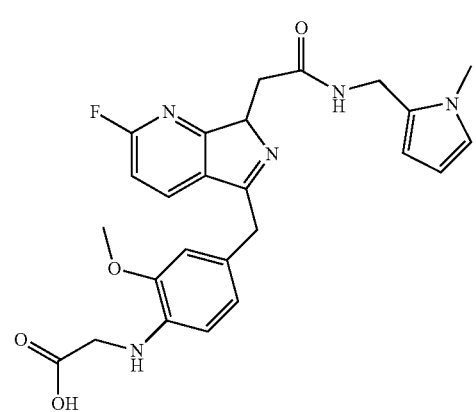
2019
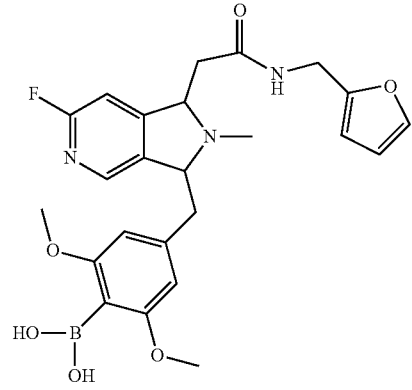

99
-continued
100
-continued
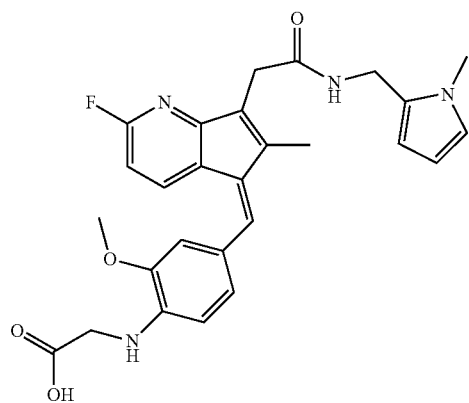
2020
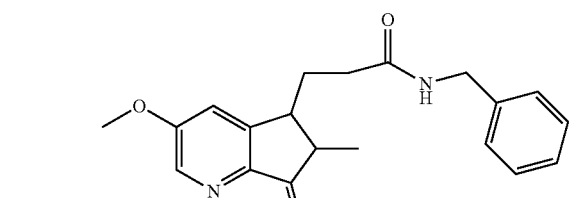
2024
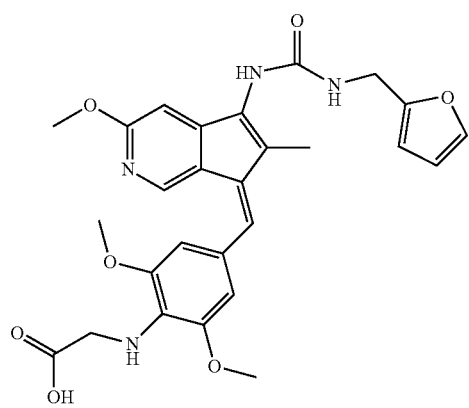
2021
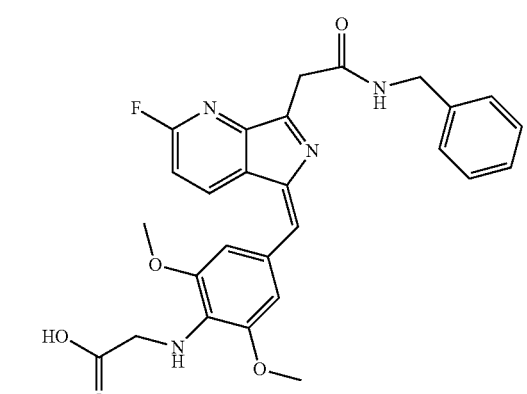
2025
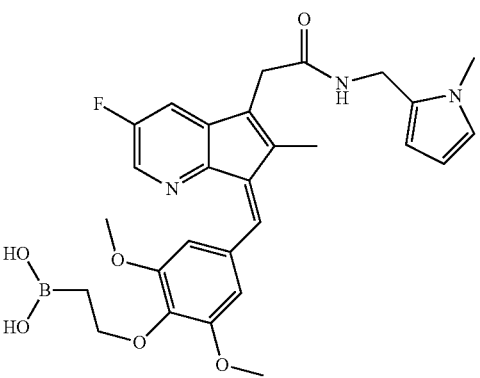
2022
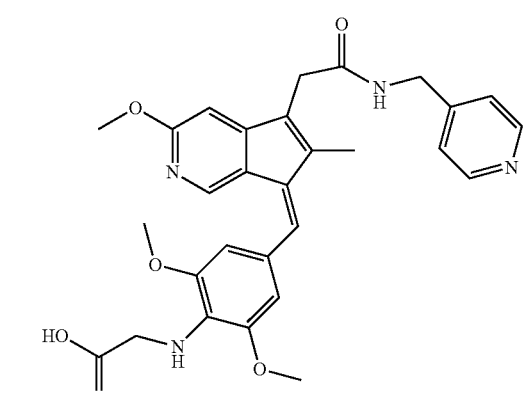
2026
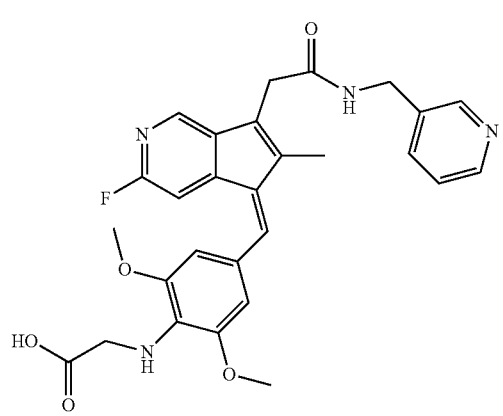
2023
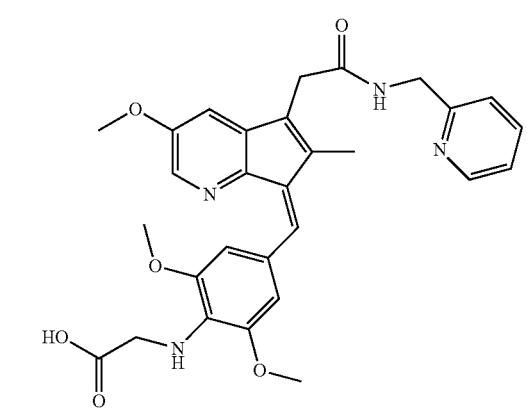
2027

2029
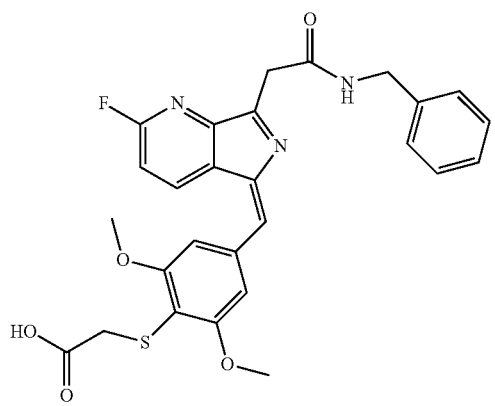
2030
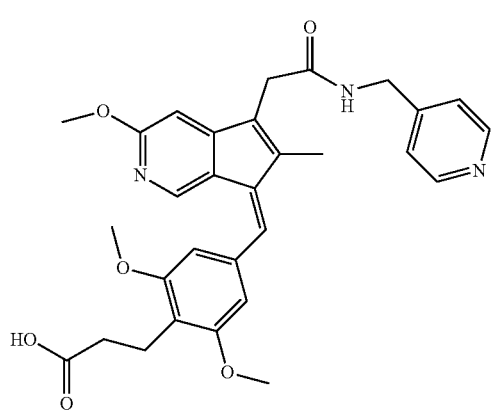
2031
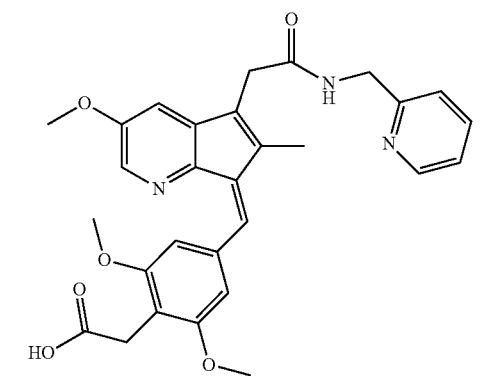
2042
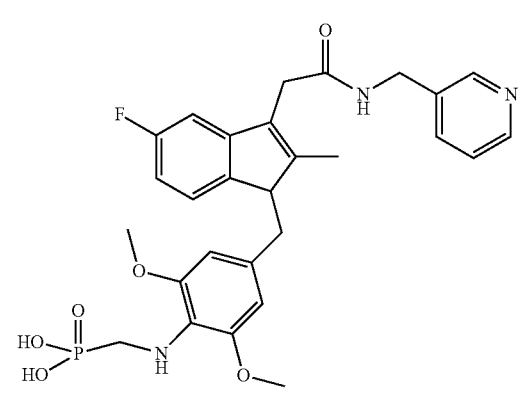
2043
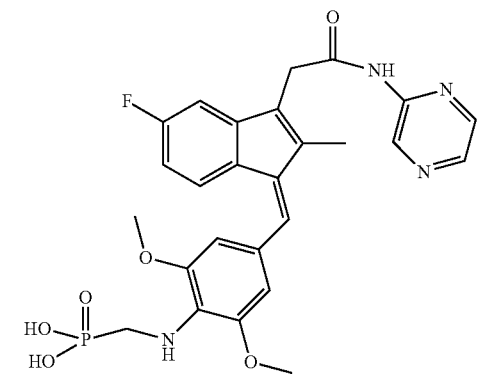
2044
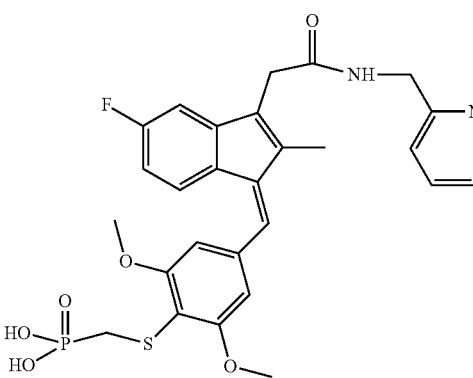
2047
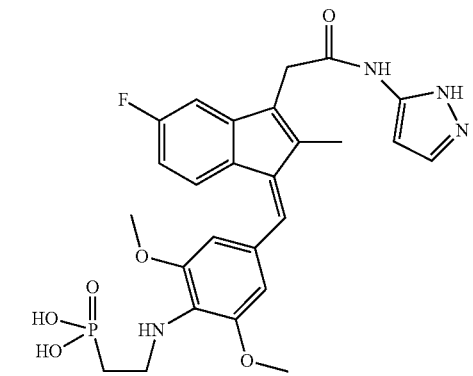
2048
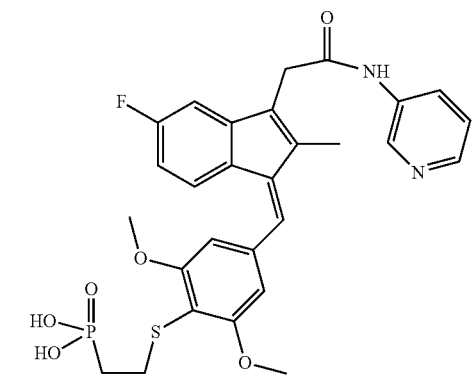

103
-continued
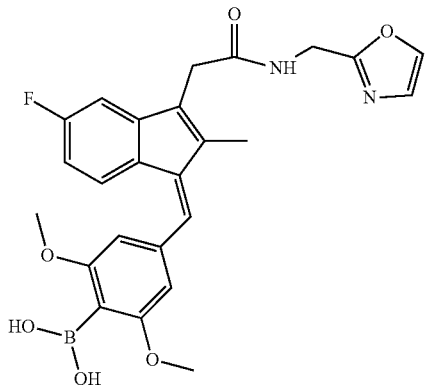
2066
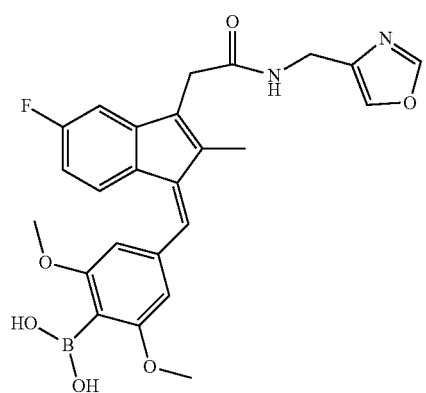
2067
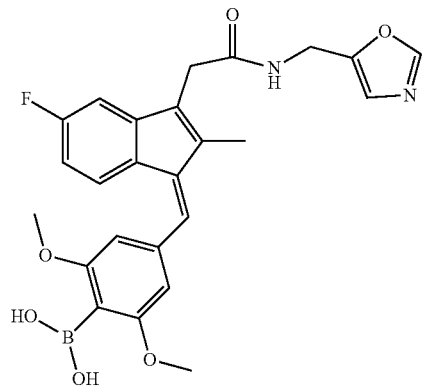
2068
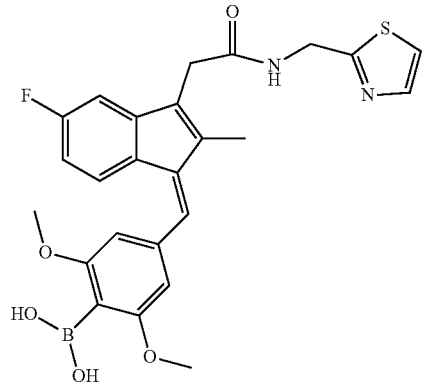
2069
104
-continued
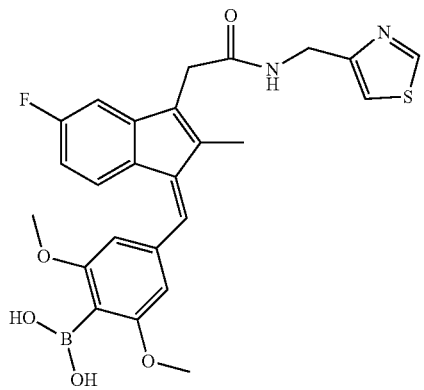
2070
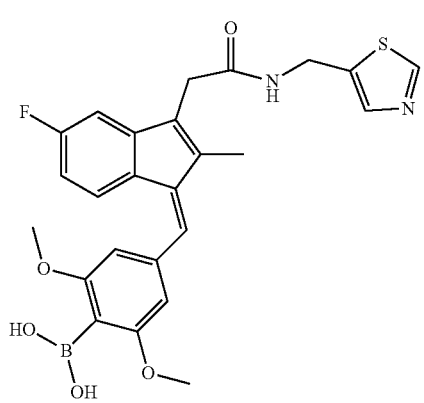
2071
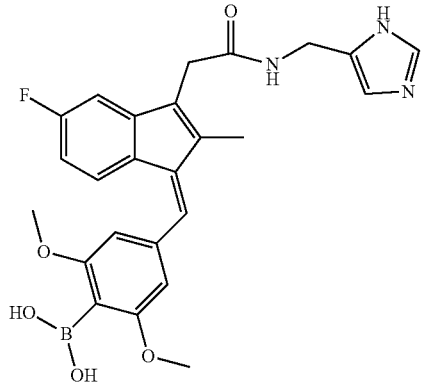
2072
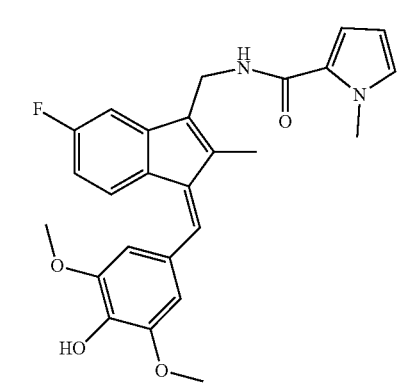
2085

2086
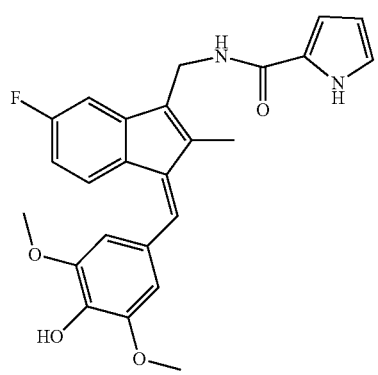
2087
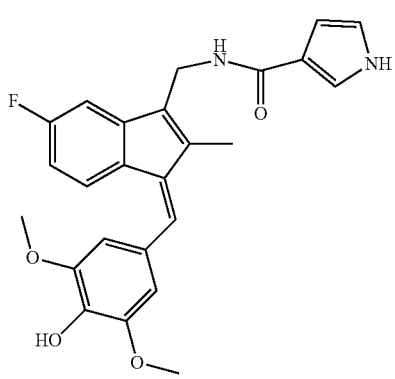
2088
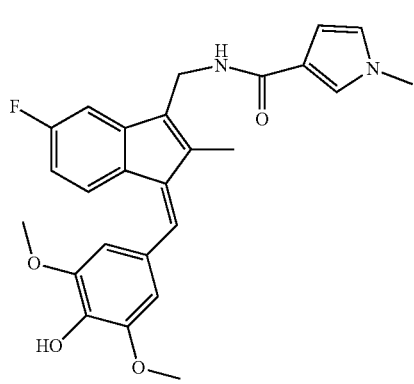
2089
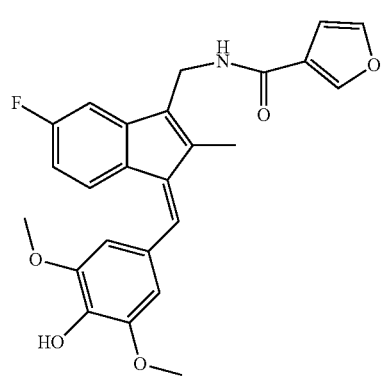
2090
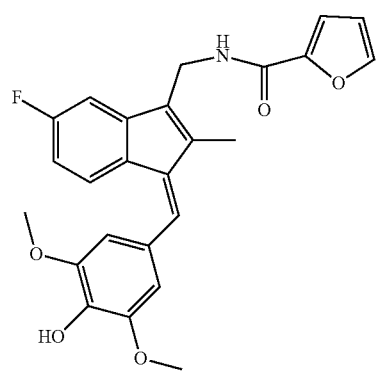
2092
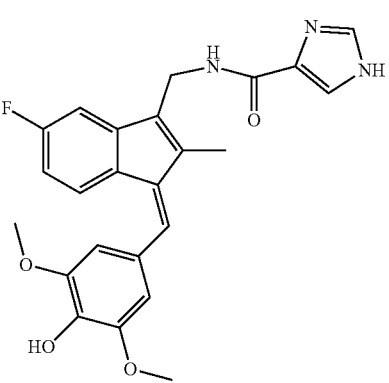
2093
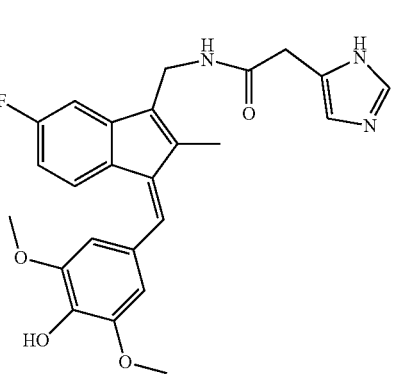
2094

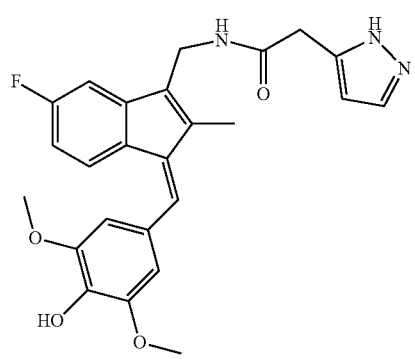
2095
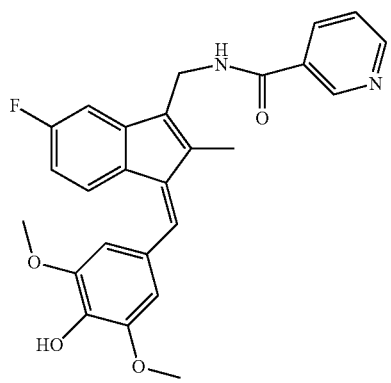
2100
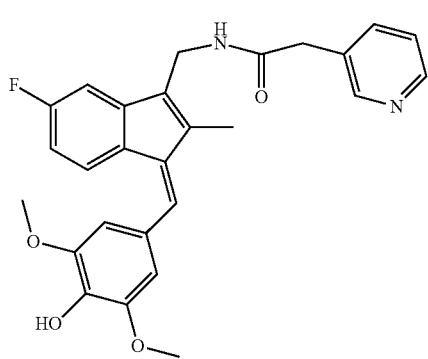
2096
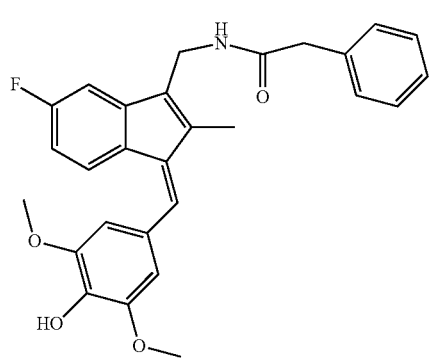
2101
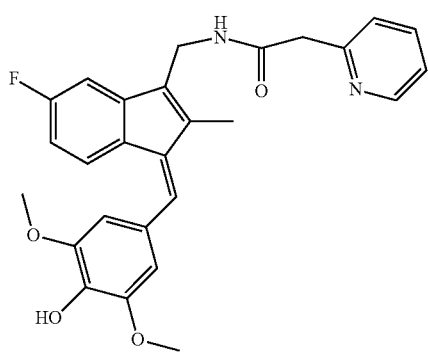
2097
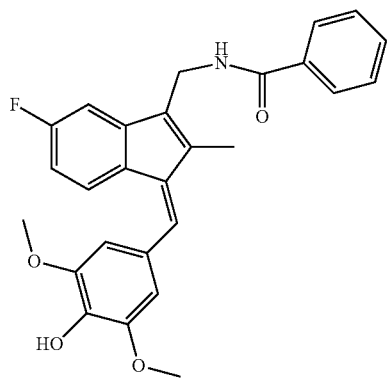
2102
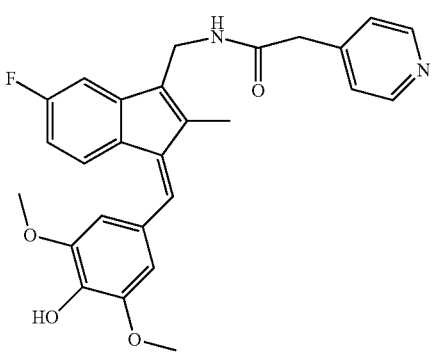
2098
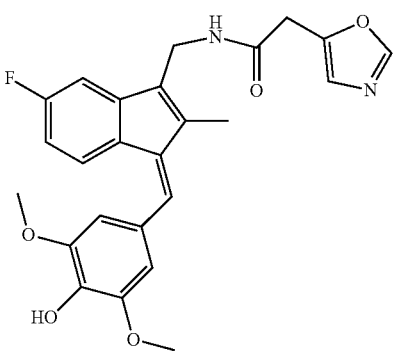
2103

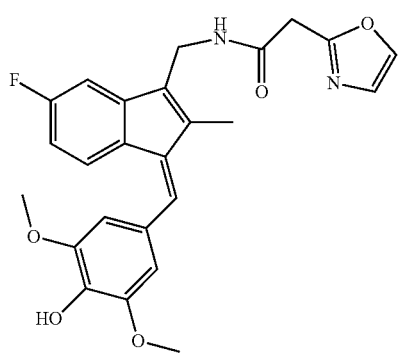
2104
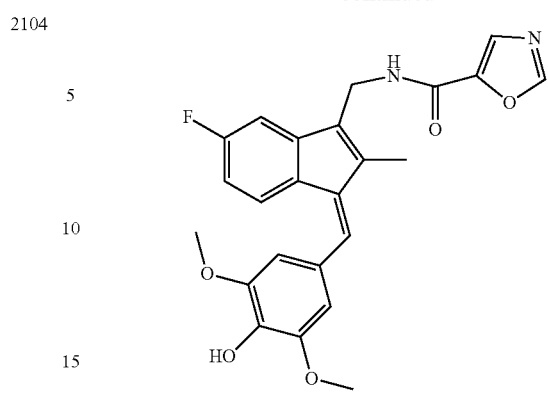
2108
2105
2109
2106
2110
2107
2111
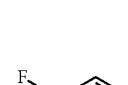

| | |
|---|---|
| 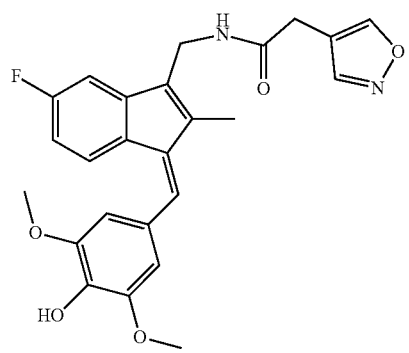 2112 | 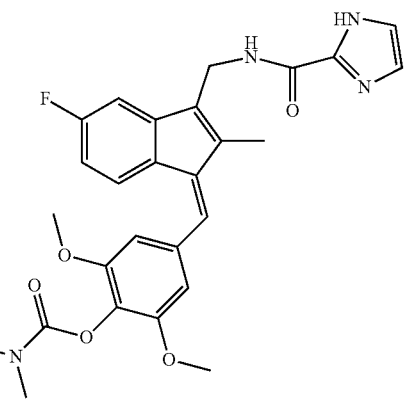 2116 |
| 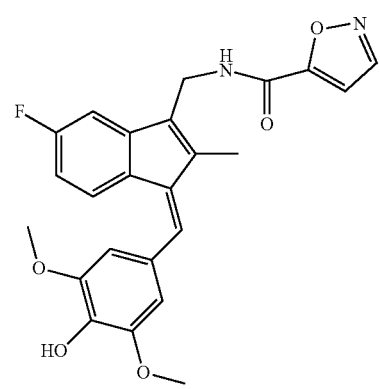 2113 | 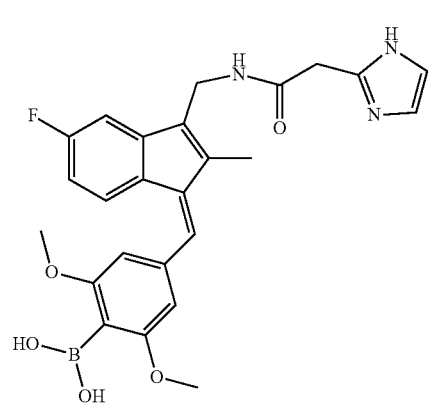 2117 |
| 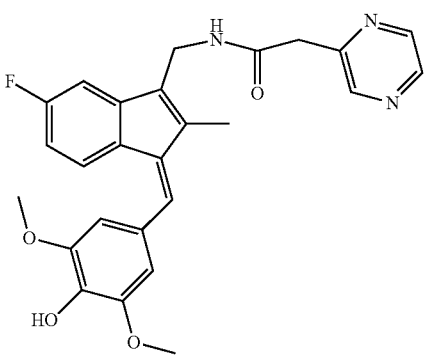 2114 | 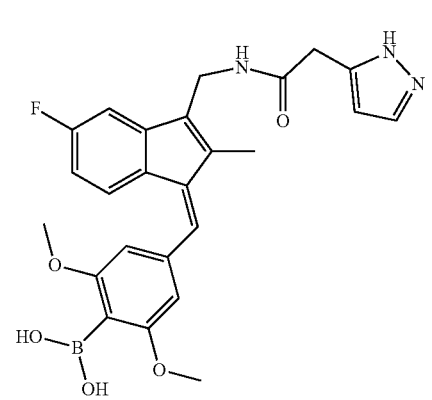 2119 |
| 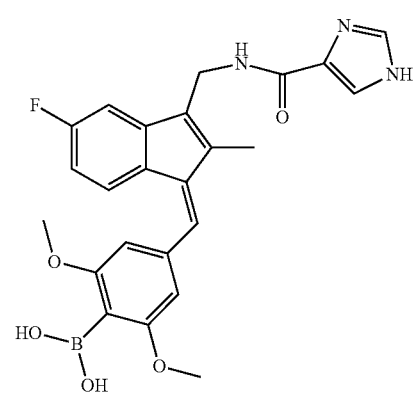 2115 | 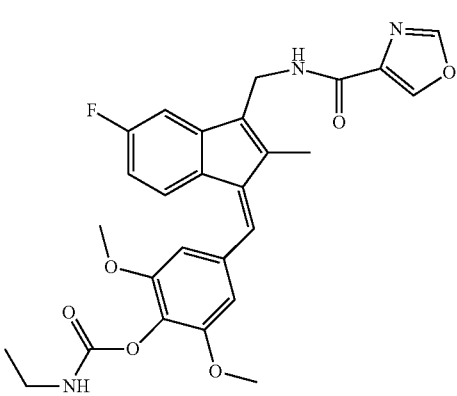 2120 |

2121
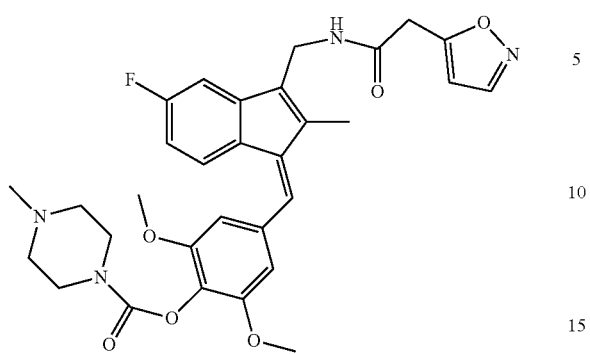
2122
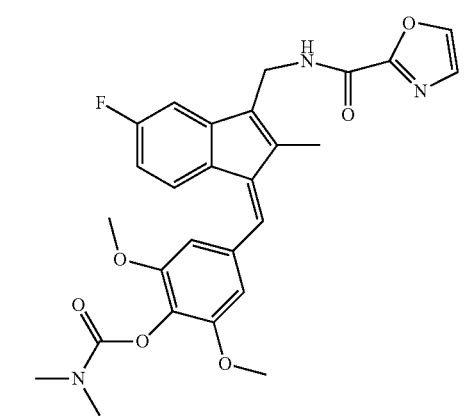
2123
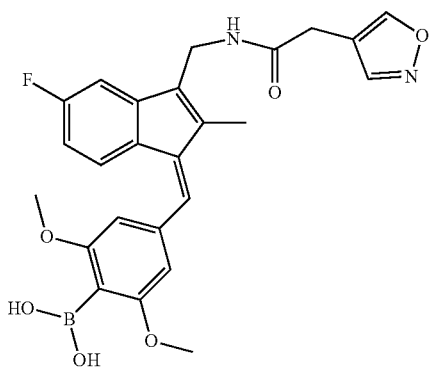
2124
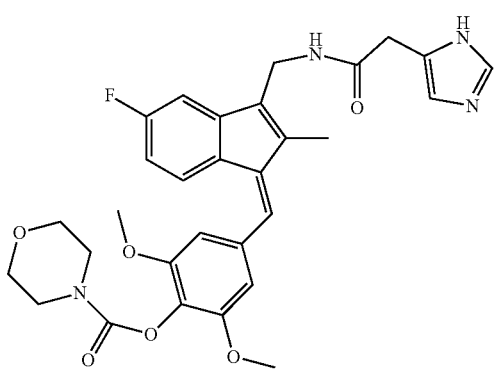
2125
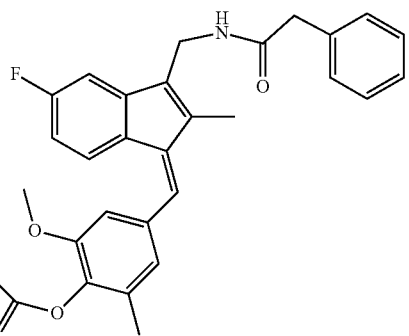
2126
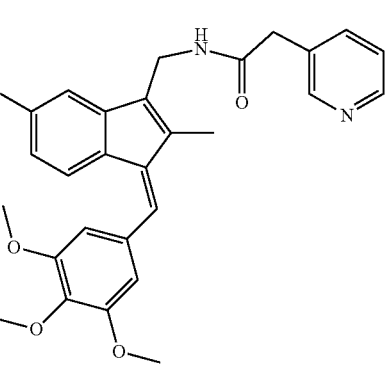
2127
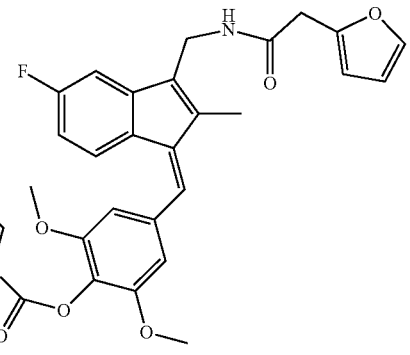
2128
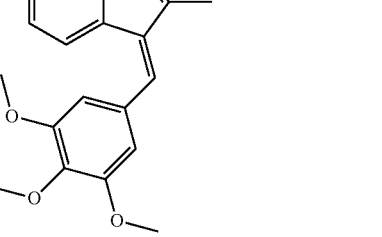

-continued

2129

2130

2131

2132

-continued

2133

2134

2135

2136

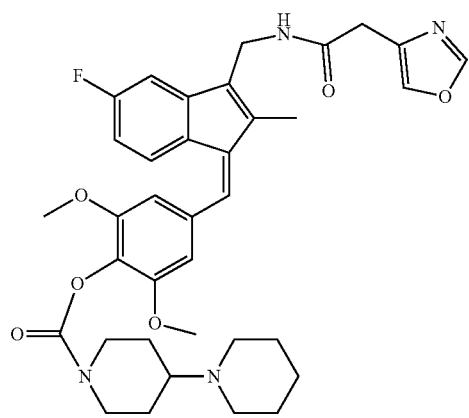
2137
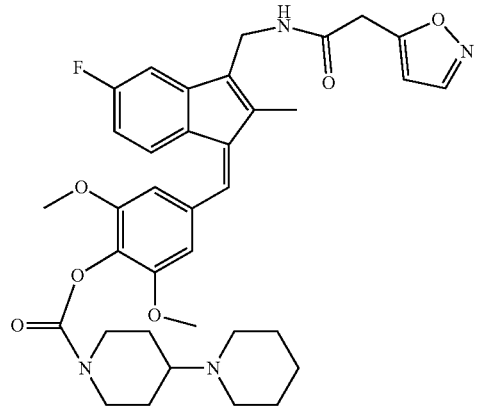
2140
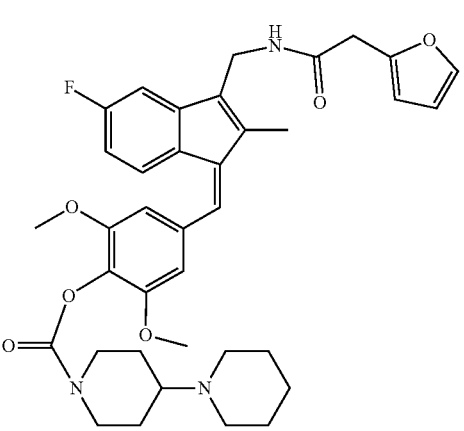
2141
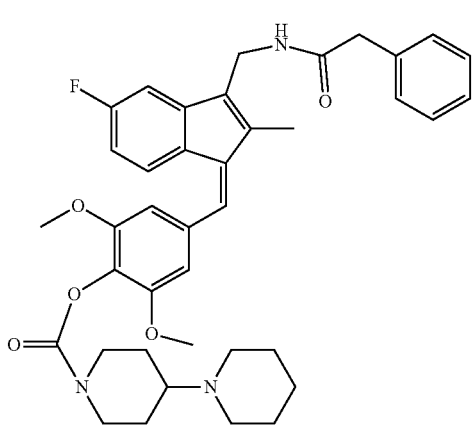
2138
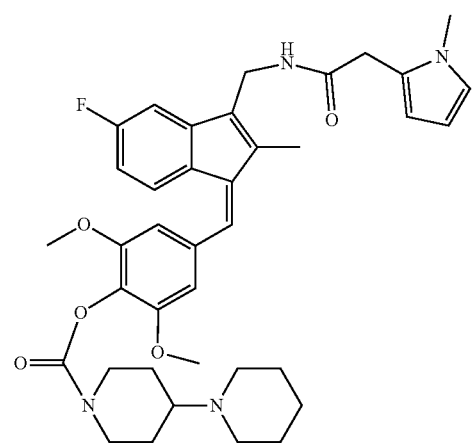
2142
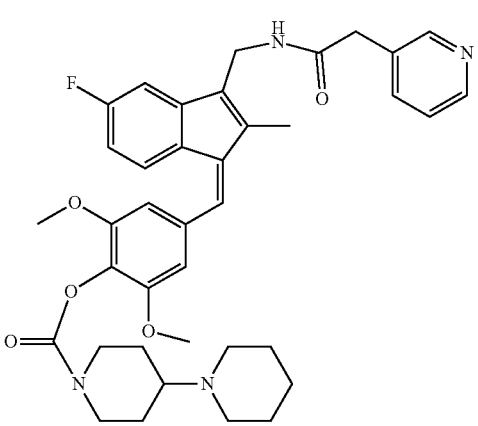
2139
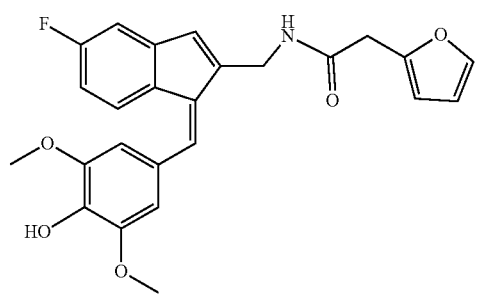
2143

2144 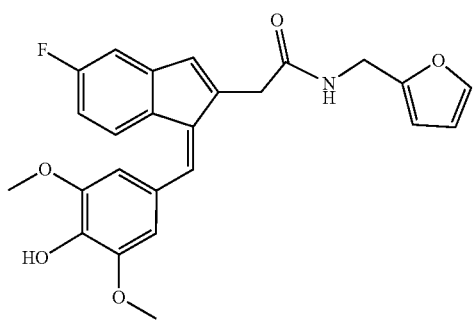
2145 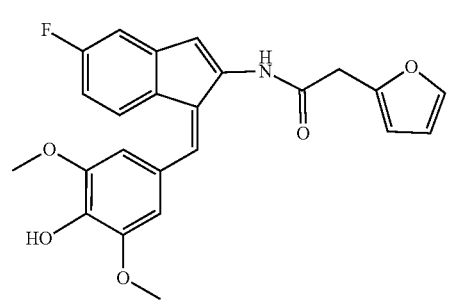
2146 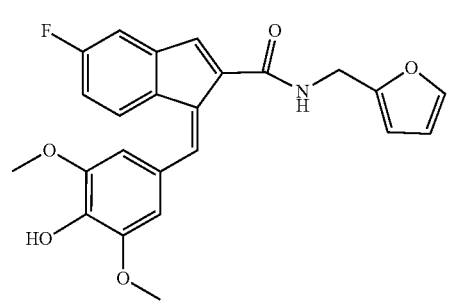
2147 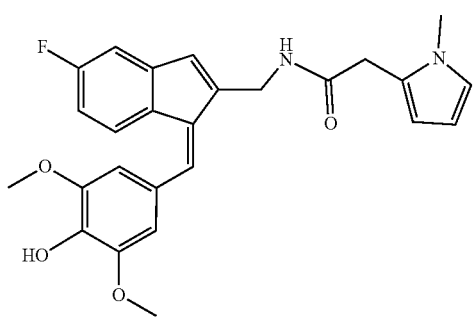
2149 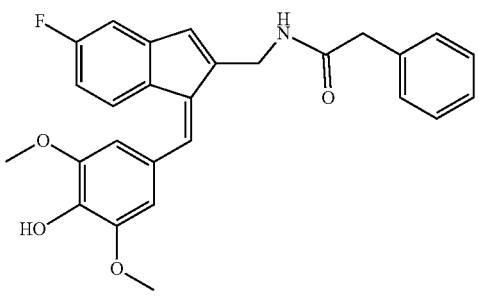
2151 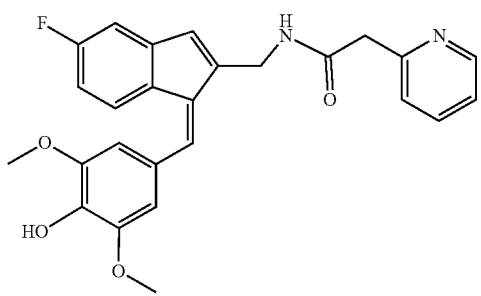
2153 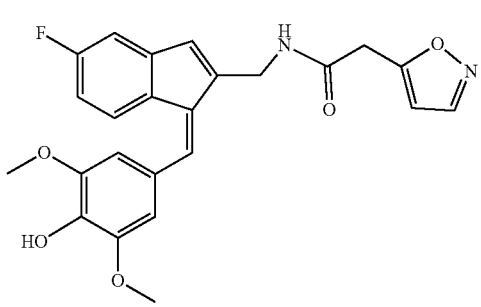
2154 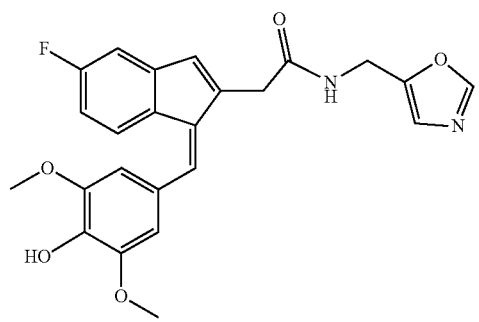
2155 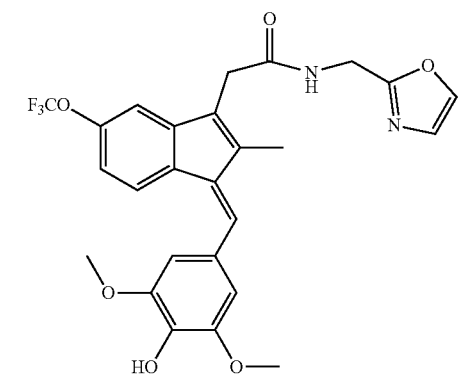

2156 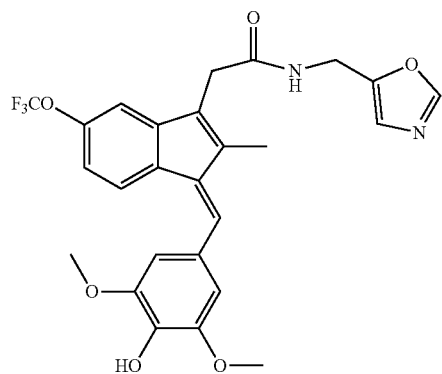
2157 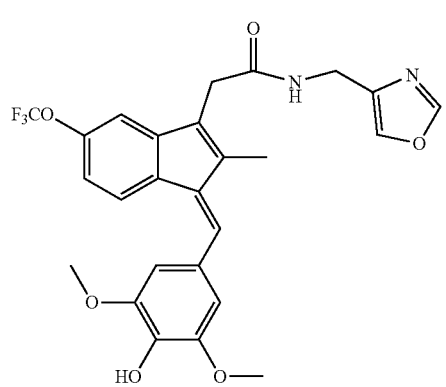
2158 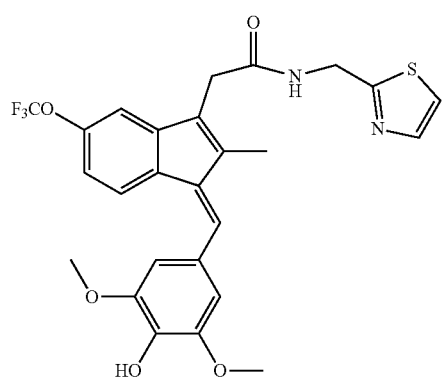
2159 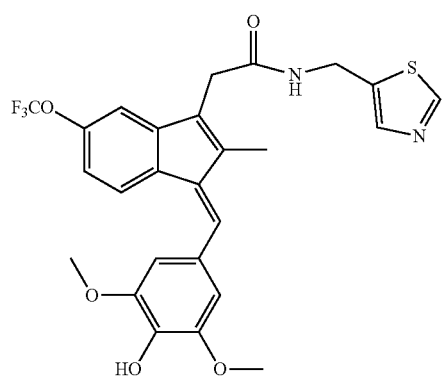
2160 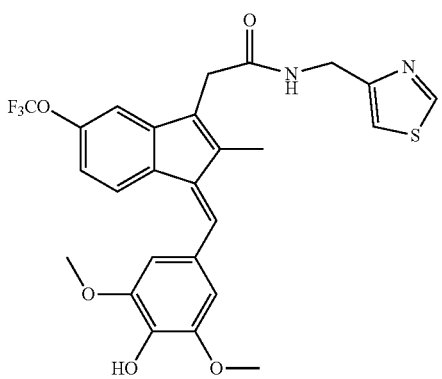
2161 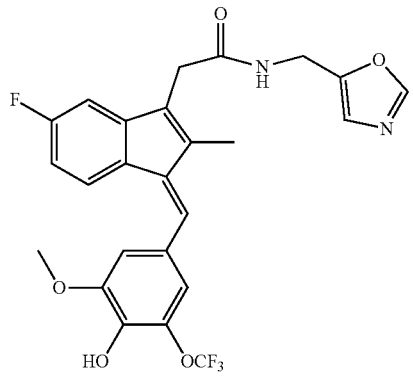
2162 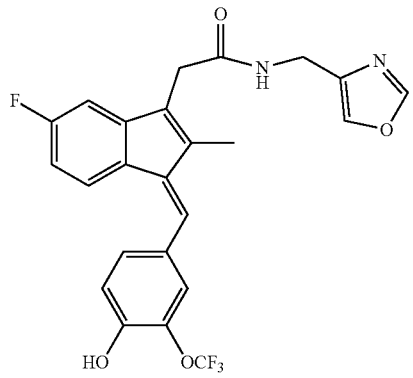
2163 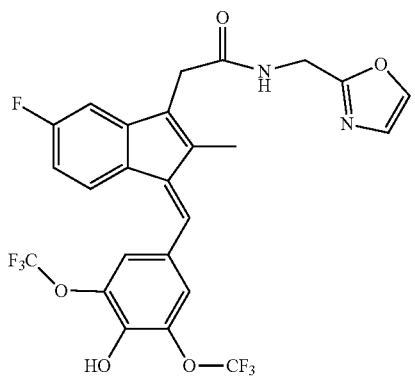

-continued
2164
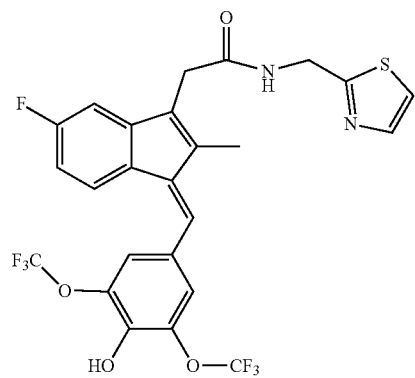
2165
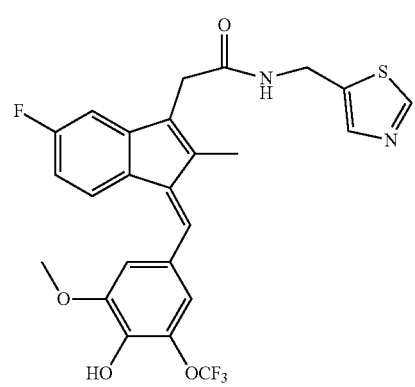
2166
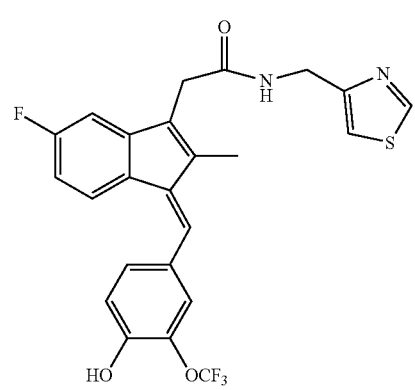
2167
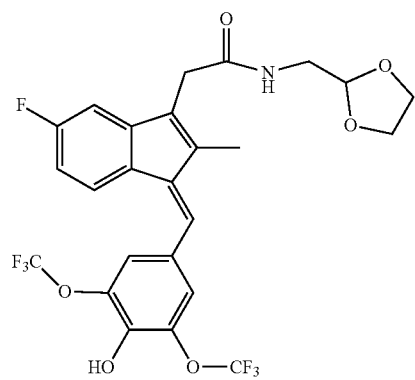
-continued
2168
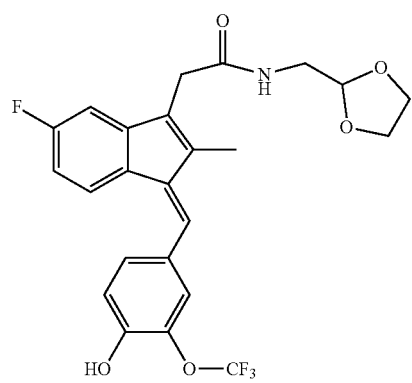
2174
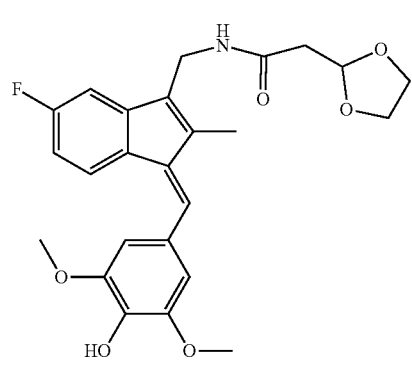
2175
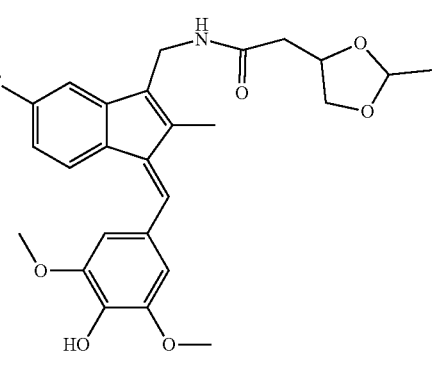
2176
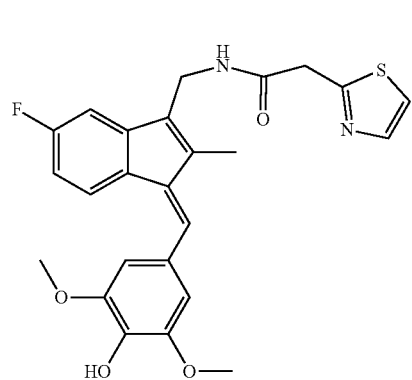

2179 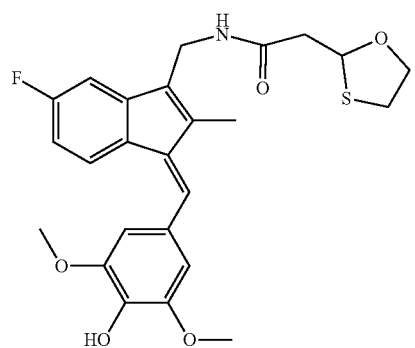
2181 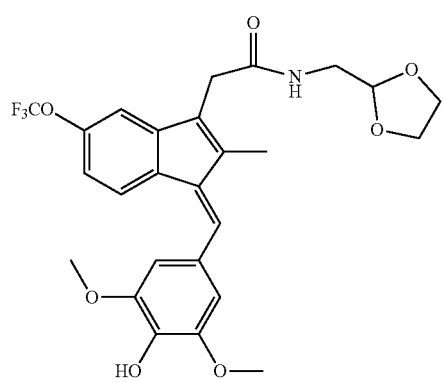
2182 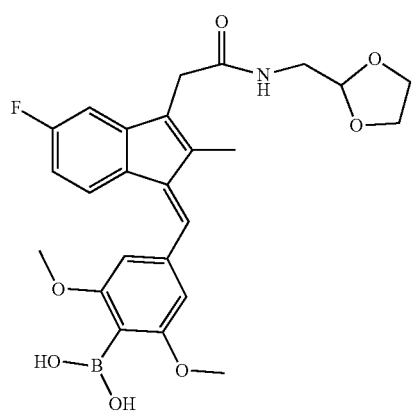
2183 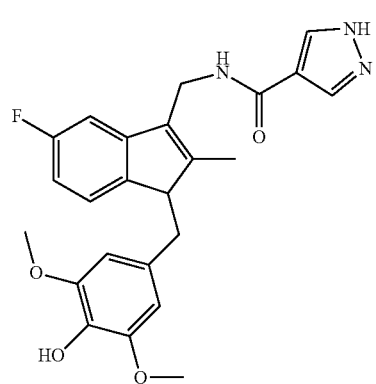
2184 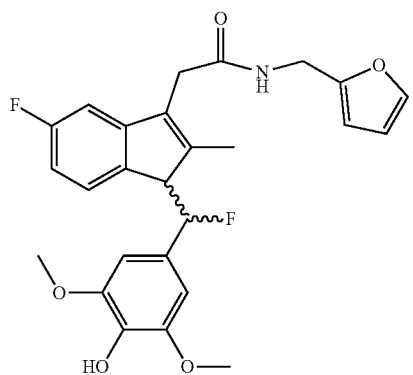
2185 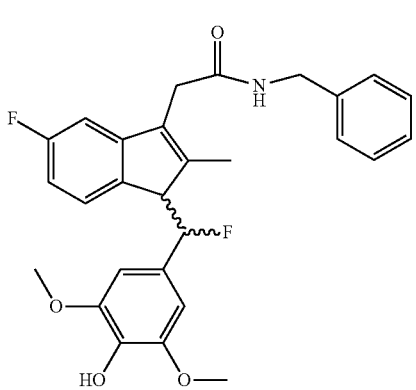
2186 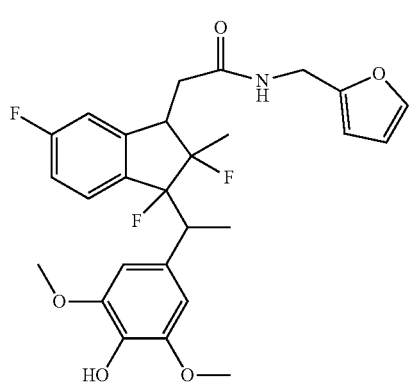
2187 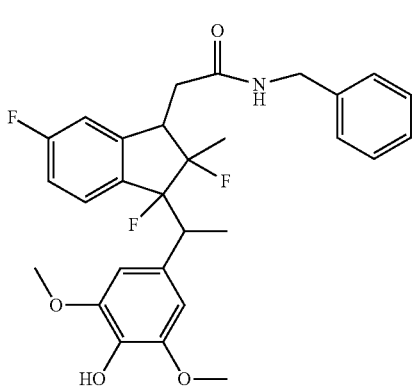

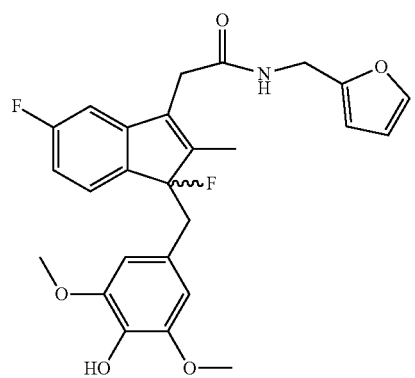
2188
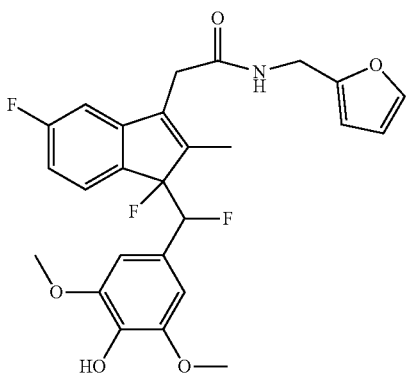
2192
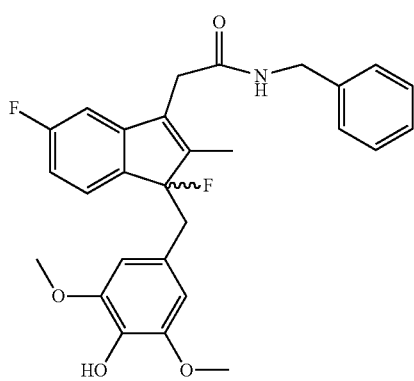
2189
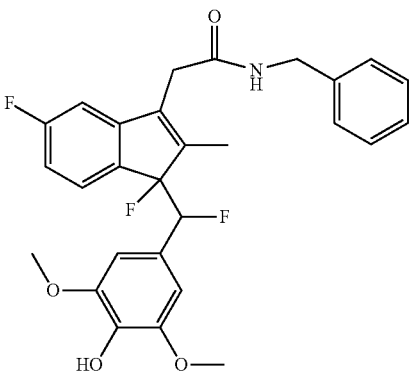
2193
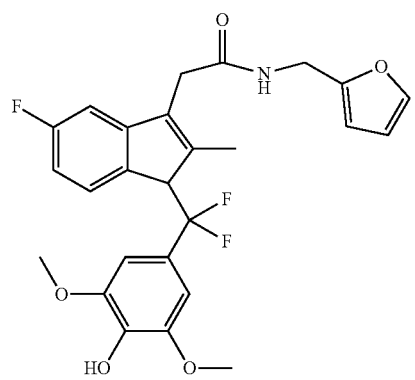
2190
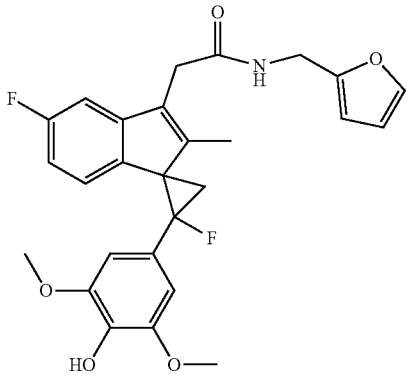
2194
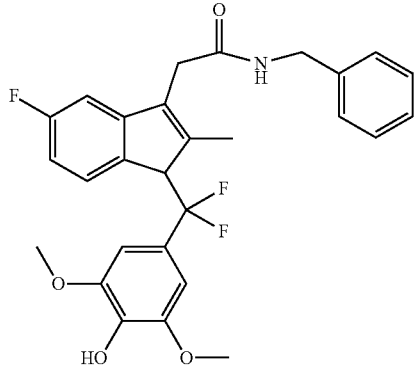
2191
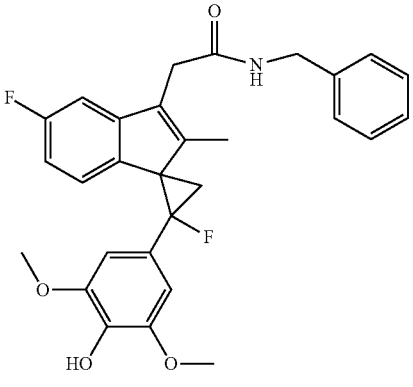
2195

2196 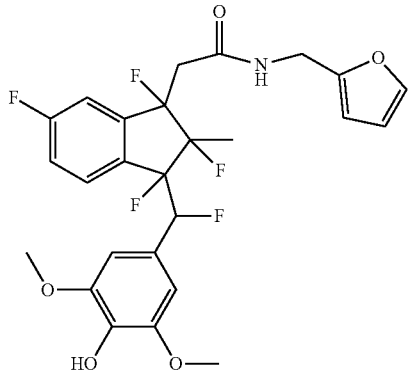

2197 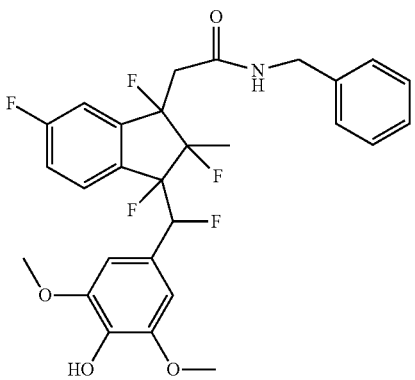

2198 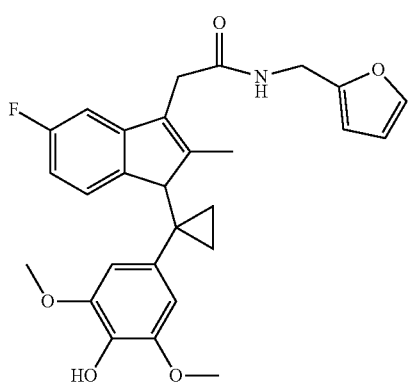

2199 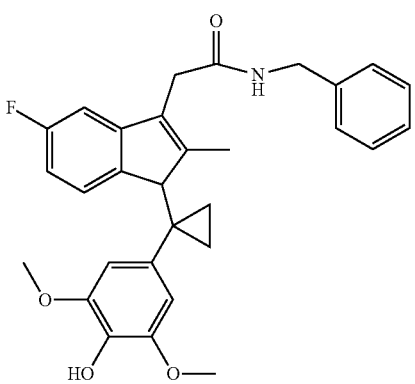

2200 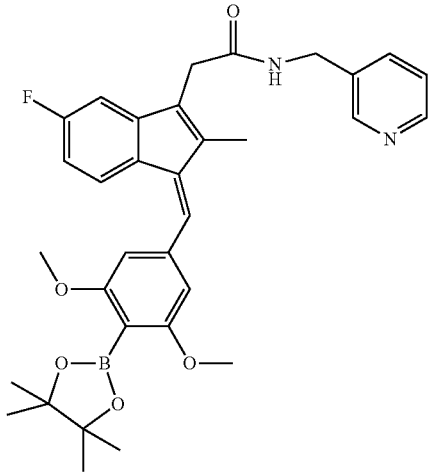

The present invention also provides a pharmaceutical composition comprising a compound of formula Ia or IIa, or pharmaceutically acceptable salt or prodrug thereof, and a pharmaceutically acceptable carrier.

In an embodiment, the pharmaceutical composition further includes at least one therapeutic agent, which is not a compound of formula Ia or IIa or salt or prodrug thereof.

The present invention further provides a method of therapeutically treating a human or nonhuman mammalian patient with cancer comprising administering to said patient an effective amount of at least one compound of Ia or IIa, or pharmaceutically acceptable salt or prodrug thereof, either alone or in combination with at least one additional agent which is selected from an anticancer agent and radiation.

In an embodiment, the patient with cancer is a patient in whom the cancer is one or more of the following types of cancer: pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, and leukemia.

In a preferred embodiment, the cancer is selected from pancreatic cancer, colorectal cancer, and lung cancer.

In another preferred embodiment, the cancer is drug-resistant or radiation-resistant.

The present invention further provides a method of treating a human or nonhuman mammalian patient with a disease or condition treatable by the inhibition of one or more neoplastic or cancerous process, which method comprises administering to a patient in need thereof an effective amount of at least one neoplastic or cancerous inhibitory compound of formula Ia or IIa, or pharmaceutically acceptable salt or prodrug thereof, either alone or in combination with at least one therapeutic agent which is not a compound of formula Ia or IIa or salt or prodrug thereof.

In a preferred embodiment, the neoplastic or cancerous process is selected from growth, proliferation, survival, metastasis, drug resistance and radiation resistance of a tumor cell.

In another preferred embodiment, the at least one therapeutic agent that is not a compound of formula Ia or IIa is selected from an anticancer drug and radiation.

The present invention additionally provides a compound of formula Ia or IIa, or pharmaceutically acceptable salt or prodrug or pharmaceutical composition thereof, for use in the treatment or prophylaxis of a human or nonhuman mammalian patient with cancer.

In a preferred embodiment, the invention provides a compound of formula Ia or IIa, or pharmaceutically acceptable salt or prodrug or pharmaceutical composition thereof, for use in treating a patient with a cancer selected from pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, and leukemia.

In a more preferred embodiment, the invention provides a compound of formula Ia or IIa, or pharmaceutically acceptable salt or prodrug or pharmaceutical composition thereof, for use in treating a patient wherein the cancer is pancreatic cancer, colorectal cancer, or lung cancer.

In another preferred embodiment, the compound of formula Ia or IIa, pharmaceutically acceptable salt or prodrug or pharmaceutical composition thereof, is for use in treating a patient with cancer wherein the cancer is drug-resistant or radiation-resistant.

In a further embodiment, the compound of formula Ia or IIa, or a pharmaceutically acceptable salt or prodrug or pharmaceutical composition thereof, is for use in the treatment or prophylaxis of a disease or condition treatable by the inhibition of one or more neoplastic or cancerous process in a human or nonhuman mammalian patient, either alone or in combination with at least one therapeutic agent which is not a compound of formula Ia or IIa or salt or prodrug thereof.

In a preferred embodiment, the compound or a pharmaceutically acceptable salt or prodrug or pharmaceutical composition thereof, is for use in inhibiting a neoplastic or cancerous process selected from growth, proliferation, survival, metastasis, drug resistance and radiation resistance of a tumor cell.

In another embodiment, the anticancer compounds provided by the invention include Ras-inhibitory compounds. A Ras-inhibitory compound can be identified from one or more compounds of formulas Ia and IIa by an assay of Ras inhibition. Some representative assays of selective Ras inhibition are illustrated in the examples that follow herein. As used herein, the terminology selective "Ras inhibition" means selective, preferential or specific inhibition of aberrant Ras-mediated cellular processes, such as, for example, accelerated or aberrant cell growth, proliferation, survival, and invasiveness, relative to these processes in cells or tissues with normal or non-aberrant Ras and Ras-mediated processes. Experimentally, selective Ras inhibition can be shown, for example, by determining the ratio (numerator/denominator) of a given compound's potency (e.g., IC50) to inhibit the growth of cells with "normal" or "wild-type" Ras (numerator) relative to that of cells with mutated and/or activated Ras (denominator). The terminology used herein for such an experimentally determined ratio is "selectivity" or "selectivity index", which is further denoted by showing the respective cell types used to determine the numerical ratio (e.g., HT-29/A549; Caco-2/SW-480; HT-29/SW-480; HT-29/CCT-116). For a given compound, a "selectivity" value or "selectivity index" of greater than 1 (one), preferably greater than 10 (ten), more preferably greater than 100 (one hundred) and even more preferably greater than 1000 (one thousand) indicates said compound selectively inhibits hyperactive Ras and/or Ras-mediated cellular functions, such as those which may drive or accelerate cancer cell growth, proliferation, metastasis, resistance to drugs or radiation, and the like.

In another preferred embodiment of the present invention, the aforementioned assay of Ras inhibition employs one or more isogenic cell line pair(s), wherein both of the lines share the same genetic background except that one of the lines ("mutant line") contains one or more mutated or hyperactive ras gene(s), Ras protein(s) and/or aberrant Ras-mediated biological process(es), and the other line ("normal line") lacks such mutation(s) or aberrant function(s).

In a further preferred embodiment of the present invention, the assay employing isogenic cell line(s), enables the determination and calculation of a Ras-Inhibitory Specificity Index (RISI). One experimental approach to determination of such a RISI may, for example, comprise determining the ratio of the concentration of a compound producing a specified effect on the normal line or Ras-deficient line, such as, for example, 50% growth inhibition in a specified period of time, divided by the concentration of the same compound producing the same specified effect (e.g., 50% growth inhibition in the same specified period of time) on the mutant line.

Whereas in the aforementioned approach, the 50% growth inhibition values may be obtained by testing the compound against both normal and mutant cell lines at multiple concentrations over a specified concentration range, for example 10 nM-10,000 nM, an alternate, more streamlined approach to determining a RISI value could comprise measuring the ratio of percentage growth inhibition in a given period of time by a specified single concentration of the compound, for example 250 nM, selected from within a range of concentrations, for example from within a range of 10 nM-10,000 nM, against the Ras mutant relative to the normal or Ras deficient cell line. This approach may be generally more applicable to larger-scale or preliminary screening of groups of individual compounds or mixtures thereof to obtain a preliminary or screening RISI, whereas a RISI determined using concentration ranges to determine 50% growth inhibition values may be more precise. A RISI value obtained for a given compound by either approach may be less than, equal to or greater than 1 (one), and a RISI value of greater than 1 (one) indicates said compound selectively inhibits Ras or Ras-mediated cellular functions.

In a highly preferred embodiment of the present invention, the employed assay of Ras inhibition enables identification of a compound from one or more compounds of formulas Ia or IIa having a RISI of greater than 1, preferably greater than 10, more preferably greater than 100, and even more preferably greater than 1000.

The present invention yet further provides a pharmaceutical composition comprising a therapeutically effective amount of Ras-inhibitory activity from one or more Ras-inhibitory compound(s) of formula Ia or IIa, or pharmaceutically acceptable salt(s) or prodrug(s) thereof, alone or in combination with at least one therapeutic agent which is not a compound of formula Ia or IIa, or salt or prodrug thereof. The therapeutically effective amount can be that amount provided by a Ras-inhibiting and/or a disease-process inhibiting effective amount, such as an anticancer effective amount, of a compound of formula Ia or IIa, or pharmaceutically acceptable salt or prodrug thereof.

In addition, the present invention provides a method of therapeutically or prophylactically treating a condition treatable by the inhibition of Ras-mediated biological processes including, for example, tumor cell growth, proliferation, survival, invasion and metastasis, as well as resistance to chemotherapy, other molecularly targeted therapeutics, and radiation; and, a method of therapeutically or prophylactically treating cancers harboring hyperactive or mutant Ras. These methods comprise administering a therapeutically or prophylactically effective amount of Ras-inhibiting activity from at least one Ras-inhibitory compound, or pharmaceutically acceptable salt or prodrug thereof, of formula Ia or IIa.

For example, the disease or condition treatable by the inhibition of one or more Ras-mediated biological process is cancer, neurofibromatosis, or Costello syndrome. In an embodiment, the Ras-mediated biological process is selected from growth, proliferation, survival, metastasis, drug resistance and radiation resistance of a tumor cell.

In an embodiment of the above method, the patient is pre-selected by utilizing an assay of the patient's tissue, blood or tumor for an abnormal, mutant or hyperactive ras gene or Ras protein, or an aberrant Ras-mediated biological process.

In an embodiment, the patient's tissue, blood or tumor contains an abnormal, mutant or hyperactive ras gene or Ras protein, or aberrant Ras-mediated biological process.

The compounds in the present invention also can be in the form of a pharmaceutically acceptable salt, which may include, for example, the salt of one or more acidic substituents (e.g. a carboxylic salt, a sulfonic acid salt, and the like) and the salt of one or more basic substituents (e.g. the salt of an amine, and the like). Suitable salts of acidic substituents include, for example, metal salts (e.g. sodium salts, potassium salts, magnesium salts, zinc salts, and the like) and ammonium salts (e.g., NH4+ salts, alkylammonium salts, quaternary ammonium salts, and the like). Suitable salts of basic substituents include, for example, acid addition salts (e.g., hydrochloride salts, hydrobromide salts, carboxylate salts (e.g., acetate salts), sulfate salts, sulfonate salts (e.g., mesylate salts), phosphate salts, quaternary ammonium salts, and the like.

A compound of the present invention can also be provided as a prodrug, which is a modified drug derivative or drug precursor compound that may have desired biological activity that is the same, similar or preferable to the original drug. Typically, the modified drug is inactive or less than fully active until it is converted in the body through a normal metabolic process, such as, for example, conversion of a promoiety to a hydroxyl group, or hydrolysis of an ester or amide form of the drug, to the active drug. A prodrug may be selected and used instead of the parent drug because, for example, in its prodrug form it is less toxic, and/or may have better absorption, distribution, metabolism and excretion (ADME) characteristics, and the like, than the parent drug. A prodrug might also be used to improve how selectively the drug interacts with cells or processes that are not its intended target. This approach may be employed particularly, for example, to prevent or decrease adverse effects, especially in cancer treatments, which may be especially prone to having severe unintended and undesirable side effects.

The term "prodrug" denotes a derivative of a compound, which derivative, when administered to warm-blooded animals, e.g. humans, is converted into the desired active compound (drug). For example, the enzymatic and/or chemical hydrolytic cleavage of a derivative compound of the present invention occurs in such a manner that the proven drug form is released, and the moiety or moieties split off remain nontoxic or are metabolized so that nontoxic metabolites are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Numerous anticancer drugs used clinically, or that have been or are in development for clinical use, are prodrugs. For example, a prodrug or masking strategy has been used for anticancer drugs such as etoposide (Schacter, Semin. Oncol. 23: (6 Suppl. 13): 1-7, 1996), irinotecan (Slatter et. al., Drug Metab. Dispos. 28: 423-433, 2000), and combretastatin-A4 (Pettit et. al., J. Med. Chem. 38: 1666-1672, 1995a; Pettit et al., Anticancer Drug Des. 10: 293-309, 1995b; Kong et. al., Chem. Biol. 12: 1007-1014, 2005), all of which drugs contain at least one hydroxyl substituent potentially compromising pharmaceutical utility in a given situation.

The phosphate prodrug of etoposide is highly water-soluble, yet with essentially identical anticancer efficacy in vivo as the parent drug (Schacter, supra). Irinotecan is a more aqueous-soluble carbamate prodrug of an anticancer active metabolite of the natural product, camptothecin (Slatter et al., supra). Combretastatin-A4 is a natural product (Pettit et al., 1995a) with anticancer properties compromised by the poor aqueous solubility of the parent compound, leading to the synthesis of a more aqueous soluble phosphate prodrug (Pettit et al., 1995b).

In another approach to remedying the poor aqueous solubility and metabolic vulnerability of the phenolic hydroxyl group contained in combretastain-A4, Kong et al., (supra) made a combretastain-A4 derivative wherein the phenolic hydroxyl was instead a boronic acid group (said group having the formula —B(OH)2, also known as a borono group, a dihydroxyboranyl group, or a dihydroxyboryl group). Although this was deemed by Kong et. el. (supra) as a "bioisosteric" substitution, other investigators have shown that the boronic acid moiety in the anticancer drug, bortezomib, is predominantly converted in vivo to a hydroxyl group (Pekol et al., Drug Metab. Dispos. 33: 771-777, 2005). Thus, the boronic acid moiety can be considered as either a bioisosteric substitution for a hydroxyl group, or as a promoiety for in vivo conversion to a desired hydroxyl group, for example the hydroxyl group at $R_{14}$ of a compound of formula Ia or IIa of the invention described herein. Such a boronic acid derivative of a compound of formula Ia or IIa can be prepared routinely by methods well-known to one skilled in the art, for example by adaptation of methodology used by Kong et. al. (supra) for replacing a hydroxyl group in combretastatin A4 with a borono group. As a more specific example, the phenolic hydroxyl group at $R_{14}$ of a compound of the invention (or a related prior-art compound) can be replaced with a borono group by one skilled in the art using well-known methods to yield a novel and distinct, medically useful, compound of formula Ia or IIa.

The desired prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched alkyl ester moieties, e.g., ethyl esters, alkenyl esters, di-alkylamino alkyl esters, e.g., dimethylaminoethyl ester, acylamino alkyl esters, acyloxy alkyl esters (e.g., pivaloyloxymethyl ester), aryl esters, e.g., phenyl ester, aryl-alkyl esters, e.g., benzyl ester, optionally substituted, e.g., with methyl, halo, or methoxy substituents aryl and aryl-alkyl esters, amides, alkyl amides, di-alkyl amides, and hydroxy amides. As another example, an alkyloxy group can serve as a prodrug moiety for a hydroxyl group; for instance, an alkoxy group on a phenyl ring can be enzymatically demethylated in vivo to yield a phenolic hydroxyl moiety.

Knowing the disclosures herein, it will be appreciated also that a compound of the present invention can be in the form of a prodrug, and that such prodrugs can be prepared using reagents and synthetic transformations that are well-known to those having ordinary skill in the art. The effectiveness of a selected prodrug can be determined using one or more analytical methods (e.g. pharmacokinetics, bioassays, in vivo efficacy studies, and the like) that are well-known to those of ordinary skill in the art.

More specifically, a prodrug having a formula of Ia or IIa may be prepared using routine chemical procedures, such as the exemplary procedures described herein. For instance, any one of $R_1$, $R_2$, $R_3$, $R_4$, R', R" or any substituent on E of formula I can be of the formula Q-U-, for example,

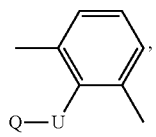

wherein U is selected from the group consisting of oxygen, sulfur, nitrogen, OCH2, SCH2 and NHCH2; and Q is selected from the group consisting of hydrogen, alkyl, PEG-CO, HCO, acetyl, amino acid, boronic acid, substituted benzoic acid and phosphoric acid; or, wherein Q-U- together is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, borono, boronoalkyl, carboxyalkyl, carboxyalkyloxy, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy.

Similarly, in a compound of formula IIa any one of $R_1$, $R_2$, $R_3$, $R_4$, $R_{12}$, $R_{13}$, $R_{14}$, $R_{15}$, $R_{16}$, R', or R" could be of the formula Q-U- wherein U is selected from the group consisting of oxygen, sulfur, nitrogen, OCH2, SCH2 and NHCH2; and Q is selected from the group consisting of hydrogen, alkyl, PEG-CO, HCO, acetyl, amino acid, boronic acid, substituted benzoic acid and phosphoric acid; or, wherein Q-U together is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, borono, boronoalkyl, carboxyalkyl, carboxyalkyloxy, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy, each of which groups is substituted or unsubstituted.

Suitable prodrugs may include, but not be limited to, those illustrated below for a compound of formula IIa, specifically as novel prodrug derivatives of a typical compound:

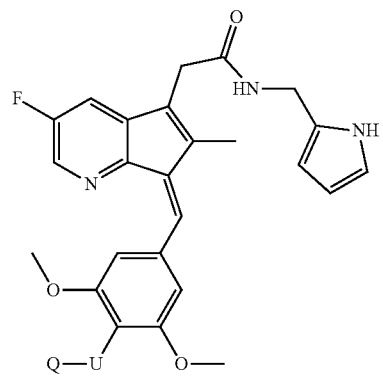

wherein U is selected from the group consisting of oxygen, sulfur, nitrogen, OCH2, SCH2 and NHCH2; and Q, for example, is selected from the group consisting of PEG-CO, HCO, acetyl, amino acid, boronic acid, substituted benzoic acid and phosphoric acid; or, Q-U together, for example, is substituted or unsubstituted phosphonooxy, phosphonooxyalkyloxy, borono, boronoalkyl, carboxyalkyl, carboxyalkyloxy, alkyloxy, alkylcarbonyloxy, alkylcarbonyloxyalkyloxy, aminocarbonyloxy, aminocarbonyloxyalkyloxy, dimethylaminocarbonyloxy, dimethylaminocarbonyloxyalkyloxy, piperidinylcarbonyloxy, piperidinylcarbonyloxyalkyloxy, dipiperidinylcarbonyloxy, or dipiperidinylcarbonyloxyalkyloxy.

As used herein, the "alkyl" part of any of the substituents described herein, e.g., including but not limited to, alkyl, alkylamino, alkylmercapto, hydroxyalkyl, polyhydroxyalkyl, alkylaminoalkyl, aminoalkyl, arylalkyl, arylcycloalkyl, heterocyclylalkyl, arylalkylenyl, arylcycloalkyl, dialkylamino, alkylcarbonyloxy, dialkylaminoalkyl, cyanoalkyl, haloalkyl, phosphonoalkyloxy, boronoalkyloxy, carboxyalkyloxy, alkylcarbonylalkylcarbonyloxy, dialkylalkylaminoalkyl, alkylsulfonyl, alkylsulfinyl, alkylsulfinyloxy, alkylsulfonyloxy, alkylenedioxy, carbocyclylalkyl, arylalkylcarbonyloxy, heteroarylcarbonyloxy, phenylalkyl, and the like, means a straight-chain or branched-chain saturated alkyl which can contain from 1-20 carbon atoms, for example from 1 to about 10 carbon atoms, or from 1 to about 8 carbon atoms, or, preferably, lower alkyl, i.e., from 1 to 6 carbon atoms. Unless otherwise specified herein, "alkyl" is assumed to mean lower alkyl.

Examples of alkyls include methyl, ethyl, propyl, isopropyl, n-butyl, sec-butyl, isobutyl, tert-butyl, pentyl, isoamyl, hexyl, octyl, dodecanyl, octadecyl, and the like. Alkyl substituents can be unsubstituted or substituted, for example with at least one substituent selected from the group consisting of a halogen, a nitro, an amino, a hydroxyl, a thio, an acyl, a mercapto, and a cyano.

The term "alkenyl" means a straight-chain or branched-chain alkenyl having one or more double bonds. Unless otherwise specified, the alkenyl can contain from 2 to about 10 carbon atoms, for example from 2 to about 8 carbon atoms, or preferably from 2 to about 6 carbon atoms. Examples of alkenyls include vinyl, allyl, 1,4-butadienyl, and isopropenyl substituents, and the like.

The term "alkynyl" means a straight-chain or branched-chain alkynyl having one or more triple bonds. Unless otherwise specified, alkynyls can contain from 2 to about 10 carbon atoms, for example, from 2 to about 8 carbon atoms, or preferably, from 2 to about 6 carbon atoms. Examples of alkynyls include ethynyl, propynyl (propargyl), butynyl, and the like. Alkenyl or alkynyl substituents can be unsubstituted or substituted, for example, with at least one substituent selected from the group consisting of a halogen, a nitro, an amino, a hydroxyl, a thio, an acyl, an alkyl, and a cyano.

The term "aryl" means an aromatic carbocyclic radical, as commonly understood in the art, and includes monocyclic and polycyclic aromatics such as, for example, phenyl and naphthyl rings. Preferably, the aryl comprises one or more six-membered rings including, for example, phenyl, naphthyl, biphenyl, and the like. Typically, the aryl comprises six or more carbon atoms in the ring skeleton thereof (e.g., from 6 to about 10 carbon atoms making up the ring). Unless specified otherwise, "aryl" by itself refers to unsubstituted aryl groups and does not cover substituted aryl groups. Substituted aryl can be an aryl substituted, for example, with at least one substituent selected from the group consisting of a halogen, a nitro, an amino, a hydroxyl, a thio, an acyl, and alkyl, and a cyano. It is to be noted that arylalkyl, benzyl, or heteroaryl groups are not considered "aryl" in accordance with the present invention.

In accordance with the invention, the term "heteroaryl" refers to a cyclic aromatic radical having from five to ten ring atoms of which at least one atom is O, S, or N, and the remaining atoms are carbon. Examples of heteroaryl radicals include pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl. Unless otherwise specified, "heteroaryl" refers to unsubstituted heteroaryl.

In further accordance with the invention, the term "heterocyclyl" refers to a stable, saturated, partially unsaturated or unsaturated monocyclic, bicyclic, or spiro ring system containing 3 to 7 ring members of carbon atoms and other atoms selected from nitrogen, sulfur, and/or oxygen. The term "heterocyclyl" includes "heteroaryl groups. Preferably, a heterocyclyl is a 5, 6, or 7-membered monocyclic ring and contains one, two, or three heteroatoms selected from nitrogen, oxygen, and/or sulfur. The heterocyclyl may be attached alone or via an alkyl linker (thus becoming a "heterocyclylalkyl") to the parent structure through a carbon atom or through any heteroatom of the heterocyclyl that results in a stable structure. Examples of such heterocyclyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl.

Further in accordance with the invention, unless otherwise specified, the term "heterocyclyl" refers to a saturated or unsaturated, unsubstituted ring consisting of 3-7 atoms, at least one of which is not a carbon atom, such as an oxygen, nitrogen or sulfur atom.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any subrange or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

Given the disclosures of the present invention, it will be appreciated that the compounds of the present invention can be made by methods well-known to those of ordinary skill in the art, for example, by structurally modifying a given compound or by direct synthesis from available building blocks using routine synthetic transformations that are well-known in the art. See for example, Sperl et al., U.S. Patent Application Publication No. US 2003/0009033 A1, Jan. 9, 2003; Sperl et al., U.S. Pat. No. 6,071,934, Jun. 6, 2000; Sperl et al., International Publication No. WO 97/47303, Dec. 18, 1997; Whitehead et al., U.S. Patent Application Publication No. US 2003/0176316 A1, Sep. 18, 2003; Thompson et al., U.S. Pat. No. 6,538,029 B1, Mar. 25, 2003; Li et al., U.S. Patent Application Publication No. US 2003/0194750 A1, Oct. 16, 2003; and Shen et al., U.S. Pat. No. 3,888,902, Jun. 10, 1975; Alcalde et al., Org. Biomol. Chem., 6, 3795-3810 (2008); Magar and Lee, Org. Lett., 15, 4288-4291 (2013).

For instance, a compound of formula Ia or IIa can be synthesized according to the general approach depicted in Scheme I

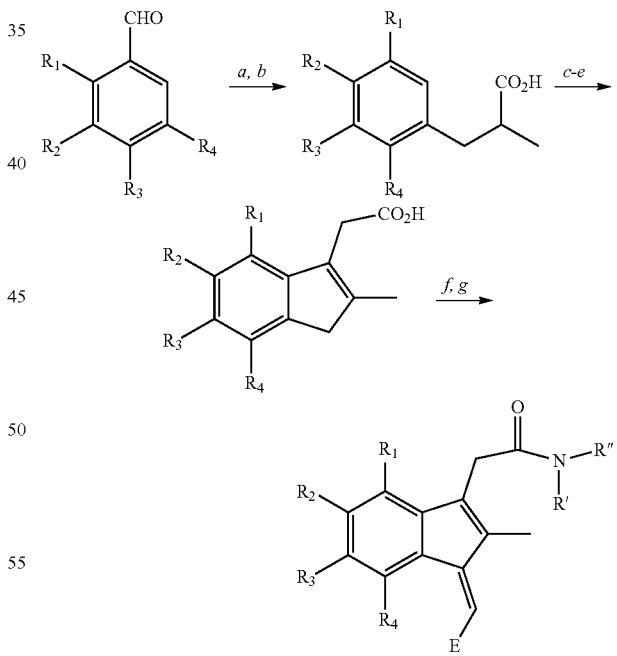

a. (EtCO)$_2$O, EtCO$_2$Na, reflux; b. H$_2$, Pd-C; c. PPA, 50-80° C.; d. NCCH$_2$CO$_2$H, AcOH, AcONH$_4$, toluene, Dean-Stark; e. KOH, H$_2$O; f. NaOCH$_3$, CH$_3$OH, E-CHO; g. (1) CDI, CH$_2$Cl$_2$, (2) R'R''NH, pyridine, warm Detailed methods to achieve all the synthesis steps depicted in Scheme I to make a desired substituted or unsubstituted indene derivative, are extensively documented in the published literature (e.g., see Sperl et al., 1997, 2000, 2003, supra; Li, et. el., 2003, supra; Thompson et al., 2003, supra; Whitehead et al., 2003, supra); Alcatel et al., 2008, supra; Magar and Lee, 2013, supra; Shen et al., 1975, supra. In Scheme I the benzaldehyde building block used for step a, and/or the aldehyde building block (E-CHO) used for step f, and/or the primary or secondary amine (R'R"NH) building block used in step g can independently be unsubstituted, or may be substituted with any desired substituent(s) required to yield the desired final product of the present invention.

For example, the benzaldehyde building block as shown in Scheme I with the desired substituents at $R_1$, $R_2$, $R_3$ and $R_4$ can be purchased commercially and/or can be prepared routinely by methods well-known to those of ordinary skill in the art. Such optional substituent(s) independently at $R_1$, $R_2$, $R_3$ and $R_4$ in Scheme I for example include but are not limited to hydrogen, halogen, alkyl, cycloalkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and a substituted or unsubstituted group selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphono, phosphonothio, phosphonoamino, phosphonoalkyl, phosphonoalkylthio, phosphonoalkylamino, phosphonooxy, phosphonoalkyloxy, sulfonamido, polyethyleneglycoxy, polyethyleneglycoxyalkyl, thioureido, borono, boronoalkyl, boronoalkyloxy, aminosulfonyl, aminocarboxyl, aminocarbonylalkyloxy, aminocarbonylalkylthio, alkylcarbonylamino, aminoalkenylamino, alkylsulfonylamino, carboxyalkyl, carboxyalkenyl, carboxyalkynyl, carboxyalkyloxy, carboxyalkylamino, carboxyalkylthio, aminoalkyloxy, aminocarbonylthio, hydroxyalkyloxy, hydroxyalkylamino, hydroxyalkylthio, dialkylaminoalkyl, aminoalkylamino, alkylaminoalkylamino, dialkylaminoalkylamino, aminoalkyloxy, alkylaminoalkyloxy, dialkylaminoalkyloxy, aminoalkylthio, alkylaminoalkylthio, dialkylaminoalkylthio and a saturated or unsaturated 3-, 4-, 5-, 6- or 7-membered carbocyclic or heterocyclic ring comprising any two of $R_1$, $R_2$, $R_3$ and $R_4$;

Likewise, the aldehyde building block (E-CHO) as shown in Scheme I with any desired group at E can be purchased and/or can be prepared by methods well-known to those of ordinary skill in the art. Such optional groups at E in Scheme I for example include but are not limited to any desired substituted or unsubstituted, saturated or unsaturated, 7-membered, 6-membered, 5-membered, 4-membered or 3-membered carbocyclic or heterocyclic ring. Substituents on said ring may include one or more of hydrogen, halogen, alkyl, cycloalkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and a substituted or unsubstituted group selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphono, phosphonothio, phosphonoamino, phosphonoalkyl, phosphonoalkylthio, phosphonoalkylamino, phosphonooxy, phosphonoalkyloxy, sulfonamido, polyethyleneglycoxy, polyethyleneglycoxyalkyl, thioureido, borono, boronoalkyl, boronoalkyloxy, aminosulfonyl, aminocarboxyl, aminocarbonylalkyloxy, aminocarbonylalkylthio, alkylcarbonylamino, aminoalkenylamino, alkylsulfonylamino, carboxyalkyl, carboxyalkenyl, carboxyalkynyl, carboxyalkyloxy, carboxyalkylamino, carboxyalkylthio, aminoalkyloxy, aminocarbonylthio, hydroxyalkyloxy, hydroxyalkylamino, hydroxyalkylthio, dialkylaminoalkyl, aminoalkylamino, alkylaminoalkylamino, dialkylaminoalkylamino, aminoalkyloxy, alkylaminoalkyloxy, dialkylaminoalkyloxy, aminoalkylthio, alkylaminoalkylthio, dialkylaminoalkylthio and a saturated or unsaturated 3-, 4-, 5-, 6- or 7-membered carbocyclic or heterocyclic ring comprising any two of $R_1$, $R_2$, $R_3$ and $R_4$;

Furthermore, the primary or secondary amine building block (R'R"NH) as shown in Scheme I can be purchased commercially and/or can be prepared routinely by methods well-known to those of ordinary skill in the art. Such optional substituents independently at R' and R" in Scheme I for example include but are not limited to hydrogen, hydroxyl, and a substituted or unsubstituted group selected from alkyl, aryloxy, cyanoalkyl, haloalkyl, alkoxy, alkenyl, alkynyl, hydroxyalkyl, polyhydroxyalkyl, alkylaminoalkyl, dialkylaminoalkyl, aminoalkyl, alkylamino, aryl, arylalkyl, arylalkenyl, arylcycloalkyl, arylcycloalkenyl, polyethyleneglycoxy, polyethyleneglycoxyalkyl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one, two or three double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, sulfonamido and $COR_{11}$, wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen and optionally oxygen or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido.

As a more specific example, a desired precursor compound for making a new compound of formula IIa can be synthesized according to the general approach depicted in Scheme II, which includes the key intermediate, a substituted indenyl acetic acid:

Scheme II

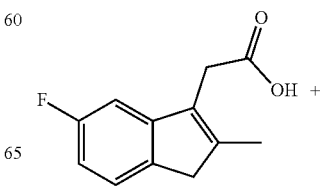

-continued

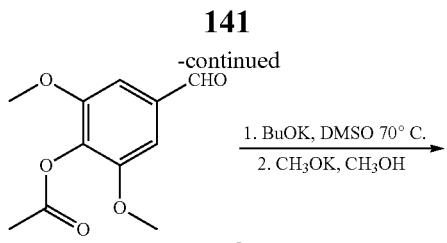

1. BuOK, DMSO 70° C.
2. CH$_3$OK, CH$_3$OH

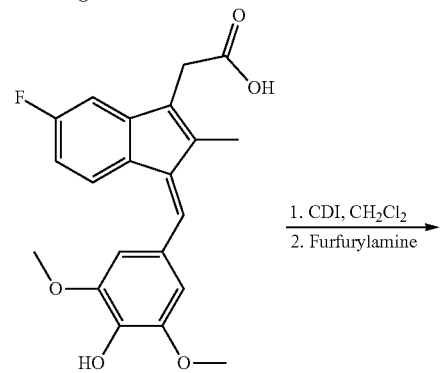

1. CDI, CH$_2$Cl$_2$
2. Furfurylamine

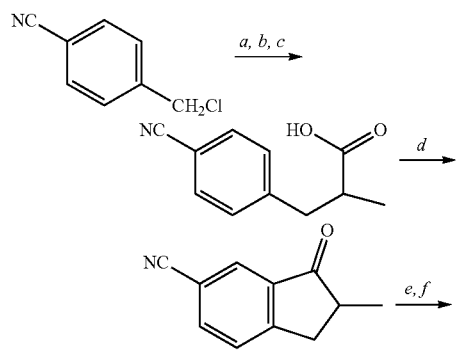

007

For certain substituents at R$_1$, R$_2$, R$_3$ or R$_4$ (e.g., in Scheme II above, R$_2$ is fluoro), the starting material for preparation of the substituted indenyl acetic acid intermediate, is optionally different than that shown in Schemes I and II, depending upon the nature of the substituent(s) desired on the intermediate and final product, and the optimum reaction conditions sought. For example, attachment of a cyano group at R$_2$ can be accomplished using as starting material a cyano-substituted benzyl halide (e.g., as adapted from Shen et al., 1975), as illustrated below in Scheme III:

Scheme III

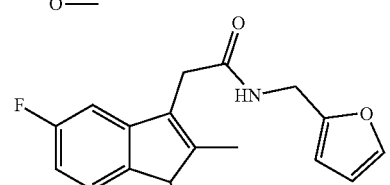

a, b, c

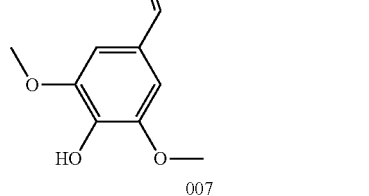

d e, f

-continued

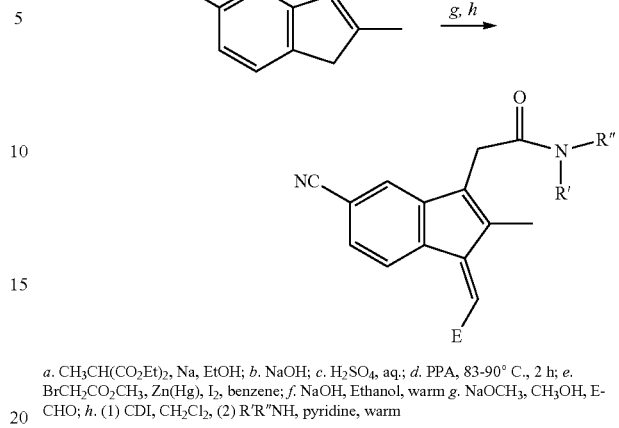

g, h a. CH$_3$CH(CO$_2$Et)$_2$, Na, EtOH; b. NaOH; c. H$_2$SO$_4$, aq.; d. PPA, 83-90° C., 2 h; e. BrCH$_2$CO$_2$CH$_3$, Zn(Hg), I$_2$, benzene; f. NaOH, Ethanol, warm g. NaOCH$_3$, CH$_3$OH, E-CHO; h. (1) CDI, CH$_2$Cl$_2$, (2) R'R"NH, pyridine, warm A wide variety of substituents can be introduced at R$_1$, R$_2$, R$_3$ and R$_4$ of a compound of formula Ia and IIa during synthesis. In addition to the above-described Schemes I-III, Scheme IV below illustrates yet another approach to making variations in substituents at R$_1$-R$_4$.

Scheme IV

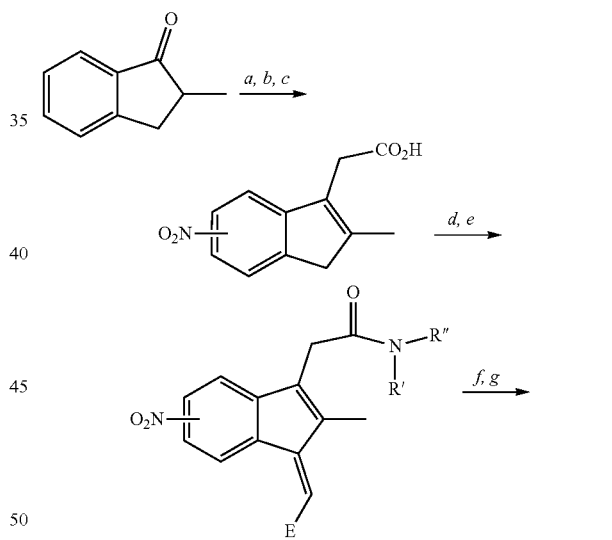

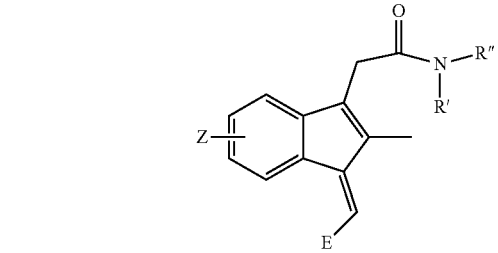

a. KNO$_3$, H$_2$SO$_4$, 46%; b. NCCH$_2$CO$_2$H, AcOH, AcONH$_4$, toluene, Dean-Stark; c. (1) KOH, EtOH, H$_2$O, (2) HOAc; d. NaOCH$_3$, CH$_3$OH, E-CHO; e. (1) CDI, CH$_2$Cl$_2$, (2) R'R"NH, pyridine, warm; f. Zn, HOAc; g. standard procedure Z = NR'R", NHSO$_2$R, isocyanide, NHCOR, azide, urea, carbamate, halogen, OH, Schiff base, etc.

Extensive variations can also be made in R and/or R$_0$ in a medically useful compound of formula Ia or IIa of the invention. For example, one skilled in the art can use or adapt as necessary the general synthesis approach illustrated by Scheme V below.

Scheme V

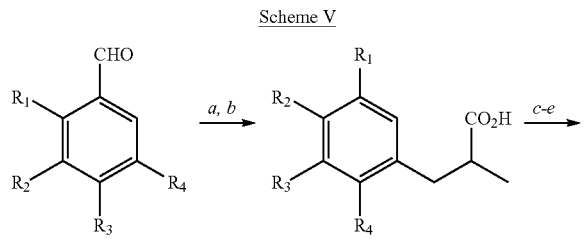

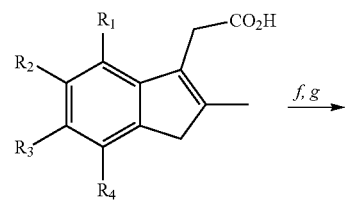

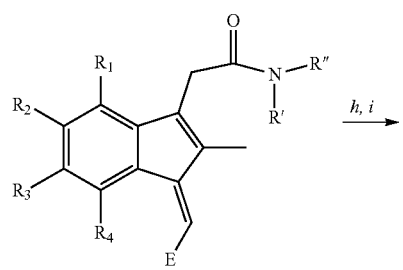

a. (EtCO)$_2$O, EtCO$_2$Na, reflux; b. H$_2$, Pd-C; c. PPA, 50-80° C.; d. NCCH$_2$CO$_2$H, AcOH, AcONH$_4$, toluene, Dean-Stark; e. KOH, H$_2$O; f. NaOCH$_3$, CH$_3$OH, E-CHO; g. (1) CDI, CH$_2$Cl$_2$, (2) R'R''NH, pyridine, warm; h. DCM, -15° C., DDQ; i. R$_0\ominus$ ethanol, 85° C.

In a more specific example illustrated in Scheme VI below, an available compound of formula Ib can serve as the starting point for making new, medically useful derivatives thereof which have various substituents at R and/or R$_0$. This approach may likewise be adapted to make novel compounds of the present invention by selection and incorporation of appropriate building block compounds into the scheme.

Scheme VI

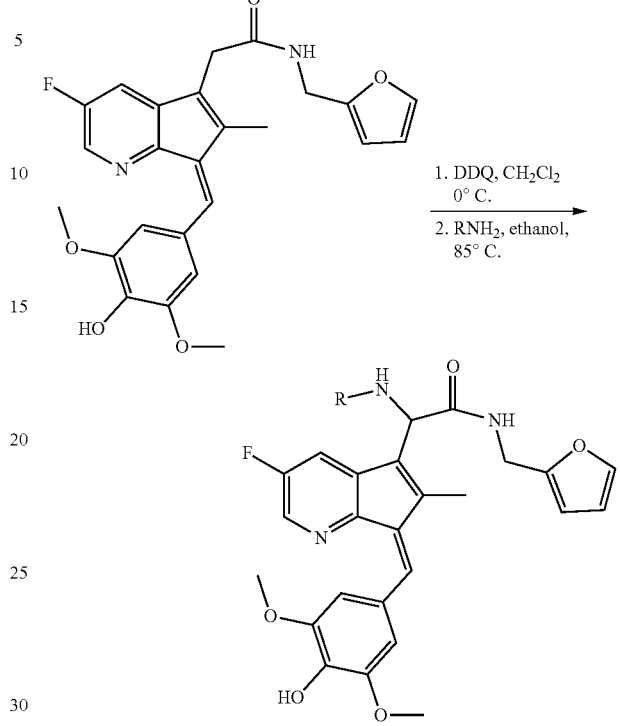

Furthermore, variations in the length of the side-chain linkers in the compounds of formula Ia and IIa can be introduced by one of ordinary skill in the art by adapting known methods. For example, adaptations of the methods of Magar and Lee 2013, supra, can be used to produce such compounds wherein n=0.

One skilled in the art will also appreciate that Schemes I-IV can be used, with routine adaptations well-known to the skilled artisan, to make compounds of formula Ia and IIa wherein R$_5$ and R$_{20}$ together form a double bond, rather than wherein R$_9$ and R$_{20}$ together form a double bond. Such variations in location of the double bond within the cyclopentene part of the indene core structure can be accomplished routinely by incorporating the appropriate presursors into the desired one or more of Scheme(s) I-VI above.

One skilled in the art will additionally know that Schemes I-VI can be used, with routine adaptations well-known to the skilled artisan, to make compounds of the invention wherein neither R$_5$ and R$_{20}$ together, nor R$_9$ and R$_{20}$ together, form a double bond. Such compounds, containing an indane core structure, rather than an indene core structure, can be synthesized routinely by using one or more of Scheme(s) I-VI and incorporating into the syntheses the appropriate precursor compound(s) which can also be made by the skilled artisan using well-established methods in the art. Compounds of formula Ia and IIa wherein the presence, absence or location of the double bond in the 5-membered ring component of the core structure can also be made by appropriate adaptations of the Scheme(s) I-VI well-known to those of ordinary skill in the art.

The skill artisan will also appreciate that additional examples of compounds of formula Ia or IIa can be made using appropriate adaptations of the well-established Scheme(s) I-VI, as well as other familiar approaches illustrated in the following schemes.

Schemes VII-X illustrate various approached to synthesis of compounds of formula Ia and IIa wherein at least one of $A_2$, $A_4$, $A_5$, $A_6$ and $A_7$ is a nitrogen atom, and Schemes XI and XII illustrate synthesis of compounds of formula Ia or IIa wherein an amido side-chain is attached to $A_1$ directly by a nitrogen-carbon bond, or where it is attached via an alkyl linker.

Scheme VII

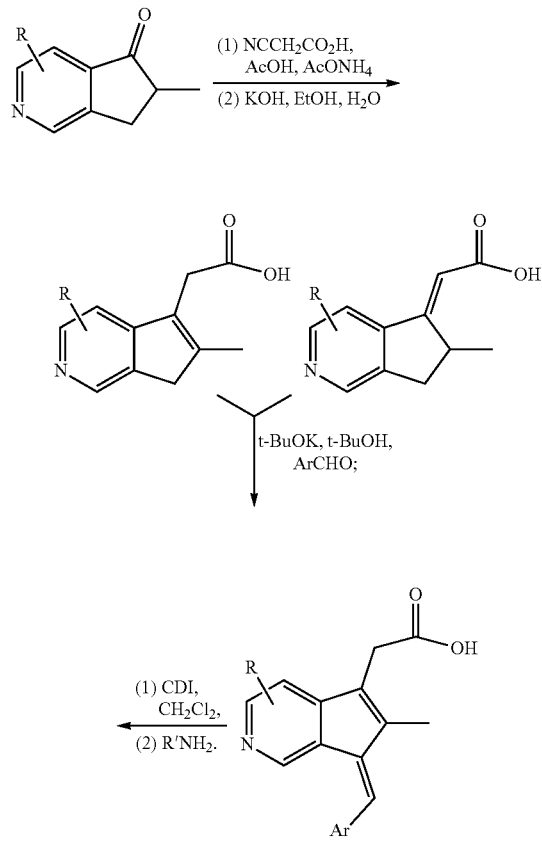

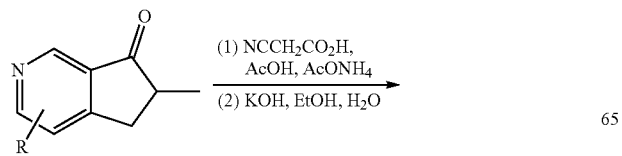

Scheme VIII

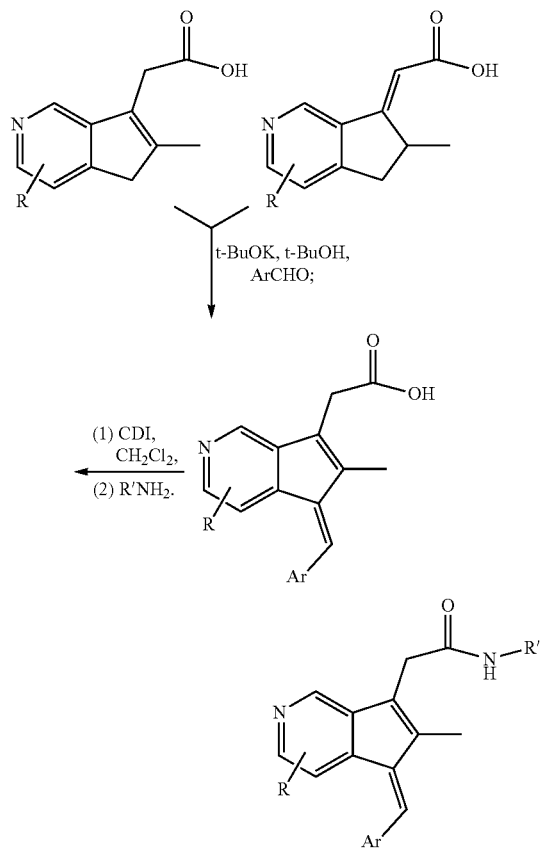

Scheme IX

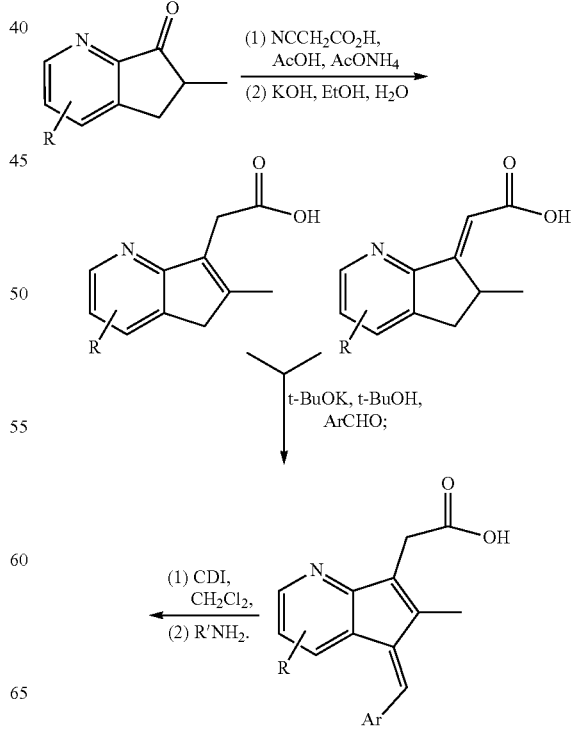

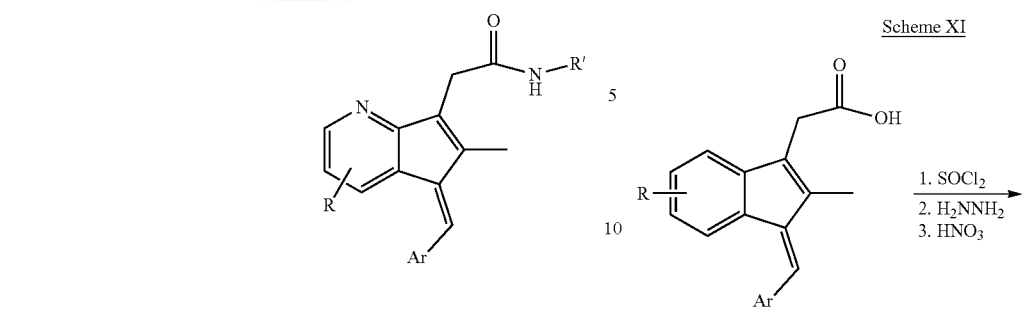
Scheme X
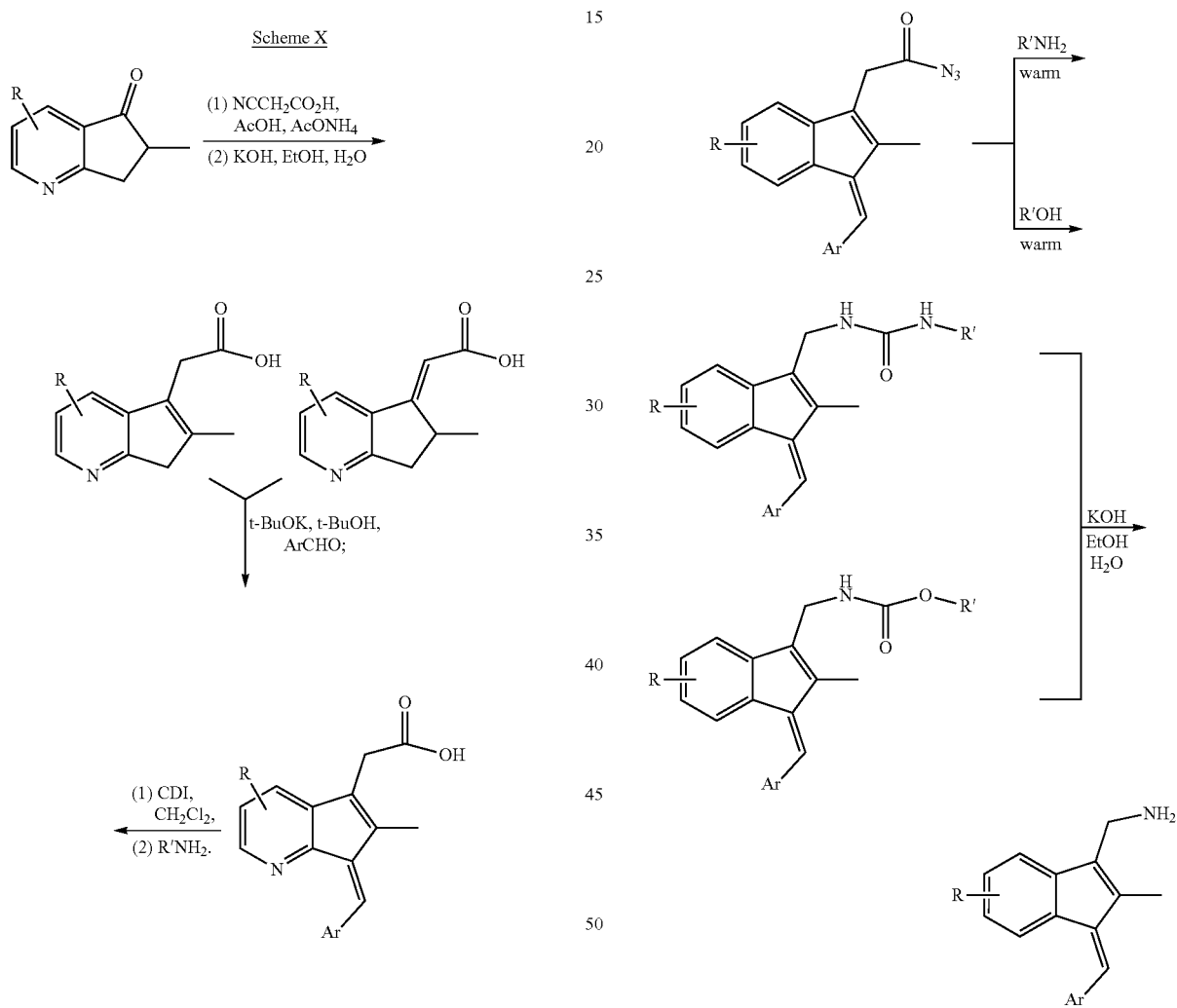
Scheme XI
Scheme XII
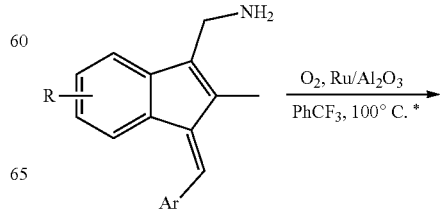

149
-continued
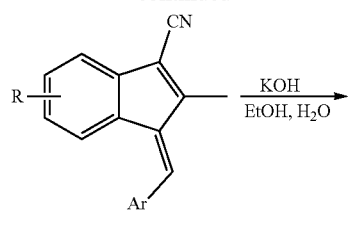
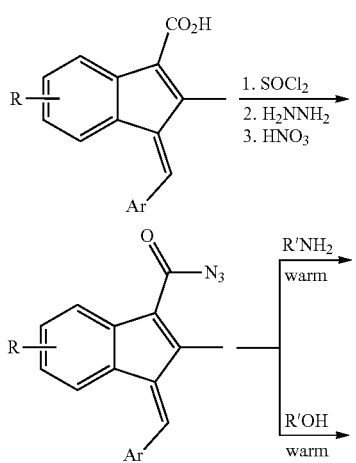
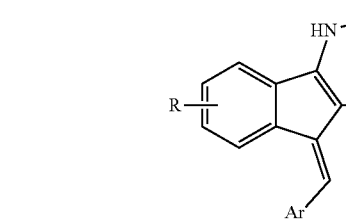
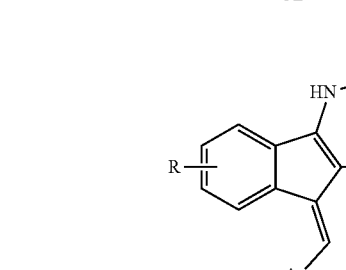
*K. Yamaguchi, N. Mizuno, *Angew. Chem. Int. Ed.*, 2003, 42, 1480-1483.
Scheme XIII (adapted from M. Murata, T. Sambommatsu, S. Watanabe, Y. Masuda, *Synlett,* 2006, 1867-1870) illustrates synthesis of a compound of formula Ia or IIa having a borono substituent on the phenyl at E:
150
-continued
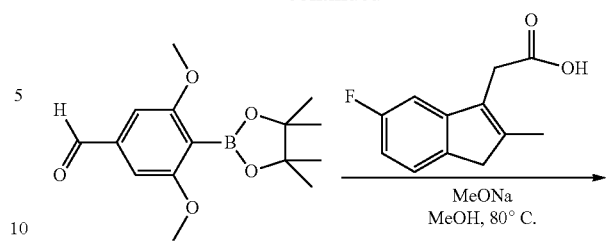
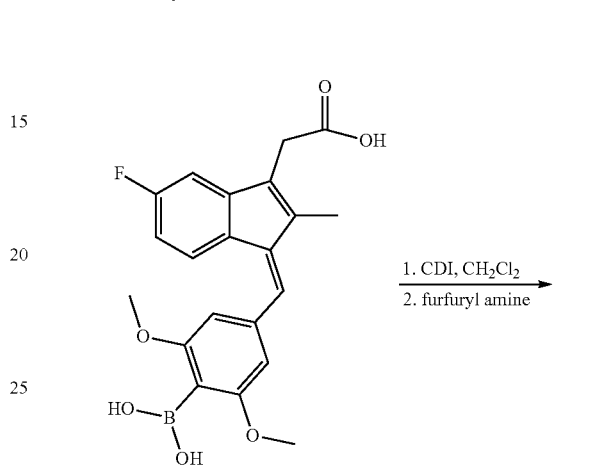
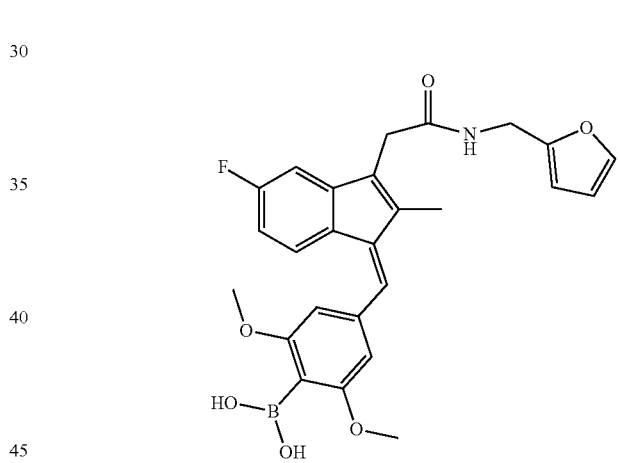
Scheme XIV illustrates synthesis of a compound of formula Ia or IIa wherein the $R_{21}$ substituent is $-(CH_2)_n NR_{22}C(O)X$:
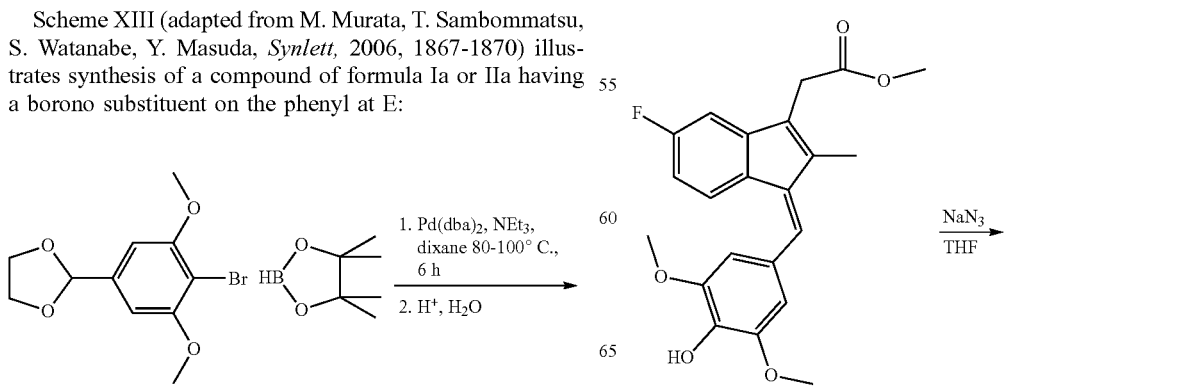

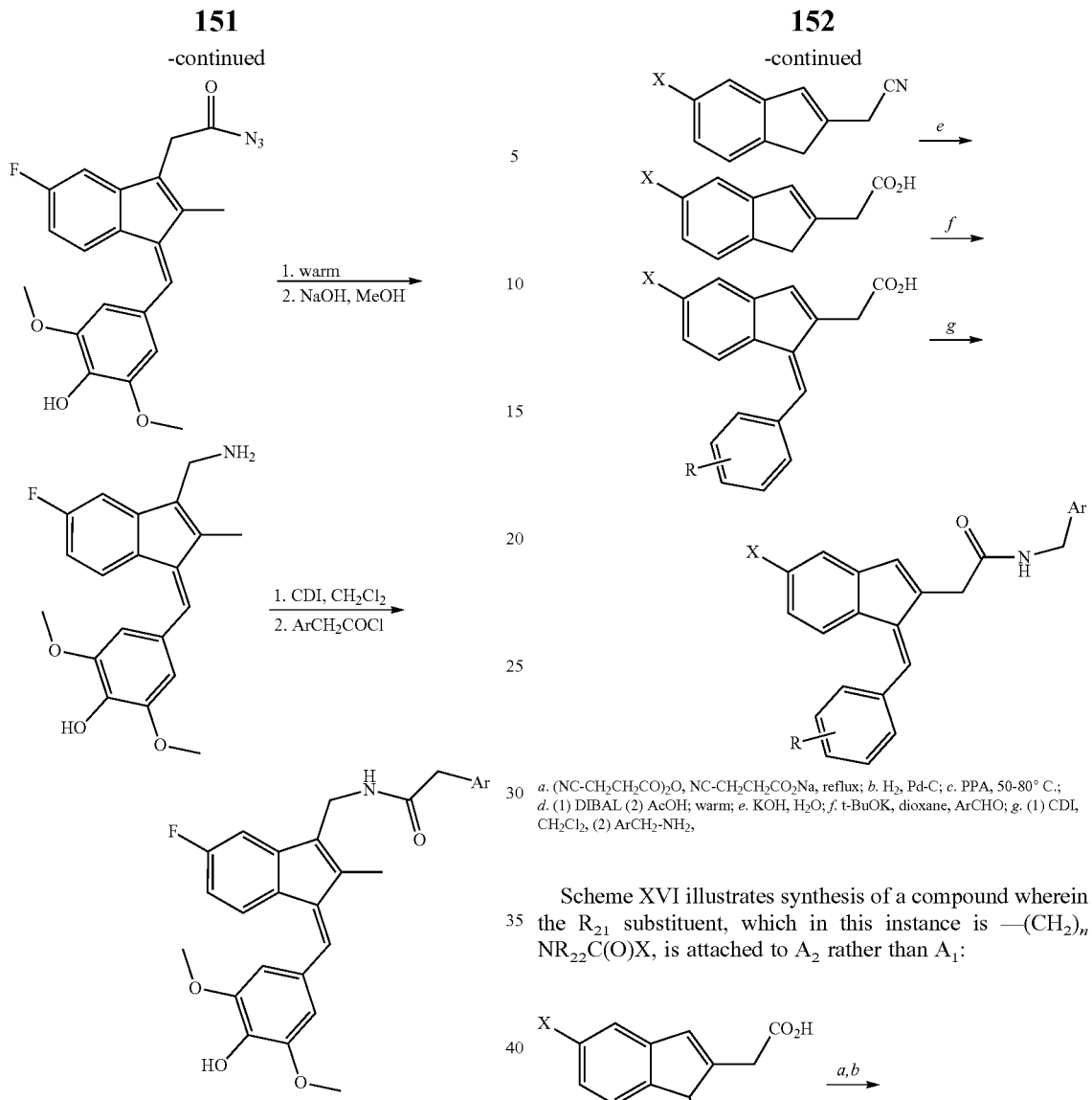

Scheme XV illustrates synthesis of a compound wherein the $R_{21}$ substituent, which in this instance is —$(CH_2)_nC(O)X$, is attached to $A_2$ rather than $A_1$:

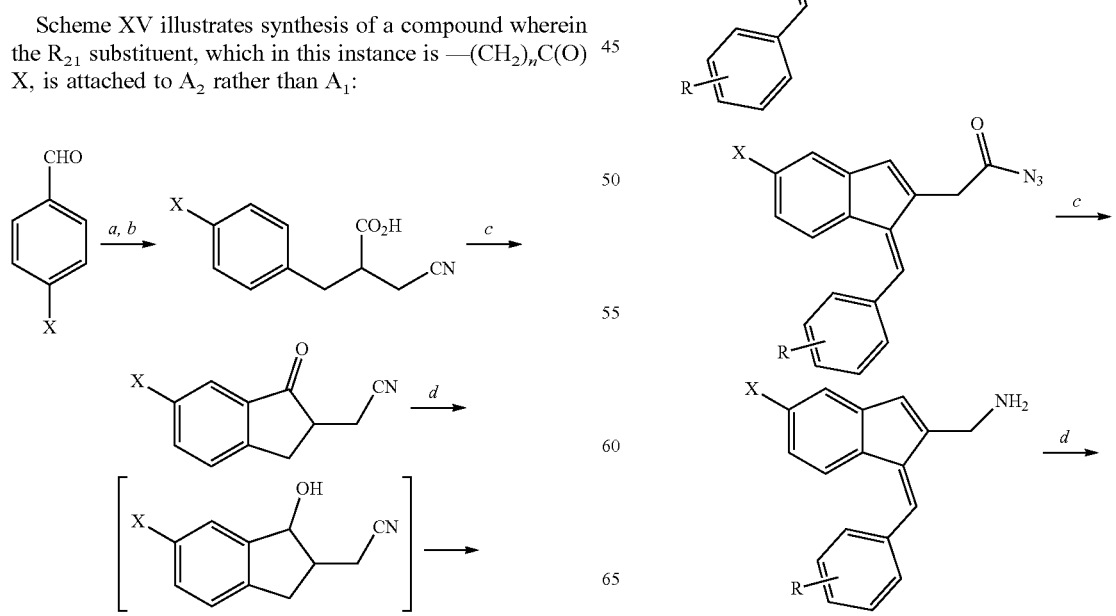

a. $(NC-CH_2CH_2CO)_2O$, $NC-CH_2CH_2CO_2Na$, reflux; b. $H_2$, Pd-C; c. PPA, 50-80° C.; d. (1) DIBAL (2) AcOH; warm; e. KOH, $H_2O$; f. t-BuOK, dioxane, ArCHO; g. (1) CDI, $CH_2Cl_2$, (2) $ArCH_2-NH_2$, Scheme XVI illustrates synthesis of a compound wherein the $R_{21}$ substituent, which in this instance is —$(CH_2)_n NR_{22}C(O)X$, is attached to $A_2$ rather than $A_1$:

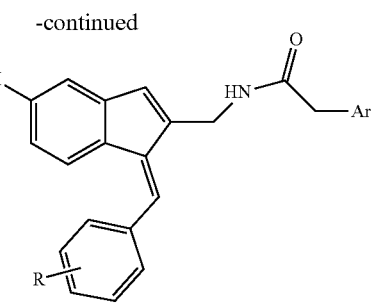

a. CH₃OH, H₃PO₄, reflux; b. NaN₃, THF; c. (1) warm, EtOH, (2) KOH, H₂O; d. (1) CDI, CH₂Cl₂, (2) ArCH₂-NH₂.

Placement, removal and/or inter-conversion of desired substituents on precursors, building blocks, intermediates or penultimate product compounds of formulas Ia and IIa can be accomplished by routine methods well-known to those of ordinary skill in the art, such as for example, briefly overviewed in the following:

One or more hydroxyl groups, for example, can be converted to the oxo derivative by direct oxidation, which can be accomplished using any known method such as, for example, a Swern oxidation, or by reaction with a metal oxidant, such as a chromium oxide (e.g., chromium trioxide), a manganese oxide (e.g., manganese dioxide or permanganate) or the like. Primary alcohols can be oxidized to aldehydes, for example, via Swern oxidation, or they can be oxidized to carboxylic acids (e.g., —CO₂H), for example by reaction with a metal oxidant. Similarly, the thiols (e.g., —SR, —SH, and the like) can be converted to oxidized sulfur derivatives (e.g., —SO₂R or the like) by reaction with an appropriate oxidant.

One or more hydroxyl groups can be converted to an ester (e.g., —CO₂R), for example, by reaction with an appropriate esterifying agent such as for example, an anhydride (e.g., (R(CO))₂O) or an acid chloride (e.g., R(CO)Cl), or the like. One or more hydroxyl groups can be converted to a sulfonate (e.g., —SO₂R) by reaction with an appropriate sulfonating agent such as, for example, a sulfonyl chloride (e.g., RSO₂Cl), or the like, wherein R is any suitable substituent including, for example, organic substituents described herein. Ester derivatives also can be obtained, for example, by reacting one or more carboxylic acid substituents (e.g., —CO₂H) with an alkylating agent such as, for example, a diazoalkane (e.g., diazomethane) an alkyl or aryl iodide, or the like. One or more amides can be obtained by reaction of one or more carboxylic acids with an amine under appropriate amide-forming conditions which include, for example, activation of a carboxylic acid (e.g., by conversion to an acid chloride or by reaction with a carbodiimide reagent) followed by coupling of the activated species with a suitable amine.

One or more hydroxyl groups can be converted to a halogen using a halogenating agent such as, for example, an N-halosuccinamide such as N-iodosuccinamide, N-bromosuccinamide, N-chlorosuccinamide, or the like, in the presence of a suitable activating agent (e.g., a phosphine, or the like). One or more hydroxyl groups also can be converted to ether by reacting one or more hydroxyls, for example, with an alkylating agent in the presence of a suitable base. Suitable alkylating agents can include, for example, an alkyl or aryl sulfonate, an alkyl or aryl halide, or the like. One or more suitably activated hydroxyls, for example a sulfonate ester, and/or one or more suitably activated halides, can be converted to the corresponding cyano, halo, or amino derivative by displacement with a nucleophile which can include, for example, a thiol, a cyano, a halide ion, or an amine (e.g., H₂NR, wherein R is a desired substituent), or the like.

Amines can be obtained by a variety of methods known in the art, for example, by hydrolysis of one or more amide groups. Amines also can be obtained by reacting one or more suitable oxo groups (e.g., an aldehyde or ketone) with one or more suitable amines under the appropriate conditions, for example, reductive amination conditions, or the like. One or more amines, in turn, can be converted to a number of other useful derivatives such as, for example, amides, sulfonamides, and the like.

Certain chemical modifications of a compound of formula Ia and IIa can be introduced as desired to obtain useful new variants with new or modified biological properties such as: new or improved potency and/or selectivity for inhibiting Ras-mediated biological processes, improved efficacy against a disease process such as, but not limited to, tumor cell growth, proliferation, survival, invasion and metastasis, as well as resistance to chemotherapy, other molecularly targeted therapeutics, and radiation, as well as enhanced oral bioavailability, less toxicity in a particular host mammal, more advantageous pharmacokinetics and/or tissue distribution in a given host mammal, and the like. Therefore, the present invention employs methods for obtaining useful new compounds of formula Ia and IIa by applying one or more well-known chemical reactions to a given compound to obtain a derivative wherein, for example, one or more phenolic hydroxyl group(s) may instead be replaced by an ester, sulfonate ester or ether group; one or more methyl ether group(s) may instead be replaced by a phenolic hydroxyl group; one or more phenolic hydroxyl group(s) may instead be replaced by an aromatic hydrocarbon substituent; a secondary amine site may instead be replaced by an amide, sulfonamide, tertiary amine, or alkyl quaternary ammonium salt; a tertiary amine site may instead be replaced by a secondary amine; and one or more aromatic hydrogen substituent(s) may instead be replaced by a halogen, nitro, amino, hydroxyl, thiol or cyano substituent.

Depending upon the stoichiometric amount of the selected reactant, a compound of formula Ia or IIa can be substituted at one, some, or all of the respective available positions. For example, when such a compound is reacted with a certain amount of CH₃COCl, an acetate substituent can be introduced a one, some, or all of the available positions, which may include, for example ether or amino positions.

Other examples may include, but are not limited to: (1) conversion to ester, sulfonate ester, and ether substituents at one or more phenolic hydroxyl positions in compounds of formula Ia and IIa; for instance, for preparation of esters or sulfonate esters a given compound can be reacted with an acid halide (e.g., RCOX or RSO₂X, where X is Cl, Br or I, and R is a C₁-C₆ aliphatic or aromatic radical) in anhydrous pyridine or triethylamine; alternatively, the given compound may be reacted with an acid (RCO₂H or RSO₃H) wherein R is an aliphatic or aromatic radical and dicyclohexylcarbodiimide in triethylamine to prepare the ester or sulfonate ester; for preparation of ethers, the given compound is reacted with an organic halide (e.g., RX or RCH₂X, where X is Cl, Br or I, and R is a C₁-C₆ aliphatic or aromatic radical) in anhydrous acetone with anhydrous potassium carbonate; (2) removal of an ether methyl group(s) to provide a phenolic hydroxyl functionality and/or conversion of that moiety to an ester, sulfonate, or other ether in a compound or derivative of formula Ia and IIa: for instance, for hydrolytic cleavage of a methyl ether substituent and conversion to a phenolic hydroxyl moiety, the given compound is reacted with $BBr_3$ or $BX_3 \cdot (CH_3)_2S$ in $CH_2Cl_2$ (where X is F, Cl or Br); the resulting phenol can be converted to an ester, sulfonate ester or ether as described above; (3) preparation of amide or sulfonamide derivatives at an amine site in a compound of formula Ia or IIa: for instance, for preparation of amides or sulfonamide derivatives, the same general procedures described above in (1) apply; in either case (procedure (1) or (3)), an appropriate functional group protection strategy (blocking/deblocking of selected group(s)) may need to be applied; (4) conversion of a secondary amine functionality in a compound of formula Ia or IIa to a tertiary amine: for instance, for preparation of a tertiary amine, the given compound is reacted with an aldehyde, and the resulting product is then reduced with NaBH4; alternatively, for preparation of an alkyl ammonium salt, the given compound is reacted with an alkyl halide (RX, where X is Cl, Br or I, and R is a $C_1$-$C_6$ aliphatic radical) in an anhydrous aprotic solvent; (5) conversion of a tertiary amine functionality in a compound of formula Ia or IIa to a secondary amine; for instance, for preparation of a secondary amine, the given compound is reacted with cyanogen bromide to give a cyanamide derivative which is then treated with $LiAlH_4$; (6) conversion of one or more phenolic hydroxyl groups in a given compound of formula Ia or IIa to an aromatic hydrogen substituent: for instance, the given compound is converted (after suitable protection of any amine substituent(s) if necessary) to the triflate ester to give the corresponding deoxy compound; (7) substitution of one or more hydrogen substituent(s) on the aryl system(s) on a compound of formula Ia or IIa by halogen, nitro, amino, hydroxyl, thiol, or cyano groups: for instance, for preparation of a bromine-substituted derivative, the given compound is reacted with $Br_2$ in $H_2O$; for the preparation of other substituted derivatives, the given compound is treated with $HNO_3$/HOAc to provide a nitro-substituted (—$NO_2$) derivative; in turn, the nitro-derivative can be reduced to an amino derivative, and the amino derivative is the point of origin of the chloro, iodo, cyano, thiol and hydroxyl substitution via well-known and practiced diazonium substitution reactions. More detailed, specific illustrations of synthesis and derivatization procedures that can be employed to access any desired member of the family of compounds represented by formulas Ia and IIa and derivatives thereof, are provided in the examples that follow herein.

It will be appreciated that certain compounds of formula Ia and, IIa can have one or more asymmetric carbon(s) and thus such compounds are capable of existing as enantiomers or diastereomers. Unless otherwise specified, the present invention includes such enantiomers or diastereomers, including any racemates thereof. If desired, the separate enantiomers or diastereomers can be synthesized from appropriate chiral starting materials, or the racemates can be resolved by conventional procedures, which are well-known to those skilled in the art, such as chiral chromatography, fractional crystallization of diastereomers or diastereomeric salts, and the like. Certain compounds can exist as geometrical isomers, such as, for example, compounds with double-bonded substituents with geometrical isomers Z and E, and the present invention includes all such isomers, including certain isomers, for example the Z isomers, which are preferred. Also, certain compounds may contain substituents wherein there is restricted rotation and/or other geometric isomers are possible. For example, certain oxime substituents may exist in syn or anti configurations. The present invention includes all such configurations, including all possible hindered-rotational isomers, and other geometric isomers. The present invention also includes all positional isomers wherein a given substituent, for example a heterocyclic substituent such as furanyl or pyrazolyl, may be connected to the core molecule via different atoms of the heterocyclic ring (e.g., 2-fuanyl, 3-furanyl, 3-pyrazolyl, 4-pyrazolyl, 5-pyrazolyl, and the like).

It will be appreciated by one skilled in the art that the proof or confirmation of the chemical structure of a compound provided by or used in the present invention can be demonstrated using at least one or more well-known and established, convergent methods including, but not limited to, for example: proton and/or carbon NMR spectroscopy, mass spectrometry, x-ray crystallography, chemical degradation, and the like.

One or more compound(s) of formula Ia or IIa or pharmaceutically acceptable salt(s) or prodrugs(s) thereof can be included in a composition, e.g., a pharmaceutical composition. In that respect, the present invention further provides a composition that includes an effective amount of at least one compound of formula Ia or IIa which may be in the form of pharmaceutically acceptable salt(s) or prodrug(s) thereof and a pharmaceutically acceptable carrier. The composition of the present invention preferably includes a therapeutically or prophylactically effective amount of at least one compound of formula Ia or IIa. The therapeutically or prophylactically effective amount can include an amount that produces a therapeutic or prophylactic response in a patient to whom a compound or composition of the present invention is administered. A therapeutically or prophylactically effective amount can include, for example, a Ras-inhibitory and/or an anticancer effective amount.

The composition of the present invention can further include a therapeutically or prophylactically effective amount of at least one additional compound other than a compound of formula Ia or IIa, which may or may not be a Ras-inhibitory compound, which may be an anticancer compound. When the additional compound is a Ras-inhibitory compound other than a compound of formula Ia or IIa, it is preferably present in the composition in a Ras-inhibiting amount. When the additional compound is an anticancer compound in general, it is preferably present in the composition in an anticancer effective amount.

The composition of the present invention can be produced by combining one or more compound(s) of formula Ia or IIa with an appropriate pharmaceutically acceptable carrier, and can be formulated into a suitable preparation, which may include, for example, preparations in solid, semi-solid, liquid or gaseous forms such as tablets, capsules, powers, granules, ointments, solutions, suppositories, injections, inhalants, and aerosols, and other formulations known in the art for their respective routes of administration. In pharmaceutical dosage forms, a compound of formula Ia or IIa can be used alone or in appropriate association, as well as in combination, with other pharmacologically active compounds, including other compounds, e.g., other Ras-inhibitory compounds, as described herein.

Any suitable pharmacologically or physiologically acceptable carrier can be utilized. The following methods and carriers are merely exemplary and are in no way limiting. In the case of oral preparations, a compound of formula Ia or IIa can be administered alone or in combination with a therapeutically or prophylactically effective amount of at least one other compound. The active ingredient(s) can be combined, if desired, with appropriate additives to make tablets, powders, granules, capsules or the like.

Suitable additives can include, for example, lactose, mannitol, corn starch or potato starch. Suitable additives also can include binders, for example crystalline cellulose, cellulose derivatives, acacia, or gelatins; disintegrants, for example, corn starch, potato starch or sodium carboxymethylcellulose; or lubricants such as talc or magnesium stearate. If desired, other additives such as, for example, diluents, buffering agents, moistening agents, preservatives, and/or flavoring agents, and the like, can be included in the composition.

The compounds used in accordance with the present invention can be formulated into a preparation for injection or infusion by dissolution, suspension, or emulsification in an aqueous or non-aqueous solvent, such as vegetable oil, synthetic aliphatic acid glycerides, esters of higher aliphatic acid or propylene glycol (if desired, with conventional additives such as solubilizers isotonic agents, suspending agents, emulsifying agents, stabilizers, and preservatives).

The compounds of formula Ia and IIa also can be made into an aerosol formulation to be administered by inhalation. Such aerosol formulations can be placed into pressurized acceptable propellants such as dichlorodifluoromethane, propane, nitrogen, and the like.

The compounds of the invention can be formulated into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature but are solid at room temperature.

Unit dosage forms for oral or rectal administration such as syrups, elixirs, and suspensions can be provided wherein each dosage unit, e.g., teaspoonful, tablet, or suppository contains a predetermined amount of the composition containing the compound of formula Ia or IIa. Similarly, unit dosage forms for injection or intravenous administration can comprise a composition as a solution in sterile water, normal saline, or other pharmaceutically acceptable carrier.

The term "unit dosage form" as used herein refers to physically discrete units suitable as unitary dosages for human and animal subjects, each unit containing a predetermined quantity of at least one compound(s) of formula Ia or IIa (alone, or if desired, with another therapeutic or prophylactic agent). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the desired effect to be achieved and the pharmacodynamics associated with the compound(s) in the individual host.

Pharmaceutically acceptable carriers, for example, vehicles, adjuvants, excipients, or diluents, are accessible to those of skill in the art and are typically available commercially. One skilled in the art can easily determine the appropriate method of administration for the exact formulation of the composition being used. Any necessary adjustments in dose can readily be made by an ordinarily skilled practitioner to address the nature or severity of the condition being treated. Adjustments in dose also can be made based on other factors such as, for example, the individual patient's overall physical health, sex age, prior medical history, and the like.

The compounds of formula Ia and IIa can be utilized in a variety of therapeutic and prophylactic (disease preventing) applications, and also in certain non-therapeutic or non-prophylactic applications. It will be appreciated that one or more of these compounds can be used, for example, as a control in diagnostic kits, bioassays, or the like. Preferably the method of the present invention is applied therapeutically or prophylactically, for example, toward treatment or prevention of cancer or toward treatment or prevention of a condition (e.g. an abnormal condition or disease) treatable by the inhibition of Ras-mediated biological process(es). The compounds of formula Ia and IIa can be administered alone, or in combination with a therapeutically or prophylactically effective amount of at least one additional compound other than a compound of formula Ia or IIa.

Accordingly, the present invention further provides a method of therapeutically or prophylactically treating a condition treatable by inhibition of one or more Ras-mediated biological processes, which method includes administering to a patient a Ras-inhibiting amount of at least one Ras-inhibitory compound of formula Ia or IIa. More particularly, the present invention provides a method of therapeutically or prophylactically treating a condition treatable by the inhibition of one or more Ras-mediated biological processes, which includes administering a Ras-inhibiting effective amount of at least one compound of formula Ia or IIa.

Many different abnormal conditions and diseases can be treated in accordance with the method of the present invention. The compounds of formulas Ia and IIa, and their compositions can be used medically to regulate biological phenomena, including but not limited to such Ras-modulated processes as tumor cell growth, proliferation, survival, invasion and metastasis, as well as resistance to chemotherapy, other molecularly targeted therapeutics, and radiation. The compounds of formula Ia and IIa are therefore useful in the treatment of diseases and conditions that can be controlled by the inhibition of Ras-mediated cellular functions. Such diseases include, for example, diseases wherein hyperactive Ras (e.g., including mutant Ras) is implicated; such diseases prominently include cancer, among others. Compounds of formula Ia and IIa can be expected to have efficacious actions in patients with cancer, especially in patients whose cancers have underlying hyperactive, overexpressed or mutant Ras-mediated pathological processes that are inhibited by a compound(s) of formula Ia or IIa. Hyperactive Ras may not only result from an activating mutation in the ras gene, but alternatively may result from an activating mutation in or overexpression of an upstream factor, such as a growth factor, that activates Ras. Compounds of the invention are expected to inhibit activated Ras and Ras-mediated disease conditions regardless of the mechanism by which the Ras is hyperactivated. Other aberrant Ras-mediated diseases or conditions that are expected to be treatable or preventable by administration of Ras-inhibiting amounts of compound(s) of the invention include for example, neurofibromatosis and Costello syndrome. In the instance of cancer particularly, compound(s) of formula Ia and IIa may promote broader sensitivity of cancer to other drugs and/or radiation therapy by inhibiting the ability of cancer cells to develop or express resistance to such drugs and/or radiation therapy making possible the effective chemotherapeutic and/or radiotherapeutic treatment of cancer.

In accordance with an embodiment of the method of the present intervention, it is preferred that a Ras-inhibiting effective amount is used. In that regard, it is preferred that the Ras-inhibiting amount is effective to inhibit one or more conditions selected from the group consisting of tumor cell growth, proliferation, survival, invasion and metastasis, as well as resistance to chemotherapy, other molecularly targeted therapeutics, and radiation.

The method of the present invention further includes administering a Ras-inhibiting effective amount of at least one additional compound other than a compound of formula Ia or IIa. In some instances, the method of the present invention can be made more effective by administering one or more other Ras-inhibitory compound(s), along with a compound of formula Ia or IIa. One or more Ras-inhibitory compound(s) of formula Ia or IIa also can be co-administered in combination with an anticancer agent other than a compound of formula Ia or IIa, for example, to cause anticancer chemotherapy-resistant and/or radiation-resistant tumor cells to become chemotherapy-sensitive and/or radiation-sensitive and/or to inhibit de novo the development of cancer cell resistance to the anticancer agent and/or to cancer cell resistance to radiation treatment.

In accordance with an embodiment of the method, the patient is pre-selected by utilizing an assay of said patient's tissue, blood or tumor for an abnormal, mutant or hyperactive ras gene or Ras protein, or an aberrant Ras-mediated biological process.

In accordance with the methods of the present invention, one or more compounds of formula Ia or IIa can be administered by any suitable route including, for example, oral or parenteral, including intravenous, subcutaneous, intraarterial, intraperitoneal, ophthalmic, intramuscular, buccal, rectal, vaginal, intraorbital, intracerebral, intracranial, intraspinal, intraventricuclar, intrathecal, intracisternal, intracapsular, intrapulmonary, intranasal, transmucosal, transdermal, or via inhalation. For example, one or more compound(s) of formula Ia or IIa can be administered as a solution that is suitable for intravenous injection or infusion, or can be administered as a tablet, a capsule, or the like, in any other suitable composition or formulation as described herein. Accordingly, there is a wide variety of suitable formulations of the pharmaceutical composition of the present invention. The formulations may also be applied topically.

The "Ras-inhibiting-effective amount" as utilized in accordance with an embodiment of the composition and method of the present invention, includes the dose necessary to achieve a "Ras-inhibiting effective level" of the active compound in an individual patient. The Ras-inhibiting-effective amount can be defined, for example, as that amount required to be administered to an individual patient to achieve in said patient a Ras-inhibiting-effective blood or tissue level, and/or intracellular target-inhibiting level of a compound of formula Ia or IIa to cause the desired medical treatment.

By way of example and not intending to limit the invention, the dose of the pharmaceutically active agent(s) described herein for methods of preventing or treating a disease or disorder can be, in embodiments, about 0.001 to about 1 mg/kg body weight of the subject being treated per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. In certain embodiments, the dose of the pharmaceutically active agent(s) described herein can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

When the effective level is used as the preferred endpoint for dosing, the actual dose and schedule can vary depending, for example, upon inter-individual differences in pharmacokinetics, drug distribution, metabolism, and the like. The effective level also can vary when one or more compound(s) of formula Ia or IIa are used in combination with other therapeutic agents, for example, one or more additional anticancer compound(s), or a combination thereof. Moreover, the effective level can vary depending upon the selected disease (e.g., cancer or neurofibromatosis) or biological process (e.g., tumor cell growth, proliferation, survival, invasion and metastasis, as well as resistance to chemotherapy, other molecularly targeted therapeutics, and radiation) for which treatment is desired. Similarly, the effective level can vary depending on whether the treatment is for therapy or prevention of a selected disease such as, for example, cancer.

Compounds of formula Ia and IIa can be expected to be broadly efficacious anticancer agents, which will inhibit or destroy human solid tumors, and as well non-solid cancer such as leukemias and certain lymphomas. Solid tumors may include particularly those tumors where ras gene mutations are highly prevalent, such as pancreatic cancer, lung cancer and colon cancer, as well as diverse other solid tumors such as, for example, melanoma, ovarian cancer, renal cancer, prostate cancer, head and neck cancer, endocrine tumors, uterine cancer, breast cancer, sarcomas, gastric cancer, hepatic cancer, esophageal cancer, central nervous system (e.g., brain) cancer, hepatic cancer, germline cancer, and the like.

In a preferred embodiment of the present invention, patients who are most likely to have a favorable response to a Ras-inhibitory compound of formula Ia or IIa can be pre-selected, prior to said treatment with said compound, by assaying said patient's blood, tissues or tumor for the presence ras gene mutations and/or abnormal Ras proteins and/or aberrant Ras-mediated biological function(s), using assay procedures (including use of commercially available assay kits) well-known to those of ordinary skill in the art.

Accordingly, the present invention further provides a method of therapeutically or prophylactically treating cancer, which method comprises administering to a patient in need thereof an anticancer effective amount of at least one Ras-inhibitory compound(s) of formula Ia or IIa. The anticancer effective amount can be determined, for example, by determining an amount to be administered effective to produce a Ras-inhibiting-effective blood or tissue level and/or intracellular target-inhibiting "effective level" in the subject patient. The effective level can be chosen, for example, as that blood and/or tissue level (e.g., $10^{-12}$-$10^{-6}$ M from examples that follow) effective to inhibit the proliferation of tumor cells in a screening assay. Similarly, the effective level can be determined, for example, based on the blood, tissue or tumor level in a patient that corresponds to a concentration of a therapeutic agent that effectively inhibits the growth of a human cancer in any assay that is clinically predictive of anticancer activity. Further, the effective level can be determined, for example based on a concentration at which certain markers of cancer in a patient's blood or tumor tissue (e.g., mutant or hyperactive ras gene(s) and/or Ras protein(s) and/or aberrant Ras-mediated biological pathway(s)) are inhibited by a selected compound that inhibits cancer. Alternatively, the effective level can be determined, for example, based on a concentration effective to slow or stop the growth of a patient's cancer, or cause a patient's cancer to regress or disappear, or render a patient asymptomatic to a selected cancer, or improve a cancer patient's subjective sense of condition. The anticancer effective level can then be used to approximate (e.g., by extrapolation) or even to determine precisely, the level which is required clinically to achieve a Ras-inhibiting-effective blood, tissue, tumor and/or intracellular level to cause the desired medical treatment. It will be appreciated that the determination of the therapeutically effective amount clinically required to effectively inhibit Ras-mediated processes also requires consideration of other variables that can influence the effective level, as discussed herein. When a fixed effective amount is used as a preferred endpoint for dosing, the actual dose and dosing schedule for drug administration can vary for each patient depending upon factors that include, for example, inter-individual differences in pharmacokinetics, drug absorption, drug disposition and tissue distribution, drug metabolism, drug excretion, whether other drugs are used in combination, or other factors described herein that influence the effective level.

One skilled in the art and knowing and understanding the disclosures of the present invention can readily determine the appropriate dose, schedule, or method of administering a selected formulation, in order to achieve the desired effective level in an individual patient. Given the disclosures herein, one skilled in the art also can readily determine and use an appropriate indicator of the effective level of the compound(s) of formula Ia and IIa. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, if the compound in question has antitumor activity, by direct or indirect observations, such as, for example, observing the shrinkage, slowing or cessation of growth or spreading of a tumor in a cancer patient. There are many references to the art that describe the protocols used in administering and monitoring responses to active compounds in a patient in need thereof. For example, drug-appropriate protocols used in the administration of different types of anticancer agents to patients are described in "*Cancer Chemotherapy and Biotherapy: Principles and Practice*" eds. Chabner and Longo, Lippincott, Williams and Wilkins (2011), and citations therein.

The present inventive method of therapeutically or prophylactically treating cancer further includes administering an anticancer effective amount of at least one additional compound other than a compound of formula Ia or IIa. For example, one or more compound(s) of formula Ia or IIa can be co-administered with an anticancer agent, and/or can be co-administered with radiation therapy, in which case the effective level is the level needed to inhibit or reverse the ability of the cancer to develop resistance to the anticancer agent and/or to the radiation therapy, respectively.

Examples of anticancer compounds include reversible DNA binders, DNA alkylators, and DNA strand breakers. Examples of suitable reversible DNA binders include topetecan hydrochloride, irinotecan (CPT11—Camptosar), rubitecan, exatecan, nalidixic acid, TAS-103, etoposide, acridines (e.g., amsacrine, aminocrine), actinomycins (e.g., actinomycin D), anthracyclines (e.g., doxorubicin, daunorubicin), benzophenainse, XR 11576/MLN 576, benzopyridoindoles, Mitoxantrone, AQ4, Etopside, Teniposide, (epipodophyllotoxins), and bisintercalating agents such as triostin A and echinomycin.

Examples of suitable DNA alkylators include sulfur mustard, the nitrogen mustards (e.g., mechlorethamine), chlorambucil, melphalan, ethyleneimines (e.g., triethylenemelamine, carboquone, diaziquone), methyl methanesulfonate, busulfan, CC-1065, duocarmycins (e.g., duocarmycin A, duocarmycin SA), metabolically activated alkylating agents such as nitrosoureas (e.g., carmustine, lomustine, (2-chloroethyl)nitrosoureas), triazine antitumor drugs such as triazenoimidazole (e.g., dacarbazine), mitomycin C, leinamycin, and the like.

Examples of suitable DNA strand breakers include doxorubicin and daunorubicin (which are also reversible DNA binders), other anthracyclines, belomycins, tirapazamine, enediyne antitumor antibiotics such as neocarzinostatin, esperamicins, calicheamicins, dynemicin A, hedarcidin, C-1027, N1999A2, esperamicins, zinostatin, and the like.

Examples of anticancer agents include abarelix, aldesleukin, alemtuzumab, altretamine, amifostine, aminoglutethimide, anastrazole, arsenic trioxide, asparaginase, azacitidine, azathioprine, BCG vaccine, bevacizumab, bexarotene, bicalutamide, bleomycin sulfate, bortezomib, bromocriptine, busulfan, capecitabine, carboplatin, carmustine, cetuximab, chlorambucil, chloroquine phosphate, cladribine, cyclophosphamide, cyclosporine, cytarabine, dacarbazine, dactinomycin, daunorubicin hydrochloride, daunorubicin citrate liposomal, dexrazoxane, docetaxel, doxorubicin hydrochloride, doxorubicin hydrochloride liposomal, epirubicin hydrochloride, estramustine phosphate sodium, etoposide, estretinate, exemestane, floxuridine, fludarabine phosphate, fluorouracil, fluoxymesterone, flutamide, fulvestrant, gefitinib, gemcitabine hydrochloride, gemtuzumab ozogamicin, goserelin acetate, hydroxyurea, idarubicin hydrochloride, ifosfamide, imtinib mesylate, interferon alfa-2a, interferon alfa-2b, irinotecan hydrochloride trihydrate, letrozole, leucovorin calcium, leuprolide acetate, levamisole hydrochloride, lomustine, lymphocyte immune anti-thymocyte globulin (equine), mechlorethamine hydrochloride, medoxyprogestone acetate, melphalan, mercaptopurine, mesna, methotrexate, mitomycin, mitotane, mitoxantrone hydrochloride, nilutamide, oxaliplatin, paclitaxel, pegaspargase, pentostatin, plicamycin, porfimer sodium, procarbazine hydrochloride, streptozocin, tamoxifen citrate, temozolomide, teniposide, testolactone, testosterone propionate, thioguaine, thiotepa, topotecan hydrochloride, tretinoin, uracil mustard, valrubicin, vinblastine sulfate, vincristine sulfate, and vinorelbine.

Suitable forms of radiation therapy include, for example, all forms of radiation therapy approved for commercial use in the United States, and those forms that will become approved in the future, for which radiation resistance thereto can be controlled by a Ras-inhibitory compound of formula Ia or IIa.

In accordance with an embodiment of the methods of the present invention, prophylaxis includes inhibition as described herein, e.g., inhibition of the growth or proliferation of cancer cells, or inhibition of aberrant Ras-mediated cellular functions. The inhibition can be less than 100% inhibition to be prophylactically effective, and a clinically desirable therapeutic benefit can be realized with less than 100% inhibition.

The compound(s) of formula Ia or IIa used in accordance with the present invention can be selected, for example, based upon the potency and/or selectivity for inhibiting Ras-mediated cellular processes, as assessed by in vitro or in vivo assays, and/or based on other pharmacological, toxicological, pharmaceutical or other pertinent considerations that are well-known to those skilled in the art. Routine methods for the specific bioassay, quantitation and comparisons of Ras-inhibitory inhibitory and other biological activities and properties of compounds of formula Ia and IIa in various tissues, cells, organelles and other preparations, as well as in vivo testing in animals are well-documented in the literature (e.g., see Teicher and Andrews (eds.), *Anticancer Drug Development Guide*, Humana (2004), and various authors and chapters therein). More specific illustrations of these and other details pertinent to enablement of the present invention are provided in the examples which follow.

The following examples further illustrate the invention but, of course, should not be construed as in any way limiting its scope.

EXAMPLE 1

One skilled in the art and knowing the disclosures of the present invention will appreciate that any of compounds of formula Ia and IIa can be made or modified with different substituents as desired to be in the final products, and/or the final product of a synthesis, for example a synthesis according to any one or more of Schemes I, II, III, IV, V, VI, VII, VIII, IX, X, XI, XII, XIII, XIV, XV and XVI can be modified with different substituents as desired.

Other modifications of molecules of formula Ia and IIa may be desirable, for example to remove extended conjugation to eliminate the potential for toxicity in certain situations, while retaining the desired Ras-inhibitory activity. For example, certain compounds of formula IIa wherein $R_5$ and $R_6$ together form a carbon-carbon bond and $R_9$ and $R_{20}$ together form a carbon-carbon bond and which have a phenolic hydroxyl group at $R_{14}$ are among the most highly potent and selective Ras inhibitors of the invention. Deprotonation of the phenolic hydroxyl in such a structure either ex vivo or in vivo may lead to the formation of a quinoid-like configuration comprising an oxo at $R_{14}$ which then creates an extended conjugation with the double bonds formed when $R_5$-$R_6$ together is a carbon-carbon bond and $R_9$-$R_{20}$ together is a carbon-carbon bond. In certain situations, it may be desirable to eliminate the possibility of such extended conjugation by not having one or both double bond(s) that exist when $R_5$ and $R_6$ together is a carbon-carbon bond and/or when $R_9$ and $R_{20}$ together is a carbon-carbon bond, and/or by having an alternative to the phenolic hydroxyl group, e.g., a bioisosteric equivalent or a cleavable alcohol promoiety or a group that is converted within or near the target tumor cells to a phenolic hydroxyl group or a bioisosteric equivalent. For making such partially reduced compounds, one skilled in the art can modify (e.g., catalytic hydrogenation of double bond(s)) existing compounds or precursors of formula Ia or IIa, and/or make use of appropriate available reduced or partially reduced, commercially or routinely available precursors for use as building blocks to synthesize the desired final compound structures, for example through use of one or more of the schemes I-XVI, or modifications or adaptations thereof or other approaches well-known to those skilled in the art. A typical hydrogenation is illustrated as follows:

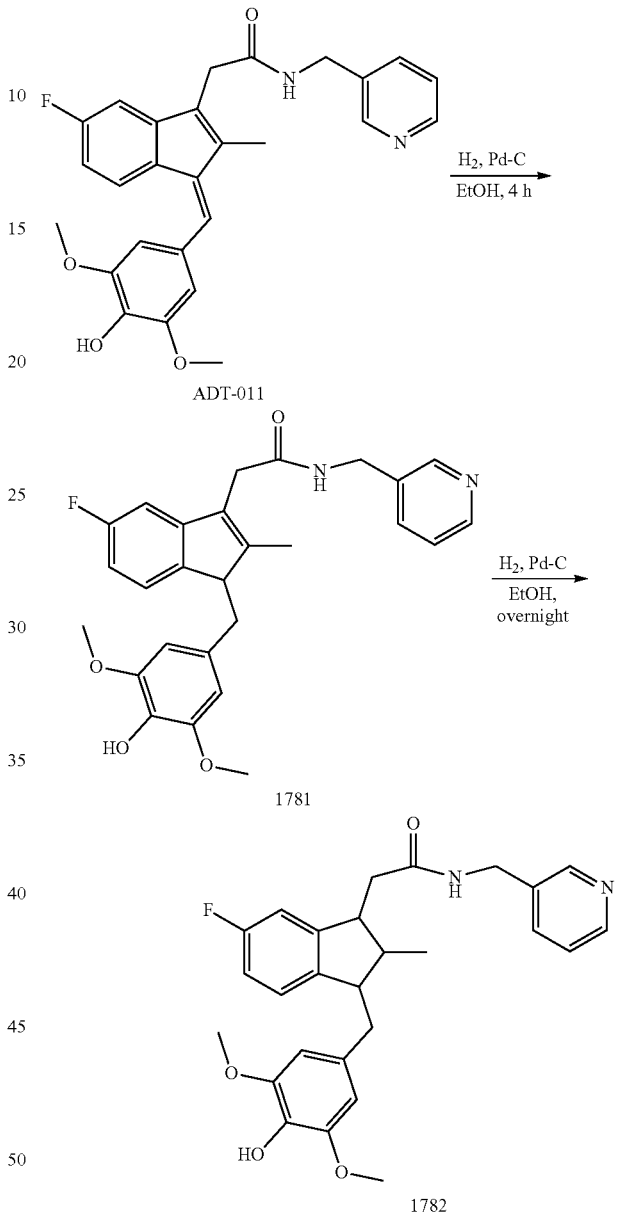

The illustrative scheme shows preparation of an exemplary compound, 1782. In a typical small-scale procedure, to a solution of the precursor compound ADT-011 (100 mg) in EtOH (10 mL), Pd/C (5%, 10 mg) is added and the suspension is stirred in an atmosphere of hydrogen at room temperature for 4 h. The catalyst is removed by filtration and the filtrate is concentrated. The residue is purified by silica gel column to afford 1781 as a colorless solid, typically in about 80% yield; then, to a solution of 1781 (100 mg) in EtOH (10 mL), Pd/C (5%, 20 mg) is added and the suspension is stirred in an atmosphere of hydrogen at room temperature overnight; the catalyst is removed by filtration and the filtrate is concentrated; the residue is purified by silica gel column to afford the 1782 as a colorless solid, typically in about 80% yield. Using a similar procedure, many different related compounds of the invention, such as for example the Ras inhibitors 1765 and 1796, can be readily prepared by one skilled in the art.

In certain situations, a compound of formula Ia or IIa may require for optimal target interaction (e.g., interaction with Ras) the molecular rigidity imposed by the double bond that exists when $R_5$ and $R_6$ together form a carbon-carbon bond. Therefore, in certain situations when $R_5$ and $R_6$ do not together form a carbon-carbon bond, it may be desirable to have substituents or connectivity at $R_5$ and $R_6$ in other ways to impose some molecular rigidity (e.g., hindered rotation about the existing carbon-carbon bond between the carbons to which the $R_5$ and $R_6$ are attached). This can be realized, for example, by imposing features such as the following in a compound of formula Ia or IIa: at least one, or preferably two or three of $R_5$, $R_6$ and $R_7$ are large bulky groups, such as halo (e.g., fluoro), t-butyl, and the like; or, $R_5$ and $R_6$ together with the atoms to which they are attached form a ring, or $R_6$ and $R_7$ together with the atom to which they are attached form a ring. Some examples of approaches that one skilled in the art may use to make such compounds are exemplified as follows;

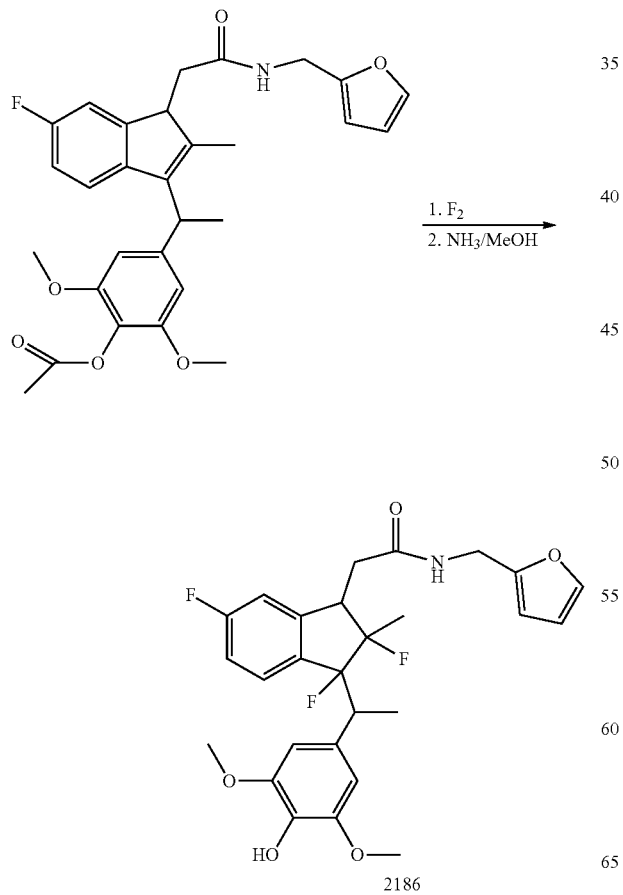

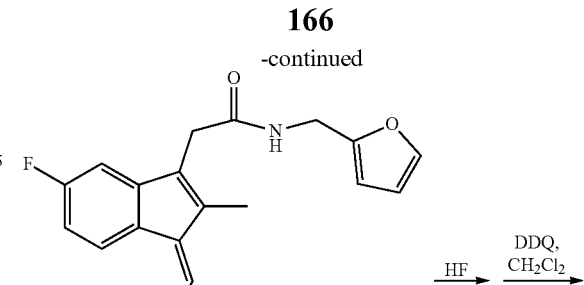

-continued

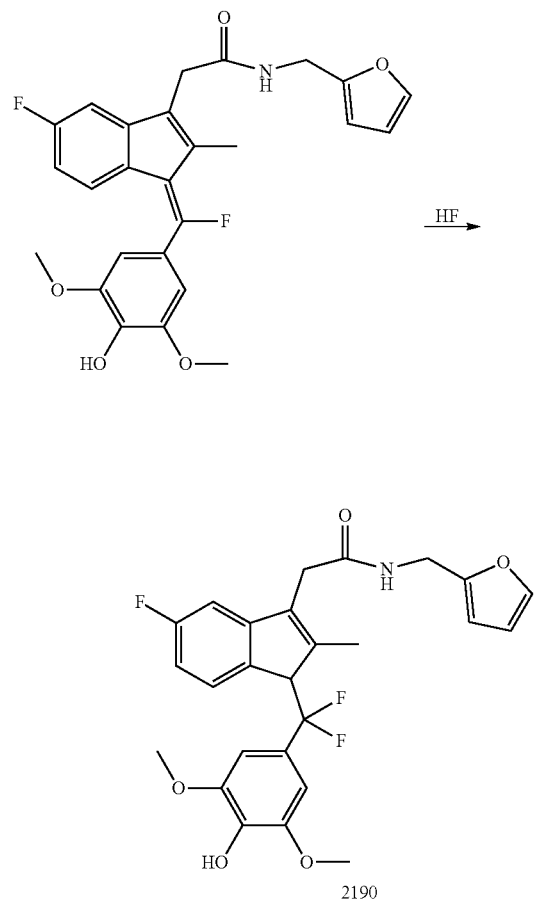

In another example, it may be desirable to have a rigid cyclic structure between the indenyl core and the attached phenyl group, such as in a compound of formula Ia or IIa when $R_5$ and $R_6$ together with the atoms to which they are attached form a ring; alternatively, or additionally, it may be desirable to have a bulky halo group located near the rigid cyclic structure. Such a compound of formula Ia or IIa can be prepared by one skilled in the art by a procedure such as exemplified in the following:

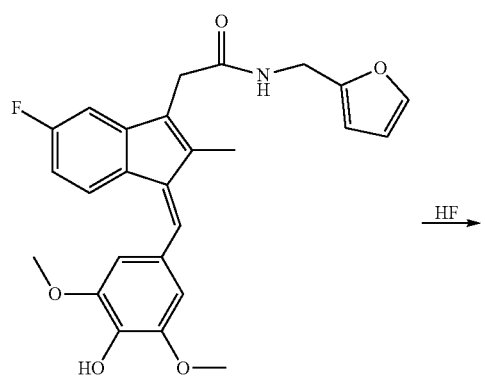

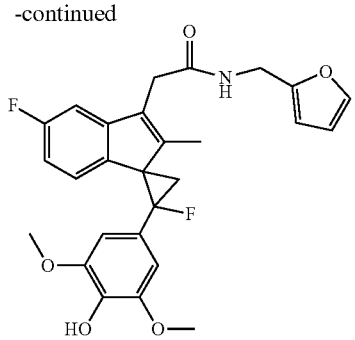

2194

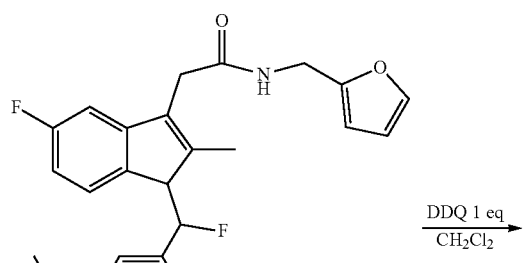

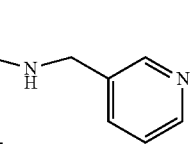

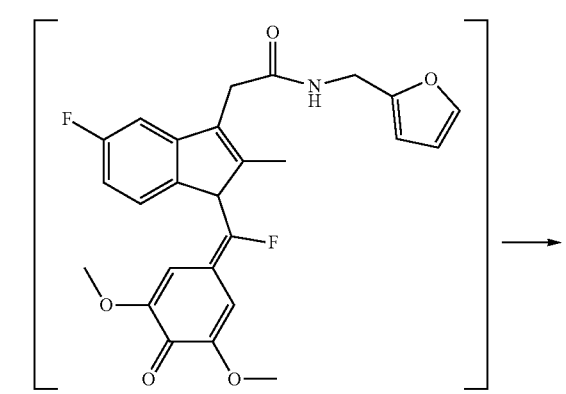

Another way to impose desired molecular rigidity with preservation of the desired biological activity in a compound of formula Ia or IIa is by having a double bond within the indene ring wherein $R_5$ and $R_{20}$ together is a carbon-carbon bond; this structural feature imposes some desired molecular rigidity as an alternative to having bulky atoms at $R_5$, $R_6$ or $R_7$ or having $R_5$ and $R_6$ together forming a carbon-carbon bond or having $R_5$, $R_6$ or $R_7$ as part of ring structures. Such a compound can be prepared, for example, by one skilled in the art using an approach such as the following:

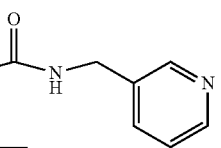

011

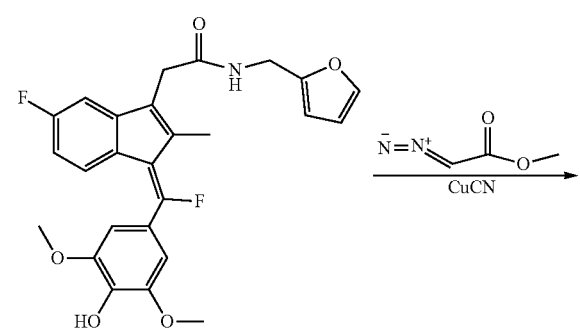

1782

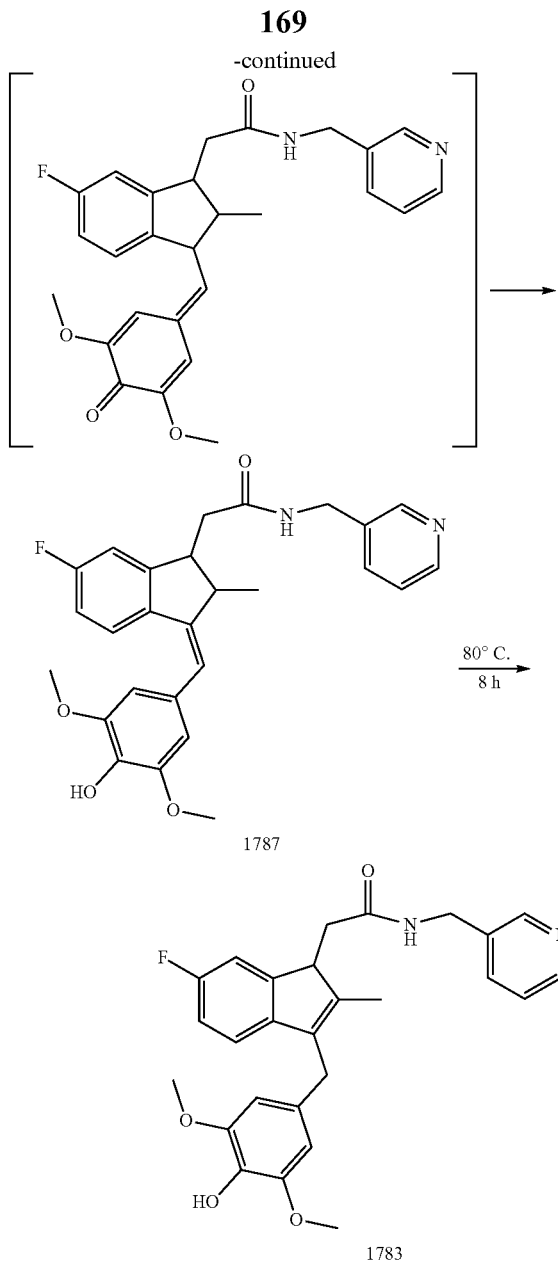

One skilled in the art can make such compounds through modification of existing compounds or precursors of formula Ia or IIa, and/or can use appropriate available commercially or routinely available precursors for use as building blocks to synthesize the desired final compound structures, for example through use of one or more of the schemes I-XVI, or modifications or adaptations thereof or other approaches well-known to those skilled in the art.

EXAMPLE 2

$^1$H-NMR data are used to confirm the structures of exemplary compounds of the invention. Spectra are routinely recorded using DMSO-$d^6$ or CDCl$_3$ as solvent, or other appropriate solvent when necessary. For illustrative purposes, the NMR data of some selected exemplary compounds (ID numbers in bold) of the invention are provided as follows: compound 2096 (CDCl$_3$) 8.547 (s, 1H); 8.515 (s, 1H); 7.706 (d, 1H, J=7.1 Hz); 7.509 (t, 1H, J=5.4 Hz); 7.194 (s, 1H); 6.830 (d, 1H, J=8.45 Hz); 6.789 (s, 2H); 6.629 (t, 1H, J=9.1 Hz); 5.735 (br, 1H); 5.551 (br, 1H); 4.371 (d, 2H, J=4.5 Hz); 3.901 (s, 6H); 3.587 (s, 2H); 2.211 (s, 3H); compound 2090: (CDCl$_3$) 7.563 (dd, 1H, J$_1$=9.65 Hz, J$_2$=13.4 Hz); 7.413 (s, 1H); 7.231 (s, 1H); 7.184 (d, 1H, J=2.0 Hz); 7.007 (d, 1H, J=8.85 Hz); 6.806 (s, 2H); 6.643 (t, 1H, J=8.00 Hz); 6.520 (s, 1H); 6.373 (br, 1H); 5.731 (br, 1H); 4.608 (d, 2H, J=5.25 Hz); 3.907 (s, 6H); 2.304 (s, 3H); compound 2183: (DMSO-d6) 8.330 (t, 1H, J=5.7 Hz); 7.589 (dd, 1H, J$_1$=5.4 Hz, J$_2$=8.45 Hz); 7.303 (s, 1H); 7.196 (dd, 1H, J$_1$=9.45 Hz, J$_2$=25 Hz); 6.855 (s, 2H); 6.227 (td, 1H, 9.1 Hz); 4.395 (d, 2H, J=5.65 Hz); 3.787 (s, 1H); 3.781 (s, 6H); 2.091 (s, 3H); compound 1736: (DMSO-d6) 8.680 (t, 1H, J=5.85 Hz); 8.476 (d, 1H, J=1.65 Hz); 8.454 (dd, 1H, J$_1$=4.75 Hz, J$_2$=1.45 Hz); 7.193 (s, 1H); 7.6420 (d, 1H, J=7.85 Hz); 7.336 (dd, 1H), 7.332 (s, 1H); 7.206 (dd, 1H, J$_1$=5.4 Hz, J$_2$=8.40 Hz); 7.058 (dd, 1H, J$_1$=9.4 Hz, J$_2$=2.40 Hz); 6.712 (td, 1H, J$_1$=9.45 Hz, J$_2$=2.45 Hz); 6.593 (d, 1H, J=1.8 Hz); 6.539 (d, 1H, J=1.8 Hz); 4.309 (d, 2H, J=5.85 Hz); 3.777 (s, 3H); 3.727 (s, 3H); 3.488 (s, 2H); 2.118 (s, 3H); compound 2200. (DMSO-d6) 8.676 (t, 1H, J=5.8 Hz); 8.475 (d, 1H, J=1.9 Hz); 8.447 (dd, 1H, J$_1$=4.75 Hz, J$_2$=1.5 Hz); 8.392 (s, br, 1H); 7.639 (d, 1H, J=7.80 Hz); 7.324 (dd, 1H, J$_1$=7.95 Hz, J$_2$=4.75 Hz), 7.242 (s, 1H); 7.068 (dd, 1H, J$_1$=9.4 Hz, J$_2$=2.5 Hz); 6.983 (dd, 1H, J$_1$=8.4 Hz, J$_2$=5.35 Hz); 6.699 (td, 1H, J$_1$=9.45 Hz, J$_2$=2.5 Hz); 6.593 (d, 1H, J=1.8 Hz); 6.546 (d, 1H, J=1.8 Hz); 4.306 (d, 2H, J=5.90 Hz); 3.762 (s, 3H); 3.750 (s, 3H); 3.482 (s, 1H); 3.174 (s, 1H); 2.136 (s, 3H); 1.20 (s, 12H).

EXAMPLE 3

Human cancer cell lines are obtained from the American Type Culture Collection (ATCC). Cells are cultured using standard methods in RPMI-1640 growth medium supplemented with 5% fetal bovine serum (FBS). CellTiter-Glo ATP cell growth assay reagents are obtained from Promega and used according to the manufacturer's protocol. Cells are plated at a density of 5,000 cells per well in 96-well microplates or 1,250 cells per well in 384-well plates, then allowed to attach for at least 4h. Test compounds are dissolved in dimethyl sulfoxide (DMSO), and this working stock is further diluted in growth medium for addition to cell cultures. Serial dilutions of the test compound are prepared in growth medium containing an equal amount of DMSO not exceeding 0.2% final concentration. Each compound concentration is tested in at least 3 separate samples per cell line. At the end of a 3-day treatment period, growth inhibition is analyzed using a bioluminescent assay of ATP concentration (Promega CellTiter-Glo) according to the manufacturer's protocol. Resulting luminescence is measured using the luminescence cartridge of the Molecular Devices Spectramax Paradigm microplate reader. Relative growth inhibition for each sample is determined by comparison with the values obtained for vehicle treated control samples. Growth inhibition values are plotted with the GraphPad Prism5 software using the 4-parameter logistic fit to obtain IC$_{50}$ values, which corresponds to the growth inhibitory potency of the compound.

EXAMPLE 4

Figure 5:
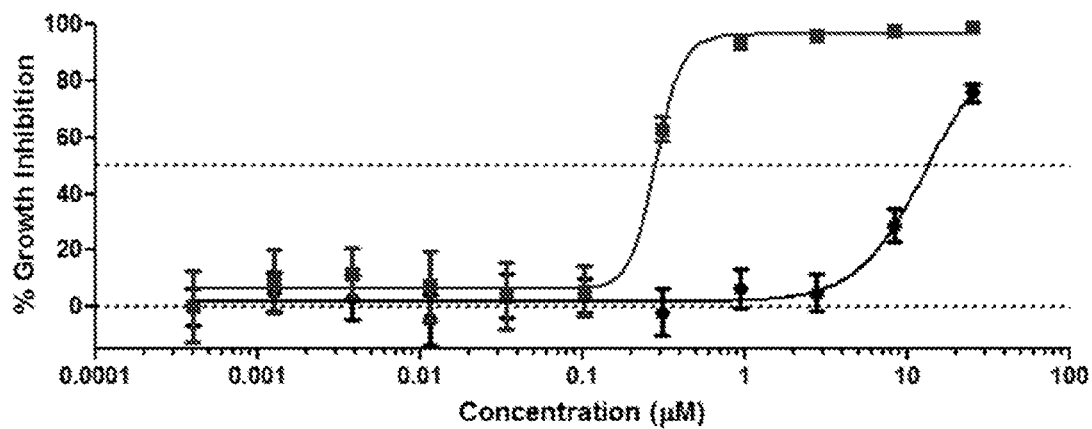
FIG. 5 shows an example of Ras-selective tumor cell growth inhibitory activity of exemplary Ras inhibitory compound 2090; the data were obtained according to the methods described in Examples 3 and 4; the square symbols are the HCT-116 data, the round symbols are the HT-29 data.
Figure 6:
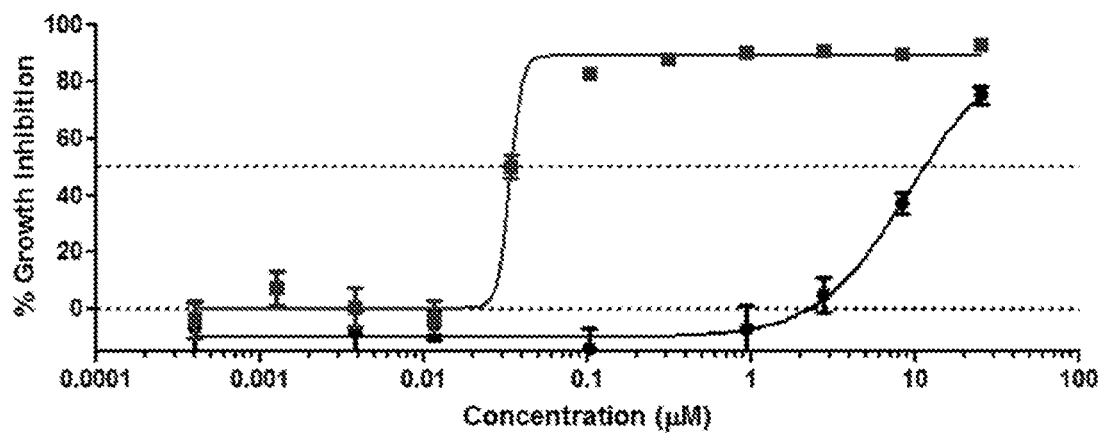
FIG. 6 shows an example of Ras-selective tumor cell growth inhibitory activity of exemplary Ras inhibitory compound 2096; the data were obtained according to the methods described in Examples 3 and 4; the square symbols are the HCT-116 data, the round symbols are the HT-29 data.
Figure 7:
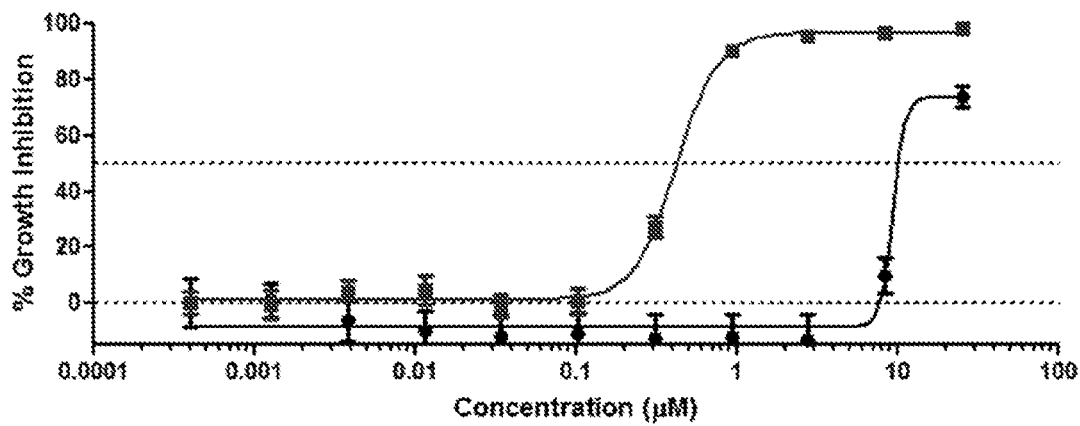
FIG. 7 shows an example of Ras-selective tumor cell growth inhibitory activity of exemplary Ras inhibitory compound 2183; the data were obtained according to the methods described in Examples 3 and 4; the square symbols are the HCT-116 data, the round symbols are the HT-29 data.

For demonstration of the Ras inhibitory properties of the compounds for use and usefulness according to the invention, any of the methods that we have disclosed and described extensively in WO 2016/100542 and WO 2016/100546, particularly with the examples contained therein, may be employed. This selected example illustrates the use of well-established human colon tumor cell lines with widely divergent Ras activation status to determine tumor cell growth inhibitory activity ($IC_{50}$ values) and Ras selectivity values for some selected exemplary compounds of the present invention. Cell lines thus employed in this example are HCT-116, a highly Ras-driven line expressing mutant Ras, and HT-29, a non-Ras-driven line expressing wild-type, non-mutated Ras. Cells are plated at 5000 cells/well in 96-well plates, ten-fold serial dilutions of compounds are tested, each tested concentration in at least 3 separate samples per cell line, and viable cell numbers are measured using the Cell Titer Glo ATP luminescence assay (Promega). To illustrate, in a typical, representative experiment the following data were obtained (compound ID numbers in bold; for each compound the first value is micromolar $IC_{50}$ for HCT-116, the second value is micromolar $IC_{50}$ for HT-29, and the third value is the HT-29/HCT-116 "Ras Inhibitory Selectivity Index" where numbers greater than one indicate Ras selectivity): compound 2096, 0.033, 9.00, 273; compound 2090, 0.300, 13.0, 43; compound 2183, 0.420, 9.28, 22; compound 1736, 5.05, 5.59, 1.11; compound 2200, 6.18, 6.65, 1.08; compound 1796, 0.212, 8.03, 38. FIGS. 5-7 provide examples of full data sets from which numerical values, including Ras selectivity indices, can be calculated; data sets are shown for selected exemplary compounds 2090, 2096 and 2183. FIGS. 5-7 provide examples of full data sets from which numerical values, including Ras selectivity indices, can be calculated; data sets are shown for selected exemplary compounds 2090, 2096 and 2183.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound, (Z)- or (E)-isomer, epimer, diastereomer, rotamer, or pharmaceutically acceptable salt thereof, wherein the compound is of formula IIa,

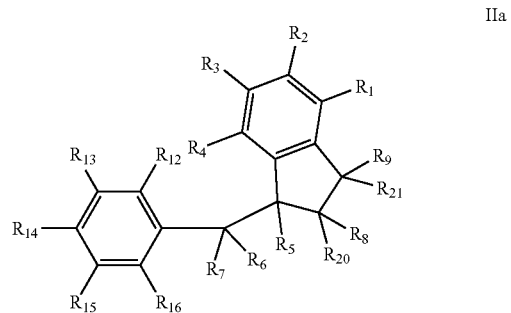

wherein:
$R_1$, $R_2$, $R_3$, and $R_4$ are independently selected from hydrogen, halo, alkyl, hydroxyl, haloalkyl, alkylmercapto, cyano, alkyloxy and haloalkyloxy;

$R_{21}$ is $—(CH_2)_nNR_{22}C(O)X$;

each of $R_5$, $R_6$, $R_7$, $R_8$, and $R_{22}$ is independently selected from hydrogen, alkyl, halo and hydroxyl; or $R_5$ and $R_6$ together is a carbon-carbon bond; $R_9$ and $R_{20}$ together is a carbon-carbon bond; or $R_6$ and $R_7$ together with the atom to which they are attached form a ring; or $R_5$ and $R_6$ together with the atoms to which they are attached, form a ring;

n is 1 or 2;

X is selected from aryl, arylalkyl, and heterocyclylalkyl, where the heterocyclyl of the heterocyclylalkyl of the X is selected from 7-membered, 6-membered and 5-membered heterocyclic rings, and the aryl of the aryl and arylalkyl, and the heterocyclyl of the heterocyclylalkyl, is optionally substituted with one or more of halo, alkyl, haloalkyl, hydroxyl, alkyloxy, amino, alkylamino, dialkylamino, mercapto, alkylmercapto, carboxamido, aldehydo, cyano, oxo, alkylcarbonyloxy and sulfonamido;

each of $R_{12}$, $R_{13}$, $R_{15}$ and $R_{16}$ is independently selected from the group consisting of hydrogen, halo, alkyl, cycloalkyl, haloalkyl, alkyloxy, haloalkyloxy, hydroxyl, carboxyl, formyloxy, hydroxyalkyl, aldehydo, amino, alkylamino, aminoalkyl, alkylaminoalkyl, dialkylamino, mercapto, alkylmercapto, cyano, cyanoalkyl, nitro and azido;

$R_{14}$ is hydroxyl, or is a cleavable alcohol prodrug moiety, or is a substituted or unsubstituted group selected from the group consisting of alkylsulfinyloxy, alkylsulfonyloxy, carbamate, alkyloxy, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, phosphonooxyalkyloxy, aminosulfonyloxy, polyethyleneglycoxy, borono, boronoalkyl, boronoalkyloxy, arylalkyloxy, aminocarbonylalkyloxy, carboxyalkyloxy, aminoalkyloxy, hydroxyalkyloxy, alkylaminoalkyloxy, dialkylaminoalkyloxy and alkyloxyaminocarbonyloxy;
  wherein the alkyl, and the alkyl of the alkylmercapto, alkyloxy haloalkyloxy, heterocyclylalkyl, cycloalkyl, haloalkyl, hydroxyalkyl, alkylamino, aminoalkyl, alkylaminoalkyl, dialkylamino, cyanoalkyl, alkylsulfinyloxy, alkylsulfonyloxy, alkylcarbonyloxy, alkylcarbonyloxyalkyloxy, aminocarbonyloxyalkyloxy, arylalkylcarbonyloxy, heterocyclylalkylcarbonyloxy, phosphonoalkyloxy, phosphonooxyalkyloxy, boronoalkyl, boronoalkyloxy, arylalkyloxy, aminocarbonylalkyloxy, carboxyalkyloxy, aminoalkyloxy, hydroxyalkyloxy, alkylaminoalkyloxy, dialkylaminoalkyloxy and alkyloxyaminocarbonyloxy, each comprises 1-6 carbon atoms; and,
  wherein the aryl, and the aryl of the arylalkyl, arylcarbonyloxy, arylalkylcarbonyloxy, aryloxycarbonyloxy and arylalkyloxy, each comprises an aromatic carbocyclic ring of 6-10 carbon atoms.

2. The compound, (Z)- or (E)-isomer, epimer, diastereomer, rotamer, or pharmaceutically acceptable salt of said compound of claim 1, wherein X is selected from phenyl, benzyl, and heterocyclylmethyl, where the heterocyclyl of the heterocyclylmethyl of the X is selected from the group consisting of piperidinyl, oxanyl, thianyl, pyridinyl, pyranyl, thiopyranyl, piperazinyl, morpholinyl, thiomorpholinyl, dioxanyl, dithianyl, pyrimidinyl, pyrazinyl, pyridizinyl, oxazinyl, thiazinyl, dioxinyl, dithiinyl, trioxanyl, trithianyl, triazinyl, tetrazinyl, pyrrolidinyl, tetrahydrofuranyl, tetrahydrothiaphenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl, wherein the phenyl and the phenyl ring of the benzyl, and the heterocyclyl of the heterocyclylmethyl, is optionally substituted with one or more of halo, alkyl, haloalkyl, hydroxyl, alkyloxy, amino, alkylamino, dialkylamino, mercapto, alkylmercapto, carboxamido, aldehydo, cyano, oxo, alkylcarbonyloxy and sulfonamide.

3. The compound, (Z)- or (E)-isomer, epimer, diastereomer, rotamer, or pharmaceutically acceptable salt of said compound of claim 2, where the heterocyclyl of the heterocyclylmethyl of the X is selected from the group consisting of furanyl, pyrrolyl, thiophenyl, oxazolyl, isoxazolyl, thiazolyl, isothiazolyl, dioxolanyl, pyrazolyl, pyridinyl and imidazolyl, wherein the phenyl and the phenyl ring of the benzyl, and the heterocyclyl of the heterocyclylmethyl are optionally substituted with one or more of halo, alkyl, haloalkyl, hydroxy, alkyloxy, amino, alkylamino, dialkylamino, mercapto, alkylmercapto, and carboxamido.

4. The compound, (Z)- or (E)-isomer, epimer, diastereomer, rotamer, or pharmaceutically acceptable salt of said compound of claim 3, wherein X is heterocyclylmethyl, where the heterocyclyl of the heterocyclylmethyl of the X is selected from the group consisting of furanyl, pyrrolyl, pyridinyl, oxazolyl, thiazolyl, dioxolanyl, imidazolyl, pyrazolyl and thiophenyl, wherein the heterocyclyl of the heterocyclylmethyl is optionally substituted with one or more of halo, alkyl, trifluoromethyl, hydroxy and methoxy.

5. The compound, (Z)- or (E)-isomer, epimer, diastereomer, rotamer, or pharmaceutically acceptable salt of said compound of claim 4, wherein the heterocyclylmethyl is selected from the group consisting of pyridin-3-ylmethyl, furan-2-ylmethyl, furan-3-ylmethyl, oxazol-2-ylmethyl, oxazol-4-ylmethyl, oxazol-5-ylmethyl, thiazol-2-ylmethyl, thiazol-4-ylmethyl, thiazol-5-ylmethyl, imidazol-2-ylmethyl, imidazol-4-ylmethyl, imidazol-5-ylmethyl, pyrazol-3-ylmethyl, pyrazol-4-ylmethyl, pyrazol-5-ylmethyl, dixolan-2-ylmethyl, and dioxolan-4-ylmethyl.

6. The compound, (Z)- or (E)-isomer, epimer, diastereomer, rotamer, or pharmaceutically acceptable salt of said compound of claim 5, wherein the heterocyclylmethyl is selected from the group consisting of pyridin-3-ylmethyl, oxazol-2-ylmethyl, thiazol-2-ylmethyl, imidazol-2-ylmethyl, pyrazol-4-ylmethyl, and dioxolan-2-ylmethyl.

7. The compound, (Z)- or (E)-isomer, epimer, diastereomer, rotamer, or pharmaceutically acceptable salt of said compound of claim 6, wherein the heterocyclylmethyl is pyridin-3-ylmethyl.

8. The compound, (Z)- or (E)-isomer, epimer, diastereomer, rotamer, or pharmaceutically acceptable salt of said compound of claim 1, wherein each of $R_1$, $R_2$, $R_3$ and $R_4$ is independently selected from the group consisting of hydrogen, halo, alkyloxy and alkyl; n is 1; each of $R_{12}$, $R_{13}$, $R_{15}$ and $R_{16}$ is independently selected from hydrogen, halo, alkyl, alkyloxy and haloalkyloxy; $R_{14}$ is selected from alkyloxy, hydroxyl, and a cleavable alcohol prodrug moiety.

9. The compound, (Z)- or (E)-isomer, epimer, diastereomer, rotamer, or pharmaceutically acceptable salt of said compound of claim 8, wherein $R_2$ is selected from halo and alkyloxy; $R_1$, $R_3$ and $R_4$ are hydrogen; and two of $R_{12}$, $R_{13}$, $R_{15}$ and $R_{16}$ are independently selected from hydrogen, alkyloxy and haloalkyloxy.

10. The compound, (Z)- or (E)-isomer, epimer, diastereomer, rotamer, or pharmaceutically acceptable salt of said compound of claim 9, wherein $R_2$ is selected from B fluoro and methoxy; and $R_{12}$ and $R_{16}$ are hydrogens.

11. The compound, (Z)- or (E)-isomer, epimer, diastereomer, rotamer, or pharmaceutically acceptable salt of said compound of claim 10, wherein each of $R_{13}$ and $R_{15}$ is independently selected from methoxy and trifluoromethoxy; and $R_{14}$ is selected from hydroxyl and methoxy.

12. The compound, (Z)- or (E)-isomer, epimer, diastereomer, rotamer, or pharmaceutically acceptable salt of said compound of claim 11, wherein each of $R_{13}$ and $R_{15}$ is methoxy; $R_7$ is hydrogen; $R_8$ is alkyl; $R_{14}$ is hydroxyl; and X is heterocyclylmethyl, where the heterocyclylmethyl of the X is pyridin-3-ylmethyl.

13. The compound, (Z)- or (E)-isomer, epimer, diastereomer, rotamer, or pharmaceutically acceptable salt of said compound of claim 1, wherein $R_5$ and $R_6$ together is a carbon-carbon bond.

14. A compound selected from the group consisting of:
  (Z)—N-((5-fluoro-1-(4-hydroxy-3,5-dimethoxybenzylidene)-2-methyl-1H-inden-3-yl)methyl)-1-methyl-1H-pyrrole-2-carboxamide (2085);
  (Z)—N-((5-fluoro-1-(4-hydroxy-3,5-dimethoxybenzylidene)-2-methyl-1H-inden-3-yl)methyl)-1H-pyrrole-2-carboxamide (2086);
  (Z)—N-((5-fluoro-1-(4-hydroxy-3,5-dimethoxybenzylidene)-2-methyl-1H-inden-3-yl)methyl)-1H-pyrrole-3-carboxamide (2087);

(Z)—N-((5-fluoro-1-(4-hydroxy-3,5-dimethoxybenzylidene)-2-methyl-1H-inden-3-yl)methyl)-1-methyl-1H-pyrrole-3-carboxamide (2088);

(Z)—N-((5-fluoro-1-(4-hydroxy-3,5-dimethoxybenzylidene)-2-methyl-1H-inden-3-yl)methyl)furan-3-carboxamide (2089);

(Z)—N-((5-fluoro-1-(4-hydroxy-3,5-dimethoxybenzylidene)-2-methyl-1H-inden-3-yl)methyl)furan-2-carboxamide (2090);

(Z)—N-((5-fluoro-1-(4-hydroxy-3,5-dimethoxybenzylidene)-2-methyl-1H-inden-3-yl)methyl)-2-(furan-3-yl)acetamide (2092);

(Z)—N-((5-fluoro-1-(4-hydroxy-3,5-dimethoxybenzylidene)-2-methyl-1H-inden-3-yl)methyl)-1H-imidazole-4-carboxamide (2093);

(Z)—N-((5-fluoro-1-(4-hydroxy-3,5-dimethoxybenzylidene)-2-methyl-1H-inden-3-yl)methyl)-2-(1H-imidazol-5-yl)acetamide (2094);

(Z)—N-((5-fluoro-1-(4-hydroxy-3,5-dimethoxybenzylidene)-2-methyl-1H-inden-3-yl)methyl)-2-(1H-pyrazol-5-yl)acetamide (2095);

(Z)—N-((5-fluoro-1-(4-hydroxy-3,5-dimethoxybenzylidene)-2-methyl-1H-inden-3-yl)methyl)-2-(pyridin-3-yl)acetamide (2096);

(Z)—N-((5-fluoro-1-(4-hydroxy-3,5-dimethoxybenzylidene)-2-methyl-1H-inden-3-yl)methyl)-2-(pyridin-2-yl)acetamide (2097);

(Z)—N-((5-fluoro-1-(4-hydroxy-3,5-dimethoxybenzylidene)-2-methyl-1H-inden-3-yl)methyl)-2-(pyridin-4-yl)acetamide (2098);

(Z)—N-((5-fluoro-1-(4-hydroxy-3,5-dimethoxybenzylidene)-2-methyl-1H-inden-3-yl)methyl)nicotinamide (2100);

(Z)—N-((5-fluoro-1-(4-hydroxy-3,5-dimethoxybenzylidene)-2-methyl-1H-inden-3-yl)methyl)-2-phenylacetamide (2101);

(Z)—N-((5-fluoro-1-(4-hydroxy-3,5-dimethoxybenzylidene)-2-methyl-1H-inden-3-yl)methyl)benzamide (2102);

(Z)—N-((5-fluoro-1-(4-hydroxy-3,5-dimethoxybenzylidene)-2-methyl-1H-inden-3-yl)methyl)-2-(oxazol-5-yl)acetamide (2103);

(Z)—N-((5-fluoro-1-(4-hydroxy-3,5-dimethoxybenzylidene)-2-methyl-1H-inden-3-yl)methyl)-2-(oxazol-2-yl)acetamide (2104);

(Z)—N-((5-fluoro-1-(4-hydroxy-3,5-dimethoxybenzylidene)-2-methyl-1H-inden-3-yl)methyl)-2-(oxazol-4-yl)acetamide (2105);

(Z)—N-((5-fluoro-1-(4-hydroxy-3,5-dimethoxybenzylidene)-2-methyl-1H-inden-3-yl)methyl)-2-(thiazol-5-yl)acetamide (2106);

(Z)—N-((5-fluoro-1-(4-hydroxy-3,5-dimethoxybenzylidene)-2-methyl-1H-inden-3-yl)methyl)oxazole-4-carboxamide (2107);

(Z)—N-((5-fluoro-1-(4-hydroxy-3,5-dimethoxybenzylidene)-2-methyl-1H-inden-3-yl)methyl)oxazole-5-carboxamide (2108);

(Z)—N-((5-fluoro-1-(4-hydroxy-3,5-dimethoxybenzylidene)-2-methyl-1H-inden-3-yl)methyl)oxazole-2-carboxamide (2109);

(Z)—N-((5-fluoro-1-(4-hydroxy-3,5-dimethoxybenzylidene)-2-methyl-1H-inden-3-yl)methyl)-2-(isoxazol-5-yl)acetamide (2110);

(Z)—N-((5-fluoro-1-(4-hydroxy-3,5-dimethoxybenzylidene)-2-methyl-1H-inden-3-yl)methyl)-2-(isoxazol-3-yl)acetamide (2111);

(Z)—N-((5-fluoro-1-(4-hydroxy-3,5-dimethoxybenzylidene)-2-methyl-1H-inden-3-yl)methyl)-2-(isoxazol-4-yl)acetamide (2112);

(Z)—N-((5-fluoro-1-(4-hydroxy-3,5-dimethoxybenzylidene)-2-methyl-1H-inden-3-yl)methyl)isoxazole-5-carboxamide (2113);

(Z)—N-((5-fluoro-1-(4-hydroxy-3,5-dimethoxybenzylidene)-2-methyl-1H-inden-3-yl)methyl)-2-(pyrazin-2-yl)acetamide (2114);

(Z)-(4-((3-((1H-imidazole-4-carboxamido)methyl)-5-fluoro-2-methyl-1H-inden-1-ylidene)methyl)-2,6-dimethoxyphenyl)boronic acid (2115);

(Z)-4-((3-((1H-imidazole-2-carboxamido)methyl)-5-fluoro-2-methyl-1H-inden-1-ylidene)methyl)-2,6-dimethoxyphenyl dimethylcarbamate (2116);

(Z)-(4-((3-((2-(1H-imidazol-2-yl)acetamido)methyl)-5-fluoro-2-methyl-1H-inden-1-ylidene)methyl)-2,6-dimethoxyphenyl)boronic acid (2117);

(Z)-(4-((3-((2-(1H-pyrazol-5-yl)acetamido)methyl)-5-fluoro-2-methyl-1H-inden-1-ylidene)methyl)-2,6-dimethoxyphenyl)boronic acid (2119);

(Z)-4-((5-fluoro-2-methyl-3-((oxazole-4-carboxamido)methyl)-1H-inden-1-ylidene)methyl)-2,6-dimethoxyphenyl ethylcarbamate (2120);

(Z)-4-((5-fluoro-3-((2-(isoxazol-5-yl)acetamido)methyl)-2-methyl-1H-inden-1-ylidene)methyl)-2,6-dimethoxyphenyl 4-methylpiperazine-1-carboxylate (2121);

(Z)-4-((5-fluoro-2-methyl-3-((oxazole-2-carboxamido)methyl)-1H-inden-1-ylidene)methyl)-2,6-dimethoxyphenyl dimethylcarbamate (2122);

(Z)-(4-((5-fluoro-3-((2-(isoxazol-4-yl)acetamido)methyl)-2-methyl-1H-inden-1-ylidene)methyl)-2,6-dimethoxyphenyl)boronic acid (2123);

(Z)-(4-((5-fluoro-3-((2-(isoxazol-5-yl)acetamido)methyl)-2-methyl-1H-inden-1-ylidene)methyl)-2,6-dimethoxyphenyl)boronic acid (2124);

(Z)-4-((5-fluoro-2-methyl-3-((2-phenylacetamido)methyl)-1H-inden-1-ylidene)methyl)-2,6-dimethoxyphenyl 4-methylpiperazine-1-carboxylate (2125);

(Z)-4-((5-fluoro-2-methyl-3-((2-(pyridin-3-yl)acetamido)methyl)-1H-inden-1-ylidene)methyl)-2,6-dimethoxyphenyl morpholine-4-carboxylate (2126);

(Z)-4-((5-fluoro-3-((2-(furan-2-yl)acetamido)methyl)-2-methyl-1H-inden-1-ylidene)methyl)-2,6-dimethoxyphenyl 4-methylpiperazine-1-carboxylate (2127);

(Z)-4-((3-((2-(1H-imidazol-5-yl)acetamido)methyl)-5-fluoro-2-methyl-1H-inden-1-ylidene)methyl)-2,6-dimethoxyphenyl morpholine-4-carboxylate (2128);

(Z)-4-((5-fluoro-2-methyl-3-((2-(thiazol-5-yl)acetamido)methyl)-1H-inden-1-ylidene)methyl)-2,6-dimethoxyphenyl morpholine-4-carboxylate (2129);

(Z)-4-((5-fluoro-2-methyl-3-((2-(pyridin-2-yl)acetamido)methyl)-1H-inden-1-ylidene)methyl)-2,6-dimethoxyphenyl ethylcarbamate (2130);

(Z)-(4-((5-fluoro-2-methyl-3-((2-(pyridin-3-yl)acetamido)methyl)-1H-inden-1-ylidene)methyl)-2,6-dimethoxyphenyl)boronic acid (2131);

(Z)-(4-((5-fluoro-3-((2-(furan-2-yl)acetamido)methyl)-2-methyl-1H-inden-1-ylidene)methyl)-2,6-dimethoxyphenyl)boronic acid (2132);

(Z)-(4-((5-fluoro-2-methyl-3-((2-(1-methyl-1H-pyrrol-2-yl)acetamido)methyl)-1H-inden-1-ylidene)methyl)-2,6-dimethoxyphenyl)boronic acid (2133);

(Z)-(4-((5-fluoro-3-((furan-2-carboxamido)methyl)-2-methyl-1H-inden-1-ylidene)methyl)-2,6-dimethoxyphenyl)boronic acid (2134);

(Z)-4-((5-fluoro-2-methyl-3-((2-(pyridin-2-yl)acetamido)methyl)-1H-inden-1-ylidene)methyl)-2,6-dimethoxyphenyl [1,4'-bipiperidine]-1'-carboxylate (2135);

(Z)-4-((5-fluoro-2-methyl-3-((2-(oxazol-5-yl)acetamido)methyl)-1H-inden-1-ylidene)methyl)-2,6-dimethoxyphenyl [1,4'-bipiperidine]-1'-carboxylate (2136);

(Z)-4-((5-fluoro-2-methyl-3-((2-(oxazol-4-yl)acetamido)methyl)-1H-inden-1-ylidene)methyl)-2,6-dimethoxyphenyl [1,4'-bipiperidine]-1'-carboxylate (2137);

(Z)-4-((5-fluoro-2-methyl-3-((2-phenylacetamido)methyl)-1H-inden-1-ylidene)methyl)-2,6-dimethoxyphenyl [1,4'-bipiperidine]-1'-carboxylate (2138);

(Z)-4-((5-fluoro-2-methyl-3-((2-(pyridin-3-yl)acetamido)methyl)-1H-inden-1-ylidene)methyl)-2,6-dimethoxyphenyl [1,4'-bipiperidine]-1'-carboxylate (2139);

(Z)-4-((5-fluoro-3-((2-(isoxazol-5-yl)acetamido)methyl)-2-methyl-1H-inden-1-ylidene)methyl)-2,6-dimethoxyphenyl [1,4'-bipiperidine]-1'-carboxylate (2140);

(Z)-4-((5-fluoro-3-((2-(furan-2-yl)acetamido)methyl)-2-methyl-1H-inden-1-ylidene)methyl)-2,6-dimethoxyphenyl [1,4'-bipiperidine]-1'-carboxylate (2141);

(Z)-4-((5-fluoro-2-methyl-3-((2-(1-methyl-1H-pyrrol-2-yl)acetamido)methyl)-1H-inden-1-ylidene)methyl)-2,6-dimethoxyphenyl [1,4'-bipiperidine]-1'-carboxylate (2142);

(Z)-2-(1,3-dioxolan-2-yl)-N-((5-fluoro-1-(4-hydroxy-3,5-dimethoxybenzylidene)-2-methyl-1H-inden-3-yl)methyl)acetamide (2174);

(Z)—N-((5-fluoro-1-(4-hydroxy-3,5-dimethoxybenzylidene)-2-methyl-1H-inden-3-yl)methyl)-2-(2-methyl-1,3-dioxolan-4-yl)acetamide (2175);

(Z)—N-((5-fluoro-1-(4-hydroxy-3,5-dimethoxybenzylidene)-2-methyl-1H-inden-3-yl)methyl)-2-(thiazol-2-yl)acetamide (2176);

(Z)—N-((5-fluoro-1-(4-hydroxy-3,5-dimethoxybenzylidene)-2-methyl-1H-inden-3-yl)methyl)-2-(1,3-oxathiolan-2-yl)acetamide (2179); and (Z)—N-((5-fluoro-1-(4-hydroxy-3,5-dimethoxybenzylidene)-2-methyl-1H-inden-3-yl)methyl)-1H-pyrazole-4-carboxamide (2183);

or (E)-isomer thereof, epimer, diastereomer or rotamer thereof, or pharmaceutically acceptable salt thereof.

15. A pharmaceutical composition comprising at least one compound, (Z)- or (E)-isomer, epimer, diastereomer, rotamer, or pharmaceutically acceptable salt of said compound, of claim 1, and a pharmaceutically acceptable carrier, said composition optionally containing at least one therapeutic agent that is not a compound of claim 1 or (E)-isomer thereof, epimer, diastereomer or rotamer thereof or pharmaceutically acceptable salt thereof.

16. A pharmaceutical composition comprising at least one compound, (Z)- or (E)-isomer, epimer, diastereomer, rotamer, or pharmaceutically acceptable salt of said compound, of claim 14, and a pharmaceutically acceptable carrier, said composition optionally containing at least one therapeutic agent that is not a compound of claim 1 or (E)-isomer thereof, epimer, diastereomer or rotamer thereof or pharmaceutically acceptable salt thereof.

17. A method of treating a patient whose cancer has been assayed and found to contain a hyperactive Ras protein or a mutant ras gene encoding for a hyperactive Ras protein, the method comprising administering to the patient an effective amount of the compound of claim 1, (Z)- or (E)-isomer, epimer, diastereomer, rotamer, or pharmaceutically acceptable salt of said compound.

18. A method of treating a patient whose cancer has been assayed and found to contain a hyperactive Ras protein or a mutant ras gene encoding for a hyperactive Ras protein, the method comprising administering to the patient an effective amount of the compound of claim 14, (Z)- or (E)-isomer, epimer, diastereomer, rotamer, or pharmaceutically acceptable salt of said compound.

19. The method according to claim 17, wherein the patient's cancer is pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, or leukemia.

20. The method according to claim 19, wherein the patient's cancer is pancreatic cancer, colorectal cancer, or lung cancer.

* * * * *